US009493466B2

(12) United States Patent
Xu et al.

(10) Patent No.: US 9,493,466 B2
(45) Date of Patent: Nov. 15, 2016

(54) TREATMENT OF CANCER WITH TOR KINASE INHIBITORS

(71) Applicant: Signal Pharmaceuticals, LLC, San Diego, CA (US)

(72) Inventors: Shuichan Xu, San Diego, CA (US); Kristen Mae Hege, Burlingame, CA (US); Antonia Lopez-Girona, San Diego, CA (US); Heather Raymon, San Diego, CA (US); Rama K. Narla, San Diego, CA (US); Rajesh Chopra, Summit, NJ (US)

(73) Assignee: Signal Pharmaceuticals, LLC, San Diego, CA (US)

( * ) Notice: Subject to any disclaimer, the term of this patent is extended or adjusted under 35 U.S.C. 154(b) by 0 days.

(21) Appl. No.: 13/654,441

(22) Filed: Oct. 18, 2012

(65) Prior Publication Data

US 2013/0102613 A1    Apr. 25, 2013

Related U.S. Application Data

(60) Provisional application No. 61/549,034, filed on Oct. 19, 2011, provisional application No. 61/591,401, filed on Jan. 27, 2012, provisional application No. 61/647,233, filed on May 15, 2012, provisional application No. 61/653,436, filed on May 31, 2012.

(51) Int. Cl.
| | |
|---|---|
| *A01N 43/58* | (2006.01) |
| *A01N 43/60* | (2006.01) |
| *A61K 31/50* | (2006.01) |
| *A61K 31/495* | (2006.01) |
| *A61K 38/00* | (2006.01) |
| *A61P 35/00* | (2006.01) |
| *C07D 487/04* | (2006.01) |
| *A61K 31/4166* | (2006.01) |
| *A61K 31/4188* | (2006.01) |
| *A61K 31/4985* | (2006.01) |
| *C07D 471/04* | (2006.01) |
| *C07D 473/00* | (2006.01) |
| *C07D 498/04* | (2006.01) |

(52) U.S. Cl.
CPC ......... *C07D 487/04* (2013.01); *A61K 31/4166* (2013.01); *A61K 31/4188* (2013.01); *A61K 31/4985* (2013.01); *C07D 471/04* (2013.01); *C07D 473/00* (2013.01); *C07D 498/04* (2013.01)

(58) Field of Classification Search
None
See application file for complete search history.

(56) References Cited

U.S. PATENT DOCUMENTS

| | | | |
|---|---|---|---|
| 3,507,866 A | 4/1970 | Jones et al. |
| 3,567,725 A | 3/1971 | Grabowki et al. |
| 4,294,836 A | 10/1981 | Lesher et al. |
| 4,294,837 A | 10/1981 | Lesher et al. |
| 4,309,537 A | 1/1982 | Lesher et al. |
| 4,317,909 A | 3/1982 | Lesher et al. |
| 4,898,872 A | 2/1990 | Campbell et al. |
| 4,963,561 A | 10/1990 | Lesher et al. |
| 5,424,311 A | 6/1995 | Billhardt-Troughton |
| 5,869,659 A | 2/1999 | Stolle et al. |
| 6,031,105 A | 2/2000 | Wright |
| 6,093,728 A | 7/2000 | McMahon et al. |
| 6,372,740 B1 | 4/2002 | Murata et al. |
| 6,566,367 B2 | 5/2003 | Bakthavatchalam et al. |
| 6,855,723 B2 | 2/2005 | McMahon et al. |
| 7,968,556 B2 | 6/2011 | Mortensen et al. |
| 7,981,893 B2 | 7/2011 | Mortensen et al. |
| 8,110,578 B2 | 2/2012 | Perrin-Ninkovic et al. |
| 8,372,976 B2 | 2/2013 | Mortensen et al. |
| 8,383,634 B2 | 2/2013 | Mortensen et al. |
| 2003/0036652 A1 | 2/2003 | Bakthavatchalam et al. |
| 2003/0162968 A1 | 8/2003 | Cirillo et al. |
| 2004/0023921 A1 | 2/2004 | Hong et al. |
| 2004/0063658 A1 | 4/2004 | Roberts et al. |
| 2004/0097485 A1 | 5/2004 | Burkitt et al. |
| 2004/0213757 A1 | 10/2004 | Zhu et al. |
| 2005/0009737 A1 | 1/2005 | Clark |
| 2006/0004014 A1 | 1/2006 | Hoffmann et al. |
| 2006/0106022 A1 | 5/2006 | Liu et al. |
| 2006/0135511 A1 | 6/2006 | Burgey |
| 2006/0142269 A1 | 6/2006 | Dykes |
| 2008/0214580 A1 | 9/2008 | Neagu et al. |
| 2009/0023724 A1 | 1/2009 | Mortensen et al. |
| 2009/0069289 A1 | 3/2009 | Neagu et al. |
| 2009/0163545 A1 | 6/2009 | Goldfarb |
| 2009/0281075 A1 | 11/2009 | Roughton et al. |
| 2010/0144738 A1 | 6/2010 | Bornmann et al. |

(Continued)

FOREIGN PATENT DOCUMENTS

| | | |
|---|---|---|
| CA | 2 458 699 A1 | 3/2003 |
| DE | 262 026 | 11/1988 |

(Continued)

OTHER PUBLICATIONS

Gruppuso, et al., The physiology and pathophysiology of rapamycin resistance, Apr. 2011, Cell Cycle, vol. 10, Iss. 7, pp. 1050-1058.*

(Continued)

*Primary Examiner* — Kortney L Klinkel
*Assistant Examiner* — Tori M Strong
(74) *Attorney, Agent, or Firm* — Jones Day

(57) ABSTRACT

Provided herein are methods for treating or preventing a solid tumor, non-Hodgkin lymphoma or multiple myeloma in a patient, comprising administering an effective amount of a TOR kinase inhibitor to a patient having a solid tumor, non-Hodgkin lymphoma or multiple myeloma.

5 Claims, 32 Drawing Sheets

(56) References Cited

U.S. PATENT DOCUMENTS

| | | |
|---|---|---|
| 2010/0249122 A1 | 9/2010 | Kalman |
| 2011/0137028 A1 | 6/2011 | Harris et al. |
| 2011/0257167 A1 | 10/2011 | Chopra et al. |
| 2012/0028972 A1 | 2/2012 | Wong et al. |
| 2012/0059164 A1 | 3/2012 | Perrin-Ninkovic et al. |
| 2012/0071658 A1 | 3/2012 | Perrin-Ninkovic et al. |

FOREIGN PATENT DOCUMENTS

| | | |
|---|---|---|
| EP | 0 385 850 | 9/1990 |
| JP | 63275582 | 5/1987 |
| JP | 2001048882 | 2/2001 |
| JP | 2002100363 | 4/2002 |
| JP | 2002167387 | 6/2002 |
| WO | WO 99/16438 | 4/1999 |
| WO | WO 99/28320 | 6/1999 |
| WO | WO 00/73306 | 12/2000 |
| WO | WO 02/48152 | 6/2002 |
| WO | WO 02/076954 | 10/2002 |
| WO | WO 03/032989 | 4/2003 |
| WO | WO 03/093290 | 11/2003 |
| WO | WO 2004/042002 | 5/2004 |
| WO | WO 2004/065378 | 8/2004 |
| WO | WO 2004/076454 | 9/2004 |
| WO | WO 2004/085409 | 10/2004 |
| WO | WO 2005/003147 | 1/2005 |
| WO | WO 2006/050076 | 5/2005 |
| WO | WO 2005/120511 | 12/2005 |
| WO | WO 2006/001266 | 1/2006 |
| WO | WO 2006/030031 | 3/2006 |
| WO | WO 2006/036883 | 4/2006 |
| WO | WO 2006/045828 | 5/2006 |
| WO | WO 2006/065703 | 6/2006 |
| WO | WO 2006/087530 | 8/2006 |
| WO | WO 2006/091737 | 8/2006 |
| WO | WO 2006/108103 | 10/2006 |
| WO | WO 2008/016669 | 2/2008 |
| WO | WO 2008/051493 | 5/2008 |
| WO | WO 2008/051494 | 5/2008 |
| WO | WO 2010/056311 | 5/2010 |
| WO | WO 2010/062571 | 6/2010 |
| WO | WO 2010/068483 | 6/2010 |
| WO | WO 2010062571 A1 * | 6/2010 |
| WO | WO 2011/053518 | 5/2011 |
| WO | WO 2011/097333 | 8/2011 |
| WO | WO 2012/016113 | 2/2012 |

OTHER PUBLICATIONS

Gulati et al., "Involvement of mTORC1 and mTORC2 in regulation of glioblastoma multiforme growth and motility," International Journal of Oncology, vol. 35, No. 4, Sep. 1, 2009, abstract.
Mortensen et al., "Use of core modification in the discovery of CC214-2, an orally available, selective inhibitor of mTOR kinase," Bioorganic & Medicinal Chemistry Letters, vol. 23, No. 6, Mar. 1, 2013, pp. 1588-1591.
U.S. Appl. No. 13/689,972, filed Nov. 30, 2012, Assaf et al.
U.S. Appl. No. 13/701,224, filed Mar. 5, 2013, Ning et al.
Barlin, "Purine analogs as amplifiers of phleomycin. VII. Some 1H-inidazo[4,5-b]pyrazines and related compound," Australian Journal of Chemistry, vol. 35, pp. 2299-2306 (1982).
Beresnev et al., "Interaction of 5-methoxy-1,2,4-traizines with uras as a new route to 6-azapurines," Medeleev Commu., vol. 2, pp. 58-59 (2000).
Bergmann et al., "2-Phenylpurines, their chemical and enzumological reactivity," J. Chem Org., pp. 3729-3735 (1963).
Booth et al., "Synthesis of 9-Hydroxyalkyl-substituted purines from the corresponding 4-(C-Cyanoformimidoyl)imidazole-5-amines," J, Chem Society, Perkin Transactions 1: Organic and Bio-Organic Chemstry, vol. pp. 2119-2126 (1992).
Booth et al., "Synthesis of [1α, 2β,3α-2,3-bis(benzyloxymethyp)cyclobutl]imidazol-5-amines: important precursors to cyclobut-A derivatives," J. Chem Society, Perkin Tranactions 1: Organic and Bio-Organic Chemistry, vol. 6, pp. 669-675 (1995).
Booth et al., "The Reactions of Diaminomaleonitrile with Isocyanates and Either Aldehydes or Ketones Revisited," J. Org Chem, vol. 66, pp. 8436-8441 (2001).
Booth, et al., "Synthesis of 4- and 5-Disubstituted 1-Benzylimidazoles, Important Precursors of Purine Analogs," J. of Heterocyclic of Chemistry, vol. 31(2), pp. 345-350 (1994).
Chupakhin et al., "A simple one pot synthesis of condensed 1,2,4-triazines by using the tandem $A_N$-$S_N$ipso and $S_N^H$ $S_N$ipso reactions," J. of Heterocyclic Chemistry, vol. 38(4), pp. 901-907 (2001).
Cohen, "The role of protein phosphorylation in human health and disease," Eur. J. Biochem, vol. 268, pp. 5001-5010 (2001).
Cohen, P. "Protein kinases—the major drug targets of the twenty-first century?" Nature Reviews/Drug Discovery, vol. 1, pp. 309-315 (2002).
Coish, et al., "Small molecule inhibitors of IKK kinase activity," Expert Opin. Ther. Patents, vol. 16(1), pp. 1-12 (2006).
Costa et al., "Aspects of mTOR biology and the use of mTOR inhibitors in non-Hodgkin's lymphoma," Cancer Treatment Reviews, Saunders, US, vol. 33(1), pp. 78-84 (2007).
Crofts et al., "Metabolism of 2-amino-1-methyl-6-phenylimidazo[4,5-b]pyridine (PhIP) by human cytochrome P4501B1," Carcinogenesis, vol. 18(9), pp. 1793-1798 (1997).
Dang et al., "Efficient synthesis of purines and purine nucelosides via an inverse electron demand diels-alder reaction," J. Am Chem Soc., vol. 121(24), pp. 5833-5834 (1999).
Database Caplus Online Chemical Abstracts Service, Columbus, Ohio, Database Accession No. 1951:49974 (XP-002472261) (1951).
Database Caplus Online Chemical Abstracts Service, Columbus, Ohio, Database Accession No. 1978:433195 (XP-002472262) (1978).
Database Caplus Online Chemical Abstracts Service, Columbus, Ohio, Database Accession No. 1966:26849 (XP-002472263) (1965).
Dornow et al., "Synthese von2-Oxy-imidazolo-(5',4':2,3)-pyridinen)," Arch Pharm. vol. 290, pp. 20-31 (1957) (w/English language abstract).
Dorwald F. Zaragoza, "Side Reactions in Organic Synthesis: a Guide to Successful Synthesis Design," Weinheim: Wiley-VCH Verlag GmbH & Co. KgaA, Preface. (2005).
Dzierba et al., "Synthesis, structure-activity relationships, and in vivo properties of 3,4-dihydro-1II-pyrido[2,3- b]pyrazin-2-ones as corticotropin-releasing factor-1 receptor antagonists," J of Medicinal Chemistry, vol. 47(23), pp. 5783-5790 (2004).
EPO Supplementary European Search Report dated Feb. 8, 2013 issued in connection with PCT/US2010/053678.
Fabbro et al., "Protein kinases as targets for anticancer agents: from inhibitors touseful drugs," Pharmacology & Therapeutics, vol. 93, pp. 79-98 (2002).
Farhadi et al., "The role of protein kinase C isoforms in modulating injury and repair of the intestinal barrier," J. Pharm Exp. Ther., vol. 316(1), pp. 1-7 (2006).
Frandsen et al., "Reaction of the N2-acetoxy derivative of 2-amino-l-methyl-6-phenylimidazo[4,5,b] pyridine . . . ," Carcinogenesis, vol. 13(4), pp. 629-635 (1992).
Frost et al., "AKT activity regulates the ability of mTOR inhibitors to prevent angiogenesis and VEGF expression in multiple myeloma cells," Oncogene, vol. 26(16), pp. 2255-2262 (2007).
Georgakis and Younes, "From rapi nui to rapamycin: targeting PI3K/Akt/mTOR for cancer therapy," Expert Rev. Anticancer Ther., vol. 6(1), 131-140 (2006).
Hamad, "A new synthesis of 4-cyano-1,3-dihydro-2-oxo-2H-imidazole-5-($N^1$-tosyl)carboxamide: Reactive precursor for thiopurine analogues," J of Heterocyclic Chemistry, vol. 38(4), pp. 939-944 (2001).
http://www.sigmaaldrich.com/catalog/product/ALDRICH/678740?lang=en&region=US, last accessed Nov. 1, 2012.
http://www.sigmaaldrich.com/catalog/product/ALDRICH/701602?lang=en&region=US#, last accessed Nov. 1, 2012.

(56) References Cited

OTHER PUBLICATIONS http://www.sigmaaldrich.com/catalog/product/aldrich/697230?lang=en&region=US, last accessed Nov. 1, 2012.
http://www.sigmaaldrich.com/chemistry/chemical-synthesis/technology-spotlights/catalysisapplicationguide.html, last accessed Nov. 1, 2012.
Irie et al., "Toward the development of new medicinal leads with selectivity for protein kinase C isozymes," The Chemical Record, vol. 5, pp. 185-195 (2005).
Itoh et al., "A novel practical synthesis of C-2-arylpurines," Advanced Synthesis & Catalysis, vol. 346, pp. 1859-1867 (2004).
Gulati et al. "Involvement of mTORC1 and mTORC2 in regulation of glioblastoma multiforme growth and motility," International Journal of Oncology, vol. 35(4) (2009), abstract.
Jones et al., "6-Substituted-5-chloro-1,3-dihydro-2H-imidazo(4,5-b)pyrazin-2-ones with hypotensive activity," J. Med. Chem., vol. 16(5), pp. 537-542 (1973).
Jordan, V.C., Nature Reviews: Drug Discover, vol. 2, p. 205 (2003).
Kazaoka et al., "Synthesis of 6-substituted 9-benzyl-8-hydroxypurines with potential interferon-indcuing activity," Chemical & Pharmaceutical Bulletin, vol. 51(5), pp. 608-611 (2003).
Killday et al., "Microxine, a new cdc2 kinase inhibitor from the Australian marine sponge Microxina species," J. of Natural Products, vol. 64(4), pp. 525-526 (2001).
Minehan et al., "Molecular recognition of DNA by Hoechst Benzimidazoles: Exploring beyond theopyrrole-imidazole-hydroxypyrrole polyamide-pairing code," Helvitica Chima Acta, vol. 83(9), pp. 2197-2213 (2000).
Mortensen et al., "Discovery and SAR exploration of a novel series of imidazo[4,5-] pyrazin-2-ones as potent and selective inTOR kinase inhibitors," Bioorganic & Medicinal Chemistry Letters, Pergamon, Elsevier Science, GB, vol. 21(22), pp. 6793-6799 (2011).
Nagashima et al., "Solution-Phase parallel synthesis of an N-Alkylated dihydropteridinone library from fluorous amino acids," J of Comb. Chemistry, vol. 6(6), pp. 942-949 (2004).
Park et al., "A novel mechanism of TRAF signaling revealed by structural and functional analyses of the TRADD-TRAF2 interaction," Cell, vol. 101, pp. 777-787 (2000).
Patani et al., "Bioisosterim: A rational approach in drug design," Chemical Reviews, vol. 96, pp. 3147-3176 (1996).
Registry File Document for RN 863501-03-5, 863502-39-0 (Sep. 20, 2005).
Seela et al., "Product Class 17: Purities," Science of Synthesis, vol. 16, pp. 945-1108 (2004).
Singh et al., 1994, "Novel cAMP PDE III Inhibitors: Imidazo[4,5-b]pyridin-2(3H)-ones and Thiazolo[4,5-b]pyridin-2(3h)-ones and Their Analogs," J. Med. Chem, vol. 37(2):248-254.
Sridhar et al., "Protein Kinasesas Therapeutic Targets," Pharm. Research, vol. 17(11), pp. 1345-1353 (2000).
Office Action mailed Jun. 11, 2009 for U.S. Appl. No. 11/975,652.
Office Action mailed Sep. 2, 2009 for U.S. Appl. No. 11/975,652.
Final Office Action mailed Feb. 2, 2010 for U.S. Appl. No. 11/975,652 with Notice of References Cited.
Office Action mailed May 12, 2010 for U.S. Appl. No. 11/975,652.
Final Office Action mailed Sep. 30, 2010 for U.S. Appl. No. 11/975,652 with Notice of References Cited.
PCT International Search Report dated Mar. 29, 2010 issued in connection with PCT/US2009/062143.
PCT Written Opinion of the International Searching Authority dated Mar. 29, 2010.
Office Action mailed Nov. 10, 2010 for U.S. Appl. No. 12/605,791.
PCT IPRP with Written Opinion of the International Searching Authority dated May 12, 2011 in connection with PCT /US2009/062143.
Office Action mailed Jan. 19, 2011 for U.S. Appl. No. 12/605,791 with Notice of References Cited.
Final Office Action mailed May 10, 2011 for U.S. Appl. No. 12/605,791.
Advisory Action mailed Aug. 17, 2011 for U.S. Appl. No. 12/605,791.
Advisory Action mailed Sep. 14, 2011 for U.S. Appl. No. 2/605,791.
PCT International Search Report dated Dec. 27, 2010 issued in connection with PCT/US2010/053678.
PCT Written Opinion dated Dec. 27, 2010 in connection with PCT/US/10/53678.
Office Action mailed Feb. 28, 2012 for U.S. Appl. No. 12/910,920 with Notice of Reference Cited.
PCT IPRP dated May 10, 2012 issued in connection with PCT/US2010/053678.
Office Action mailed Jun. 28, 2012 for U.S. Appl. No. 12/910,920 with Notice of Reference Cited.
Final Office Action mailed Nov. 6, 2012 for U.S. Appl. No. 12/910,920 with Notice of Reference Cited.
Office Action mailed Apr. 2, 2012 for U.S. Appl. No. 13/295,513.
Office Action mailed Aug. 27, 2012 for U.S. Appl. No. 13/295,513 with Notice of References Cited.
PCT Partial International Search dated Feb. 21, 2013 issued in connection with PCT/US2012/060723.
PCT International Search Report dated Feb. 13, 2013 issued in connection with PCT/US2012/067172.
PCT Written Opinion dated Feb. 13, 2013 issued in connection with PCT/US/2012/067172.
Vippagunta et al., Advanced Drug Delivery Reviews, vol. 48, pp. 3-26 (2001) (Cited in Office Action in connection with U.S. Appl. No. 12/605,791).
Wallace, "Palladium-catalyzed synthesis of quinoxaline derivatives," Tetrahedron, vol. 64, pp. 9675-9684 (2008).
Westover et al., "Synthesis and antiviral activity of certain 9-β-D-Riofuranoaylpurine-6-carboxamides," J.Med. Chem., vol. 24(8), pp. 941-946 (1981).
Wolff, Manfred E., Ed. Burger's Medicinal Chemistry and Drug Discovery—Fifth Edition, New York: John Wiley & Sons, vol. 1, pp. 975-976 (1996).
Yoneda et al., "A transformation of 7-azapteridines into 6-azapurines (Imidazo[4,5-e]- as -triazines)," Heterocycles, vol. 4(9), pp. 1503-1508 (1976).
Yoneda et al., "Synthesis of imadazo[4,5-e]-as-triazine (6-Azapurine) Deriviatives," Chem & Pharm Bulletin, vol. 26(10), pp. 3154-3160 (1978).
Zaki et al., "The synthesis of imidazol[4,5-d]pyridines from a substituted imidazole and acyl or sulfonyl acetonitrile," Tetrahedron, vol. 63(18), pp. 3745-3753 (2007).
PCT Partial International Search dated Nov. 15, 2012 issued in connection with PCT/US2012/049281.
PCT International Search Report dated Jan. 11, 2013 issued in connection with PCT/US2012/049281.
PCT Written Opinion dated Feb. 13, 2013 issued in connection with PCT/US2012/049281.
Yuan et al., "Targeting tumorigenesis: development and use of mTOR inhibitors in cancer therapy," Journal of Hematology & Oncology, vol. 2(1), p. 45 (2009).
Carretero et al., "Integrative Genomic and Proteomic Analyses Identify Targets for Lkb1-Deficient Metastatic Lung Tumors," Cancer Cell, vol. 17( 6), pp. 547-559 (2010).
Gao et al., "LKB1 in lung cancerigenesis: a serine/threonine kinase as tumor suppressor," Protein & Cell, vol. 2(2), pp. 99-107 (2011).
Gao et al., "LKB1 inhibits lung cancer progression through lysyl oxidase and extracellular matrix remodeling," Proceedings of the National Academy of Sciences, vol. 107(44), pp. 18892-18897 (2010).
Inge et al., "Expression of LKB1 tumor suppressor in non-small cell lung cancer determines sensitivity to 2-deoxyglucose," Journal of Thoracic and Cardiovascular Surgery, vol. 137(3), pp. 580-558 (2009).

(56) References Cited

OTHER PUBLICATIONS

Wingo et al., "Somatic LKB1 Mutations Promote Cervical Cancer Progression," Plos One, vol. 4(4), pp. 5137-5138 (2009).
Shaw et al., "The LKB1 tumor suppressor negatively regulates mTOR signaling," Cancer Cell, vol. 6(1), pp. 91-99 (2004).
Huang et al., "Genetic and epigenetic silencing of SCARA5 may contribute to human hepatocellular carcinoma by activating FAK signaling," Journal of Clinical Investigation, vol. 120(1), pp. 223-241 (2010).
Gini et al., (2013) "The mTOR kinase inhibitors, CC214-1 and CC214-2, preferentially block the growth of EGFRvIII-activated glioblastomas." Clinical Cancer Research 19.20 (2013): 5722-5732.

* cited by examiner

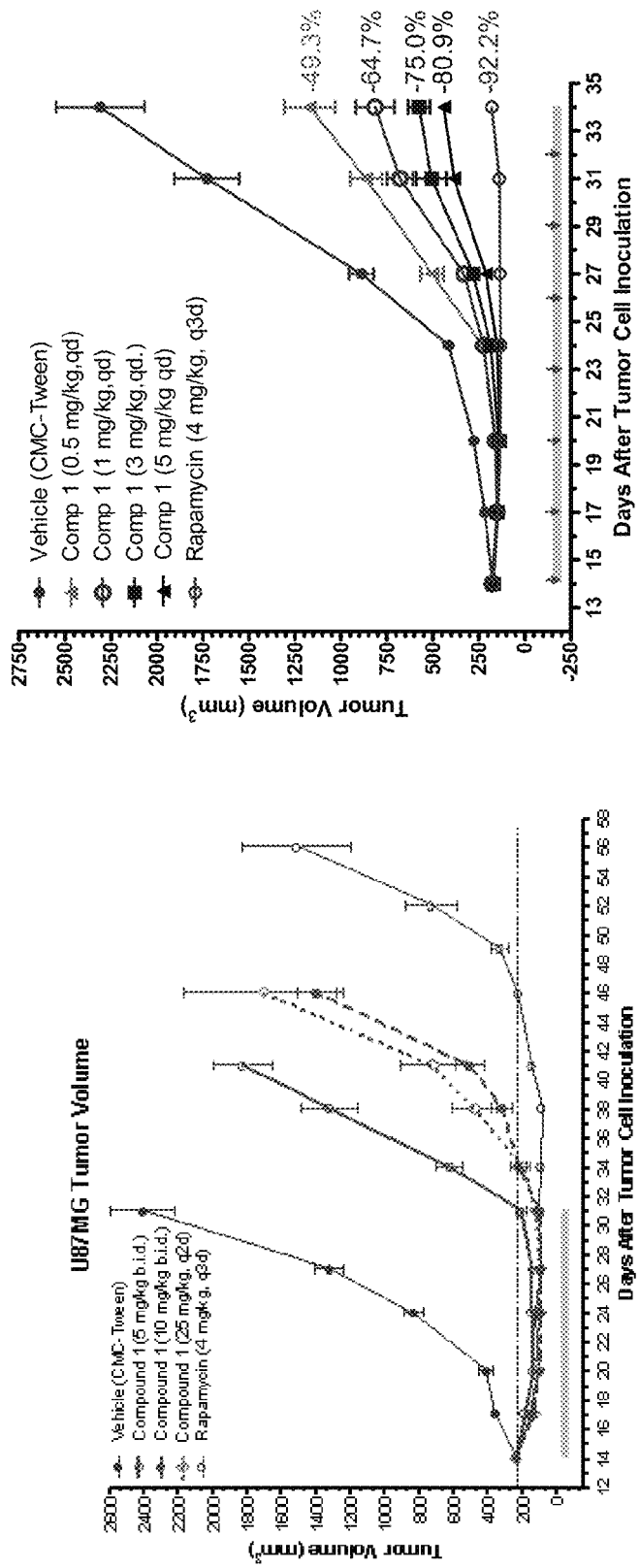
FIG. 10A-B

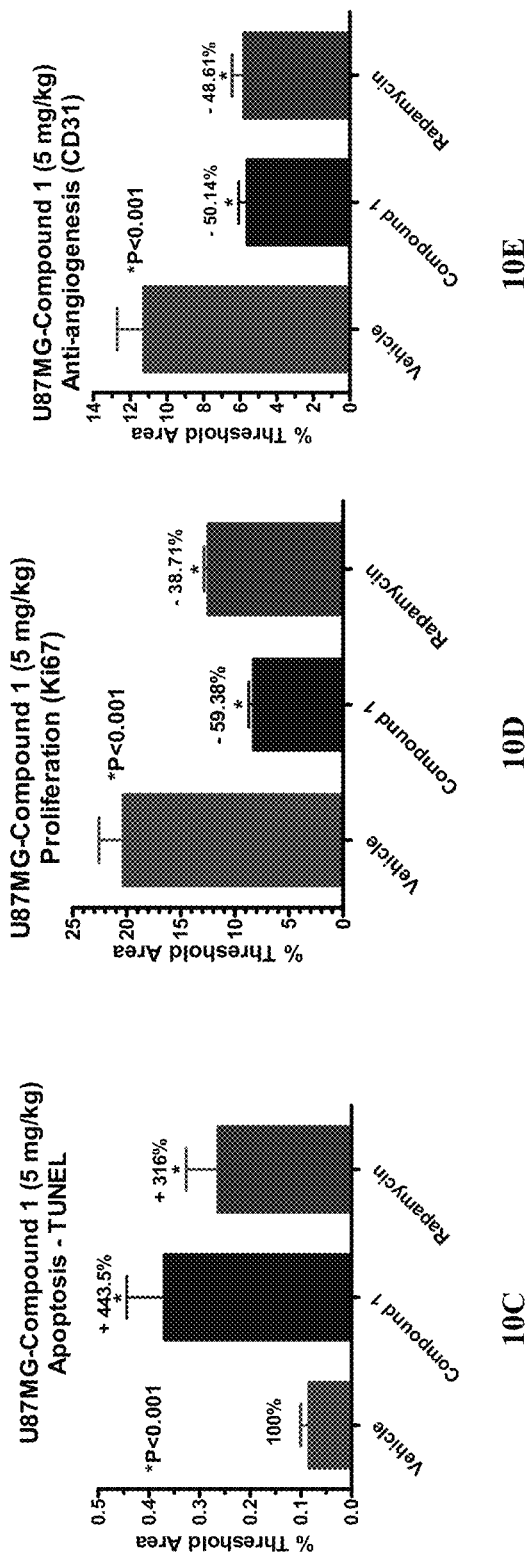
FIG. 10C-E

Tumor Growth Delay (median time to endpoint versus control group)

| Compound 1 Dose (mg/kg) | % Tumor Growth Inhibition (Day 12) | % Tumor Growth Delay |
|---|---|---|
| 0 | - | - |
| 0.3 | -8 | 4 |
| 3 | 44 * | 25 |
| 10 | -3 | -6 * |

* statistically significant

FIG. 19

| | | |
|---|---|---|
| Age | | |
| Mean (Range) | 50 | 25-80 |
| Gender (n, %) | | |
| M | 9 | 32 |
| F | 19 | 68 |
| ECOG (n, %) | | |
| 0 | 16 | 57 |
| 1 | 11 | 39 |
| 2 | 1 | 4 |
| Tumor Type (n, %) | | |
| CRC | 6 | 21 |
| Breast | 3 | 11 |
| Pancreas | 3 | 11 |
| NSCLC | 2 | 7 |
| GBM | 2 | 7 |
| HCC | 2 | 7 |
| Salivary | 2 | 7 |
| Other* (1 each) | 8 | 29 |
| No. Prior Therapies (n, %) | | |
| 1-3 | 14 | 50 |
| >3 | 14 | 50 |

FIG. 21

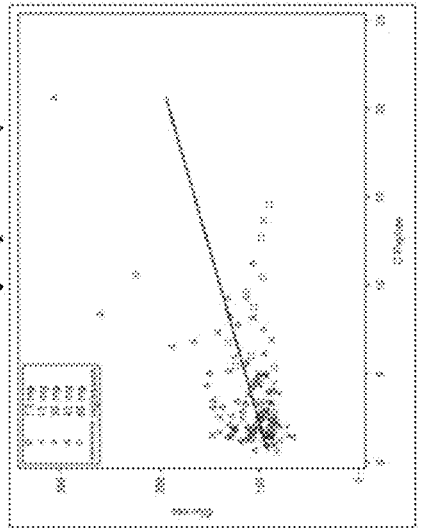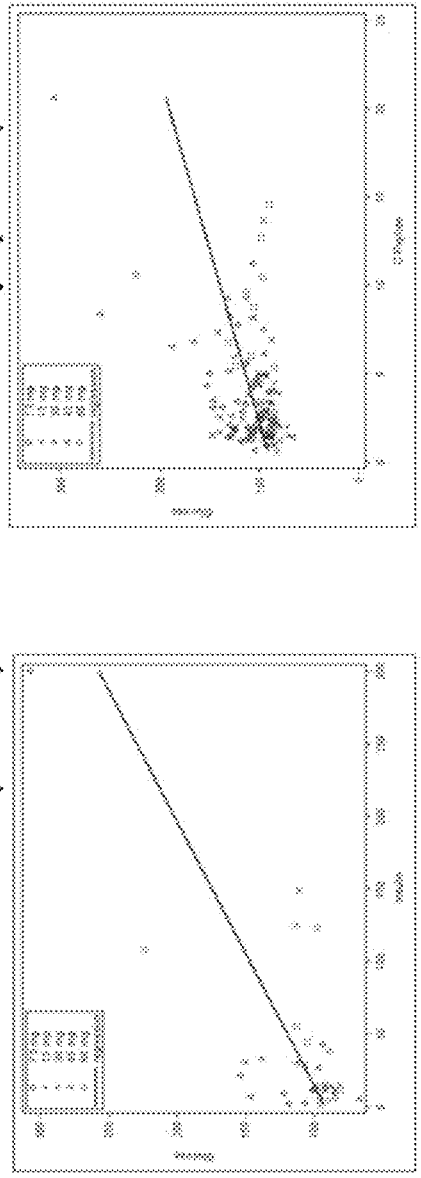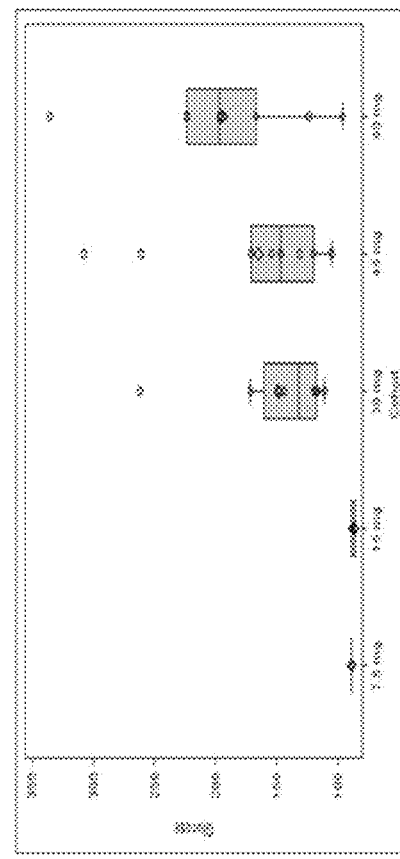
FIG. 24

TREATMENT OF CANCER WITH TOR KINASE INHIBITORS

This application claims the benefit of U.S. Provisional Application No. 61/549,034, filed Oct. 19, 2011, claims the benefit of U.S. Provisional Application No. 61/591,401, filed Jan. 27, 2012, claims the benefit of U.S. Provisional Application No. 61/647,233, filed May 15, 2012 and claims the benefit of U.S. Provisional Application No. 61/653,436, filed May 31, 2012, the entire contents of each of which are incorporated herein by reference.

1. FIELD

Provided herein are methods for treating or preventing a solid tumor, non-Hodgkin lymphoma or multiple myeloma in a patient, comprising administering an effective amount of a TOR kinase inhibitor to a patient having a solid tumor, non-Hodgkin lymphoma or multiple myeloma.

2. BACKGROUND

The connection between abnormal protein phosphorylation and the cause or consequence of diseases has been known for over 20 years. Accordingly, protein kinases have become a very important group of drug targets. See Cohen, *Nature*, 1:309-315 (2002). Various protein kinase inhibitors have been used clinically in the treatment of a wide variety of diseases, such as cancer and chronic inflammatory diseases, including diabetes and stroke. See Cohen, *Eur. J. Biochem.*, 268:5001-5010 (2001), *Protein Kinase Inhibitors for the Treatment of Disease: The Promise and the Problems*, Handbook of Experimental Pharmacology, Springer Berlin Heidelberg, 167 (2005).

The protein kinases are a large and diverse family of enzymes that catalyze protein phosphorylation and play a critical role in cellular signaling. Protein kinases may exert positive or negative regulatory effects, depending upon their target protein. Protein kinases are involved in specific signaling pathways which regulate cell functions such as, but not limited to, metabolism, cell cycle progression, cell adhesion, vascular function, apoptosis, and angiogenesis. Malfunctions of cellular signaling have been associated with many diseases, the most characterized of which include cancer and diabetes. The regulation of signal transduction by cytokines and the association of signal molecules with protooncogenes and tumor suppressor genes have been well documented. Similarly, the connection between diabetes and related conditions, and deregulated levels of protein kinases, has been demonstrated. See e.g., Sridhar et al. *Pharmaceutical Research*, 17(11):1345-1353 (2000). Viral infections and the conditions related thereto have also been associated with the regulation of protein kinases. Park et al. *Cell* 101 (7): 777-787 (2000).

Because protein kinases regulate nearly every cellular process, including metabolism, cell proliferation, cell differentiation, and cell survival, they are attractive targets for therapeutic intervention for various disease states. For example, cell-cycle control and angiogenesis, in which protein kinases play a pivotal role are cellular processes associated with numerous disease conditions such as but not limited to cancer, inflammatory diseases, abnormal angiogenesis and diseases related thereto, atherosclerosis, macular degeneration, diabetes, obesity, and pain.

Protein kinases have become attractive targets for the treatment of cancers. Fabbro et al., *Pharmacology & Therapeutics* 93:79-98 (2002). It has been proposed that the involvement of protein kinases in the development of human malignancies may occur by: (1) genomic rearrangements (e.g., BCR-ABL in chronic myelogenous leukemia), (2) mutations leading to constitutively active kinase activity, such as acute myelogenous leukemia and gastrointestinal tumors, (3) deregulation of kinase activity by activation of oncogenes or loss of tumor suppressor functions, such as in cancers with oncogenic RAS, (4) deregulation of kinase activity by over-expression, as in the case of EGFR and (5) ectopic expression of growth factors that can contribute to the development and maintenance of the neoplastic phenotype. Fabbro et al., *Pharmacology & Therapeutics* 93:79-98 (2002).

The elucidation of the intricacy of protein kinase pathways and the complexity of the relationship and interaction among and between the various protein kinases and kinase pathways highlights the importance of developing pharmaceutical agents capable of acting as protein kinase modulators, regulators or inhibitors that have beneficial activity on multiple kinases or multiple kinase pathways. Accordingly, there remains a need for new kinase modulators.

The protein named mTOR (mammalian target of rapamycin), which is also called FRAP, RAFTI or RAPT1), is a 2549-amino acid Ser/Thr protein kinase, that has been shown to be one of the most critical proteins in the mTOR/PI3K/Akt pathway that regulates cell growth and proliferation. Georgakis and Younes *Expert Rev. Anticancer Ther.* 6(1):131-140 (2006). mTOR exists within two complexes, mTORC1 and mTORC2. While mTORC1 is sensitive to rapamycin analogs (such as temsirolimus or everolimus), mTORC2 is largely rapamycin-insensitive. Notably, rapamycin is not a TOR kinase inhibitor. Several mTOR inhibitors have been or are being evaluated in clinical trials for the treatment of cancer. Temsirolimus was approved for use in renal cell carcinoma in 2007 and sirolimus was approved in 1999 for the prophylaxis of renal transplant rejection. Everolimus was approved in 2009 for renal cell carcinoma patients that have progressed on vascular endothelial growth factor receptor inhibitors, in 2010 for subependymal giant cell astrocytoma (SEGA) associated with tuberous sclerosis (TS) in patients who require therapy but are not candidates for surgical resection, and in 2011 for progressive neuroendocrine tumors of pancreatic origin (PNET) in patients with unresectable, locally advanced or metastatic disease. There remains a need for TOR kinase inhibitors that inhibit both mTORC1 and mTORC2 complexes.

Citation or identification of any reference in Section 2 of this application is not to be construed as an admission that the reference is prior art to the present application.

3. SUMMARY

Provided herein are methods for treating or preventing a solid tumor, non-Hodgkin lymphoma or multiple myeloma, comprising administering an effective amount of a TOR kinase inhibitor to a patient having a solid tumor, non-Hodgkin lymphoma or multiple myeloma.

In certain embodiments, provided herein are methods for achieving a Response Evaluation Criteria in Solid Tumors (RECIST 1.1) of complete response, partial response or stable disease, improving International Workshop Criteria (IWC) for NHL, improving International Uniform Response Criteria for Multiple Myeloma (IURC), improving Eastern Cooperative Oncology Group Performance Status (ECOG) or improving Response Assessment for Neuro-Oncology (RANO) Working Group for GBM comprising administering an effective amount of a TOR kinase inhibitor to a patient having a solid tumor, non-Hodgkin lymphoma or multiple myeloma. In some embodiments, the TOR kinase inhibitor is a compound as described herein.

The present embodiments can be understood more fully by reference to the detailed description and examples, which are intended to exemplify non-limiting embodiments.

4. DETAILED DESCRIPTION

4.1 Definitions

An "alkyl" group is a saturated, partially saturated, or unsaturated straight chain or branched non-cyclic hydrocarbon having from 1 to 10 carbon atoms, typically from 1 to 8 carbons or, in some embodiments, from 1 to 6, 1 to 4, or 2 to 6 or carbon atoms. Representative alkyl groups include -methyl, -ethyl, -n-propyl, -n-butyl, -n-pentyl and -n-hexyl; while saturated branched alkyls include -isopropyl, -sec-butyl, -isobutyl, -tert-butyl, -isopentyl, 2-methylpentyl, 3-methylpentyl, 4-methylpentyl, 2,3-dimethylbutyl and the like. Examples of unsaturated alkyl groups include, but are not limited to, vinyl, allyl, —CH═CH(CH$_3$), —CH═C(CH$_3$)$_2$, —C(CH$_3$)═CH$_2$, —C(CH$_3$)═CH(CH$_3$), —C(CH$_2$CH$_3$)═CH$_2$, —C≡CH, —C≡C(CH$_3$), —C≡C(CH$_2$CH$_3$), —CH$_2$C≡CH, —CH$_2$C≡C(CH$_3$) and —CH$_2$C≡C(CH$_7$CH$_3$), among others. An alkyl group can be substituted or unsubstituted. In certain embodiments, when the alkyl groups described herein are said to be "substituted," they may be substituted with any substituent or substituents as those found in the exemplary compounds and embodiments disclosed herein, as well as halogen (chloro, iodo, bromo, or fluoro); hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonato; phosphine; thiocarbonyl; sulfonyl; sulfone; sulfonamide; ketone; aldehyde; ester; urea; urethane; oxime; hydroxylamine; alkoxyamine; aralkoxyamine; N-oxide; hydrazine; hydrazide; hydrazone; azide; isocyanate; isothiocyanate; cyanate; thiocyanate; B(OH)$_2$, or O(alkyl)aminocarbonyl.

An "alkenyl" group is a straight chain or branched non-cyclic hydrocarbon having from 2 to 10 carbon atoms, typically from 2 to 8 carbon atoms, and including at least one carbon-carbon double bond. Representative straight chain and branched (C$_2$-C$_8$)alkenyls include -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl and the like. The double bond of an alkenyl group can be unconjugated or conjugated to another unsaturated group. An alkenyl group can be unsubstituted or substituted.

A "cycloalkyl" group is a saturated, partially saturated, or unsaturated cyclic alkyl group of from 3 to 10 carbon atoms having a single cyclic ring or multiple condensed or bridged rings which can be optionally substituted with from 1 to 3 alkyl groups. In some embodiments, the cycloalkyl group has 3 to 8 ring members, whereas in other embodiments the number of ring carbon atoms ranges from 3 to 5, 3 to 6, or 3 to 7. Such cycloalkyl groups include, by way of example, single ring structures such as cyclopropyl, cyclobutyl, cyclopentyl, cyclohexyl, cycloheptyl, cyclooctyl, 1-methylcyclopropyl, 2-methylcyclopentyl, 2-methylcyclooctyl, and the like, or multiple or bridged ring structures such as adamantyl and the like. Examples of unsaturated cycloalkyl groups include cyclohexenyl, cyclopentenyl, cyclohexadienyl, butadienyl, pentadienyl, hexadienyl, among others. A cycloalkyl group can be substituted or unsubstituted. Such substituted cycloalkyl groups include, by way of example, cyclohexanone and the like.

An "aryl" group is an aromatic carbocyclic group of from 6 to 14 carbon atoms having a single ring (e.g., phenyl) or multiple condensed rings (e.g., naphthyl or anthryl). In some embodiments, aryl groups contain 6-14 carbons, and in others from 6 to 12 or even 6 to 10 carbon atoms in the ring portions of the groups. Particular aryls include phenyl, biphenyl, naphthyl and the like. An aryl group can be substituted or unsubstituted. The phrase "aryl groups" also includes groups containing fused rings, such as fused aromatic-aliphatic ring systems (e.g., indanyl, tetrahydronaphthyl, and the like).

A "heteroaryl" group is an aryl ring system having one to four heteroatoms as ring atoms in a heteroaromatic ring system, wherein the remainder of the atoms are carbon atoms. In some embodiments, heteroaryl groups contain 5 to 6 ring atoms, and in others from 6 to 9 or even 6 to 10 atoms in the ring portions of the groups. Suitable heteroatoms include oxygen, sulfur and nitrogen. In certain embodiments, the heteroaryl ring system is monocyclic or bicyclic. Non-limiting examples include but are not limited to, groups such as pyrrolyl, pyrazolyl, imidazolyl, triazolyl, tetrazolyl, oxazolyl, isoxazolyl, thiazolyl, pyrolyl, pyridyl, pyridazinyl, pyrimidinyl, pyrazinyl, thiophenyl, benzothiophenyl, furanyl, benzofuranyl (for example, isobenzofuran-1,3-diimine), indolyl, azaindolyl (for example, pyrrolopyridyl or 1H-pyrrolo[2,3-b]pyridyl), indazolyl, benzimidazolyl (for example, 1H-benzo[d]imidazolyl), imidazopyridyl (for example, azabenzimidazolyl, 3H-imidazo[4,5-b]pyridyl or 1H-imidazo[4,5-b]pyridyl), pyrazolopyridyl, triazolopyridyl, benzotriazolyl, benzoxazolyl, benzothiazolyl, benzothiadiazolyl, isoxazolopyridyl, thianaphthalenyl, purinyl, xanthinyl, adeninyl, guaninyl, quinolinyl, isoquinolinyl, tetrahydroquinolinyl, quinoxalinyl, and quinazolinyl groups.

A "heterocyclyl" is an aromatic (also referred to as heteroaryl) or non-aromatic cycloalkyl in which one to four of the ring carbon atoms are independently replaced with a heteroatom from the group consisting of O, S and N. In some embodiments, heterocyclyl groups include 3 to 10 ring members, whereas other such groups have 3 to 5, 3 to 6, or 3 to 8 ring members. Heterocyclyls can also be bonded to other groups at any ring atom (i.e., at any carbon atom or heteroatom of the heterocyclic ring). A heterocyclylalkyl group can be substituted or unsubstituted. Heterocyclyl groups encompass unsaturated, partially saturated and saturated ring systems, such as, for example, imidazolyl, imidazolinyl and imidazolidinyl groups. The phrase heterocyclyl includes fused ring species, including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. Representative examples of a heterocyclyl group include, but are not limited to, aziridinyl, azetidinyl, pyrrolidyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl (for example, tetrahydro-2H-pyranyl), tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl; for example, 1H-imidazo[4,5-b]pyridyl, or 1H-imidazo[4,5-b]pyridin-2(3H)-onyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthalenyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed below.

An "cycloalkylalkyl" group is a radical of the formula: -alkyl-cycloalkyl, wherein alkyl and cycloalkyl are defined above. Substituted cycloalkylalkyl groups may be substituted at the alkyl, the cycloalkyl, or both the alkyl and the cycloalkyl portions of the group. Representative cycloalkylalkyl groups include but are not limited to cyclopentylmethyl, cyclopentylethyl, cyclohexylmethyl, cyclohexylethyl, and cyclohexylpropyl. Representative substituted cycloalkylalkyl groups may be mono-substituted or substituted more than once.

An "aralkyl" group is a radical of the formula: -alkyl-aryl, wherein alkyl and aryl are defined above. Substituted aralkyl groups may be substituted at the alkyl, the aryl, or both the alkyl and the aryl portions of the group. Representative aralkyl groups include but are not limited to benzyl and phenethyl groups and fused (cycloalkylaryl)alkyl groups such as 4-ethyl-indanyl.

A "heterocyclylalkyl" group is a radical of the formula: -alkyl-heterocyclyl, wherein alkyl and heterocyclyl are defined above. Substituted heterocyclylalkyl groups may be substituted at the alkyl, the heterocyclyl, or both the alkyl and the heterocyclyl portions of the group. Representative heterocylylalkyl groups include but are not limited to 4-ethyl-morpholinyl, 4-propylmorpholinyl, furan-2-yl methyl, furan-3-yl methyl, pyridine-3-yl methyl, (tetrahydro-2H-pyran-4-yl)methyl, (tetrahydro-2H-pyran-4-yl) ethyl, tetrahydrofuran-2-yl methyl, tetrahydrofuran-2-yl ethyl, and indol-2-yl propyl.

A "halogen" is fluorine, chlorine, bromine or iodine.

A "hydroxyalkyl" group is an alkyl group as described above substituted with one or more hydroxy groups.

An "alkoxy" group is —O-(alkyl), wherein alkyl is defined above.

An "alkoxyalkyl" group is -(alkyl)-O-(alkyl), wherein alkyl is defined above.

An "amino" group is a radical of the formula: —$NH_2$.

An "alkylamino" group is a radical of the formula: —NH-alkyl or —N(alkyl)$_2$, wherein each alkyl is independently as defined above.

A "carboxy" group is a radical of the formula: —C(O)OH.

An "aminocarbonyl" group is a radical of the formula: —C(O)N($R^\#$)$_2$, —C(O)NH($R^\#$) or —C(O)$NH_2$, wherein each $R^\#$ is independently a substituted or unsubstituted alkyl, cycloalkyl, aryl, aralkyl, heterocyclyl or heterocyclyl group as defined herein.

An "acylamino" group is a radical of the formula: —NHC(O)($R^\#$) or —N(alkyl)C(O)($R^\#$), wherein each alkyl and $R^\#$ are independently as defined above.

An "alkylsulfonylamino" group is a radical of the formula: —$NHSO_2$($R^\#$) or —N(alkyl)$SO_2$($R^\#$), wherein each alkyl and $R^\#$ are defined above.

A "urea" group is a radical of the formula: —N(alkyl)C(O)N($R^\#$)$_2$, —N(alkyl)C(O)NH($R^\#$), —N(alkyl)C(O)$NH_2$, —NHC(O)N($R^\#$)$_2$, —NHC(O)NH($R^\#$), or —NH(CO)$NHR^\#$, wherein each alkyl and $R^\#$ are independently as defined above.

When the groups described herein, with the exception of alkyl group are said to be "substituted," they may be substituted with any appropriate substituent or substituents. Illustrative examples of substituents are those found in the exemplary compounds and embodiments disclosed herein, as well as halogen (chloro, iodo, bromo, or fluoro); alkyl; hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonato; phosphine; thiocarbonyl; sulfonyl; sulfone; sulfonamide; ketone; aldehyde; ester; urea; urethane; oxime; hydroxylamine; alkoxyamine; aralkoxyamine; N-oxide; hydrazine; hydrazide; hydrazone; azide; isocyanate; isothiocyanate; cyanate; thiocyanate; oxygen (=O); B(OH)$_2$, O(alkyl)aminocarbonyl; cycloalkyl, which may be monocyclic or fused or non-fused polycyclic (e.g., cyclopropyl, cyclobutyl, cyclopentyl, or cyclohexyl), or a heterocyclyl, which may be monocyclic or fused or non-fused polycyclic (e.g., pyrrolidyl, piperidyl, piperazinyl, morpholinyl, or thiazinyl); monocyclic or fused or non-fused polycyclic aryl or heteroaryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl) aryloxy; aralkyloxy; heterocyclyloxy; and heterocyclyl alkoxy.

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts of the TOR kinase inhibitors include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art, see for example, *Remington's Pharmaceutical Sciences*, 18$^{th}$ eds., Mack Publishing, Easton Pa. (1990) or *Remington: The Science and Practice of Pharmacy*, 19$^{th}$ eds., Mack Publishing, Easton Pa. (1995).

As used herein and unless otherwise indicated, the term "clathrate" means a TOR kinase inhibitor, or a salt thereof, in the form of a crystal lattice that contains spaces (e.g., channels) that have a guest molecule (e.g., a solvent or water) trapped within or a crystal lattice wherein a TOR kinase inhibitor is a guest molecule.

As used herein and unless otherwise indicated, the term "solvate" means a TOR kinase inhibitor, or a salt thereof, that further includes a stoichiometric or non-stoichiometric amount of a solvent bound by non-covalent intermolecular forces. In one embodiment, the solvate is a hydrate.

As used herein and unless otherwise indicated, the term "hydrate" means a TOR kinase inhibitor, or a salt thereof, that further includes a stoichiometric or non-stoichiometric amount of water bound by non-covalent intermolecular forces.

As used herein and unless otherwise indicated, the term "prodrug" means a TOR kinase inhibitor derivative that can hydrolyze, oxidize, or otherwise react under biological conditions (in vitro or in vivo) to provide an active compound, particularly a TOR kinase inhibitor. Examples of prodrugs include, but are not limited to, derivatives and metabolites of a TOR kinase inhibitor that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. In certain embodiments, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by *Burger's Medicinal Chemistry and Drug Discovery* 6$^{th}$ ed. (Donald J. Abraham ed., 2001, Wiley) and *Design and Application of Prodrugs* (H. Bundgaard ed., 1985, Harwood Academic Publishers Gmfh).

As used herein and unless otherwise indicated, the term "stereoisomer" or "stereomerically pure" means one stereoisomer of a TOR kinase inhibitor that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. The TOR kinase inhibitors can have chiral centers and can occur as racemates, individual enantiomers or diastereomers, and mixtures thereof. All such isomeric forms are included within the embodiments disclosed herein, including mixtures thereof. The use of stereomerically pure forms of such TOR kinase inhibitors, as well as the use of mixtures of those forms are encompassed by the embodiments disclosed herein. For example, mixtures comprising equal or unequal amounts of the enantiomers of a particular TOR kinase inhibitor may be used in methods and compositions disclosed herein. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, NY, 1962); and Wilen, S. H., *Tables of Resolving Agents and Optical Resolutions* p. 268 (E. L. Eliel, Ed., Univ. of Notre Dame Press, Notre Dame, Ind., 1972).

It should also be noted the TOR kinase inhibitors can include E and Z isomers, or a mixture thereof, and cis and trans isomers or a mixture thereof. In certain embodiments, the TOR kinase inhibitors are isolated as either the cis or trans isomer. In other embodiments, the TOR kinase inhibitors are a mixture of the cis and trans isomers.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

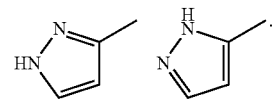

As readily understood by one skilled in the art, a wide variety of functional groups and other structures may exhibit tautomerism and all tautomers of the TOR kinase inhibitors are within the scope of the present invention.

It should also be noted the TOR kinase inhibitors can contain unnatural proportions of atomic isotopes at one or more of the atoms. For example, the compounds may be radiolabeled with radioactive isotopes, such as for example tritium ($^3$H), iodine-125 ($^{125}$I), sulfur-35 ($^{35}$S), or carbon-14 ($^{14}$C), or may be isotopically enriched, such as with deuterium ($^2$H), carbon-13 ($^{13}$C), or nitrogen-15 ($^{15}$N). As used herein, an "isotopologue" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom. Radiolabeled and isotopically enriched compounds are useful as therapeutic agents, e.g., cancer and inflammation therapeutic agents, research reagents, e.g., binding assay reagents, and diagnostic agents, e.g., in vivo imaging agents. All isotopic variations of the TOR kinase inhibitors as described herein, whether radioactive or not, are intended to be encompassed within the scope of the embodiments provided herein. In some embodiments, there are provided isotopologues of the TOR kinase inhibitors, for example, the isotopologues are deuterium, carbon-13, or nitrogen-15 enriched TOR kinase inhibitors.

An "advanced solid tumor" as used herein, means a solid tumor that has spread locally or metastasized or spread to another part of the body.

"Treating" as used herein, means an alleviation, in whole or in part, of symptoms associated with a disorder or disease (e.g., a solid tumor (for example, a neuroendocrine tumor, non-small cell lung cancer, glioblastoma multiforme, hepatocellular carcinoma breast cancer, colorectal cancer, salivary cancer, pancreatic cancer, adenocystic cancer or adrenal cancer), non-Hodgkin lymphoma or multiple myeloma), or slowing, or halting of further progression or worsening of those symptoms. In another embodiment, the solid tumor is esophageal cancer, renal cancer, leiomyosarcoma, or paraganglioma.

"Preventing" as used herein, means the prevention of the onset, recurrence or spread, in whole or in part, of the disease or disorder (e.g., a solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer or adrenal cancer), non-Hodgkin lymphoma or multiple myeloma), or a symptom thereof. In another embodiment, the solid tumor is esophageal cancer, renal cancer, leiomyosarcoma, or paraganglioma.

The term "effective amount" in connection with an TOR kinase inhibitor means an amount capable of alleviating, in whole or in part, symptoms associated with a solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer or adrenal cancer), non-Hodgkin lymphoma or multiple myeloma, or slowing or halting further progression or worsening of those symptoms, or treating or preventing a solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer or adrenal cancer), non-Hodgkin lymphoma or multiple myeloma in a subject having or at risk for having a solid tumor, non-Hodgkin lymphoma or multiple myeloma. In another embodiment, the solid tumor is esophageal cancer, renal cancer, leiomyosarcoma, or paraganglioma. The effective amount of the TOR kinase inhibitor, for example in a pharmaceutical composition, may be at a level that will exercise the desired effect; for example, about 0.005 mg/kg of a subject's body weight to about 100 mg/kg of a patient's body weight in unit dosage for both oral and parenteral administration. As will be apparent to those skilled in the art, it is to be expected that the effective amount of a TOR kinase inhibitor disclosed herein may vary depending on the severity of the indication being treated.

The terms "patient" and "subject" as used herein include an animal, including, but not limited to, an animal such as a cow, monkey, horse, sheep, pig, chicken, turkey, quail, cat, dog, mouse, rat, rabbit or guinea pig, in one embodiment a mammal, in another embodiment a human. In one embodiment, a "patient" or "subject" is a human having a solid tumor, non-Hodgkin lymphoma or multiple myeloma. In one embodiment, a patient is a human having histologically or cytologically-confirmed, advanced non-Hodgkin lymphoma, multiple myeloma, or advanced unresectable solid tumors including subjects who have progressed on (or not been able to tolerate) standard anticancer therapy or for whom no standard anticancer therapy exists. In one embodiment, a "patient" or "subject" is a breast cancer patient who has previously had a mastectomy or who has previously undergone one or more of the following therapies: chemotherapy (including adjuvant chemotherapy (AC)) (for example, doxorubicin, amrubicin, cyclophosphamide, vinorelbine, methotrexate, or 5-fluorouracil), taxane therapy (for example docetaxel or paclitaxel), ER receptor modulator therapy (for example tamoxifen or fulvestrant), gonadotropin-releasing hormone (GnRH) agonist therapy (for example Lupron®); HER2/neu receptor directed antibody therapy (for example, trastuzumab), vascular endothelial growth factor A inhibitor therapy (for example bevacizumab), aromatase inhibitor therapy (for example anastrazole, letrozole, or exemestane), anti-IGFR mAb therapy, PI3K inhibitor therapy, gemcitabine therapy, Mek inhibitor therapy, cMet inhibitor therapy (for example ARC197), PI3K/mTor inhibitor therapy (for example XL765), capecitabine therapy, or whole breast external-beam radiation therapy (WB XRT).

In the context of a solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer or adrenal cancer), non-Hodgkin lymphoma or multiple myeloma, treatment may be assessed by inhibition or retarding of disease progression, inhibition of tumor growth, reduction or regression of primary and/or secondary tumor(s), relief of tumor-related symptoms, improvement in quality of life, inhibition of tumor-secreted factors (including tumor-secreted hormones, such as those that contribute to carcinoid syndrome), reductions in endocrine hormone markers (for example, chromogranin, gastrin, serotonin, and/or glucagon), delayed appearance or recurrence of primary and/or secondary tumor(s), slowed development of primary and/or secondary tumor(s), decreased occurrence of primary and/or secondary tumor(s), slowed or decreased severity of secondary effects of disease, arrested tumor growth and/or regression of tumors, increased Time To Progression (TTP), increased Progression Free Survival (PFS), increased Overall Survival (OS), among others. OS as used herein means the time from randomization until death from any cause, and is measured in the intent-to-treat population. TTP as used herein means the time from randomization until objective tumor progression; TTP does not include deaths. As used herein, PFS means the time from randomization until objective tumor progression or death. In one embodiment, PFS rates will be computed using the Kaplan-Meier estimates. In another embodiment, the solid tumor is esophageal cancer, renal cancer, leiomyosarcoma, or paraganglioma.

In certain embodiments, the treatment of solid tumors may be assessed by Response Evaluation Criteria in Solid Tumors (RECIST 1.1) (see Thereasse P., et al. New Guidelines to Evaluate the Response to Treatment in Solid Tumors. J. of the National Cancer Institute; 2000; (92) 205-216 and Eisenhauer E. A., Therasse P., Bogaerts J., et al. New response evaluation criteria in solid tumours: Revised RECIST guideline (version 1.1). European J. Cancer; 2009; (45) 228-247). Overall responses for all possible combinations of tumor responses in target and non-target lesions with our without the appearance of new lesions are as follows:

| Target lesions | Non-target lesions | New lesions | Overall response |
|---|---|---|---|
| CR | CR | No | CR |
| CR | Incomplete response/SD | No | PR |
| PR | Non-PD | No | PR |
| SD | Non-PD | No | SD |
| PD | Any | Yes or no | PD |
| Any | PD | Yes or no | PD |
| Any | Any | Yes | PD |

CR = complete response;
PR = partial response;
SD = stable disease; and
PD = progressive disease.

With respect to the evaluation of target lesions, complete response (CR) is the disappearance of all target lesions, partial response (PR) is at least a 30% decrease in the sum of the longest diameter of target lesions, taking as reference the baseline sum longest diameter, progressive disease (PD) is at least a 20% increase in the sum of the longest diameter of target lesions, taking as reference the smallest sum longest diameter recorded since the treatment started or the appearance of one or more new lesions and stable disease (SD) is neither sufficient shrinkage to qualify for partial response nor sufficient increase to qualify for progressive disease, taking as reference the smallest sum longest diameter since the treatment started.

With respect to the evaluation of non-target lesions, complete response (CR) is the disappearance of all non-target lesions and normalization of tumor marker level; incomplete response/stable disease (SD) is the persistence of one or more non-target lesion(s) and/or the maintenance of tumor marker level above the normal limits, and progressive disease (PD) is the appearance of one or more new lesions and/or unequivocal progression of existing non-target lesions.

In certain embodiments, the treatment of lymphoma may be assessed by the International Workshop Criteria (IWC) for non-Hodgkin lymphoma (NHL) (see Cheson B D, Pfistner B, Juweid, M E, et. al. Revised Response Criteria for Malignant Lymphoma. J. Clin. Oncol: 2007: (25) 579-586), using the response and endpoint definitions shown below:

| Response | Definition | Nodal Masses | Spleen, liver | Bone Marrow |
| --- | --- | --- | --- | --- |
| CR | Disappearance of all evidence of disease | (a) FDG-avid or PET positive prior to therapy; mass of any size permitted if PET negative (b) Variably FDG-avid or PET negative; regression to normal size on CT | Not palpable, nodules disappeared | Infiltrate cleared on repeat biopsy; if indeterminate by morphology, immunohistochemistry should be negative |
| PR | Regression of measurable disease and no new sites | $\geq 50\%$ decrease in SPD of up to 6 largest dominant masses; no increase in size of other nodes (a) FDG-avid or PET positive prior to therapy; one or more PET positive at previously involved site (b) Variably FDG-avid or PET negative; regression on CT | $\geq 50\%$ decrease in SPD of nodules (for single nodule in greatest transverse diameter); no increase in size of liver or spleen | Irrelevant if positive prior to therapy; cell type should be specified |
| SD | Failure to attain CR/PR or PD | (a) FDG-avid or PET positive prior to therapy; PET positive at prior sites of disease and no new sites on CT or PET (b) Variably FDG-avid or PET negative; no change in size of previous lesions on CT | | |
| PD or relapsed disease | Any new lesion or increase by $\geq 50\%$ of previously involved sites from nadir | Appearance of a new lesion(s) $\geq 1.5$ cm in any axis, $\geq 50\%$ increase in SPD of more than one node, or $\geq 50\%$ increase in longest diameter of a previously identifed node $\geq 1$ cm in short axis Lesions PET positive if FDG-avid lymphoma or PET positive prior to therapy | $\geq 50\%$ increase from nadir in the SPD of any previous lesions | New or recurrent involvement |

Abbreviations:
CR, complete remission;
FDG, [$^{18}$F]fluorodeoxyglucose;
PET, positron emission tomography;
CT, computed tomography;
PR, partial remission;
SPD, sum of the product of the diameters;
SD, stable disease;
PD, progressive disease.

| End point | Patients | Definition | Measured from |
|---|---|---|---|
| Primary | | | |
| Overall survival | All | Death as a result of any cause | Entry onto study |
| Progression-free survival | All | Disease progression or death as a result of any cause | Entry onto study |
| Secondary | | | |
| Event-free survival | All | Failure of treatment or death as result of any cause | Entry onto study |
| Time to progression | All | Time to progression or death as a result of lymphoma | Entry onto study |
| Disease-free survival | In CR | Time to relapse or death as a result of lymphoma or acute toxicity of treatment | Documentation of response |
| Response duration | In CR or PR | Time to relapse or progression | Documentation of response |
| Lymphoma-specific survival | All | Time to death as a result of lymphoma | Entry onto study |
| Time to next treatment | All | Time to new treatment | End of primary treatment |

Abbreviations:
CR: complete remission;
PR: partial remission

In one embodiment, the end point for lymphoma is evidence of clinical benefit. Clinical benefit may reflect improvement in quality of life, or reduction in patient symptoms, transfusion requirements, frequent infections, or other parameters. Time to reappearance or progression of lymphoma-related symptoms can also be used in this end point.

In certain embodiments, the treatment of multiple myeloma may be assessed by the International Uniform Response Criteria for Multiple Myeloma (IURC) (see Durie B G M, Harousseau J-L, Miguel J S, et al. International uniform response criteria for multiple myeloma. Leukemia, 2006; (10) 10:1-7), using the response and endpoint definitions shown below:

| Response Subcategory | Response Criteria[a] |
|---|---|
| sCR | CR as defined below plus<br>Normal FLC ratio and<br>Absence of clonal cells in bone marrow[b] by immunohistochemistry or immunofluorescence[c] |
| CR | Negative immunofixation on the serum and urine and Disappearance of any soft tissue plasmacytomas and <5% plasma cells in bone marrow[b] |
| VGPR | Serum and urine M-protein detectable by immunofixation but not on electrophoresis or 90% or greater reduction in serum M-protein plus urine M-protein level <100 mg per 24 h |
| PR | ≥50% reduction of serum M-protein and reduction in 24-h urinary M-protein by≥90% or to <200 mg per 24 h<br>If the serum and urine M-protein are unmeasurable,[d] a ≥50% decrease in the difference between involved and uninvolved FLC levels is required in place of the M-protein criteria<br>If serum and urine M-protein are unmeasurable, and serum free light assay is also unmeasurable, ≥50% reduction in plasma cells is required in place of M-protein, provided baseline bone marrow plasma cell percentage was ≥30%<br>In addition to the above listed criteria, if present at baseline, a ≥50% reduction in the size of soft tissue plasmacytomas is also required |
| SD (not recommended for use as an indicator of response; stability of disease is best described by providing the time to progression estimates) | Not meeting criteria for CR, VGPR, PR or progressive disease |

Abbreviations:
CR, complete response;
FLC, free light chain;
PR, partial response;
SD, stable disease;
sCR, stringent complete response;
VGPR, very good partial response;

[a]All response categories require two consecutive assessments made at anytime before the institution of any new therapy; all categories also require no known evidence of progressive or new bone lesions if radiographic studies were performed. Radiographic studies are not required to satisfy these response requirements;
[b]Confirmation with repeat bone marrow biopsy not needed;
[c]Presence/absence of clonal cells is based upon the κ/λ ratio. An abnormal κ/λ ratio by immunohistochemistry and/or immunofluorescence requires a minimum of 100 plasma cells for analysis. An abnormal ratio reflecting presence of an abnormal clone is κ/λ of >4:1 or <1:2.
[d]Measurable disease defined by at least one of the following measurements: Bone marrow plasma cells ≥30%; Serum M-protein ≥1 g/dl (≥10 gm/l)[10 g/l]; Urine M-protein ≥200 mg/24 h; Serum FLC assay: Involved FLC level ≥10 mg/dl (≥100 mg/l); provided serum FLC ratio is abnormal.

The procedures, conventions, and definitions described below provide guidance for implementing the recommendations from the Response Assessment for Neuro-Oncology (RANO) Working Group regarding response criteria for high-grade gliomas (Wen P., Macdonald, D R., Reardon, D A., et al. Updated response assessment criteria for highgrade gliomas: Response assessment in neuro-oncology working group. J Clin Oncol 2010; 28: 1963-1972). Primary modifications to the RANO criteria for Criteria for Time Point Responses (TPR) can include the addition of operational conventions for defining changes in glucocorticoid dose, and the removal of subjects' clinical deterioration component to focus on objective radiologic assessments. The baseline MRI scan is defined as the assessment performed at the end of the post-surgery rest period, prior to re-initiating compound treatment. The baseline MRI is used as the reference for assessing complete response (CR) and partial response (PR). Whereas, the smallest SPD (sum of the products of perpendicular diameters) obtained either at baseline or at subsequent assessments will be designated the nadir assessment and utilized as the reference for determining progression. For the 5 days preceding any protocol-defined MRI scan, subjects receive either no glucocorticoids or are on a stable dose of glucocorticoids. A stable dose is defined as the same daily dose for the 5 consecutive days preceding the MRI scan. If the prescribed glucocorticoid dose is changed in the 5 days before the baseline scan, a new baseline scan is required with glucocorticoid use meeting the criteria described above. The following definitions will be used.

Measurable Lesions: Measurable lesions are contrast-enhancing lesions that can be measured bidimensionally. A measurement is made of the maximal enhancing tumor diameter (also known as the longest diameter, LD). The greatest perpendicular diameter is measured on the same image. The cross hairs of bidimensional measurements should cross and the product of these diameters will be calculated.

Minimal Diameter: T1-weighted image in which the sections are 5 mm with 1 mm skip. The minimal LD of a measurable lesion is set as 5 mm by 5 mm. Larger diameters may be required for inclusion and/or designation as target lesions. After baseline, target lesions that become smaller than the minimum requirement for measurement or become no longer amenable to bidimensional measurement will be recorded at the default value of 5 mm for each diameter below 5 mm. Lesions that disappear will be recorded as 0 mm by 0 mm.

Multicentric Lesions: Lesions that are considered multicentric (as opposed to continuous) are lesions where there is normal intervening brain tissue between the two (or more) lesions. For multicentric lesions that are discrete foci of enhancement, the approach is to separately measure each enhancing lesion that meets the inclusion criteria. If there is no normal brain tissue between two (or more) lesions, they will be considered the same lesion.

Nonmeasurable Lesions: All lesions that do not meet the criteria for measurable disease as defined above will be considered non-measurable lesions, as well as all nonenhancing and other truly nonmeasurable lesions. Nonmeasurable lesions include foci of enhancement that are less than the specified smallest diameter (ie., less than 5 mm by 5 mm), nonenhancing lesions (eg., as seen on T1-weighted post-contrast, T2-weighted, or fluid-attenuated inversion recovery [FLAIR] images), hemorrhagic or predominantly cystic or necrotic lesions, and leptomeningeal tumor. Hemorrhagic lesions often have intrinsic T1-weighted hyperintensity that could be misinterpreted as enhancing tumor, and for this reason, the pre-contrast T1-weighted image may be examined to exclude baseline or interval sub-acute hemorrhage.

At baseline, lesions will be classified as follows: Target lesions: Up to 5 measurable lesions can be selected as target lesions with each measuring at least 10 mm by 5 mm, representative of the subject's disease; Non-target lesions: All other lesions, including all nonmeasurable lesions (including mass effects and T2/FLAIR findings) and any measurable lesion not selected as a target lesion. At baseline, target lesions are to be measured as described in the definition for measurable lesions and the SPD of all target lesions is to be determined. The presence of all other lesions is to be documented. At all post-treatment evaluations, the baseline classification of lesions as target and non-target lesions will be maintained and lesions will be documented and described in a consistent fashion over time (eg., recorded in the same order on source documents and eCRFs). All measurable and nonmeasurable lesions must be assessed using the same technique as at baseline (e.g., subjects should be imaged on the same MRI scanner or at least with the same magnet strength) for the duration of the study to reduce difficulties in interpreting changes. At each evaluation, target lesions will be measured and the SPD calculated. Non-target lesions will be assessed qualitatively and new lesions, if any, will be documented separately. At each evaluation, a time point response will be determined for target lesions, non-target lesions, and new lesion. Tumor progression can be established even if only a subset of lesions is assessed. However, unless progression is observed, objective status (stable disease, PR or CR) can only be determined when all lesions are assessed.

Confirmation assessments for overall time point responses of CR and PR will be performed at the next scheduled assessment, but confirmation may not occur if scans have an interval of <28 days. Best response, incorporating confirmation requirements, will be derived from the series of time points.

In certain embodiments, treatment of a solid tumor (for example, a neuroendocrine tumor, non-small cell lung cancer, glioblastoma multiforme, hepatocellular carcinoma or breast cancer) may be assessed by the inhibition of phosphorylation of S6RP, 4E-BP1 and/or AKT in circulating blood and/or tumor cells and/or skin biopsies or tumor biopsies/aspirates, before, during and/or after treatment with a TOR kinase inhibitor. For example, the inhibition of phosphorylation of S6RP, 4E-BP1 and/or AKT is assessed in B-cells, T-cells and/or monocytes. In other embodiments, treatment of a solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer or adrenal cancer) may be assessed by the inhibition of DNA-dependent protein kinase (DNA-PK) activity in skin samples and/or tumor biopsies/aspirates, such as by assessment of the amount of pDNA-PK S2056 as a biomarker for DNA damage pathways, before, during, and/or after TOR kinase inhibitor treatment. In another embodiment, the solid tumor is esophageal cancer, renal cancer, leiomyosarcoma, or paraganglioma. In one embodiment, the skin sample is irradiated by UV light. In the extreme, complete inhibition, is referred to herein as prevention or chemoprevention. In this context, the term "prevention" includes either preventing the onset of clinically evident a solid tumor altogether or preventing the onset of a preclinically evident stage of a solid tumor. Also intended to be encompassed by this definition is the prevention of transformation into malignant cells or to arrest or reverse the progression of premalignant cells to malignant cells. This includes prophylactic treatment of those at risk of developing a solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer or adrenal cancer). In another embodiment, the solid tumor is esophageal cancer, renal cancer, leiomyosarcoma, or paraganglioma

4.2 BRIEF DESCRIPTION OF THE DRAWINGS

FIG. 1 provides $GI_{50}$ values of Compound 1 (FIG. 1A) and Compound 2 (FIG. 1B) against certain NHL cell lines.

FIGS. 10A and 10B depict anti-tumor activity of Compound 1 in a U87MG human glioblastoma xenograft model, using different dosing paradigms. FIG. 10C depicts the quantitation of apoptotic cells in U87MG tumors by TUNEL staining FIGS. 10D and 10E depict the quantitation of Ki67 and CD31, respectively, in U87MG tumors.

FIG. 19 depicts the efficacy of Compound 1 in the NCI-H929 human plasma cell myeloma xenograft model in SCID mice.

FIG. 21 depicts the baseline characteristics of the Part A subjects.

FIG. 24 depicts the hyperglycemia associated elevations of insulin and C-peptide.

4.3 TOR KINASE INHIBITORS

Figure 1A:
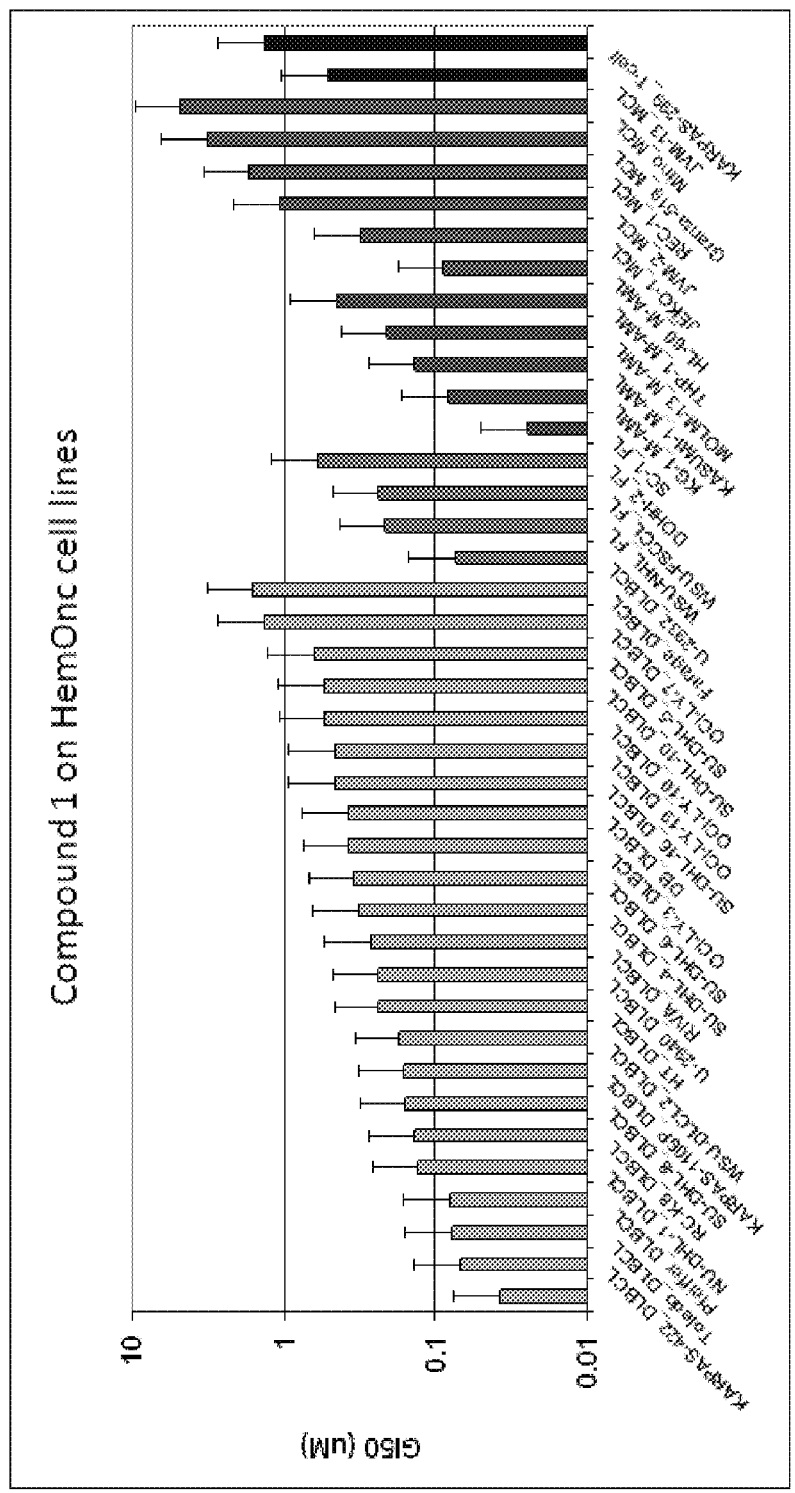

The compounds provided herein are generally referred to as "TOR kinase inhibitor(s)." In a specific embodiment, the TOR kinase inhibitors do not include rapamycin or rapamycin analogs (rapalogs).

In one embodiment, the TOR kinase inhibitors include compounds having the following formula (I):

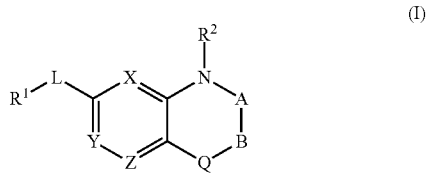

and pharmaceutically acceptable salts, clathrates, solvates, stereoisomers, tautomers, and prodrugs thereof, wherein:

X, Y and Z are at each occurrence independently N or $CR^3$, wherein at least one of X, Y and Z is N and at least one of X, Y and Z is $CR^3$;

-A-B-Q- taken together form —$CHR^4C(O)NH$—, —$C(O)CHR^4NH$—, —$C(O)NH$—, —$CH_2C(O)O$—, —$C(O)CH_2O$—, —$C(O)O$— or $C(O)NR^3$;

L is a direct bond, NH or O;

$R^1$ is H, substituted or unsubstituted $C_{1-8}$alkyl, substituted or unsubstituted $C_{2-8}$alkenyl, substituted or unsubstituted aryl, substituted or unsubstituted heteroaryl, substituted or unsubstituted cycloalkyl or substituted or unsubstituted heterocyclylalkyl;

$R^2$ is H, substituted or unsubstituted $C_{1-8}$alkyl, substituted or unsubstituted aryl, substituted or unsubstituted heteroaryl, substituted or unsubstituted cycloalkyl, or substituted or unsubstituted heterocyclylalkyl;

$R^3$ is H, substituted or unsubstituted $C_{1-8}$alkyl, substituted or unsubstituted aryl, substituted or unsubstituted heteroaryl, substituted or unsubstituted cycloalkyl, substituted or unsubstituted heterocyclylalkyl, —$NHR^4$ or —$N(R^4)_2$; and $R^4$ is at each occurrence independently substituted or unsubstituted $C_{1-8}$alkyl, substituted or unsubstituted aryl, substituted or unsubstituted heteroaryl, substituted or unsubstituted cycloalkyl, or substituted or unsubstituted heterocyclylalkyl.

In one embodiment, the TOR kinase inhibitors of formula (I) are those wherein -A-B-Q- taken together form —$CH_2C(O)NH$—.

In another embodiment, the TOR kinase inhibitors of formula (I) are those wherein -A-B-Q- taken together form —$C(O)CH_2NH$—.

In another embodiment, the TOR kinase inhibitors of formula (I) are those wherein -A-B-Q- taken together form —$C(O)NH$—.

In another embodiment, the TOR kinase inhibitors of formula (I) are those wherein -A-B-Q- taken together form —$CH_2C(O)O$—.

In another embodiment, the TOR kinase inhibitors of formula (I) are those wherein -A-B-Q- taken together form —$C(O)CH_2O$—.

In another embodiment, the TOR kinase inhibitors of formula (I) are those wherein -A-B-Q- taken together form —$C(O)O$—.

In another embodiment, the TOR kinase inhibitors of formula (I) are those wherein -A-B-Q- taken together form —$C(O)NR^3$—.

In another embodiment, the TOR kinase inhibitors of formula (I) are those wherein Y is $CR^3$.

In another embodiment, the TOR kinase inhibitors of formula (I) are those wherein X and Z are N and Y is $CR^3$.

In another embodiment, the TOR kinase inhibitors of formula (I) are those wherein X and Z are N and Y is CH.

In another embodiment, the TOR kinase inhibitors of formula (I) are those wherein X and Z are CH and Y is N.

In another embodiment, the TOR kinase inhibitors of formula (I) are those wherein Y and Z are CH and X is N.

In another embodiment, the TOR kinase inhibitors of formula (I) are those wherein X and Y are CH and Z is N.

In another embodiment, the TOR kinase inhibitors of formula (I) are those wherein $R^1$ is substituted aryl, such as substituted phenyl.

In another embodiment, the TOR kinase inhibitors of formula (I) are those wherein $R^1$ is substituted or unsubstituted aryl, such as substituted or unsubstituted phenyl or substituted or unsubstituted naphthyl.

In another embodiment, the TOR kinase inhibitors of formula (I) are those wherein $R^1$ is substituted or unsubstituted heteroaryl, such as substituted or unsubstituted quinoline, substituted or unsubstituted pyridine, substituted or unsubstituted pyrimidine, substituted or unsubstituted indole, or substituted or unsubstituted thiophene.

In another embodiment, the TOR kinase inhibitors of formula (I) are those wherein $R^1$ is H.

In another embodiment, the TOR kinase inhibitors of formula (I) are those wherein $R^2$ is substituted $C_{1-8}$alkyl.

In another embodiment, the TOR kinase inhibitors of formula (I) are those wherein $R^2$ is methyl or ethyl substituted with substituted or unsubstituted aryl, substituted or unsubstituted heteroaryl, substituted or unsubstituted cycloalkyl, or substituted or unsubstituted heterocyclylalkyl.

In another embodiment, the TOR kinase inhibitors of formula (I) are those wherein $R^2$ is substituted or unsubstituted cycloalkyl or substituted or unsubstituted heterocyclylalkyl.

In another embodiment, the TOR kinase inhibitors of formula (I) are those wherein $R^2$ is substituted or unsubstituted aryl, such as substituted or unsubstituted phenyl.

In another embodiment, the TOR kinase inhibitors of formula (I) are those wherein $R^2$ is H.

In another embodiment, the TOR kinase inhibitors of formula (I) are those wherein L is a direct bond.

In another embodiment, the TOR kinase inhibitors of formula (I) are those wherein -A-B-Q- taken together form —C(O)NH—, X and Z are N and Y is CH, $R^1$ is substituted or unsubstituted aryl or substituted or unsubstituted heteroaryl, L is a direct bond, and $R^2$ is substituted or unsubstituted $C_{1-8}$alkyl.

In another embodiment, the TOR kinase inhibitors of formula (I) are those wherein -A-B-Q- taken together form —C(O)NH—, X and Z are N and Y is CH, $R^1$ is substituted or unsubstituted aryl, L is a direct bond, and $R^2$ is substituted or unsubstituted $C_{1-8}$alkyl.

In another embodiment, the TOR kinase inhibitors of formula (I) are those wherein -A-B-Q- taken together form —C(O)NH—, X and Z are N and Y is CH, $R^1$ is substituted or unsubstituted aryl, and $R^2$ is $C_{1-8}$alkyl substituted with one or more substituents selected from alkoxy, amino, hydroxy, cycloalkyl, or heterocyclylalkyl.

In another embodiment, the TOR kinase inhibitors of formula (I) are those wherein -A-B-Q- taken together form —C(O)NH—, X and Z are N and Y is CH, $R^1$ is substituted or unsubstituted aryl, and $R^2$ is substituted or unsubstituted cycloalkyl, or substituted or unsubstituted heterocyclylalkyl.

In another embodiment, the TOR kinase inhibitors of formula (I) are those wherein -A-B-Q- taken together form —C(O)NH—, X and Z are N and Y is CH, $R^1$ is substituted phenyl, L is a direct bond, and $R^2$ is substituted $C_{1-8}$alkyl.

In another embodiment, the TOR kinase inhibitors of formula (I) do not include compounds wherein X and Z are both N and Y is CH, -A-B-Q- is —C(O)NH—, L is a direct bond, $R^1$ is substituted or unsubstituted aryl or substituted or unsubstituted heteroaryl, and $R^2$ is $C_{1-8}$alkyl substituted with substituted or unsubstituted aryl or substituted or unsubstituted heteroaryl.

In another embodiment, the TOR kinase inhibitors of formula (I) do not include compounds wherein X and Z are both N and Y is CH, -A-B-Q- is —C(O)NH—, L is a direct bond, $R^1$ is phenyl, naphthyl, indanyl or biphenyl, each of which may be optionally substituted with one or more substituents independently selected from the group consisting substituted or unsubstituted $C_{1-8}$alkyl, substituted or unsubstituted $C_{2-8}$alkenyl, substituted or unsubstituted aryl, substituted or unsubstituted cycloalkyl or substituted or unsubstituted heterocyclylalkyl.

In another embodiment, the TOR kinase inhibitors of formula (I) do not include compounds wherein X and Z are both N and Y is CH, -A-B-Q- is —C(O)NH—, L is a direct bond, $R^1$ is phenyl, naphthyl or biphenyl, each of which may be optionally substituted with one or more substituents each independently selected from the group consisting of $C_{1-4}$alkyl, amino, amino$C_{1-12}$alkyl, halogen, hydroxy, hydroxy$C_{1-4}$alkyl, $C_{1-4}$alkyloxy$C_{1-4}$alkyl, —$CF_3$, $C_{1-12}$alkoxy, aryloxy, aryl$C_{1-12}$alkoxy, —CN, —$OCF_3$, —$COR_g$, —$COOR_g$, —$CONR_gR_h$, —$NR_gCOR_h$, —$SO_2R_g$, —$SO_3R_g$ or —$SO_2NR_gR_h$, wherein each $R_g$ and $R_h$ are independently selected from the group consisting of hydrogen, $C_{1-4}$alkyl, $C_{3-6}$cycloalkyl, aryl, aryl$C_{1-6}$alkyl, heteroaryl or heteroaryl$C_{1-6}$alkyl; or A is a 5- to 6-membered monocyclic heteroaromatic ring having from one, two, three or four heteroatoms independently selected from the group consisting of N, O and S, that monocyclic heteroaromatic ring may be optionally substituted with one or more substituents each independently selected from the group consisting of $C_{1-6}$alkyl, amino, amino$C_{1-12}$alkyl, halogen, hydroxy, hydroxy$C_{1-4}$alkyl, $C_{1-4}$alkyloxy$C_{1-4}$alkyl, $C_{1-12}$alkoxy, aryloxy, aryl $C_{1-12}$alkoxy, —CN, —$CF_3$, —$OCF_3$, —$COR_i$, —$COOR_i$, —$CONR_iR_j$, —$NR_iCOR_j$, —$NR_iSO_2R_j$, —$SO_2R_i$, —$SO_3R_i$ or —$SO_2NR_iR_j$, wherein each $R_i$ and $R_j$ are independently selected from the group consisting of hydrogen, $C_{1-4}$ alkyl, $C_{3-6}$cycloalkyl, aryl, aryl$C_{1-6}$alkyl, heteroaryl or heteroaryl$C_{1-6}$alkyl; or A is a 8- to 10 membered bicyclic heteroaromatic ring from one, two, three or four heteroatoms selected from the group consisting of N, O and S, and may be optionally substituted with one, two or three substituents each independently selected from the group consisting of $C_{1-6}$alkyl, amino, amino$C_{1-12}$alkyl, halogen, hydroxy, hydroxyC$_{1-4}$alkyl, C$_{1-4}$alkyloxyC$_{1-4}$alkyl, aryloxy, aryl C$_{1-12}$alkoxy, —CN, —CF$_3$, —COR$_k$, —CO-OR$_k$, —CONR$_k$R$_l$, —NR$_k$COR$_l$, —NR$_k$SO$_2$R$_l$, —SO$_2$R$_k$, —SO$_3$R$_k$ or —SO$_2$NR$_k$R$_l$, wherein each R$_k$ and R$_l$ are independently selected from the group consisting of hydrogen, C$_{1-4}$ alkyl, C$_{3-6}$ cycloalkyl, aryl, arylC$_{1-6}$alkyl, heteroaryl or heteroarylC$_{1-6}$alkyl, and R$^2$ is C$_{1-8}$alkyl substituted with substituted or unsubstituted aryl or substituted or unsubstituted heteroaryl.

In another embodiment, the TOR kinase inhibitors of formula (I) do not include compounds wherein X and Y are both N and Z is CH, -A-B-Q- is —C(O)NH—, L is a direct bond, R$^1$ is substituted or unsubstituted phenyl or substituted or unsubstituted heteroaryl, and R$^2$ is substituted or unsubstituted methyl, unsubstituted ethyl, unsubstituted propyl, or an acetamide.

In another embodiment, the TOR kinase inhibitors of formula (I) do not include compounds wherein X and Y are both N and Z is CH, -A-B-Q- is —C(O)NH—, L is a direct bond, R$^1$ is substituted or unsubstituted phenyl or substituted or unsubstituted heteroaryl, and R$^2$ is an acetamide.

In another embodiment, the TOR kinase inhibitors of formula (I) do not include compounds wherein X is N and Y and Z are both CH, -A-B-Q- is —C(O)NH—, L is a direct bond, R$^1$ is a (2,5'-Bi-1H-benzimidazole)-5-carboxamide, and R$^2$ is H.

In another embodiment, the TOR kinase inhibitors of formula (I) do not include compounds wherein one of X and Z is CH and the other is N, Y is CH, -A-B-Q- is —C(O)NH—, L is a direct bond, R$^1$ is unsubstituted pyridine, and R$^2$ is H, methyl or substituted ethyl.

In another embodiment, the TOR kinase inhibitors of formula (I) do not include compounds wherein X and Z are both N and Y is CH, -A-B-Q- is —C(O)NH—, R$^1$ is H, C$_{1-8}$alkyl, C$_{2-8}$alkenyl, aryl or cycloalkyl, and L is NH.

In another embodiment, the TOR kinase inhibitors of formula (I) do not include compounds wherein X and Z are both N and Y is CH, -A-B-Q- is —C(O)NR$^3$—, R$^2$ is H, substituted or unsubstituted C$_{1-8}$alkyl, substituted or unsubstituted phenyl, substituted or unsubstituted cycloalkyl, or substituted or unsubstituted heterocyclylalkyl, and L is NH.

In another embodiment, the TOR kinase inhibitors of formula (I) do not include compounds wherein R$^1$ is a substituted or unsubstituted oxazolidinone.

In another embodiment, the TOR kinase inhibitors of formula (I) do not include one or more of the following compounds: 1,7-dihydro-2-phenyl-8H-Purin-8-one, 1,2-dihydro-3-phenyl-6H-Imidazo[4,5-e]-1,2,4-triazin-6-one, 1,3-dihydro-6-(4-pyridinyl)-2H-Imidazo[4,5-b]pyridin-2-one, 6-(1,3-benzodioxol-5-yl)-1,3-dihydro-1-[(1S)-1-phenylethyl]-2H-Imidazo[4,5-b]pyrazin-2-one, 3-[2,3-dihydro-2-oxo-3-(4-pyridinylmethyl)-1H-imidazo[4,5-b]pyrazin-5-yl]-Benzamide, 1-[2-(dimethylamino)ethyl]-1,3-dihydro-6-(3,4,5-trimethoxyphenyl)-2H-Imidazo[4,5-b]pyrazin-2-one, N-[5-(1,1-dimethylethyl)-2-methoxyphenyl]-N'-[4-(1,2,3,4-tetrahydro-2-oxopyrido[2,3-b]pyrazin-7-yl)-1-naphthalenyl]-Urea, N-[4-(2,3-dihydro-2-oxo-1H-imidazo[4,5-b]pyridin-6-yl)-1-naphthalenyl]-N'-[5-(1,1-dimethylethyl)-2-methoxyphenyl]-Urea, 1,3-dihydro-5-phenyl-2H-Imidazo[4,5-b]pyrazin-2-one, 1,3-dihydro-5-phenoxy-2H-Imidazo[4,5-b]pyridin-2-one, 1,3-dihydro-1-methyl-6-phenyl-2H-Imidazo[4,5-b]pyridin-2-one, 1,3-dihydro-5-(1H-imidazol-1-yl) 2H-Imidazo[4,5-b]pyridin-2-one, 6-(2,3-dihydro-2-oxo-1H-imidazo[4,5-b]pyridin-6-yl)-8-methyl-2(1H)-Quinolinone and 7,8-dihydro-8-oxo-2-phenyl-9H-purine-9-acetic acid.

In one embodiment, the TOR kinase inhibitors include compounds having the following formula (Ia):

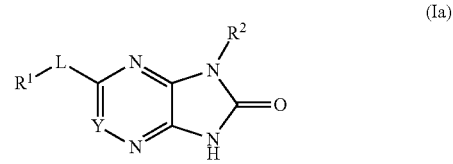

(Ia)

and pharmaceutically acceptable salts, clathrates, solvates, stereoisomers, tautomers, and prodrugs thereof, wherein:

L is a direct bond, NH or O;

Y is N or CR$^3$;

R$^1$ is H, substituted or unsubstituted C$_{1-8}$alkyl, substituted or unsubstituted C$_{2-8}$alkenyl, substituted or unsubstituted aryl, substituted or unsubstituted heteroaryl, substituted or unsubstituted cycloalkyl or substituted or unsubstituted heterocyclylalkyl;

R$^2$ is H, substituted or unsubstituted C$_{1-8}$alkyl, substituted or unsubstituted aryl, substituted or unsubstituted heteroaryl, substituted or unsubstituted cycloalkyl, or substituted or unsubstituted heterocyclylalkyl;

R$^3$ is H, substituted or unsubstituted C$_{1-8}$alkyl, substituted or unsubstituted aryl, substituted or unsubstituted heteroaryl, substituted or unsubstituted cycloalkyl, substituted or unsubstituted heterocyclylalkyl, —NHR$^4$ or —N(R$^4$)$_2$; and R$^4$ is at each occurrence independently substituted or unsubstituted C$_{1-8}$alkyl, substituted or unsubstituted aryl, substituted or unsubstituted heteroaryl, substituted or unsubstituted cycloalkyl, or substituted or unsubstituted heterocyclylalkyl.

In one embodiment, the TOR kinase inhibitors of formula (Ia) are those wherein R$^1$ is substituted aryl, such as substituted phenyl.

In another embodiment, the TOR kinase inhibitors of formula (Ia) are those wherein R$^1$ is substituted or unsubstituted aryl, such as substituted or unsubstituted phenyl or substituted or unsubstituted naphthyl.

In another embodiment, the TOR kinase inhibitors of formula (Ia) are those wherein R$^1$ is substituted or unsubstituted heteroaryl, such as substituted or unsubstituted quinoline, substituted or unsubstituted pyridine, substituted or unsubstituted pyrimidine, substituted or unsubstituted indole, or substituted or unsubstituted thiophene.

In another embodiment, the TOR kinase inhibitors of formula (Ia) are those wherein R$^1$ is H.

In another embodiment, the TOR kinase inhibitors of formula (Ia) are those wherein R$^2$ is substituted C$_{1-8}$alkyl.

In another embodiment, the TOR kinase inhibitors of formula (Ia) are those wherein R$^2$ is methyl or ethyl substituted with substituted or unsubstituted aryl, substituted or unsubstituted heteroaryl, substituted or unsubstituted cycloalkyl, or substituted or unsubstituted heterocyclylalkyl.

In another embodiment, the TOR kinase inhibitors of formula (Ia) are those wherein R$^2$ is substituted or unsubstituted cycloalkyl or substituted or unsubstituted heterocyclylalkyl.

In another embodiment, the TOR kinase inhibitors of formula (Ia) are those wherein R$^2$ is substituted or unsubstituted aryl, such as substituted or unsubstituted phenyl.

In another embodiment, the TOR kinase inhibitors of formula (Ia) are those wherein R$^2$ is H.

In another embodiment, the TOR kinase inhibitors of formula (Ia) are those wherein Y is CH.

In another embodiment, the TOR kinase inhibitors of formula (Ia) are those wherein L is a direct bond.

In another embodiment, the TOR kinase inhibitors of formula (Ia) are those wherein $R^1$ is substituted or unsubstituted aryl and $R^2$ is unsubstituted $C_{1-8}$alkyl.

In another embodiment, the TOR kinase inhibitors of formula (Ia) are those wherein $R^1$ is substituted or unsubstituted aryl and $R^2$ is $C_{1-8}$alkyl substituted with one or more substituents selected from alkoxy, amino, hydroxy, cycloalkyl, or heterocyclylalkyl.

In another embodiment, the TOR kinase inhibitors of formula (Ia) are those wherein $R^1$ is substituted or unsubstituted aryl and $R^2$ is substituted or unsubstituted cycloalkyl, or substituted or unsubstituted heterocyclylalkyl.

In another embodiment, the TOR kinase inhibitors of formula (Ia) do not include compounds wherein Y is CH, L is a direct bond, $R^1$ is substituted or unsubstituted aryl or substituted or unsubstituted heteroaryl, and $R^2$ is $C_{1-8}$alkyl substituted with substituted or unsubstituted aryl or substituted or unsubstituted heteroaryl.

In one embodiment, the TOR kinase inhibitors include compounds having the following formula (Ib):

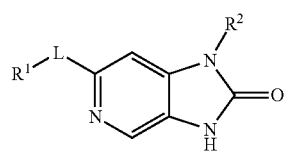

(Ib)

and pharmaceutically acceptable salts, clathrates, solvates, stereoisomers, tautomers, and prodrugs thereof, wherein:

L is a direct bond, NH or O;

$R^1$ is H, substituted or unsubstituted $C_{1-8}$alkyl, substituted or unsubstituted $C_{2-8}$alkenyl, substituted or unsubstituted aryl, substituted or unsubstituted heteroaryl, substituted or unsubstituted cycloalkyl or substituted or unsubstituted heterocyclylalkyl; and $R^2$ is H, substituted or unsubstituted $C_{1-8}$alkyl, substituted or unsubstituted aryl, substituted or unsubstituted heteroaryl, substituted or unsubstituted cycloalkyl, or substituted or unsubstituted heterocyclylalkyl.

In one embodiment, the TOR kinase inhibitors of formula (Ib) are those wherein $R^1$ is substituted aryl, such as substituted phenyl.

In another embodiment, the TOR kinase inhibitors of formula (Ib) are those wherein $R^1$ is substituted or unsubstituted aryl, such as substituted or unsubstituted phenyl or substituted or unsubstituted naphthyl.

In another embodiment, the TOR kinase inhibitors of formula (Ib) are those wherein $R^1$ is substituted or unsubstituted heteroaryl, such as substituted or unsubstituted quinoline, substituted or unsubstituted pyridine, substituted or unsubstituted pyrimidine, substituted or unsubstituted indole, or substituted or unsubstituted thiophene.

In another embodiment, the TOR kinase inhibitors of formula (Ib) are those wherein $R^1$ is H.

In another embodiment, the TOR kinase inhibitors of formula (Ib) are those wherein $R^2$ is substituted $C_{1-8}$alkyl.

In another embodiment, the TOR kinase inhibitors of formula (Ib) are those wherein $R^2$ is methyl or ethyl substituted with substituted or unsubstituted aryl, substituted or unsubstituted heteroaryl, substituted or unsubstituted cycloalkyl, or substituted or unsubstituted heterocyclylalkyl.

In another embodiment, the TOR kinase inhibitors of formula (Ib) are those wherein $R^2$ is substituted or unsubstituted cycloalkyl or substituted or unsubstituted heterocyclylalkyl.

In another embodiment, the TOR kinase inhibitors of formula (Ib) are those wherein $R^2$ is substituted or unsubstituted aryl, such as substituted or unsubstituted phenyl.

In another embodiment, the TOR kinase inhibitors of formula (Ib) are those wherein $R^2$ is H.

In another embodiment, the TOR kinase inhibitors of formula (Ib) are those wherein L is a direct bond.

In another embodiment, the TOR kinase inhibitors of formula (Ib) are those wherein $R^1$ is substituted or unsubstituted aryl and $R^2$ is unsubstituted $C_{1-8}$alkyl.

In another embodiment, the TOR kinase inhibitors of formula (Ib) are those wherein $R^1$ is substituted or unsubstituted aryl and $R^2$ is $C_{1-8}$alkyl substituted with one or more substituents selected from alkoxy, amino, hydroxy, cycloalkyl, or heterocyclylalkyl.

In another embodiment, the TOR kinase inhibitors of formula (Ib) are those wherein $R^1$ is substituted or unsubstituted aryl and $R^2$ is substituted or unsubstituted cycloalkyl, or substituted or unsubstituted heterocyclylalkyl.

In one embodiment, the TOR kinase inhibitors include compounds having the following formula (Ic):

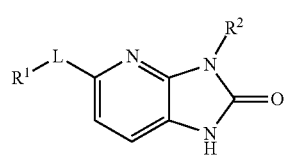

(Ic)

and pharmaceutically acceptable salts, clathrates, solvates, stereoisomers, tautomers, and prodrugs thereof, wherein:

L is a direct bond, NH or O;

$R^1$ is H, substituted or unsubstituted $C_{1-8}$alkyl, substituted or unsubstituted $C_{2-8}$alkenyl, substituted or unsubstituted aryl, substituted or unsubstituted heteroaryl, substituted or unsubstituted cycloalkyl or substituted or unsubstituted heterocyclylalkyl; and $R^2$ is H, substituted or unsubstituted $C_{1-8}$alkyl, substituted or unsubstituted aryl, substituted or unsubstituted heteroaryl, substituted or unsubstituted cycloalkyl, or substituted or unsubstituted heterocyclylalkyl.

In one embodiment, the TOR kinase inhibitors of formula (Ic) are those wherein $R^1$ is substituted aryl, such as substituted phenyl.

In another embodiment, the TOR kinase inhibitors of formula (Ic) are those wherein $R^1$ is substituted or unsubstituted aryl, such as substituted or unsubstituted phenyl or substituted or unsubstituted naphthyl.

In another embodiment, the TOR kinase inhibitors of formula (Ic) are those wherein $R^1$ is substituted or unsubstituted heteroaryl, such as substituted or unsubstituted quinoline, substituted or unsubstituted pyridine, substituted or unsubstituted pyrimidine, substituted or unsubstituted indole, or substituted or unsubstituted thiophene.

In another embodiment, the TOR kinase inhibitors of formula (Ic) are those wherein $R^1$ is H.

In another embodiment, the TOR kinase inhibitors of formula (Ic) are those wherein $R^2$ is substituted $C_{1-8}$alkyl.

In another embodiment, the TOR kinase inhibitors of formula (Ic) are those wherein $R^2$ is methyl or ethyl substituted with substituted or unsubstituted aryl, substituted or unsubstituted heteroaryl, substituted or unsubstituted cycloalkyl, or substituted or unsubstituted heterocyclylalkyl.

In another embodiment, the TOR kinase inhibitors of formula (Ic) are those wherein $R^2$ is substituted or unsubstituted cycloalkyl or substituted or unsubstituted heterocyclylalkyl.

In another embodiment, the TOR kinase inhibitors of formula (Ic) are those wherein $R^2$ is substituted or unsubstituted aryl, such as substituted or unsubstituted phenyl.

In another embodiment, the TOR kinase inhibitors of formula (Ic) are those wherein $R^2$ is H.

In another embodiment, the TOR kinase inhibitors of formula (Ic) are those wherein L is a direct bond.

In another embodiment, the TOR kinase inhibitors of formula (Ic) are those wherein $R^1$ is substituted or unsubstituted aryl and $R^2$ is unsubstituted $C_{1-8}$alkyl.

In another embodiment, the TOR kinase inhibitors of formula (Ic) are those wherein $R^1$ is substituted or unsubstituted aryl and $R^2$ is $C_{1-8}$alkyl substituted with one or more substituents selected from alkoxy, amino, hydroxy, cycloalkyl, or heterocyclylalkyl.

In another embodiment, the TOR kinase inhibitors of formula (Ic) are those wherein $R^1$ is substituted or unsubstituted aryl and $R^2$ is substituted or unsubstituted cycloalkyl, or substituted or unsubstituted heterocyclylalkyl.

In one embodiment, the TOR kinase inhibitors include compounds having the following formula (Id):

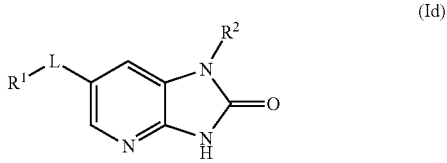

(Id)

and pharmaceutically acceptable salts, clathrates, solvates, stereoisomers, tautomers, and prodrugs thereof, wherein:

L is a direct bond, NH or O;

$R^1$ is H, substituted or unsubstituted $C_{1-8}$alkyl, substituted or unsubstituted $C_{2-8}$alkenyl, substituted or unsubstituted aryl, substituted or unsubstituted heteroaryl, substituted or unsubstituted cycloalkyl or substituted or unsubstituted heterocyclylalkyl; and $R^2$ is H, substituted or unsubstituted $C_{1-8}$alkyl, substituted or unsubstituted aryl, substituted or unsubstituted heteroaryl, substituted or unsubstituted cycloalkyl, or substituted or unsubstituted heterocyclylalkyl.

In one embodiment, the TOR kinase inhibitors of formula (Id) are those wherein $R^1$ is substituted aryl, such as substituted phenyl.

In another embodiment, the TOR kinase inhibitors of formula (Id) are those wherein $R^1$ is substituted or unsubstituted aryl, such as substituted or unsubstituted phenyl or substituted or unsubstituted naphthyl.

In another embodiment, the TOR kinase inhibitors of formula (Id) are those wherein $R^1$ is substituted or unsubstituted heteroaryl, such as substituted or unsubstituted quinoline, substituted or unsubstituted pyridine, substituted or unsubstituted pyrimidine, substituted or unsubstituted indole, or substituted or unsubstituted thiophene.

In another embodiment, the TOR kinase inhibitors of formula (Id) are those wherein $R^1$ is H.

In another embodiment, the TOR kinase inhibitors of formula (Id) are those wherein $R^2$ is substituted $C_{1-8}$alkyl.

In another embodiment, the TOR kinase inhibitors of formula (Id) are those wherein $R^2$ is methyl or ethyl substituted with substituted or unsubstituted aryl, substituted or unsubstituted heteroaryl, substituted or unsubstituted cycloalkyl, or substituted or unsubstituted heterocyclylalkyl.

In another embodiment, the TOR kinase inhibitors of formula (Id) are those wherein $R^2$ is substituted or unsubstituted cycloalkyl or substituted or unsubstituted heterocyclylalkyl.

In another embodiment, the TOR kinase inhibitors of formula (Id) are those wherein $R^2$ is substituted or unsubstituted aryl, such as substituted or unsubstituted phenyl.

In another embodiment, the Heteroaryl Compounds of formula (Id) are those wherein $R^2$ is H.

In another embodiment, the TOR kinase inhibitors of formula (Id) are those wherein L is a direct bond.

In another embodiment, the TOR kinase inhibitors of formula (Id) are those wherein $R^1$ is substituted or unsubstituted aryl and $R^2$ is unsubstituted $C_{1-8}$alkyl.

In another embodiment, the TOR kinase inhibitors of formula (Id) are those wherein $R^1$ is substituted or unsubstituted aryl and $R^2$ is $C_{1-8}$alkyl substituted with one or more substituents selected from alkoxy, amino, hydroxy, cycloalkyl, or heterocyclylalkyl.

In another embodiment, the TOR kinase inhibitors of formula (Id) are those wherein $R^1$ is substituted or unsubstituted aryl and $R^2$ is substituted or unsubstituted cycloalkyl, or substituted or unsubstituted heterocyclylalkyl.

In one embodiment, the TOR kinase inhibitors include compounds having the following formula (Ie):

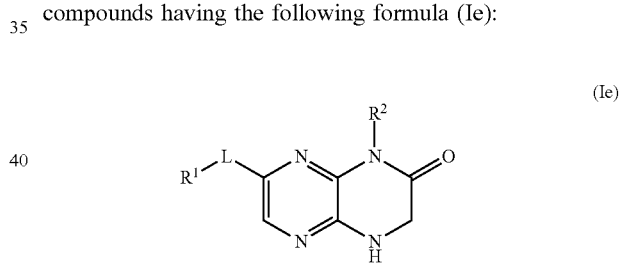

(Ie)

and pharmaceutically acceptable salts, clathrates, solvates, stereoisomers, tautomers, and prodrugs thereof, wherein:

L is a direct bond, NH or O;

$R^1$ is H, substituted or unsubstituted $C_{1-8}$alkyl, substituted or unsubstituted $C_{2-8}$alkenyl, substituted or unsubstituted aryl, substituted or unsubstituted heteroaryl, substituted or unsubstituted cycloalkyl or substituted or unsubstituted heterocyclylalkyl; and $R^2$ is H, substituted or unsubstituted $C_{1-8}$alkyl, substituted or unsubstituted aryl, substituted or unsubstituted heteroaryl, substituted or unsubstituted cycloalkyl, or substituted or unsubstituted heterocyclylalkyl.

In one embodiment, the TOR kinase inhibitors of formula (Ie) are those wherein $R^1$ is substituted aryl, such as substituted phenyl.

In another embodiment, the TOR kinase inhibitors of formula (Ie) are those wherein $R^1$ is substituted or unsubstituted aryl, such as substituted or unsubstituted phenyl or substituted or unsubstituted naphthyl.

In another embodiment, the TOR kinase inhibitors of formula (Ie) are those wherein $R^1$ is substituted or unsubstituted heteroaryl, such as substituted or unsubstituted quinoline, substituted or unsubstituted pyridine, substituted or unsubstituted pyrimidine, substituted or unsubstituted indole, or substituted or unsubstituted thiophene.

In another embodiment, the TOR kinase inhibitors of formula (Ie) are those wherein $R^1$ is H.

In another embodiment, the TOR kinase inhibitors of formula (Ie) are those wherein $R^2$ is substituted $C_{1-8}$alkyl.

In another embodiment, the TOR kinase inhibitors of formula (Ie) are those wherein $R^2$ is methyl or ethyl substituted with substituted or unsubstituted aryl, substituted or unsubstituted heteroaryl, substituted or unsubstituted cycloalkyl, or substituted or unsubstituted heterocyclylalkyl.

In another embodiment, the TOR kinase inhibitors of formula (Ie) are those wherein $R^2$ is substituted or unsubstituted cycloalkyl or substituted or unsubstituted heterocyclylalkyl.

In another embodiment, the TOR kinase inhibitors of formula (Ie) are those wherein $R^2$ is substituted or unsubstituted aryl, such as substituted or unsubstituted phenyl.

In another embodiment, the TOR kinase inhibitors of formula (Ie) are those wherein $R^2$ is H.

In another embodiment, the TOR kinase inhibitors of formula (Ie) are those wherein L is a direct bond.

In another embodiment, the TOR kinase inhibitors of formula (Ie) are those wherein $R^1$ is substituted or unsubstituted aryl and $R^2$ is unsubstituted $C_{1-8}$alkyl.

In another embodiment, the TOR kinase inhibitors of formula (Ie) are those wherein $R^1$ is substituted or unsubstituted aryl and $R^2$ is $C_{1-8}$alkyl substituted with one or more substituents selected from alkoxy, amino, hydroxy, cycloalkyl, or heterocyclylalkyl.

In another embodiment, the TOR kinase inhibitors of formula (Ie) are those wherein $R^1$ is substituted or unsubstituted aryl and $R^2$ is substituted or unsubstituted cycloalkyl, or substituted or unsubstituted heterocyclylalkyl.

In one embodiment, the TOR kinase inhibitors include compounds having the following formula (If):

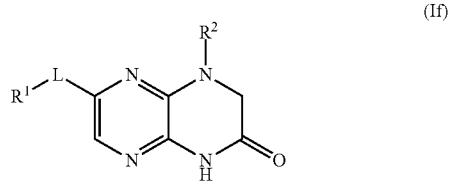

(If)

and pharmaceutically acceptable salts, clathrates, solvates, stereoisomers, tautomers, and prodrugs thereof, wherein:

L is a direct bond, NH or O;

$R^1$ is H, substituted or unsubstituted $C_{1-8}$alkyl, substituted or unsubstituted $C_{2-8}$alkenyl, substituted or unsubstituted aryl, substituted or unsubstituted heteroaryl, substituted or unsubstituted cycloalkyl or substituted or unsubstituted heterocyclylalkyl; and $R^2$ is H, substituted or unsubstituted $C_{1-8}$alkyl, substituted or unsubstituted aryl, substituted or unsubstituted heteroaryl, substituted or unsubstituted cycloalkyl, or substituted or unsubstituted heterocyclylalkyl.

In one embodiment, the TOR kinase inhibitors of formula (If) are those wherein $R^1$ is substituted aryl, such as substituted phenyl.

In another embodiment, the TOR kinase inhibitors of formula (If) are those wherein $R^1$ is substituted or unsubstituted aryl, such as substituted or unsubstituted phenyl or substituted or unsubstituted naphthyl.

In another embodiment, the TOR kinase inhibitors of formula (If) are those wherein $R^1$ is substituted or unsubstituted heteroaryl, such as substituted or unsubstituted quinoline, substituted or unsubstituted pyridine, substituted or unsubstituted pyrimidine, substituted or unsubstituted indole, or substituted or unsubstituted thiophene.

In another embodiment, the TOR kinase inhibitors of formula (If) are those wherein $R^1$ is H.

In another embodiment, the TOR kinase inhibitors of formula (If) are those wherein $R^2$ is substituted $C_{1-8}$alkyl.

In another embodiment, the TOR kinase inhibitors of formula (If) are those wherein $R^2$ is methyl or ethyl substituted with substituted or unsubstituted aryl, substituted or unsubstituted heteroaryl, substituted or unsubstituted cycloalkyl, or substituted or unsubstituted heterocyclylalkyl.

In another embodiment, the TOR kinase inhibitors of formula (If) are those wherein $R^2$ is substituted or unsubstituted cycloalkyl or substituted or unsubstituted heterocyclylalkyl.

In another embodiment, the TOR kinase inhibitors of formula (If) are those wherein $R^2$ is substituted or unsubstituted aryl, such as substituted or unsubstituted phenyl.

In another embodiment, the TOR kinase inhibitors of formula (If) are those wherein $R^2$ is H.

In another embodiment, the TOR kinase inhibitors of formula (If) are those wherein L is a direct bond.

In another embodiment, the TOR kinase inhibitors of formula (If) are those wherein $R^1$ is substituted or unsubstituted aryl and $R^2$ is unsubstituted $C_{1-8}$alkyl.

In another embodiment, the TOR kinase inhibitors of formula (If) are those wherein $R^1$ is substituted or unsubstituted aryl and $R^2$ is $C_{1-8}$alkyl substituted with one or more substituents selected from alkoxy, amino, hydroxy, cycloalkyl, or heterocyclylalkyl.

In another embodiment, the TOR kinase inhibitors of formula (If) are those wherein $R^1$ is substituted or unsubstituted aryl and $R^2$ is substituted or unsubstituted cycloalkyl, or substituted or unsubstituted heterocyclylalkyl.

In one embodiment, the TOR kinase inhibitors include compounds having the following formula (Ig):

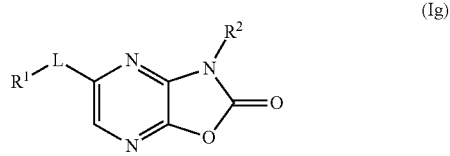

(Ig)

and pharmaceutically acceptable salts, clathrates, solvates, stereoisomers, tautomers, and prodrugs thereof, wherein:

L is a direct bond, NH or O;

$R^1$ is H, substituted or unsubstituted $C_{1-8}$alkyl, substituted or unsubstituted $C_{2-8}$alkenyl, substituted or unsubstituted aryl, substituted or unsubstituted heteroaryl, substituted or unsubstituted cycloalkyl or substituted or unsubstituted heterocyclylalkyl; and $R^2$ is H, substituted or unsubstituted $C_{1-8}$alkyl, substituted or unsubstituted aryl, substituted or unsubstituted heteroaryl, substituted or unsubstituted cycloalkyl, or substituted or unsubstituted heterocyclylalkyl.

In one embodiment, the TOR kinase inhibitors of formula (Ig) are those wherein $R^1$ is substituted aryl, such as substituted phenyl.

In another embodiment, the TOR kinase inhibitors of formula (Ig) are those wherein $R^1$ is substituted or unsubstituted aryl, such as substituted or unsubstituted phenyl or substituted or unsubstituted naphthyl.

In another embodiment, the TOR kinase inhibitors of formula (Ig) are those wherein $R^1$ is substituted or unsubstituted heteroaryl, such as substituted or unsubstituted quinoline, substituted or unsubstituted pyridine, substituted or unsubstituted pyrimidine, substituted or unsubstituted indole, or substituted or unsubstituted thiophene.

In another embodiment, the TOR kinase inhibitors of formula (Ig) are those wherein $R^1$ is H.

In another embodiment, the TOR kinase inhibitors of formula (Ig) are those wherein $R^2$ is substituted $C_{1-8}$alkyl.

In another embodiment, the TOR kinase inhibitors of formula (Ig) are those wherein $R^2$ is methyl or ethyl substituted with substituted or unsubstituted aryl, substituted or unsubstituted heteroaryl, substituted or unsubstituted cycloalkyl, or substituted or unsubstituted heterocyclylalkyl.

In another embodiment, the TOR kinase inhibitors of formula (Ig) are those wherein $R^2$ is substituted or unsubstituted cycloalkyl or substituted or unsubstituted heterocyclylalkyl.

In another embodiment, the TOR kinase inhibitors of formula (Ig) are those wherein $R^2$ is substituted or unsubstituted aryl, such as substituted or unsubstituted phenyl.

In another embodiment, the TOR kinase inhibitors of formula (Ig) are those wherein $R^2$ is H.

In another embodiment, the TOR kinase inhibitors of formula (Ig) are those wherein L is a direct bond.

In another embodiment, the TOR kinase inhibitors of formula (Ig) are those wherein $R^1$ is substituted or unsubstituted aryl and $R^2$ is unsubstituted $C_{1-8}$alkyl.

In another embodiment, the TOR kinase inhibitors of formula (Ig) are those wherein $R^1$ is substituted or unsubstituted aryl and $R^2$ is $C_{1-8}$alkyl substituted with one or more substituents selected from alkoxy, amino, hydroxy, cycloalkyl, or heterocyclylalkyl.

In another embodiment, the TOR kinase inhibitors of formula (Ig) are those wherein $R^1$ is substituted or unsubstituted aryl and $R^2$ is substituted or unsubstituted cycloalkyl, or substituted or unsubstituted heterocyclylalkyl.

Representative TOR kinase inhibitors of formula (I) include compounds from Table A. PGPubs, can be done by text.

Table A (S)-1-(1-hydroxy-3-methylbutan-2-yl)-6-phenyl-1H-imidazo[4,5-b]pyrazin-2(3H)-one;
1-((tetrahydro-2H-pyran-4-yl)methyl)-6-(3,4,5-trimethoxyphenyl)-1H-imidazo[4,5-b]pyrazin-2(3H)-one;
(R)-6-(naphthalen-1-yl)-1-(1-phenylethyl)-1H-imidazo[4,5-b]pyrazin-2(3H)-one;
1-(3-methoxybenzyl)-6-(4-(methylsulfonyl)phenyl)-1H-imidazo[4,5-b]pyrazin-2(3H)-one;
(S)-1-(1-phenylethyl)-6-(quinolin-5-yl)-1H-imidazo[4,5-b]pyrazin-2(3H)-one;
6-(4-hydroxyphenyl)-1-((tetrahydro-2H-pyran-4-yl)methyl)-1H-imidazo[4,5-b]pyrazin-2(3H)-one;
(S)-6-(naphthalen-1-yl)-1-(1-phenylethyl)-1H-imidazo[4,5-b]pyrazin-2(3H)-one;
(S)-1-(1-hydroxy-3-methylbutan-2-yl)-6-(5-isopropyl-2-methoxyphenyl)-1H-imidazo[4,5-b]pyrazin-2(3H)-one;
(R)-1-(1-hydroxy-3-methylbutan-2-yl)-6-phenyl-1H-imidazo[4,5-b]pyrazin-2(3H)-one;
(R)-1-(1-phenylethyl)-6-(quinolin-5-yl)-1H-imidazo[4,5-b]pyrazin-2(3H)-one;
(S)-1-(1-hydroxy-3-methylbutan-2-yl)-6-(quinolin-5-yl)-1H-imidazo[4,5-b]pyrazin-2(3H)-one;
(R)-1-(1-hydroxy-3-methylbutan-2-yl)-6-(quinolin-5-yl)-1H-imidazo[4,5-b]pyrazin-2(3H)-one;
(R)-1-(1-hydroxy-3-methylbutan-2-yl)-6-(5-isopropyl-2-methoxyphenyl)-1H-imidazo[4,5-b]pyrazin-2(3H)-one;
1-benzyl-6-(quinolin-5-yl)-1H-imidazo[4,5-b]pyrazin-2(3H)-one;
1-(4-methoxybenzyl)-6-(quinolin-5-yl)-1H-imidazo[4,5-b]pyrazin-2(3H)-one;
(R)-1-(1-phenylethyl)-1H-imidazo[4,5-b]pyrazin-2(3H)-one;
(S)-1-(1-phenylethyl)-1H-imidazo[4,5-b]pyrazin-2(3H)-one;
1-isopropyl-6-(5-isopropyl-2-methoxyphenyl)-1H-imidazo[4,5-b]pyrazin-2(3H)-one;
1-cyclohexyl-6-(5-isopropyl-2-methoxyphenyl)-1H-imidazo[4,5-b]pyrazin-2(3H)-one;
5-(quinolin-5-yl)-1H-imidazo[4,5-b]pyrazin-2(3H)-one;
1-isobutyl-6-(5-isopropyl-2-methoxyphenyl)-1H-imidazo[4,5-b]pyrazin-2(3H)-one;
1-(2-hydroxyethyl)-6-(5-isopropyl-2-methoxyphenyl)-1H-imidazo[4,5-b]pyrazin-2(3H)-one;
6-(5-isopropyl-2-methoxyphenyl)-1-(tetrahydro-2H-pyran-4-yl)-1H-imidazo[4,5-b]pyrazin-2(3H)-one;
(R)-1-(1-phenylethyl)-6-(quinolin-5-yl)-1H-imidazo[4,5-c]pyridin-2(3H)-one;
(S)-1-(1-phenylethyl)-6-(quinolin-5-yl)-1H-imidazo[4,5-c]pyridin-2(3H)-one;
3-(1-phenylethyl)-5-(quinolin-5-yl)-1H-imidazo[4,5-b]pyridin-2(3H)-one;
(R)-3-(1-phenylethyl)-5-(quinolin-5-yl)-1H-imidazo[4,5-b]pyridin-2(3H)-one;
(R)-6-(5-isopropyl-2-methoxyphenyl)-1-(3-methylbutan-2-yl)-1H-imidazo[4,5-b]pyrazin-2(3H)-one;
(S)-6-(5-isopropyl-2-methoxyphenyl)-1-(tetrahydrofuran-3-yl)-1H-imidazo[4,5-b]pyrazin-2(3H)-one;
(S)-6-(5-isopropyl-2-methoxyphenyl)-1-(3-methylbutan-2-yl)-1H-imidazo[4,5-b]pyrazin-2(3H)-one;
1-cyclopentyl-6-(5-isopropyl-2-methoxyphenyl)-1H-imidazo[4,5-b]pyrazin-2(3H)-one;
(R)-6-(5-isopropyl-2-methoxyphenyl)-1-(tetrahydrofuran-3-yl)-1H-imidazo[4,5-b]pyrazin-2(3H)-one;
1-(cyclopropylmethyl)-6-(5-isopropyl-2-methoxyphenyl)-1H-imidazo[4,5-b]pyrazin-2(3H)-one;
1-(cyclopentylmethyl)-6-(5-isopropyl-2-methoxyphenyl)-1H-imidazo[4,5-b]pyrazin-2(3H)-one;
1-(cyclohexylmethyl)-6-(5-isopropyl-2-methoxyphenyl)-1H-imidazo[4,5-b]pyrazin-2(3H)-one;
6-(5-isopropyl-2-methoxyphenyl)-1-neopentyl-1H-imidazo[4,5-b]pyrazin-2(3H)-one;
1-isopropyl-6-(3-isopropylphenyl)-1H-imidazo[4,5-b]pyrazin-2(3H)-one;
1-isopropyl-6-(2-methoxyphenyl)-1H-imidazo[4,5-b]pyrazin-2(3H)-one;
(S)-3-(1-hydroxy-3-methylbutan-2-yl)-5-(5-isopropyl-2-methoxyphenyl)-1H-imidazo[4,5-b]pyridin-2(3H)-one;
(R)-1-(2-hydroxy-1-phenylethyl)-6-(quinolin-5-yl)-1H-imidazo[4,5-b]pyrazin-2(3H)-one;
(S)-1-(2-hydroxy-1-phenylethyl)-6-(quinolin-5-yl)-1H-imidazo[4,5-b]pyrazin-2(3H)-one;
1-(1-phenylethyl)-6-(quinolin-5-yl)-1H-imidazo[4,5-b]pyrazin-2(3H)-one;
1-benzhydryl-6-(quinolin-5-yl)-1H-imidazo[4,5-b]pyrazin-2(3H)-one;

(S)-1-(1-phenylpropyl)-6-(quinolin-5-yl)-1H-imidazo[4,5-b]pyrazin-2(3H)-one;
(R)-1-(1-phenylpropyl)-6-(quinolin-5-yl)-1H-imidazo[4,5-b]pyrazin-2(3H)-one;
6-(5-isopropyl-2-methoxyphenyl)-1-(tetrahydro-2H-pyran-3-yl)-1H-imidazo[4,5-b]pyrazin-2(3H)-one;
1-(3-methoxybenzyl)-6-(quinolin-5-yl)-1H-imidazo[4,5-b]pyrazin-2(3H)-one;
(R)-1-methyl-3-(1-phenylethyl)-5-(quinolin-5-yl)-1H-imidazo[4,5-b]pyrazin-2(3H)-one;
(S)-1-methyl-3-(1-phenylethyl)-5-(quinolin-5-yl)-1H-imidazo[4,5-b]pyrazin-2(3H)-one;
1-(cyclopentylmethyl)-6-(quinolin-5-yl)-1H-imidazo[4,5-b]pyrazin-2(3H)-one;
1-(1-(2-fluorophenyl)ethyl)-6-(quinolin-5-yl)-1H-imidazo[4,5-b]pyrazin-2(3H)-one;
1-(1-(4-fluorophenyl)ethyl)-6-(quinolin-5-yl)-1H-imidazo[4,5-b]pyrazin-2(3H)-one;
1-cyclopentyl-6-(quinolin-5-yl)-1H-imidazo[4,5-b]pyrazin-2(3H)-one;
1-(1-(3-fluorophenyl)ethyl)-6-(quinolin-5-yl)-1H-imidazo[4,5-b]pyrazin-2(3H)-one;
1-(1-(3-methoxyphenyl)ethyl)-6-(quinolin-5-yl)-1H-imidazo[4,5-b]pyrazin-2(3H)-one;
1-(1-(4-methoxyphenyl)ethyl)-6-(quinolin-5-yl)-1H-imidazo[4,5-b]pyrazin-2(3H)-one;
6-(quinolin-5-yl)-1-(tetrahydro-2H-pyran-4-yl)-1H-imidazo[4,5-b]pyrazin-2(3H)-one;
6-(quinolin-5-yl)-1-(tetrahydro-2H-pyran-3-yl)-1H-imidazo[4,5-b]pyrazin-2(3H)-one;
1-((1s,4s)-4-hydroxycyclohexyl)-6-(quinolin-5-yl)-1H-imidazo[4,5-b]pyrazin-2(3H)-one;
1-((1r,4r)-4-hydroxycyclohexyl)-6-(quinolin-5-yl)-1H-imidazo[4,5-b]pyrazin-2(3H)-one;
6-(isoquinolin-5-yl)-1-(1-phenylethyl)-1H-imidazo[4,5-b]pyrazin-2(3H)-one;
(R)-1-(1-phenylethyl)-6-(quinolin-5-yl)-1H-imidazo[4,5-b]pyridin-2(3H)-one;
1-(1-phenylethyl)-6-(quinolin-5-yl)-1H-imidazo[4,5-b]pyridin-2(3H)-one;
1-isopropyl-6-(quinolin-5-yl)-1H-imidazo[4,5-b]pyrazin-2(3H)-one;
1-(1-(4-chlorophenyl)ethyl)-6-(quinolin-5-yl)-1H-imidazo[4,5-b]pyrazin-2(3H)-one;
1-(1-(4-(methylsulfonyl)phenyl)ethyl)-6-(quinolin-5-yl)-1H-imidazo[4,5-b]pyrazin-2(3H)-one;
1-(1-(pyridin-4-yl)ethyl)-6-(quinolin-5-yl)-1H-imidazo[4,5-b]pyrazin-2(3H)-one;
5-methyl-1-((S)-1-phenylethyl)-6-(quinolin-5-yl)-1H-imidazo[4,5-b]pyrazin-2(3H)-one;
5-methyl-1-((R)-1-phenylethyl)-6-(quinolin-5-yl)-1H-imidazo[4,5-b]pyrazin-2(3H)-one;
1-(1-phenylethyl)-6-(quinolin-4-yl)-1H-imidazo[4,5-b]pyrazin-2(3H)-one;
6-(3-fluorophenyl)-1-(1-phenylethyl)-1H-imidazo[4,5-b]pyrazin-2(3H)-one;
6-(2-fluorophenyl)-1-(1-phenylethyl)-1H-imidazo[4,5-b]pyrazin-2(3H)-one;
1-(1-phenylethyl)-6-(quinolin-6-yl)-1H-imidazo[4,5-b]pyrazin-2(3H)-one;
1-(piperidin-4-ylmethyl)-6-(quinolin-5-yl)-1H-imidazo[4,5-b]pyrazin-2(3H)-one;
1-(1-(pyridin-2-yl)ethyl)-6-(quinolin-5-yl)-1H-imidazo[4,5-b]pyrazin-2(3H)-one;
1-(1-(pyridin-3-yl)ethyl)-6-(quinolin-5-yl)-1H-imidazo[4,5-b]pyrazin-2(3H)-one;
1-((1s,4s)-4-(hydroxymethyl)cyclohexyl)-6-(quinolin-5-yl)-1H-imidazo[4,5-b]pyrazin-2(3H)-one;
N-(4-(2-oxo-3-(1-phenylethyl)-2,3-dihydro-1H-imidazo[4,5-b]pyrazin-5-yl)phenyl)methanesulfonamide;
6-(3-(methylsulfonyl)phenyl)-1-(1-phenylethyl)-1H-imidazo[4,5-b]pyrazin-2(3H)-one;
6-(3-aminophenyl)-1-(1-phenylethyl)-1H-imidazo[4,5-b]pyrazin-2(3H)-one;
6-(3-(dimethylamino)phenyl)-1-(1-phenylethyl)-1H-imidazo[4,5-b]pyrazin-2(3H)-one;
1-phenyl-6-(quinolin-5-yl)-1H-imidazo[4,5-b]pyrazin-2(3H)-one;
1-(1-phenylethyl)-6-(4-(trifluoromethyl)phenyl)-1H-imidazo[4,5-b]pyrazin-2(3H)-one;
N-(3-(2-oxo-3-(1-phenylethyl)-2,3-dihydro-1H-imidazo[4,5-b]pyrazin-5-yl)phenyl)methanesulfonamide;
6-(4-(methylsulfonyl)phenyl)-1-(1-phenylethyl)-1H-imidazo[4,5-b]pyrazin-2(3H)-one;
3-(1-phenylethyl)-5-(quinolin-5-yl)oxazolo[5,4-b]pyrazin-2(3H)-one;
1-(cyclopentylmethyl)-6-(4-hydroxyphenyl)-1H-imidazo[4,5-b]pyrazin-2(3H)-one
6-(4-hydroxyphenyl)-1-isopropyl-1H-imidazo[4,5-b]pyrazin-2(3H)-one;
6-(4-hydroxyphenyl)-1-isobutyl-1H-imidazo[4,5-b]pyrazin-2(3H)-one;
6-(4-hydroxyphenyl)-1-((tetrahydro-2H-pyran-3-yl)methyl)-1H-imidazo[4,5-b]pyrazin-2(3H)-one;
1-(cyclohexylmethyl)-6-(4-hydroxyphenyl)-1H-imidazo[4,5-b]pyrazin-2(3H)-one;
5-(3-Hydroxyphenyl)-3-(2-methoxyphenyl)-1H-imidazo[4,5-b]pyridin-2(3H)-one;
4-(3-(3-Methoxybenzyl)-2-oxo-2,3-dihydrooxazolo[5,4-b]pyrazin-5-yl)-N-methyl benzamide;
1-Cyclopentyl-6-(4-hydroxyphenyl)-1H-imidazo[4,5-b]pyrazin-2(3H)-one;
1-Cyclohexyl-6-(4-hydroxyphenyl)-1H-imidazo[4,5-b]pyrazin-2(3H)-one;
4-(3-(Cyclohexylmethyl)-2-oxo-2,3-dihydro-1H-imidazo[4,5-b]pyrazin-5-yl)benzamide;
Methyl 4-(3-(cyclohexylmethyl)-2-oxo-2,3-dihydro-1H-imidazo[4,5-b]pyrazin-5-yl)benzoate;
1-(Cyclohexylmethyl)-6-(pyridin-4-yl)-1H-imidazo[4,5-b]pyrazin-2(3H)-one;
4-(3-(Cyclohexylmethyl)-2-oxo-2,3-dihydro-1H-imidazo[4,5-b]pyrazin-5-yl)-N-methylbenzamide;
1-(Cyclohexylmethyl)-6-(4-(hydroxymethyl)phenyl)-1H-imidazo[4,5-b]pyrazin-2(3H)-one;
1-(Cyclohexylmethyl)-6-(pyridin-3-yl)-1H-imidazo[4,5-b]pyrazin-2(3H)-one;
3-(Cyclohexylmethyl)-2-oxo-2,3-dihydro-1H-imidazo[4,5-b]pyrazin-5-yl)benzonitrile;
1-(Cyclohexylmethyl)-6-(1H-indol-5-yl)-1H-imidazo[4,5-b]pyrazin-2(3H)-one;
4-(3-(Cyclohexylmethyl)-2-oxo-2,3-dihydro-1H-imidazo[4,5-b]pyrazin-5-yl)-N-isopropylbenzamide;
1-(2-Hydroxyethyl)-6-(4-hydroxyphenyl)-1H-imidazo[4,5-b]pyrazin-2(3H)-one;
1-(Cyclohexylmethyl)-6-(1H-indol-6-yl)-1H-imidazo[4,5-b]pyrazin-2(3H)-one;
3-(3-(Cyclohexylmethyl)-2-oxo-2,3-dihydro-1H-imidazo[4,5-b]pyrazin-5-yl)benzamide;
6-(4-(Aminomethyl)phenyl)-1-(cyclohexylmethyl)-1H-imidazo[4,5-b]pyrazin-2(3H)-one;
6-(4-Hydroxyphenyl)-1-((1-methylpiperidin-4-yl)methyl)-1H-imidazo[4,5-b]pyrazin-2(3H)-one;

4-(3-(Cyclohexylmethyl)-2-oxo-2,3-dihydro-1H-imidazo[4,5-b]pyrazin-5-yl)benzonitrile;
1-((1s,4s)-4-Hydroxycyclohexyl)-6-(4-hydroxyphenyl)-1H-imidazo[4,5-b]pyrazin-2(3H)-one;
1-(Cyclohexylmethyl)-6-(pyridin-2-yl)-1H-imidazo[4,5-b]pyrazin-2(3H)-one;
4-(3-(Cyclohexylmethyl)-2-oxo-2,3-dihydro-1H-imidazo[4,5-b]pyrazin-5-yl)-N-ethylbenzamide;
1-(Cyclohexylmethyl)-6-(4-(2-hydroxypropan-2-yl)phenyl)-1H-imidazo[4,5-b]pyrazin-2(3H)-one;
1-(Cyclohexylmethyl)-6-(4-hydroxy-2-methylphenyl)-1H-imidazo[4,5-b]pyrazin-2(3H)-one;
4-(3-(Cyclohexylmethyl)-2-oxo-2,3-dihydro-1H-imidazo[4,5-b]pyrazin-5-yl)benzoic acid;
6-(4-Hydroxyphenyl)-1-(2-methoxyethyl)-1H-imidazo[4,5-b]pyrazin-2(3H)-one;
6-(4-Hydroxyphenyl)-1-(3-methoxypropyl)-1H-imidazo[4,5-b]pyrazin-2(3H)-one;
6-(4-Hydroxyphenyl)-4-(3-methoxybenzyl)-3,4-dihydropyrazino[2,3-b]pyrazin-2(1H)-one;
6-(4-Hydroxyphenyl)-1-(2-(tetrahydro-2H-pyran-4-yl)ethyl)-1H-imidazo[4,5-b]pyrazin-2(3H)-one;
6-(4-Hydroxyphenyl)-1-phenethyl-1H-imidazo[4,5-b]pyrazin-2(3H)-one;
1-((1r,4r)-4-Hydroxycyclohexyl)-6-(4-hydroxyphenyl)-1H-imidazo[4,5-b]pyrazin-2(3H)-one;
6-(4-(1H-1,2,4-Triazol-3-yl)phenyl)-1-(cyclohexylmethyl)-1H-imidazo[4,5-b]pyrazin-2(3H)-one;
1-(Cyclohexylmethyl)-6-phenyl-1H-imidazo[4,5-b]pyrazin-2(3H)-one;
1-(Cyclohexylmethyl)-6-(1H-pyrazol-5-yl)-1H-imidazo[4,5-b]pyrazin-2(3H)-one;
1-(Cyclohexylmethyl)-6-(1H-pyrazol-4-yl)-1H-imidazo[4,5-b]pyrazin-2(3H)-one;
1-(Cyclohexylmethyl)-6-(1-oxoisoindolin-5-yl)-1H-imidazo[4,5-b]pyrazin-2(3H)-one;
6-(3-(1H-Tetrazol-5-yl)phenyl)-1-(cyclohexylmethyl)-1H-imidazo[4,5-b]pyrazin-2(3H)-one;
1-(Cyclohexylmethyl)-6-(2-oxoindolin-5-yl)-1H-imidazo[4,5-b]pyrazin-2(3H)-one;
1-(Cyclohexylmethyl)-6-(1H-indazol-5-yl)-1H-imidazo[4,5-b]pyrazin-2(3H)-one;
1-(Cyclohexylmethyl)-6-(6-methoxypyridin-3-yl)-1H-imidazo[4,5-b]pyrazin-2(3H)-one;
6-(4-Hydroxyphenyl)-1-(tetrahydro-2H-pyran-4-yl)-1H-imidazo[4,5-b]pyrazin-2(3H)-one;
6-(4-Hydroxyphenyl)-1-(piperidin-4-ylmethyl)-1H-imidazo[4,5-b]pyrazin-2(3H)-one;
1-(((1r,4r)-4-Aminocyclohexyl)methyl)-6-(4-hydroxyphenyl)-1H-imidazo[4,5-b]pyrazin-2(3H)-one;
1-(Cyclohexylmethyl)-6-(6-hydroxypyridin-3-yl)-1H-imidazo[4,5-b]pyrazin-2(3H)-one;
1-(Cyclohexylmethyl)-6-(2-methoxypyridin-4-yl)-1H-imidazo[4,5-b]pyrazin-2(3H)-one;
4-(3-((1r,4r)-4-Hydroxycyclohexyl)-2-oxo-2,3-dihydro-1H-imidazo[4,5-b]pyrazin-5-yl)benzamide;
2-(4-(3-(Cyclohexylmethyl)-2-oxo-2,3-dihydro-1H-imidazo[4,5-b]pyrazin-5-yl)phenyl)acetic acid;
2-(4-(3-(Cyclohexylmethyl)-2-oxo-2,3-dihydro-1H-imidazo[4,5-b]pyrazin-5-yl)phenyl)acetamide;
1-(Cyclohexylmethyl)-6-(2-oxoindolin-6-yl)-1H-imidazo[4,5-b]pyrazin-2(3H)-one;
4-(3-(Cyclohexylmethyl)-2-oxo-2,3-dihydro-1H-imidazo[4,5-b]pyrazin-5-yl)-3-methyl benzoic acid;
N-Methyl-4-(2-oxo-3-((tetrahydro-2H-pyran-4-yl)methyl)-2,3-dihydro-1H-imidazo[4,5-b]pyrazin-5-yl)benzamide;
4-(2-oxo-3-((Tetrahydro-2H-pyran-4-yl)methyl)-2,3-dihydro-1H-imidazo[4,5-b]pyrazin-5-yl)benzamide;
7-(4-Hydroxyphenyl)-1-(3-methoxybenzyl)-3,4-dihydropyrazino[2,3-b]pyrazin-2(1H)-one;
6-(4-(2-Hydroxypropan-2-yl)phenyl)-1-((tetrahydro-2H-pyran-4-yl)methyl)-1H-imidazo[4,5-b]pyrazin-2(3H)-one;
6-(1H-Indol-5-yl)-1-((tetrahydro-2H-pyran-4-yl)methyl)-1H-imidazo[4,5-b]pyrazin-2(3H)-one;
6-(4-(4H-1,2,4-Triazol-3-yl)phenyl)-1-((tetrahydro-2H-pyran-4-yl)methyl)-1H-imidazo[4,5-b]pyrazin-2(3H)-one;
6-(1H-Benzo[d]imidazol-5-yl)-1-(cyclohexylmethyl)-1H-imidazo[4,5-b]pyrazin-2(3H)-one;
4-(2-oxo-3-(2-(Tetrahydro-2H-pyran-4-yl)ethyl)-2,3-dihydro-1H-imidazo[4,5-b]pyrazin-5-yl)benzamide;
6-(3-(2H-1,2,3-Triazol-4-yl)phenyl)-1-(cyclohexylmethyl)-1H-imidazo[4,5-b]pyrazin-2(3H)-one;
6-(4-(1H-Imidazol-1-yl)phenyl)-1-(cyclohexylmethyl)-1H-imidazo[4,5-b]pyrazin-2(3H)-one;
6-(4-(1H-1,2,4-Triazol-3-yl)phenyl)-1-((1r,4r)-4-hydroxycyclohexyl)-1H-imidazo[4,5-b]pyrazin-2(3H)-one;
6-(4-(2H-tetrazol-5-yl)phenyl)-1-(cyclohexylmethyl)-1H-imidazo[4,5-b]pyrazin-2(3H)-one;
1-(Cyclohexylmethyl)-6-(2-hydroxypyridin-4-yl)-1H-imidazo[4,5-b]pyrazin-2(3H)-one;
6-(4-(1H-1,2,4-Triazol-3-yl)phenyl)-1-(2-(tetrahydro-2H-pyran-4-yl)ethyl)-1H-imidazo[4,5-b]pyrazin-2(3H)-one;
6-(4-(1H-Imidazol-2-yl)phenyl)-1-(cyclohexylmethyl)-1H-imidazo[4,5-b]pyrazin-2(3H)-one;
6-(4-(1H-1,2,3-Triazol-1-yl)phenyl)-1-(cyclohexylmethyl)-1H-imidazo[4,5-b]pyrazin-2(3H)-one;
6-(4-(2-Hydroxypropan-2-yl)phenyl)-1-(2-(tetrahydro-2H-pyran-4-yl)ethyl)-1H-imidazo[4,5-b]pyrazin-2(3H)-one;
1-(Cyclohexylmethyl)-6-(4-(5-methyl-1H-1,2,4-triazol-3-yl)phenyl)-1H-imidazo[4,5-b]pyrazin-2(3H)-one;
6-(4-(1H-Pyrazol-3-yl)phenyl)-1-(cyclohexylmethyl)-1H-imidazo[4,5-b]pyrazin-2(3H)-one;
6-(4-(1H-Pyrazol-4-yl)phenyl)-1-(cyclohexylmethyl)-1H-imidazo[4,5-b]pyrazin-2(3H)-one;
6-(4-(5-(Aminomethyl)-1H-1,2,4-triazol-3-yl)phenyl)-1-(cyclohexylmethyl)-1H-imidazo[4,5-b]pyrazin-2(3H)-one hydrochloride;
1-(Cyclohexylmethyl)-6-(4-(5-(trifluoromethyl)-1H-1,2,4-triazol-3-yl)phenyl)-1H-imidazo[4,5-b]pyrazin-2(3H)-one;
6-(4-Hydroxyphenyl)-1-((1r,4r)-4-methoxycyclohexyl)-1H-imidazo[4,5-b]pyrazin-2(3H)-one;
6-(4-Hydroxyphenyl)-1-((tetrahydrofuran-2-yl)methyl)-1H-imidazo[4,5-b]pyrazin-2(3H)-one;
6-(3-(1H-1,2,4-Triazol-3-yl)phenyl)-1-(cyclohexylmethyl)-1H-imidazo[4,5-b]pyrazin-2(3H)-one;
1-((1r,4r)-4-(Hydroxymethyl)cyclohexyl)-6-(4-hydroxyphenyl)-1H-imidazo[4,5-b]pyrazin-2(3H)-one;
6-(4-Hydroxyphenyl)-1-((1s,4s)-4-methoxycyclohexyl)-1H-imidazo[4,5-b]pyrazin-2(3H)-one;
6-(4-Hydroxyphenyl)-1-((1r,4r)-4-(methoxymethyl)cyclohexyl)-1H-imidazo[4,5-b]pyrazin-2(3H)-one;
6-(1-Methyl-1H-pyrazol-4-yl)-1-((tetrahydro-2H-pyran-4-yl)methyl)-1H-imidazo[4,5-b]pyrazin-2(3H)-one;
1-(((1r,4r)-4-Hydroxycyclohexyl)methyl)-6-(4-hydroxyphenyl)-1H-imidazo[4,5-b]pyrazin-2(3H)-one;
6-(4-Hydroxyphenyl)-1-((tetrahydrofuran-3-yl)methyl)-1H-imidazo[4,5-b]pyrazin-2(3H)-one;
1-(((1s,4s)-4-Hydroxycyclohexyl)methyl)-6-(4-hydroxyphenyl)-1H-imidazo[4,5-b]pyrazin-2(3H)-one;

6-(1H-Benzo[d]imidazol-5-yl)-1-((tetrahydro-2H-pyran-4-yl)methyl)-1H-imidazo[4,5-b]pyrazin-2(3H)-one hydrochloride;
6-(4-(5-(Morpholinomethyl)-1H-1,2,4-triazol-3-yl)phenyl)-1-((tetrahydro-2H-pyran-4-yl)methyl)-1H-imidazo[4,5-b]pyrazin-2(3H)-one;
6-(4-Hydroxyphenyl)-1-(3-(2-oxopyrrolidin-1-yl)propyl)-1H-imidazo[4,5-b]pyrazin-2(3H)-one;
6-(4-Hydroxyphenyl)-1-(2-morpholinoethyl)-1H-imidazo[4,5-b]pyrazin-2(3H)-one hydrochloride;
1-(Cyclohexylmethyl)-6-(4-(oxazol-5-yl)phenyl)-1H-imidazo[4,5-b]pyrazin-2(3H)-one;
6-(2-Methyl-1H-benzo[d]imidazol-5-yl)-1-((tetrahydro-2H-pyran-4-yl)methyl)-1H-imidazo[4,5-b]pyrazin-2(3H)-one hydrocholoride;
6-(4-(5-(Methoxymethyl)-1H-1,2,4-triazol-3-yl)phenyl)-1-((tetrahydro-2H-pyran-4-yl)methyl)-1H-imidazo[4,5-b]pyrazin-2(3H)-one;
1-((1s,4s)-4-(Hydroxymethyl)cyclohexyl)-6-(4-hydroxyphenyl)-1H-imidazo[4,5-b]pyrazin-2(3H)-one;
6-(3-Methyl-1H-pyrazol-4-yl)-1-((tetrahydro-2H-pyran-4-yl)methyl)-1H-imidazo[4,5-b]pyrazin-2(3H)-one;
6-(1H-Pyrazol-4-yl)-1-((tetrahydro-2H-pyran-4-yl)methyl)-1H-imidazo[4,5-b]pyrazin-2(3H)-one;
6-(2-Amino-1H-benzo[d]imidazol-5-yl)-1-((tetrahydro-2H-pyran-4-yl)methyl)-1H-imidazo[4,5-b]pyrazin-2(3H)-one dihydrochloride;
6-(4-(5-(2-Hydroxypropan-2-yl)-1H-1,2,4-triazol-3-yl)phenyl)-1-((tetrahydro-2H-pyran-4-yl)methyl)-1H-imidazo[4,5-b]pyrazin-2(3H)-one;
6-(4-(5-Isopropyl-1H-1,2,4-triazol-3-yl)phenyl)-1-((tetrahydro-2H-pyran-4-yl)methyl)-1H-imidazo[4,5-b]pyrazin-2(3H)-one;
4-(2-Methoxy-1-(2-morpholinoethyl)-1H-imidazo[4,5-b]pyrazin-6-yl)benzamide hydrochloride;
4-(1-((1s,4s)-4-Hydroxycyclohexyl)-2-methoxy-1H-imidazo[4,5-b]pyrazin-6-yl)benzamide;
6-(4-Hydroxyphenyl)-1-((1s,4s)-4-(methoxymethyl)cyclohexyl)-1H-imidazo[4,5-b]pyrazin-2(3H)-one;
6-(3H-imidazo[4,5-b]pyridin-6-yl)-1-((tetrahydro-2H-pyran-4-yl)methyl)-1H-imidazo[4,5-b]pyrazin-2(3H)-one;
1-(2-(2,2-Dimethyltetrahydro-2H-pyran-4-yl)ethyl)-6-(4-hydroxyphenyl)-1H-imidazo[4,5-b]pyrazin-2(3H)-one;
6-(4-(1H-Pyrazol-1-yl)phenyl)-1-((tetrahydro-2H-pyran-4-yl)methyl)-1H-imidazo[4,5-b]pyrazin-2(3H)-one;
6-(4-(4H-1,2,4-Triazol-3-yl)phenyl)-1-(2-morpholinoethyl)-1H-imidazo[4,5-b]pyrazin-2(3H)-one;
6-(4-(1H-Benzo[d]imidazol-2-yl)phenyl)-1-((tetrahydro-2H-pyran-4-yl)methyl)-1H-imidazo[4,5-b]pyrazin-2(3H)-one;
6-(4-(1H-Imidazol-2-yl)phenyl)-1-((tetrahydro-2H-pyran-4-yl)methyl)-1H-imidazo[4,5-b]pyrazin-2(3H)-one hydrochloride;
6-(4-(5-(Hydroxymethyl)-1H-1,2,4-triazol-3-yl)phenyl)-1-((tetrahydro-2H-pyran-4-yl)methyl)-1H-imidazo[4,5-b]pyrazin-2(3H)-one;
6-(4-(1H-Imidazol-5-yl)phenyl)-1-((tetrahydro-2H-pyran-4-yl)methyl)-1H-imidazo[4,5-b]pyrazin-2(3H)-one hydrochloride;
6-(4-Hydroxyphenyl)-1-((5-oxopyrrolidin-2-yl)methyl)-1H-imidazo[4,5-b]pyrazin-2(3H)-one;
6-(4-(4,5-Dimethyl-1H-imidazol-2-yl)phenyl)-1-((tetrahydro-2H-pyran-4-yl)methyl)-1H-imidazo[4,5-b]pyrazin-2(3H)-one;
6-(4-(1H-1,2,4-Triazol-5-yl)phenyl)-1-(((1s,4s)-4-methoxycyclohexyl)methyl)-1H-imidazo[4,5-b]pyrazin-2(3H)-one;
6-(4-(1H-1,2,4-Triazol-5-yl)phenyl)-1-(((1r,4r)-4-methoxycyclohexyl)methyl)-1H-imidazo[4,5-b]pyrazin-2(3H)-one;
6-(6-(1H-1,2,4-Triazol-3-yl)pyridin-3-yl)-1-((tetrahydro-2H-pyran-4-yl)methyl)-1H-imidazo[4,5-b]pyrazin-2(3H)-one;
6-(4-(1H-1,2,4-Triazol-3-yl)phenyl)-1-(2-(2-oxopyrrolidin-1-yl)ethyl)-1H-imidazo[4,5-b]pyrazin-2(3H)-one;
6-(4-(5-((dimethylamino)methyl)-1H-1,2,4-triazol-3-yl)phenyl)-1-((tetrahydro-2H-pyran-4-yl)methyl)-1H-imidazo[4,5-b]pyrazin-2(3H)-one;
6-(4-Hydroxyphenyl)-1-(pyrrolidin-2-ylmethyl)-1H-imidazo[4,5-b]pyrazin-2(3H)-one hydrochloride;
6-(2-Aminobenzimidazol-5-yl)-1-(cyclohexylmethyl)-4-imidazolino[4,5-b]pyrazin-2-one dihydrochloride;
6-(2-(Dimethylamino)-1H-benzo[d]imidazol-5-yl)-1-((tetrahydro-2H-pyran-4-yl)methyl)-1H-imidazo[4,5-b]pyrazin-2(3H)-one;
6-(4-Hydroxyphenyl)-1-(piperidin-3-ylmethyl)-1H-imidazo[4,5-b]pyrazin-2(3H)-one;
6-(4-(4H-1,2,4-triazol-3-yl)phenyl)-1-(2-(piperidin-1-yl)ethyl)-1H-imidazo[4,5-b]pyrazin-2(3H)-one hydrochloride;
1-(Cyclohexylmethyl)-6-(2-(methylamino)pyrimidin-5-yl)-1H-imidazo[4,5-b]pyrazin-2(3H)-one;
6-(3-methyl-4-(1H-1,2,4-triazol-3-yl)phenyl)-1-((tetrahydro-2H-pyran-4-yl)methyl)-1H-imidazo[4,5-b]pyrazin-2(3H)-one;
1-(Cyclohexylmethyl)-6-(2-(2-methoxyethylamino)pyrimidin-5-yl)-1H-imidazo[4,5-b]pyrazin-2(3H)-one;
6-(4-(5-((methylamino)methyl)-1H-1,2,4-triazol-3-yl)phenyl)-1-((tetrahydro-2H-pyran-4-yl)methyl)-1H-imidazo[4,5-b]pyrazin-2(3H)-one;
6-(4-(5-Oxopyrrolidin-2-yl)phenyl)-1-(2-(tetrahydro-2H-pyran-4-yl)ethyl)-1H-imidazo[4,5-b]pyrazin-2(3H)-one;
6-(4-(5-methyl-1H-1,2,4-triazol-3-yl)phenyl)-1-(2-(tetrahydro-2H-pyran-4-yl)ethyl)-1H-imidazo[4,5-b]pyrazin-2(3H)-one;
6-(4-(1H-imidazol-2-yl)phenyl)-1-(2-(tetrahydro-2H-pyran-4-yl)ethyl)-1H-imidazo[4,5-b]pyrazin-2(3H)-one;
6-(4-(4H-1,2,4-triazol-3-yl)phenyl)-1-(2-methyl-2-morpholinopropyl)-1H-imidazo[4,5-b]pyrazin-2(3H)-one;
6-(4-(4H-1,2,4-Triazol-3-yl)phenyl)-1-(1-morpholinopropan-2-yl)-1H-imidazo[4,5-b]pyrazin-2(3H)-one;
6-(4-(Pyrrolidin-2-yl)phenyl)-1-(2-(tetrahydro-2H-pyran-4-yl)ethyl)-1H-imidazo[4,5-b]pyrazin-2(3H)-one;
6-(4-(5-(aminomethyl)-1H-1,2,4-triazol-3-yl)phenyl)-1-(2-(tetrahydro-2H-pyran-4-yl)ethyl)-1H-imidazo[4,5-b]pyrazin-2(3H)-one;
6-(5-(Hydroxymethyl)thiophen-2-yl)-1-((tetrahydro-2H-pyran-4-yl)methyl)-1H-imidazo[4,5-b]pyrazin-2(3H)-one;
(1r,4r)-4-(6-(4-Hydroxyphenyl)-2-oxo-2,3-dihydro-1H-imidazo[4,5-b]pyrazin-1-yl)cyclo-hexanecarboxamide;
(1s,4s)-4-(6-(4-Hydroxyphenyl)-2-oxo-2,3-dihydro-1H-imidazo[4,5-b]pyrazin-1-yl)cyclohexanecarboxamide;
6-(4-(5-methyl-1H-1,2,4-triazol-3-yl)phenyl)-1-(2-morpholinoethyl)-1H-imidazo[4,5-b]pyrazin-2(3H)-one;
6-(4-(5-Oxopyrrolidin-3-yl)phenyl)-1-(2-(tetrahydro-2H-pyran-4-yl)ethyl)-1H-imidazo[4,5-b]pyrazin-2(3H)-one;
6-(4-(Pyrrolidin-3-yl)phenyl)-1-(2-(tetrahydro-2H-pyran-4-yl)ethyl)-1H-imidazo[4,5-b]pyrazin-2(3H)-one;
6-(1H-benzo[d]imidazol-5-yl)-1-(2-(tetrahydro-2H-pyran-4-yl)ethyl)-1H-imidazo[4,5-b]pyrazin-2(3H)-one;

6-(3-(Hydroxymethyl)thiophen-2-yl)-1-((tetrahydro-2H-pyran-4-yl)methyl)-1H-imidazo[4,5-b]pyrazin-2(3H)-one;

6-(5-(2-Hydroxyethyl)thiophen-2-yl)-1-((tetrahydro-2H-pyran-4-yl)methyl)-1H-imidazo[4,5-b]pyrazin-2(3H)-one;

1-(Cyclohexylmethyl)-6-(pyrimidin-5-yl)-1H-imidazo[4,5-b]pyrazin-2(3H)-one;

6-(6-Fluoropyridin-3-yl)-1-((tetrahydro-2H-pyran-4-yl)methyl)-1H-imidazo[4,5-b]pyrazin-2(3H)-one;

6-(6-Aminopyridin-3-yl)-1-((tetrahydro-2H-pyran-4-yl)methyl)-1H-imidazo[4,5-b]pyrazin-2(3H)-one;

6-(4-(5-methyl-1H-imidazol-2-yl)phenyl)-1-((tetrahydro-2H-pyran-4-yl)methyl)-1H-imidazo[4,5-b]pyrazin-2(3H)-one;

6-(4-(5-Methyl-1H-1,2,4-triazol-3-yl)phenyl)-1-(2-(2-oxopyrrolidin-1-yl)ethyl)-1H-imidazo[4,5-b]pyrazin-2(3H)-one;

6-(6-(Methylamino)pyridin-3-yl)-1-((tetrahydro-2H-pyran-4-yl)methyl)-1H-imidazo[4,5-b]pyrazin-2(3H)-one;

6-(2-aminopyrimidin-5-yl)-1-(cyclohexylmethyl)-1H-imidazo[4,5-b]pyrazin-2(3H)-one;

6-(4-(2-hydroxypropan-2-yl)phenyl)-1-(((1r,4r)-4-methoxycyclohexyl)methyl)-1H-imidazo[4,5-b]pyrazin-2(3H)-one;

6-(4-hydroxyphenyl)-1-((1-methylpiperidin-3-yl)methyl)-1H-imidazo[4,5-b]pyrazin-2(3H)-one;

6-(2-methyl-4-(1H-1,2,4-triazol-3-yl)phenyl)-1-(2-(tetrahydro-2H-pyran-4-yl)ethyl)-1H-imidazo[4,5-b]pyrazin-2(3H)-one;

1-(cyclohexylmethyl)-6-(6-(2-hydroxypropan-2-yl)pyridin-3-yl)-1H-imidazo[4,5-b]pyrazin-2(3H)-one;

6-(4-(hydroxymethyl)thiophen-2-yl)-1-((tetrahydro-2H-pyran-4-yl)methyl)-1H-imidazo[4,5-b]pyrazin-2(3H)-one;

6-(1H-benzo[d]imidazol-6-yl)-1-(((1r,4r)-4-methoxycyclohexyl)methyl)-1H-imidazo[4,5-b]pyrazin-2(3H)-one;

6-(4-(4,5-dimethyl-1H-imidazol-2-yl)phenyl)-1-(2-morpholinoethyl)-1H-imidazo[4,5-b]pyrazin-2(3H)-one;

6-(6-(2-hydroxypropan-2-yl)pyridin-3-yl)-1-((tetrahydro-2H-pyran-4-yl)methyl)-1H-imidazo[4,5-b]pyrazin-2(3H)-one;

6-(6-(2-hydroxypropan-2-yl)pyridin-3-yl)-1-(2-(tetrahydro-2H-pyran-4-yl)ethyl)-1H-imidazo[4,5-b]pyrazin-2(3H)-one;

6-(4-(4H-1,2,4-triazol-3-yl)phenyl)-1-(2-morpholino-2-oxoethyl)-1H-imidazo[4,5-b]pyrazin-2(3H)-one;

6-(4-(4H-1,2,4-triazol-3-yl)phenyl)-3-(cyclohexylmethyl)-3,4-dihydropyrazino[2,3-b]pyrazin-2(1H)-one;

6-(4-(1H-1,2,4-triazol-3-yl)phenyl)-1-(2-(tetrahydro-2H-pyran-4-yl)ethyl)-1H-imidazo[4,5-b]pyridin-2(3H)-one;

(R)-6-(4-(1H-1,2,4-triazol-3-yl)phenyl)-1-(1-phenylethyl)-1H-imidazo[4,5-b]pyrazin-2(3H)-one;

(S)-6-(4-(1H-1,2,4-triazol-3-yl)phenyl)-1-(1-phenylethyl)-1H-imidazo[4,5-b]pyrazin-2(3H)-one;

(1r,4r)-4-(6-(4-(2-Hydroxypropan-2-yl)phenyl)-2-oxo-2,3-dihydro-1H-imidazo[4,5-b]pyrazin-1-yl)cyclohexanecarboxamide;

6-(3-Methyl-4-(1H-1,2,4-Triazol-3-yl)phenyl)-1-((tetrahydro-2H-pyran-4-yl)methyl)-1H-imidazo[4,5-B]pyrazin-2(3H)-one;

6-(4-(1H-imidazol-2-yl)phenyl)-1-(2-(tetrahydro-2H-pyran-4-yl)ethyl)-1H-imidazo[4,5-b]pyrazin-2(3H)-one;

6-(4-(5-(Aminomethyl)-1H-1,2,4-triazol-3-yl)phenyl)-1-(2-(tetrahydro-2H-pyran-4-yl)ethyl)-1H-imidazo[4,5-b]pyrazin-2(3H)-one;

6-(1H-benzo[d]imidazol-5-yl)-1-(2-(tetrahydro-2H-pyran-4-yl)ethyl)-1H-imidazo[4,5-b]pyrazin-2(3H)-one;

6-(2-Aminopyrimidin-5-yl)-1-(cyclohexylmethyl)-1H-imidazo[4,5-b]pyrazin-2(3H)-one;

6-(4-Hydroxyphenyl)-1-((1-methylpiperidin-2-yl)methyl)-1H-imidazo[4,5-b]pyrazin-2(3H)-one hydrochloride;

6-(3-Methyl-4-(1H-1,2,4-Triazol-3-yl)phenyl)-1-((tetrahydro-2H-pyran-4-yl)methyl)-1H-imidazo[4,5-B]pyrazin-2(3H)-one;

1-(Cyclohexylmethyl)-6-(6-(2-hydroxypropan-2-yl)pyridin-3-yl)-1H-imidazo[4,5-b]pyrazin-2(3H)-one;

6-(6-(2-Hydroxypropan-2-yl)pyridin-3-yl)-1-((tetrahydro-2H-pyran-4-yl)methyl)-1H-imidazo[4,5-b]pyrazin-2(3H)-one;

6-(6-(2-Hydroxypropan-2-yl)pyridin-3-yl)-1-(2-(tetrahydro-2H-pyran-4-yl)ethyl)-1H-imidazo[4,5-b]pyrazin-2(3H)-one;

6-(4-(4H-1,2,4-Triazol-3-yl)phenyl)-1-(2-morpholino-2-oxoethyl)-1H-imidazo[4,5-b]pyrazin-2(3H)-one;

(R)-6-(4-(4H-1,2,4-Triazol-3-yl)phenyl)-3-(cyclohexylmethyl)-3,4-dihydropyrazino[2,3-b]pyrazin-2(1H)-one;

(R)-6-(4-(1H-1,2,4-Triazol-3-yl)phenyl)-1-(1-phenylethyl)-1H-imidazo[4,5-B]pyrazin-2(3H)-one;

(S)-6-(4-(4H-1,2,4-Triazol-3-yl)phenyl)-1-(1-phenylethyl)-1H-imidazo[4,5-b]pyrazin-2(3H)-one;

(1r,4r)-4-(6-(4-(2-Hydroxypropan-2-yl)phenyl)-2-oxo-2,3-dihydro-1H-imidazo[4,5-b]pyrazin-1-yl)cyclohexanecarboxamide; and 6-(4-(5-Methyl-1H-1,2,4-triazol-3-yl)phenyl)-1-(2-(tetrahydro-2H-pyran-4-yl)ethyl)-1H-imidazo[4,5-b]pyrazin-2(3H)-one, and pharmaceutically acceptable salts, clathrates, solvates, stereoisomers, tautomers, and prodrugs thereof.

In one embodiment, the TOR kinase inhibitors include compounds having the following formula (II):

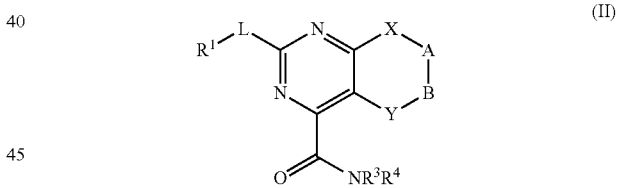

and pharmaceutically acceptable salts, clathrates, solvates, stereoisomers, tautomers, and prodrugs thereof, wherein:

$R^1$ is substituted or unsubstituted $C_{1-8}$alkyl, substituted or unsubstituted aryl, substituted or unsubstituted heteroaryl, substituted or unsubstituted cycloalkyl, or substituted or unsubstituted heterocyclylalkyl;

—X-A-B—Y— taken together form —N($R^2$)CH$_2$C(O)NH—, —N($R^2$)C(O)CH$_2$NH—, —N($R^2$)C(O)NH—, —N($R^2$)C=N—, or —C($R^2$)=CHNH—;

L is a direct bond, NH or O;

$R^2$ is substituted or unsubstituted $C_{1-8}$alkyl, substituted or unsubstituted aryl, substituted or unsubstituted heteroaryl, substituted or unsubstituted cycloalkyl, or substituted or unsubstituted heterocyclylalkyl; and $R^3$ and $R^4$ are independently H or $C_{1-8}$alkyl.

In one embodiment, the TOR kinase inhibitors of formula (II) are those wherein —X-A-B—Y— taken together form —N($R^2$)CH$_2$C(O)NH—.

In another embodiment, the TOR kinase inhibitors of formula (II) are those wherein —X-A-B—Y— taken together form —N(R$^2$)C(O)CH$_2$NH—.

In another embodiment, the TOR kinase inhibitors of formula (II) are those wherein —X-A-B—Y— taken together form —N(R$^2$)C(O)NH—.

In another embodiment, the TOR kinase inhibitors of formula (II) are those wherein —X-A-B—Y— taken together form —N(R$^2$)C=N—.

In another embodiment, the TOR kinase inhibitors of formula (II) are those wherein —X-A-B—Y— taken together form —C(R$^2$)=CHNH—.

In another embodiment, the TOR kinase inhibitors of formula (II) are those wherein L is a direct bond.

In another embodiment, the TOR kinase inhibitors of formula (II) are those wherein R$^1$ is substituted aryl, such as substituted phenyl.

In another embodiment, the TOR kinase inhibitors of formula (II) are those wherein R$^1$ is substituted or unsubstituted heteroaryl, such as substituted or unsubstituted pyridine, substituted or unsubstituted indole or substituted or unsubstituted quinoline.

In another embodiment, the TOR kinase inhibitors of formula (II) are those wherein R$^1$ is substituted or unsubstituted cycloalkyl, such as substituted or unsubstituted cyclopentyl.

In another embodiment, the TOR kinase inhibitors of formula (II) are those wherein —X-A-B—Y— taken together form —N(R$^2$)C(O)NH— and R$^1$ is substituted aryl, such as phenyl.

In another embodiment, the TOR kinase inhibitors of formula (II) are those wherein —X-A-B—Y— taken together form —N(R$^2$)C(O)NH— and R$^1$ is substituted or unsubstituted heteroaryl, such as substituted or unsubstituted pyridine, substituted or unsubstituted indole or substituted or unsubstituted quinoline.

In another embodiment, the TOR kinase inhibitors of formula (II) are those wherein —X-A-B—Y— taken together form —N(R$^2$)C(O)NH— and R$^1$ is substituted or unsubstituted cycloalkyl, such as substituted or unsubstituted cyclopentyl.

In another embodiment, the TOR kinase inhibitors of formula (II) are those wherein R$^2$ is substituted C$_{1-8}$alkyl, such as —CH$_2$C$_6$H$_5$.

In another embodiment, the TOR kinase inhibitors of formula (II) are those wherein R$^2$ is unsubstituted C$_{1-8}$alkyl, such as unsubstituted methyl.

In another embodiment, the TOR kinase inhibitors of formula (II) are those wherein R$^2$ is substituted or unsubstituted aryl, such as substituted or unsubstituted phenyl.

In another embodiment, the TOR kinase inhibitors of formula (II) are those wherein R$^2$ is substituted aryl, such as halo, haloalkyl or alkoxy substituted phenyl.

In another embodiment, the TOR kinase inhibitors of formula (II) are those wherein R$^2$ is substituted or unsubstituted cycloalkyl, such as substituted or unsubstituted cyclohexyl or substituted or unsubstituted cycloheptyl.

In another embodiment, the TOR kinase inhibitors of formula (II) are those wherein R$^2$ is substituted heterocyclylalkyl, such as substituted piperidine.

In another embodiment, the TOR kinase inhibitors of formula (II) are those wherein R$^3$ and R$^4$ are H.

In another embodiment, the TOR kinase inhibitors of formula (II) are those wherein —X-A-B—Y— taken together form —N(R$^2$)C(O)NH— and R$^2$ is unsubstituted aryl, such as unsubstituted phenyl.

In another embodiment, the TOR kinase inhibitors of formula (II) are those wherein —X-A-B—Y— taken together form —N(R$^2$)C(O)NH—, R$^1$ is substituted or unsubstituted heteroaryl, such as substituted or unsubstituted pyridine, and R$^2$ is substituted or unsubstituted aryl, such as substituted or unsubstituted phenyl.

In another embodiment, the TOR kinase inhibitors of formula (II) are those wherein —X-A-B—Y— taken together form —N(R$^2$)C(O)NH—, R$^1$ is substituted or unsubstituted heteroaryl, such as substituted or unsubstituted pyridine, R$^2$ is substituted or unsubstituted aryl, such as substituted or unsubstituted phenyl, and R$^3$ and R$^4$ are H.

In another embodiment, the TOR kinase inhibitors of formula (II) are those wherein —X-A-B—Y— taken together form —N(R$^2$)C(O)NH—, L is a direct bond, R$^1$ is substituted or unsubstituted heteroaryl, such as substituted or unsubstituted pyridine, R$^2$ is substituted or unsubstituted aryl, such as substituted or unsubstituted phenyl, and R$^3$ and R$^4$ are H.

In another embodiment, the TOR kinase inhibitors of formula (II) are those wherein —X-A-B—Y— taken together form —N(R$^2$)C(O)NH—, R$^1$ is substituted or unsubstituted aryl, such as substituted or unsubstituted phenyl, and R$^2$ is substituted or unsubstituted aryl, such as substituted or unsubstituted phenyl.

In another embodiment, the TOR kinase inhibitors of formula (II) are those wherein —X-A-B—Y— taken together form —N(R$^2$)C(O)NH—, R$^1$ is substituted or unsubstituted aryl, such as substituted or unsubstituted phenyl, R$^2$ is substituted or unsubstituted aryl, such as substituted or unsubstituted phenyl, and R$^3$ and R$^4$ are H.

In another embodiment, the TOR kinase inhibitors of formula (II) are those wherein —X-A-B—Y— taken together form —N(R$^2$)C(O)NH—, L is a direct bond, R$^1$ is substituted or unsubstituted aryl, such as substituted or unsubstituted phenyl, R$^2$ is substituted or unsubstituted aryl, such as substituted or unsubstituted phenyl, and R$^3$ and R$^4$ are H.

In another embodiment, the TOR kinase inhibitors of formula (II) are those wherein —X-A-B—Y— taken together form —N(R$^2$)C(O)NH—, R$^1$ is substituted or unsubstituted heteroaryl, L is a direct bond and R$^2$ is substituted or unsubstituted C$_{1-8}$alkyl or substituted or unsubstituted cycloalkyl.

In another embodiment, the TOR kinase inhibitors of formula (II) are those wherein —X-A-B—Y— taken together form —N(R$^2$)C(O)NH—, R$^1$ is substituted or unsubstituted aryl, L is a direct bond and R$^2$ is substituted or unsubstituted C$_{1-8}$alkyl or substituted or unsubstituted cycloalkyl.

In another embodiment, the TOR kinase inhibitors of formula (II) do not include 8,9-dihydro-8-oxo-9-phenyl-2-(3-pyridinyl)-7H-purine-6-carboxamide, 8,9-dihydro-8-oxo-9-phenyl-2-(3-pyridinyl)-7H-purine-6-carboxamide, 8,9-dihydro-8-oxo-9-phenyl-2-(3-pyridinyl)-7H-purine-6-carboxamide, 2-(4-cyanophenyl)-8-oxo-9-phenyl-8,9-dihydro-7H-purine-6-carboxamide, 2-(4-nitrophenyl)-8-oxo-9-phenyl-8,9-dihydro-7H-purine-6-carboxamide, 9-benzyl-2-(4-methoxyphenyl)-8-oxo-8,9-dihydro-7H-purine-6-carboxamide, 2-methyl-8-oxo-9-phenyl-8,9-dihydro-7H-purine-6-carboxamide, 9-benzyl-9H-purine-2,6-dicarboxamide, 9-[2,3-bis[(benzoyloxy)methyl]cyclobutyl]-2-methyl-9H-Purine-6-carboxamide, 9-benzyl-2-methyl-9H-purine-6-carboxamide, 9-(2-hydroxyethyl)-2-methyl-9H-purine-6-carboxamide, 9-(2-hydroxyethyl)-2-(trifluoromethyl)-9H-purine-6-carboxamide, 9-(2-hydroxyethyl)-2-(prop-1-enyl)-9H-purine-6-carboxamide, 9-(2-hydroxyethyl)-2-phenyl-9H-purine-6-carboxamide, 9-(3-hydroxypropyl)-2-methyl-9H-purine-6-carboxamide, 9-(3-hydroxypropyl)-2-(trifluoromethyl)-9H-purine-6-carboxamide, 2-methyl-9-phenylmethyl-9H-purine-6-carboxamide or 2-methyl-9-β-D-ribofuranosyl-9H-purine-6-carboxamide.

In another embodiment, the TOR kinase inhibitors of formula (II) do not include compounds wherein $R^2$ is a substituted furanoside.

In another embodiment, the TOR kinase inhibitors of formula (II) do not include compounds wherein $R^2$ is a substituted or unsubstituted furanoside.

In another embodiment, the TOR kinase inhibitors of formula (II) do not include (2'R)-2'-deoxy-2'-fluoro-2'-C-methyl nucleosides.

In one embodiment, the TOR kinase inhibitors include compounds having the following formula (IIa):

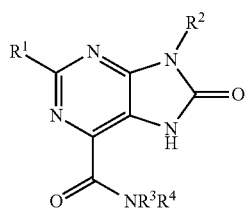

(IIa)

and pharmaceutically acceptable salts, clathrates, solvates, stereoisomers, tautomers, and prodrugs thereof, wherein:

$R^1$ is substituted or unsubstituted $C_{1-8}$alkyl, substituted or unsubstituted aryl, substituted or unsubstituted heteroaryl, substituted or unsubstituted cycloalkyl, or substituted or unsubstituted heterocyclylalkyl;

$R^2$ is substituted or unsubstituted $C_{1-8}$alkyl, substituted or unsubstituted aryl, substituted or unsubstituted heteroaryl, substituted or unsubstituted cycloalkyl, or substituted or unsubstituted heterocyclylalkyl; and $R^3$ and $R^4$ are independently H or $C_{1-8}$alkyl.

In one embodiment, the TOR kinase inhibitors of formula (IIa) are those wherein $R^1$ is substituted aryl, substituted or unsubstituted heteroaryl, such as substituted phenyl.

In another embodiment, the TOR kinase inhibitors of formula (IIa) are those wherein $R^1$ is substituted or unsubstituted heteroaryl, such as substituted or unsubstituted pyridine, substituted or unsubstituted indole or substituted or unsubstituted quinoline.

In another embodiment, the TOR kinase inhibitors of formula (IIa) are those wherein $R^1$ is substituted or unsubstituted cycloalkyl, such as substituted or unsubstituted cyclopentyl.

In another embodiment, the TOR kinase inhibitors of formula (IIa) are those wherein $R^2$ is substituted $C_{1-8}$alkyl, such as —$CH_2C_6H_5$.

In another embodiment, the TOR kinase inhibitors of formula (IIa) are those wherein $R^2$ is unsubstituted $C_{1-8}$alkyl, such as unsubstituted methyl.

In another embodiment, the TOR kinase inhibitors of formula (IIa) are those wherein $R^2$ is substituted or unsubstituted aryl, such as substituted or unsubstituted phenyl.

In another embodiment, the TOR kinase inhibitors of formula (IIa) are those wherein $R^2$ is substituted aryl, such as halo, haloalkyl or alkoxy substituted phenyl.

In another embodiment, the TOR kinase inhibitors of formula (IIa) are those wherein $R^2$ is substituted or unsubstituted cycloalkyl, such as substituted or unsubstituted cyclohexyl or substituted or unsubstituted cycloheptyl.

In another embodiment, the TOR kinase inhibitors of formula (IIa) are those wherein $R^2$ is substituted heterocyclylalkyl, such as substituted piperidine.

In another embodiment, the TOR kinase inhibitors of formula (IIa) are those wherein $R^3$ and $R^4$ are H.

In another embodiment, the TOR kinase inhibitors of formula (IIa) do not include 8,9-dihydro-8-oxo-9-phenyl-2-(3-pyridinyl)-7H-Purine-6-carboxamide, 8,9-dihydro-8-oxo-9-phenyl-2-(3-pyridinyl)-7H-Purine-6-carboxamide, 8,9-dihydro-8-oxo-9-phenyl-2-(3-pyridinyl)-7H-Purine-6-carboxamide, 2-(4-cyanophenyl)-8-oxo-9-phenyl-8,9-dihydro-7H-purine-6-carboxamide, 2-(4-nitrophenyl)-8-oxo-9-phenyl-8,9-dihydro-7H-purine-6-carboxamide, 9-benzyl-2-(4-methoxyphenyl)-8-oxo-8,9-dihydro-7H-purine-6-carboxamide, 9-phenylmethyl-9H-purine-2,6-dicarboxamide, or 2-methyl-8-oxo-9-phenyl-8,9-dihydro-7H-purine-6-carboxamide.

In another embodiment, the TOR kinase inhibitors of formula (IIa) do not include compounds wherein $R^2$ is a substituted furanoside.

In another embodiment, the TOR kinase inhibitors of formula (IIa) do not include compounds wherein $R^2$ is a substituted or unsubstituted furanoside.

In another embodiment, the TOR kinase inhibitors of formula (IIa) do not include (2'R)-2'-deoxy-2'-fluoro-2'-C-methyl nucleosides.

In one embodiment, the TOR kinase inhibitors include compounds having the following formula (IIb):

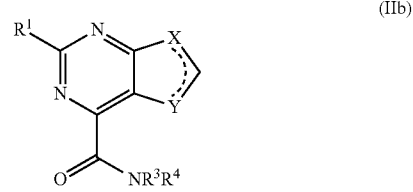

(IIb)

and pharmaceutically acceptable salts, clathrates, solvates, stereoisomers, tautomers, and prodrugs thereof, wherein:

is —$C(R^2)$=CH—NH— or —$N(R^2)$—CH=N—;

$R^1$ is substituted or unsubstituted $C_{1-8}$alkyl, substituted or unsubstituted aryl, substituted or unsubstituted heteroaryl, substituted or unsubstituted cycloalkyl, or substituted or unsubstituted heterocyclylalkyl;

$R^2$ is substituted or unsubstituted $C_{1-8}$alkyl, substituted or unsubstituted aryl, substituted or unsubstituted heteroaryl, substituted or unsubstituted cycloalkyl, or substituted or unsubstituted heterocyclylalkyl; and $R^3$ and $R^4$ are independently H or $C_{1-8}$alkyl.

In one embodiment, the TOR kinase inhibitors of formula (IIb) are those wherein $R^1$ is substituted aryl, such as substituted phenyl.

In another embodiment, the TOR kinase inhibitors of formula (IIb) are those wherein $R^1$ is substituted or unsubstituted heteroaryl, such as substituted or unsubstituted pyridine, substituted or unsubstituted indole or substituted or unsubstituted quinoline.

In another embodiment, the TOR kinase inhibitors of formula (IIb) are those wherein R¹ is substituted or unsubstituted cycloalkyl, such as substituted or unsubstituted cyclopentyl.

In another embodiment, the TOR kinase inhibitors of formula (IIb) are those wherein R² is substituted $C_{1-8}$alkyl, such as —CH₂C₆H₅.

In another embodiment, the TOR kinase inhibitors of formula (IIb) are those wherein R² is unsubstituted $C_{1-8}$alkyl, such as unsubstituted methyl.

In another embodiment, the TOR kinase inhibitors of formula (IIb) are those wherein R² is substituted or unsubstituted aryl, such as substituted or unsubstituted phenyl.

In another embodiment, the TOR kinase inhibitors of formula (IIb) are those wherein R² is substituted aryl, such as halo, haloalkyl or alkoxy substituted phenyl.

In another embodiment, the TOR kinase inhibitors of formula (IIb) are those wherein R² is substituted or unsubstituted cycloalkyl, such as substituted or unsubstituted cyclohexyl or substituted or unsubstituted cycloheptyl.

In another embodiment, the TOR kinase inhibitors of formula (IIb) are those wherein R² is substituted heterocyclylalkyl, such as substituted piperidine.

In another embodiment, the TOR kinase inhibitors of formula (IIb) are those wherein R³ and R⁴ are H.

In another embodiment, the TOR kinase inhibitors of formula (IIb) are those wherein

is —C(R²)=CH—NH— and R² is substituted aryl, such as substituted phenyl.

In another embodiment, the TOR kinase inhibitors of formula (IIb) are those wherein

is —N(R²)—CH=N— and R² is substituted aryl, such as substituted phenyl.

In another embodiment, the TOR kinase inhibitors of formula (IIb) are those wherein R¹ is substituted aryl, such as phenyl, and R² is substituted aryl, such as substituted phenyl.

In another embodiment, the TOR kinase inhibitors of formula (IIb) do not include 9-benzyl-9H-purine-2,6-dicarboxamide, 9-[2,3-bis[(benzoyloxy)methyl]cyclobutyl]-2-methyl-9H-Purine-6-carboxamide, 9-benzyl-2-methyl-9H-purine-6-carboxamide, 9-(2-hydroxyethyl)-2-methyl-9H-purine-6-carboxamide, 9-(2-hydroxyethyl)-2-(trifluoromethyl)-9H-purine-6-carboxamide, 9-(2-hydroxyethyl)-2-(prop-1-enyl)-9H-purine-6-carboxamide, 9-(2-hydroxyethyl)-2-phenyl-9H-purine-6-carboxamide, 9-(3-hydroxypropyl)-2-methyl-9H-purine-6-carboxamide, 9-(3-hydroxypropyl)-2-(trifluoromethyl)-9H-purine-6-carboxamide, 9-phenylmethyl-9H-purine-2,6-dicarboxamide, 2-methyl-9-phenylmethyl-9H-purine-6-carboxamide or 2-methyl-9-β-D-ribofuranosyl-9H-purine-6-carboxamide.

In another embodiment, the TOR kinase inhibitors of formula (IIb) do not include compounds wherein R² is substituted cyclobutyl when

is —N(R²)—CH=N—.

In another embodiment, the TOR kinase inhibitors of formula (IIb) do not include compounds wherein R² is a substituted furanoside when

is —N(R²)—CH=N—.

In another embodiment, the TOR kinase inhibitors of formula (IIb) do not include compounds wherein R² is substituted pyrimidine when

is —C(R²)=CH—NH—.

In another embodiment, the TOR kinase inhibitors of formula (IIb) do not include compounds wherein R² is substituted oxetane when

is —N(R²)—CH=N—.

In another embodiment, the TOR kinase inhibitors of formula (IIb) do not include compounds wherein R² is substituted cyclopentyl or a heterocyclopentyl when

is —N(R²)—CH=N—.

In one embodiment, the TOR kinase inhibitors include compounds having the following formula (IIc):

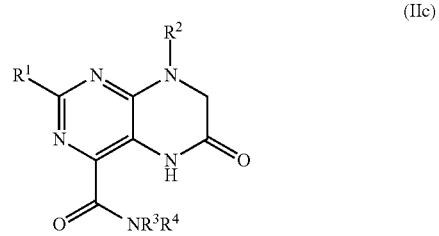

(IIc)

and pharmaceutically acceptable salts, clathrates, solvates, stereoisomers, tautomers, and prodrugs thereof, wherein:

R¹ is substituted or unsubstituted $C_{1-8}$alkyl, substituted or unsubstituted aryl, substituted or unsubstituted heteroaryl, substituted or unsubstituted cycloalkyl, or substituted or unsubstituted heterocyclylalkyl;

R² is substituted or unsubstituted $C_{1-8}$alkyl, substituted or unsubstituted aryl, substituted or unsubstituted heteroaryl, substituted or unsubstituted cycloalkyl, or substituted or unsubstituted heterocyclylalkyl; and R³ and R⁴ are independently H or $C_{1-8}$alkyl.

In one embodiment, the TOR kinase inhibitors of formula (IIc) are those wherein R¹ is substituted aryl, such as substituted phenyl.

In another embodiment, the TOR kinase inhibitors of formula (IIc) are those wherein R¹ is substituted or unsubstituted heteroaryl, such as substituted or unsubstituted pyridine, substituted or unsubstituted indole or substituted or unsubstituted quinoline.

In another embodiment, the TOR kinase inhibitors of formula (IIc) are those wherein $R^1$ is substituted or unsubstituted cycloalkyl, such as substituted or unsubstituted cyclopentyl.

In another embodiment, the TOR kinase inhibitors of formula (IIc) are those wherein $R^2$ is substituted $C_{1-8}$alkyl, such as —$CH_2C_6H_5$.

In another embodiment, the TOR kinase inhibitors of formula (IIc) are those wherein $R^2$ is unsubstituted $C_{1-8}$alkyl, such as unsubstituted methyl.

In another embodiment, the TOR kinase inhibitors of formula (IIc) are those wherein $R^2$ is substituted or unsubstituted aryl, such as substituted or unsubstituted phenyl.

In another embodiment, the TOR kinase inhibitors of formula (IIc) are those wherein $R^2$ is substituted aryl, such as halo, haloalkyl or alkoxy substituted phenyl.

In another embodiment, the TOR kinase inhibitors of formula (IIc) are those wherein $R^2$ is substituted or unsubstituted cycloalkyl, such as substituted or unsubstituted cyclohexyl or substituted or unsubstituted cycloheptyl.

In another embodiment, the TOR kinase inhibitors of formula (IIc) are those wherein $R^2$ is substituted heterocyclylalkyl, such as substituted piperidine.

In another embodiment, the TOR kinase inhibitors of formula (IIc) are those wherein $R^3$ and $R^4$ are H.

In one embodiment, the TOR kinase inhibitors include compounds having the following formula (IId):

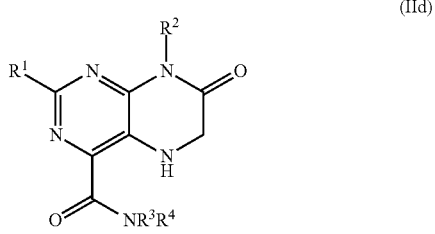

(IId)

and pharmaceutically acceptable salts, clathrates, solvates, stereoisomers, tautomers, and prodrugs thereof, wherein:

$R^1$ is substituted or unsubstituted $C_{1-8}$alkyl, substituted or unsubstituted aryl, substituted or unsubstituted heteroaryl, substituted or unsubstituted cycloalkyl, or substituted or unsubstituted heterocyclylalkyl;

$R^2$ is substituted or unsubstituted $C_{1-8}$alkyl, substituted or unsubstituted aryl, substituted or unsubstituted heteroaryl, substituted or unsubstituted cycloalkyl, or substituted or unsubstituted heterocyclylalkyl; and $R^3$ and $R^4$ are independently H or $C_{1-8}$alkyl.

In one embodiment, the TOR kinase inhibitors of formula (IId) are those wherein $R^1$ is substituted aryl, such as substituted phenyl.

In another embodiment, the TOR kinase inhibitors of formula (IId) are those wherein $R^1$ is substituted or unsubstituted heteroaryl, such as substituted or unsubstituted pyridine, substituted or unsubstituted indole or substituted or unsubstituted quinoline.

In another embodiment, the TOR kinase inhibitors of formula (IId) are those wherein $R^1$ is substituted or unsubstituted cycloalkyl, such as substituted or unsubstituted cyclopentyl.

In another embodiment, the TOR kinase inhibitors of formula (IId) are those wherein $R^2$ is substituted $C_{1-8}$alkyl, such as —$CH_2C_6H_5$.

In another embodiment, the TOR kinase inhibitors of formula (IId) are those wherein $R^2$ is unsubstituted $C_{1-8}$alkyl, such as unsubstituted methyl.

In another embodiment, the TOR kinase inhibitors of formula (IId) are those wherein $R^2$ is substituted or unsubstituted aryl, such as substituted or unsubstituted phenyl.

In another embodiment, the TOR kinase inhibitors of formula (IId) are those wherein $R^2$ is substituted aryl, such as halo, haloalkyl or alkoxy substituted phenyl.

In another embodiment, the TOR kinase inhibitors of formula (IId) are those wherein $R^2$ is substituted or unsubstituted cycloalkyl, such as substituted or unsubstituted cyclohexyl or substituted or unsubstituted cycloheptyl.

In another embodiment, the TOR kinase inhibitors of formula (IId) are those wherein $R^2$ is substituted heterocyclylalkyl, such as substituted piperidine.

In another embodiment, the TOR kinase inhibitors of formula (IId) are those wherein $R^3$ and $R^4$ are H.

Representative TOR kinase inhibitors of formula (II) include compounds from Table B.

Table B.

9-benzyl-8-oxo-2-(pyridin-3-yl)-8,9-dihydro-7H-purine-6-carboxamide;
N-methyl-8-oxo-9-phenyl-2-(pyridin-3-yl)-8,9-dihydro-7H-purine-6-carboxamide;
8-oxo-9-phenyl-2-(pyridin-2-yl)-8,9-dihydro-7H-purine-6-carboxamide;
2-(2-chloropyridin-3-yl)-8-oxo-9-phenyl-8,9-dihydro-7H-purine-6-carboxamide;
2-(2-methoxypyridin-3-yl)-8-oxo-9-phenyl-8,9-dihydro-7H-purine-6-carboxamide;
N,N-dimethyl-8-oxo-9-phenyl-2-(pyridin-3-yl)-8,9-dihydro-7H-purine-6-carboxamide;
9-methyl-8-oxo-2-(pyridin-3-yl)-8,9-dihydro-7H-purine-6-carboxamide;
2-(4-hydroxyphenyl)-9-(2-methoxyphenyl)-8-oxo-8,9-dihydro-7H-purine-6-carboxamide;
2-(3-hydroxyphenyl)-8-oxo-9-o-tolyl-8,9-dihydro-7H-purine-6-carboxamide;
2-(1H-indol-4-yl)-9-(2-methoxyphenyl)-8-oxo-8,9-dihydro-7H-purine-6-carboxamide;
2-(1H-indol-6-yl)-9-(2-methoxyphenyl)-8-oxo-8,9-dihydro-7H-purine-6-carboxamide;
2-(3-hydroxyphenyl)-9-(4-methoxyphenyl)-8-oxo-8,9-dihydro-7H-purine-6-carboxamide;
2-(2-hydroxypyridin-4-yl)-9-(2-methoxyphenyl)-8-oxo-8,9-dihydro-7H-purine-6-carboxamide;
9-(2-chlorophenyl)-2-(3-hydroxyphenyl)-8-oxo-8,9-dihydro-7H-purine-6-carboxamide;
9-(2-fluorophenyl)-2-(3-hydroxyphenyl)-8-oxo-8,9-dihydro-7H-purine-6-carboxamide;
9-(2,6-difluorophenyl)-2-(3-hydroxyphenyl)-8-oxo-8,9-dihydro-7H-purine-6-carboxamide;
9-cycloheptyl-8-oxo-2-(pyridin-3-yl)-8,9-dihydro-7H-purine-6-carboxamide;
9-(2-methoxyphenyl)-8-oxo-2-(quinolin-5-yl)-8,9-dihydro-7H-purine-6-carboxamide;
2-cyclopentyl-9-(2-methoxyphenyl)-8-oxo-8,9-dihydro-7H-purine-6-carboxamide;
9-(2-methoxyphenyl)-8-oxo-2-(3-(trifluoromethyl)phenyl)-8,9-dihydro-7H-purine-6-carboxamide;
9-(2-methoxyphenyl)-2-(6-methoxypyridin-3-yl)-8-oxo-8,9-dihydro-7H-purine-6-carboxamide;

2-(3-hydroxyphenyl)-8-oxo-9-(4-(trifluoromethyl)phenyl)-8,9-dihydro-7H-purine-6-carboxamide;
9-benzyl-2-(3-hydroxyphenyl)-8-oxo-8,9-dihydro-7H-purine-6-carboxamide;
2-(3-hydroxyphenyl)-8-oxo-9-(2-(trifluoromethoxy)phenyl)-8,9-dihydro-7H-purine-6-carboxamide;
9-(2,4-dichlorophenyl)-2-(3-hydroxyphenyl)-8-oxo-8,9-dihydro-7H-purine-6-carboxamide;
9-(2-methoxyphenyl)-2-(3-nitrophenyl)-8-oxo-8,9-dihydro-7H-purine-6-carboxamide;
2-(3-cyanophenyl)-8-oxo-9-phenyl-8,9-dihydro-7H-purine-6-carboxamide;
9-(3-fluorophenyl)-2-(3-hydroxyphenyl)-8-oxo-8,9-dihydro-7H-purine-6-carboxamide;
9-(2-methoxyphenyl)-8-oxo-2-(2-(trifluoromethyl)phenyl)-8,9-dihydro-7H-purine-6-carboxamide;
2-(5-fluoropyridin-3-yl)-9-(2-methoxyphenyl)-8-oxo-8,9-dihydro-7H-purine-6-carboxamide;
2-(1-benzylpiperidin-4-yl)-9-(2-methoxyphenyl)-8-oxo-8,9-dihydro-7H-purine-6-carboxamide;
benzyl 4-(6-carbamoyl-8-oxo-2-(pyridin-3-yl)-7H-purin-9(8H)-yl)piperidine-1-carboxylate;
9-cyclohexyl-2-(3-hydroxyphenyl)-8-oxo-8,9-dihydro-7H-purine-6-carboxamide;
9-(2-methoxyphenyl)-8-oxo-2-(3-(trifluoromethoxy)phenyl)-8,9-dihydro-7H-purine-6-carboxamide;
9-phenyl-2-(pyridin-3-yl)-9H-purine-6-carboxamide;
6-oxo-8-phenyl-2-(pyridin-3-yl)-5,6,7,8-tetrahydropteridine-4-carboxamide;
6-oxo-8-phenyl-2-(pyridin-4-yl)-5,6,7,8-tetrahydropteridine-4-carboxamide;
2-(3-aminophenyl)-9-(2-methoxyphenyl)-8-oxo-8,9-dihydro-7H-purine-6-carboxamide;
2-(3-hydroxyphenyl)-9-(2-methoxyphenyl)-9H-purine-6-carboxamide;
9-Cyclopentyl-2-(3-hydroxyphenyl)-8-oxo-8,9-dihydro-7H-purine-6-carboxamide;
9-tert-Butyl-2-(3-hydroxy-phenyl)-8-oxo-8,9-dihydro-7H-purine-6-carboxamide;
[2-(3-Hydroxyphenyl)-9-(2-methoxyphenyl)-8-oxo(7-hydropurin-6-yl)]-N-methylcarboxamide;
2-phenyl-5H-pyrrolo[3,2-d]pyrimidine-4-carboxamide;
[2-(3-Hydroxyphenyl)-9-(2-methoxyphenyl)-8-oxo(7-hydropurin-6-yl)]-N,N-dimethyl carboxamide;
2-(3-Hydroxyphenylamino)-9-(2-methoxyphenyl)-8-oxo-8,9-dihydro-7H-purine-6-carboxamide;
2-(4-Hydroxyphenylamino)-9-(2-methoxyphenyl)-8-oxo-8,9-dihydro-7H-purine-6-carboxamide;
9-(trans-4-Hydroxycyclohexyl)-2-(3-hydroxyphenyl)-8-oxo-8,9-dihydro-7H-purine-6-carboxamide;
9-(trans-4-Hydroxycyclohexyl)-8-oxo-2-(pyridin-3-yl)-8,9-dihydro-7H-purine-6-carboxamide;
9-(trans-4-Hydroxycyclohexyl)-2-(3-hydroxyphenyl)-8-oxo-8,9-dihydro-7H-purine-6-carboxamide;
9-(trans-4-Hydroxycyclohexyl)-8-oxo-2-(pyridin-3-yl)-8,9-dihydro-7H-purine-6-carboxamide;
2-(3-Hydroxyphenylamino)-9-(2-methoxyphenyl)-9H-purine-6-carboxamide;
9-Isopropyl-2-(3-hydroxy-phenyl)-8-oxo-8,9-dihydro-7H-purine-6-carboxamide;
Methyl 4-(6-carbamoyl-9-(2-methoxyphenyl)-8-oxo-8,9-dihydro-7H-purin-2-yl)benzoate;
2-(2-Chloro-3-hydroxyphenyl)-9-(2-methoxyphenyl)-8-oxo-7-hydropurine-6-carboxamide;
2-(3-Cyanophenyl)-9-(2-methoxyphenyl)-8-oxo-8,9-dihydro-7H-purine-6-carboxamide;
2-(2-Hydroxyphenylamino)-9-(2-methoxyphenyl)-8-oxo-8,9-dihydro-7H-purine-6-carboxamide;
2-(3-Hydroxyphenyl)-9-(4-methoxy-2-methylphenyl)-8-oxo-8,9-dihydro-7H-purine-6-carboxamide;
2-(3-Hydroxyphenyl)-8-oxo-9-(2-(trifluoromethyl)phenyl)-8,9-dihydro-7H-purine-6-carboxamide;
2-(4-Cyano-phenyl)-9-(2-methoxy-phenyl)-8-oxo-8,9-dihydro-7H-purine-6-carboxamide;
4-[6-Carbamoyl-9-(2-methoxy-phenyl)-8-oxo-8,9-dihydro-7H-purin-2-yl]-benzoic acid;
Methyl 3-(6-carbamoyl-9-(2-methoxyphenyl)-8-oxo-8,9-dihydro-7H-purin-2-yl)benzoate;
3-(6-Carbamoyl-9-(2-methoxyphenyl)-8-oxo-8,9-dihydro-7H-purin-2-yl)benzoic acid;
2-(3-Hydroxyphenyl)-9-(2-isopropylphenyl)-8-oxo-8,9-dihydro-7H-purine-6-carboxamide;
2-(1H-Indazol-6-yl)-9-(2-methoxyphenyl)-8-oxo-7-hydropurine-6-carboxamide;
2-(4-Carbamoylphenyl)-9-(2-methoxyphenyl)-8-oxo-8,9-dihydro-7H-purine-6-carboxamide;
9-(2-Ethylphenyl)-2-(3-hydroxyphenyl)-8-oxo-8,9-dihydro-7H-purine-6-carboxamide;
9-(2,5-Dichlorophenyl)-2-(3-hydroxyphenyl)-8-oxo-7-hydropurine-6-carboxamide;
2-(3-Carbamoylphenyl)-9-(2-methoxyphenyl)-8-oxo-8,9-dihydro-7H-purine-6-carboxamide;
9-(2,6-Dichlorophenyl)-2-(3-hydroxyphenyl)-8-oxo-7-hydropurine-6-carboxamide;
2-(2-Hydroxyphenyl)-9-(2-methoxyphenyl)purine-6-carboxamide;
2-(1H-Indazol-5-yl)-9-(2-methoxyphenyl)-8-oxo-7-hydropurine-6-carboxamide;
9-(2,3-Dichlorophenyl)-2-(3-hydroxyphenyl)-8-oxo-7-hydropurine-6-carboxamide;
2-[4-(Hydroxymethyl)phenyl]-9-(2-methoxyphenyl)-8-oxo-7-hydropurine-6-carbox-amide;
2-[3-(Hydroxymethyl)phenyl]-9-(2-methoxyphenyl)-8-oxo-7-hydropurine-6-carbox-amide;
9-(2-Methoxyphenyl)-8-oxo-2-(pyridin-4-yl)-8,9-dihydro-7H-purine-6-carboxamide;
2-(4-Fluoro-3-hydroxyphenyl)-9-(2-methoxyphenyl)-8-oxo-7-hydropurine-6-carbox-amide;
2-(2-Fluoro-3-hydroxyphenyl)-9-(2-methoxyphenyl)-8-oxo-7-hydropurine-6-carbox-amide;
2-[4-(1-Hydroxy-isopropyl)phenyl]-9-(2-methoxyphenyl)-8-oxo-7-hydropurine-6-carboxamide;
2-[3-(1-Hydroxy-isopropyl)phenyl]-9-(2-methoxyphenyl)-8-oxo-7-hydropurine-6-carboxamide;
9-(2-Methoxyphenyl)-2-(2-nitrophenyl)-8-oxo-7-hydropurine-6-carboxamide;
9-(2-Methoxyphenyl)-2-(4-nitrophenyl)-8-oxo-7-hydropurine-6-carboxamide;
9-(2-Methoxyphenyl)-2-(2-nitrophenyl)-8-oxo-7-hydropurine-6-carboxamide;
9-(2,4-Difluorophenyl)-2-(3-hydroxyphenyl)-8-oxo-7-hydropurine-6-carboxamide;
9-(2-Methoxyphenyl)-2-{3-[(methylsulfonyl)amino]phenyl}-8-oxo-7-hydropurine-6-carboxamide;
9-(4-Chloro-2-fluorophenyl)-2-(3-hydroxyphenyl)-8-oxo-7-hydropurine-6-carboxamide;
9-(2-Chlorophenyl)-8-oxo-2-(3-pyridyl)-7-hydropurine-6-carboxamide;
8-oxo-2-(3-pyridyl)-9-[2-(trifluoromethyl)phenyl]-7-hydropurine-6-carboxamide;
9-(3-Chloro-2-fluorophenyl)-2-(3-hydroxyphenyl)-8-oxo-7-hydropurine-6-carboxamide;

9-(2-Fluoro-3-trifluoromethylphenyl)-2-(3-hydroxyphenyl)-8-oxo-7-hydropurine-6-carboxamide;
9-(2,3,4-Trifluorophenyl)-2-(3-hydroxyphenyl)-8-oxo-7-hydropurine-6-carboxamide;
2-(1H-Benzo[d]imidazol-6-yl)-9-(2-methoxyphenyl)-8-oxo-8,9-dihydro-7H-purine-6-carboxamide;
2-[3-(Acetylamino)phenyl]-9-(2-methoxyphenyl)-8-oxo-7-hydropurine-6-carboxamide;
2-(3-hydroxyphenyl)-8-(2-methoxyphenyl)-6-oxo-5,6,7,8-tetrahydropteridine-4-carbox-amide;
9-(2-Methoxyphenyl)-8-oxo-2-pyrazol-4-yl-7-hydropurine-6-carboxamide;
9-(2-Methoxyphenyl)-8-oxo-2-pyrazol-3-yl-7-hydropurine-6-carboxamide;
9-(4-Aminocyclohexyl)-2-(3-hydroxyphenyl)-8-oxo-7-hydropurine-6-carboxamide;
2-[3-(Difluoromethyl)phenyl]-9-(2-methoxyphenyl)-8-oxo-7-hydropurine-6-carbox-amide;
2-[5-(Difluoromethyl)-2-fluorophenyl]-9-(2-methoxyphenyl)-8-oxo-7-hydropurine-6-carboxamide;
2-(1H-benzo[d]imidazol-4-yl)-9-(2-methoxyphenyl)-8-oxo-8,9-dihydro-7H-purine-6-carboxamide;
2-(6-Hydroxypyridin-3-yl)-8-oxo-9-(2-(trifluoromethyl)phenyl)-8,9-dihydro-7H-purine-6-carboxamide;
2-(1H-benzo[d]imidazol-6-yl)-9-(2-fluorophenyl)-8-oxo-8,9-dihydro-7H-purine-6-carboxamide;
2-Benzimidazol-6-yl-8-oxo-9-[2-(trifluoromethyl)phenyl]-7-hydropurine-6-carboxamide;
2-(5-Chloropyridin-3-yl)-8-oxo-9-(2-(trifluoromethyl)phenyl)-8,9-dihydro-7H-purine-6-carboxamide;
trans-4-(6-Carbamoyl-9-(2-methoxyphenyl)-8-oxo-8,9-dihydro-7H-purin-2-ylamino)cyclohexyl carbamate;
(R)-9-(2-Methoxyphenyl)-8-oxo-2-(pyrrolidin-3-ylamino)-8,9-dihydro-7H-purine-6-carboxamide;
(S)-9-(2-Methoxyphenyl)-8-oxo-2-(pyrrolidin-3-ylamino)-8,9-dihydro-7H-purine-6-carboxamide;
(cis)-4-(6-Carbamoyl-9-(2-methoxyphenyl)-8-oxo-8,9-dihydro-7H-purin-2-ylamino)cyclohexyl carbamate;
2-(trans-4-Hydroxycyclohexylamino)-9-(2-methoxyphenyl)-8-oxo-8,9-dihydro-7H-purine-6-carboxamide;
2-(4-Chloropyridin-3-yl)-8-oxo-9-(2-(trifluoromethyl)phenyl)-8,9-dihydro-7H-purine-6-carboxamide;
2-(cis-4-Hydroxycyclohexylamino)-9-(2-methoxyphenyl)-8-oxo-8,9-dihydro-7H-purine-6-carboxamide;
2-(4-((1H-Imidazol-1-yl)methyl)phenylamino)-9-(2-methoxyphenyl)-8-oxo-8,9-dihydro-7H-purine-6-carboxamide;
2-(4-Hydroxypyridin-3-yl)-8-oxo-9-(2-(trifluoromethyl)phenyl)-8,9-dihydro-7H-purine-6-carboxamide;
(R)-9-(2-Methoxyphenyl)-8-oxo-2-(pyrrolidin-2-ylmethylamino)-8,9-dihydro-7H-purine-6-carboxamide;
(S)-9-(2-Methoxyphenyl)-8-oxo-2-(pyrrolidin-2-ylmethylamino)-8,9-dihydro-7H-purine-6-carboxamide;
2-(4-(1H-1,2,4-Triazol-3-yl)phenyl)-9-(2-methoxyphenyl)-8-oxo-7-hydropurine-6-carboxamide;
2-(2-Hydroxyethylamino)-9-(2-methoxyphenyl)-8-oxo-8,9-dihydro-7H-purine-6-carboxamide;
9-(2-Methoxyphenyl)-8-oxo-2-(2-(trifluoromethyl)-1H-benzo[d]imidazol-6-yl)-8,9-dihydro-7H-purine-6-carboxamide;
2-(3-(1H-1,2,4-Triazol-3-yl)phenyl)-9-(2-methoxyphenyl)-8-oxo-7-hydropurine-6-carboxamide;
9-(Biphenyl-2-yl)-2-(3-hydroxyphenyl)-8-oxo-7-hydropurine-6-carboxamide;
2-(4-(1H-1,2,4-Triazol-3-yl)phenyl)-9-(2-fluorophenyl)-8-oxo-7-hydropurine-6-carboxamide;
2-(4-(1H-1,2,4-Triazol-3-yl)phenyl)-9-(2-isopropylphenyl)-8-oxo-8,9-dihydro-7H-purine-6-carboxamide;
9-(2-Methoxyphenyl)-2-(2-methyl-1H-benzo[d]imidazol-6-yl)-8-oxo-8,9-dihydro-7H-purine-6-carboxamide;
2-(3-(Hydroxymethyl)phenylamino)-9-(2-methoxyphenyl)-8-oxo-8,9-dihydro-7H-purine-6-carboxamide;
2-(2-(Hydroxymethyl)phenylamino)-9-(2-methoxyphenyl)-8-oxo-8,9-dihydro-7H-purine-6-carboxamide;
9-(2-tert-Butylphenyl)-2-(3-hydroxyphenyl)-8-oxo-8,9-dihydro-7H-purine-6-carboxamide;
2-(3-Hydroxyphenyl)-8-oxo-9-(2-phenoxyphenyl)-8,9-dihydro-7H-purine-6-carboxamide;
2-(1H-Benzo[d]imidazol-6-yl)-9-(2-isopropylphenyl)-8-oxo-8,9-dihydro-7H-purine-6-carboxamide;
2-(1H-Indazol-4-yl)-9-(2-methoxyphenyl)-8-oxo-8,9-dihydro-7H-purine-6-carboxamide;
2-(2-Hydroxypyridin-3-yl)-8-oxo-9-(2-(trifluoromethyl)phenyl)-8,9-dihydro-7H-purine-6-carboxamide;
2-(1H-Imidazo[4,5-b]pyridin-6-yl)-9-(2-methoxyphenyl)-8-oxo-8,9-dihydro-7H-purine-6-carboxamide;
2-(4-(1H-Imidazol-1-yl)phenyl)-9-(2-isopropylphenyl)-8-oxo-8,9-dihydro-7H-purine-6-carboxamide;
9-(2-Cyclohexylphenyl)-2-(3-hydroxyphenyl)-8-oxo-8,9-dihydro-7H-purine-6-carboxamide;
2-(4-(1H-Imidazol-2-yl)phenyl)-9-(2-isopropylphenyl)-8-oxo-8,9-dihydro-7H-purine-6-carboxamide;
2-(1H-Benzo[d]imidazol-1-yl)-9-(2-methoxyphenyl)-8-oxo-8,9-dihydro-7H-purine-6-carboxamide;
2-(1H-Imidazo[4,5-b]pyridin-6-yl)-9-(2-isopropylphenyl)-8-oxo-8,9-dihydro-7H-purine-6-carboxamide;
9-(2-Isopropylphenyl)-8-oxo-2-(1H-pyrrolo[2,3-b]pyridin-5-yl)-8,9-dihydro-7H-purine-6-carboxamide;
2-(1H-Imidazo[4,5-b]pyridin-6-yl)-8-oxo-9-(2-(trifluoromethyl)phenyl)-8,9-dihydro-7H-purine-6-carboxamide;
9-(2-Methoxyphenyl)-2-(2-(methylthio)-1H-benzo[d]imidazol-5-yl)-8-oxo-8,9-dihydro-7H-purine-6-carboxamide;
2-(1H-Indol-5-yl)-9-(2-isopropylphenyl)-8-oxo-8,9-dihydro-7H-purine-6-carboxamide;
9-(Cyclohexylmethyl)-2-(3-hydroxyphenyl)-8-oxo-8,9-dihydro-7H-purine-6-carboxamide;
9-(2,3-Dihydro-1H-inden-1-yl)-2-(3-hydroxyphenyl)-8-oxo-8,9-dihydro-7H-purine-6-carboxamide;
2-(3-Hydroxyphenyl)-9-isobutyl-8-oxo-8,9-dihydro-7H-purine-6-carboxamide;
9-(trans-4-Methoxycyclohexyl)-2-(3-hydroxyphenyl)-8-oxo-8,9-dihydro-7H-purine-6-carboxamide;
9-(cis-4-Methoxycyclohexyl)-2-(3-hydroxyphenyl)-8-oxo-8,9-dihydro-7H-purine-6-carboxamide;
2-(3-Hydroxyphenyl)-8-oxo-9-(5,6,7,8-tetrahydronaphthalen-1-yl)-8,9-dihydro-7H-purine-6-carboxamide;
2-(4-(1H-1,2,4-Triazol-3-yl)phenyl)-9-cyclohexyl-8-oxo-8,9-dihydro-7H-purine-6-carboxamide;
2-(3-Hydroxyphenyl)-9-(1H-indol-4-yl)-8-oxo-8,9-dihydro-7H-purine-6-carboxamide;
9-(2-Fluoro-3-methoxyphenyl)-2-(3-hydroxyphenyl)-8-oxo-8,9-dihydro-7H-purine-6-carboxamide;
9-(2-Fluoro-5-methoxyphenyl)-2-(3-hydroxyphenyl)-8-oxo-8,9-dihydro-7H-purine-6-carboxamide;
9-Cyclohexyl-2-(1H-imidazo[4,5-b]pyridin-6-yl)-8-oxo-8,9-dihydro-7H-purine-6-carboxamide;
2-(3-Hydroxyphenyl)-8-oxo-9-(tetrahydro-2H-pyran-4-yl)-8,9-dihydro-7H-purine-6-carboxamide;
2-(3-Hydroxyphenyl)-8-oxo-9-((tetrahydro-2H-pyran-4-yl)methyl)-8,9-dihydro-7H-purine-6-carboxamide;
9-(2-Cyclopentylphenyl)-2-(3-hydroxyphenyl)-8-oxo-8,9-dihydro-7H-purine-6-carboxamide;

2-(3-Hydroxyphenyl)-8-oxo-9-(piperidin-4-yl)-8,9-dihydro-7H-purine-6-carboxamide;
9-(2-Fluoro-4-methoxyphenyl)-2-(3-hydroxyphenyl)-8-oxo-8,9-dihydro-7H-purine-6-carboxamide;
2-(1H-benzo[d]imidazol-6-yl)-9-cyclohexyl-8-oxo-8,9-dihydro-7H-purine-6-carboxamide;
2-Benzimidazol-6-yl-9-(trans-4-methoxycyclohexyl)-8-oxo-7-hydropurine-6-carboxamide;
2-(4-(Aminomethyl)phenyl)-9-(2-methoxyphenyl)-8-oxo-8,9-dihydro-7H-purine-6-carboxamide;
2-(3-Hydroxyphenyl)-9-(cis-4-(methoxymethyl)cyclohexyl)-8-oxo-8,9-dihydro-7H-purine-6-carboxamide;
9-(trans-4-Aminocyclohexyl)-2-(3-hydroxyphenyl)-8-oxo-8,9-dihydro-7H-purine-6-carboxamide;
2-(3-Hydroxyphenyl)-9-(2-isobutylphenyl)-8-oxo-8,9-dihydro-7H-purine-6-carboxamide;
(R)-2-(3-Hydroxyphenyl)-8-oxo-9-(tetrahydrofuran-3-yl)-8,9-dihydro-7H-purine-6-carboxamide;
(S)-2-(3-Hydroxyphenyl)-8-oxo-9-(tetrahydrofuran-3-yl)-8,9-dihydro-7H-purine-6-carboxamide;
2-(3-(Aminomethyl)phenyl)-9-(2-methoxyphenyl)-8-oxo-8,9-dihydro-7H-purine-6-carboxamide;
2-(4-(1H-1,2,3-Triazol-5-yl)phenyl)-9-(2-isopropylphenyl)-8-oxo-8,9-dihydro-7H-purine-6-carboxamide;
2-(4-(1H-1,2,4-Triazol-3-yl)phenyl)-9-(cis-4-methoxycyclohexyl)-8-oxo-8,9-dihydro-7H-purine-6-carboxamide;
2-(1H-Benzo[d]imidazol-6-yl)-9-(cis-4-methoxycyclohexyl)-8-oxo-8,9-dihydro-7H-purine-6-carboxamide;
2-(1H-Imidazo[4,5-b]pyridin-6-yl)-9-(cis-4-methoxycyclohexyl)-8-oxo-8,9-dihydro-7H-purine-6-carboxamide;
2-(3-Hydroxyphenyl)-9-((1r,4r)-4-(methoxymethyl)cyclohexyl)-8-oxo-8,9-dihydro-7H-purine-6-carboxamide; and
9-(2-Isopropylphenyl)-2-(4-(5-methyl-4H-1,2,4-triazol-3-yl)phenyl)-8-oxo-8,9-dihydro-7H-purine-6-carboxamide,
and pharmaceutically acceptable salts, clathrates, solvates, stereoisomers, tautomers, and prodrugs thereof.

In one embodiment, the TOR kinase inhibitors include compounds having the following formula (III):

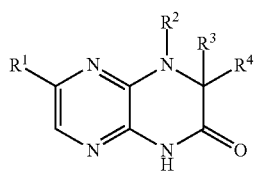

(III)

and pharmaceutically acceptable salts, clathrates, solvates, stereoisomers, tautomers, and prodrugs thereof, wherein:

$R^1$ is substituted or unsubstituted $C_{1-8}$ alkyl, substituted or unsubstituted aryl, substituted or unsubstituted cycloalkyl, substituted or unsubstituted heterocyclyl, or substituted or unsubstituted heterocyclylalkyl;

$R^2$ is H, substituted or unsubstituted $C_{1-8}$ alkyl, substituted or unsubstituted cycloalkyl, substituted or unsubstituted heterocyclyl, substituted or unsubstituted heterocyclylalkyl, substituted or unsubstituted aralkyl, or substituted or unsubstituted cycloalkylalkyl;

$R^3$ and $R^4$ are each independently H, substituted or unsubstituted $C_{1-8}$ alkyl, substituted or unsubstituted aryl, substituted or unsubstituted cycloalkyl, substituted or unsubstituted heterocyclyl, substituted or unsubstituted heterocyclylalkyl, substituted or unsubstituted aralkyl, substituted or unsubstituted cycloalkylalkyl, or $R^3$ and $R^4$, together with the atoms to which they are attached, form a substituted or unsubstituted cycloalkyl or substituted or unsubstituted heterocyclyl;

or $R^2$ and one of $R^3$ and $R^4$, together with the atoms to which they are attached, form a substituted or unsubstituted heterocyclyl, wherein in certain embodiments, the TOR kinase inhibitors do not include the compounds depicted below, namely:

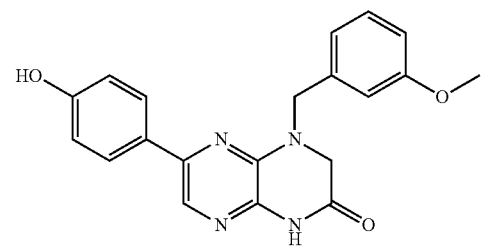 [SMILES: COc1cccc(CN2CC(=O)Nc3ncc(-c4ccc(O)cc4)nc32)c1]

6-(4-hydroxyphenyl)-4-(3-methoxybenzyl)-3,4-dihydropyrazino[2,3-b]pyrazin-2(1H)-one;

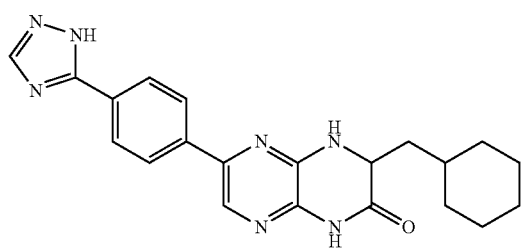 [SMILES: O=C1Nc2ncc(-c3ccc(-c4ncn[nH]4)cc3)nc2NC1CC1CCCCC1]

6-(4-(1H-1,2,4-triazol-5-yl)phenyl)-3-(cyclohexylmethyl)-3,4-dihydropyrazino[2,3-b]pyrazin-2(1H)-one; or

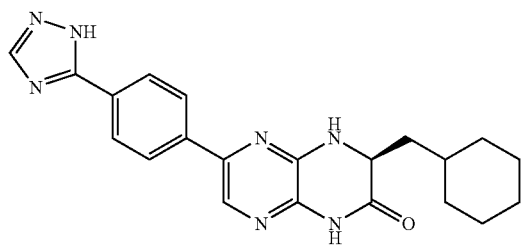 [SMILES: O=C1Nc2ncc(-c3ccc(-c4ncn[nH]4)cc3)nc2N[C@H]1CC1CCCCC1]

(R)-6-(4-(1H-1,2,4-triazol-5-yl)phenyl)-3-(cyclohexylmethyl)-3,4-dihydropyrazino[2,3-b]pyrazin-2(1H)-one.

In some embodiments of compounds of formula (III), $R^1$ is substituted or unsubstituted aryl or substituted or unsubstituted heteroaryl. In one embodiment, $R^1$ is phenyl, pyridyl, pyrimidyl, benzimidazolyl, indolyl, indazolyl, 1H-pyrrolo[2,3-b]pyridyl, 1H-imidazo[4,5-b]pyridyl, 1H-imidazo[4,5-b]pyridin-2(3H)-onyl, 3H-imidazo[4,5-b]pyridyl, or pyrazolyl, each optionally substituted. In some embodiments, $R^1$ is phenyl substituted with one or more substituents independently selected from the group consisting of substituted or unsubstituted $C_{1-8}$ alkyl (for example, methyl), substituted or unsubstituted heterocyclyl (for example, substituted or unsubstituted triazolyl or pyrazolyl), halogen (for example, fluorine), aminocarbonyl, cyano, hydroxyalkyl (for example, hydroxypropyl), and hydroxy. In other embodiments, $R^1$ is pyridyl substituted with one or more substituents independently selected from the group consisting of substituted or unsubstituted $C_{1-8}$ alkyl, substituted or unsubstituted heterocyclyl (for example, substituted or unsubstituted triazolyl), halogen, aminocarbonyl, cyano, hydroxyalkyl, —OR, and —NR$_2$, wherein each R is independently H, or a substituted or unsubstituted $C_{1-4}$ alkyl. In yet other embodiments, $R^1$ is 1H-pyrrolo[2,3-b]pyridyl or benzimidazolyl, each optionally substituted with one or more substituents independently selected from the group consisting of substituted or unsubstituted $C_{1-8}$ alkyl, and —NR$_2$, wherein each R is independently H, or a substituted or unsubstituted $C_{1-4}$ alkyl.

In some embodiments of compounds of formula (III), $R^1$ is

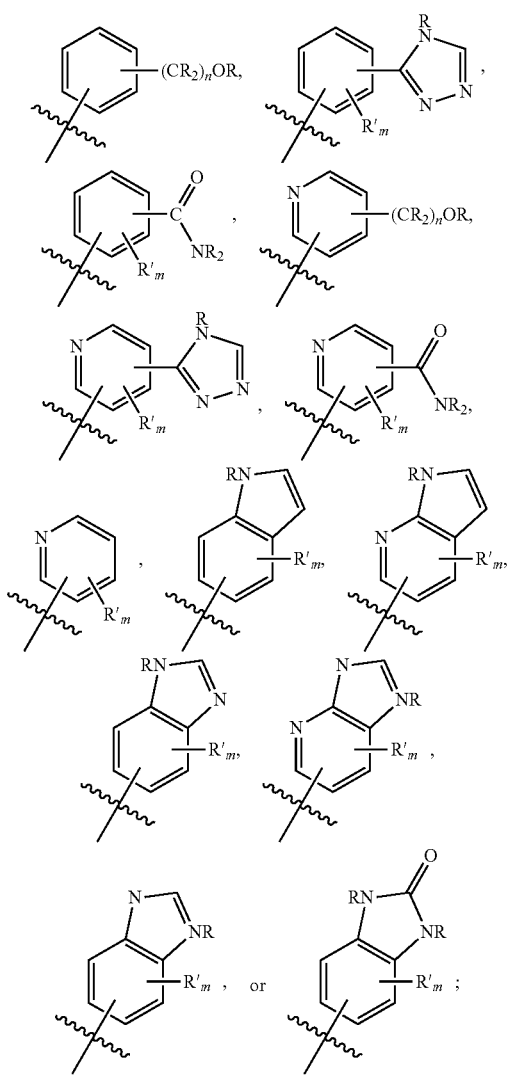

wherein R is at each occurrence independently H, or a substituted or unsubstituted $C_{1-4}$ alkyl (for example, methyl); R' is at each occurrence independently a substituted or unsubstituted $C_{1-4}$ alkyl, halogen (for example, fluorine), cyano, —OR, or —NR$_2$; m is 0-3; and n is 0-3. It will be understood by those skilled in the art that any of the substitutents R' may be attached to any suitable atom of any of the rings in the fused ring systems. It will also be understood by those skilled in the art that the connecting bond of $R^1$ (designated by the bisecting wavy line) may be attached to any of the atoms in any of the rings in the fused ring systems.

In some embodiments of compounds of formula (III), $R^1$ is

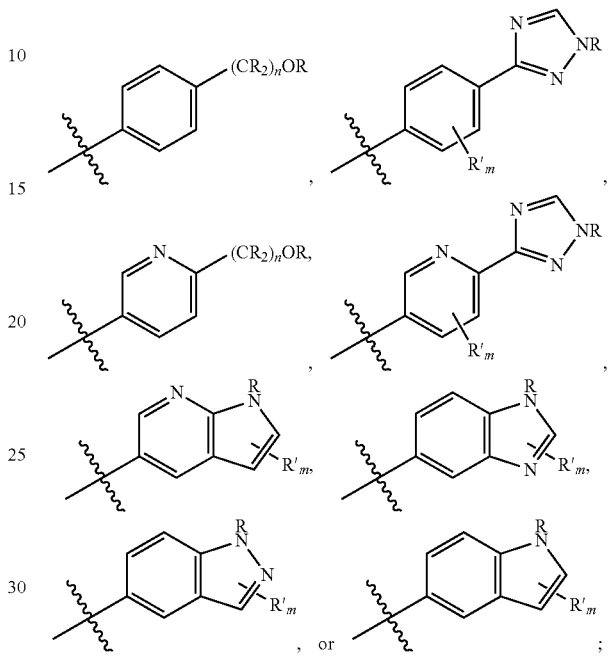

wherein R is at each occurrence independently H, or a substituted or unsubstituted $C_{1-4}$ alkyl; R' is at each occurrence independently a substituted or unsubstituted $C_{1-4}$ alkyl, halogen, cyano, —OR, or —NR$_2$; m is 0-3; and n is 0-3.

In some embodiments of compounds of formula (III), $R^2$ is H, substituted or unsubstituted $C_{1-8}$ alkyl, substituted or unsubstituted cycloalkyl, substituted or unsubstituted heterocyclyl, substituted or unsubstituted $C_{1-4}$ alkyl-heterocyclyl, substituted or unsubstituted $C_{1-4}$ alkyl-aryl, or substituted or unsubstituted $C_{1-4}$ alkyl-cycloalkyl. For example, $R^2$ is H, methyl, ethyl, n-propyl, isopropyl, n-butyl, sec-butyl, isobutyl, tert-butyl, n-pentyl, isopentyl, cyclopentyl, cyclohexyl, tetrahydrofuranyl, tetrahydropyranyl, ($C_{1-4}$ alkyl)-phenyl, ($C_{1-4}$ alkyl)-cyclopropyl, ($C_{1-4}$ alkyl)-cyclobutyl, ($C_{1-4}$ alkyl)-cyclopentyl, ($C_{1-4}$ alkyl)-cyclohexyl, ($C_{1-4}$ alkyl)-pyrrolidyl, ($C_{1-4}$ alkyl)-piperidyl, ($C_{1-4}$ alkyl)-piperazinyl, ($C_{1-4}$ alkyl)-morpholinyl, ($C_{1-4}$ alkyl)-tetrahydrofuranyl, or ($C_{1-4}$ alkyl)-tetrahydropyranyl, each optionally substituted.

In other embodiments, $R^2$ is H, $C_{1-4}$ alkyl, ($C_{1-4}$alkyl) (OR),

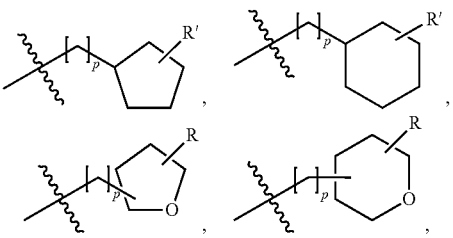

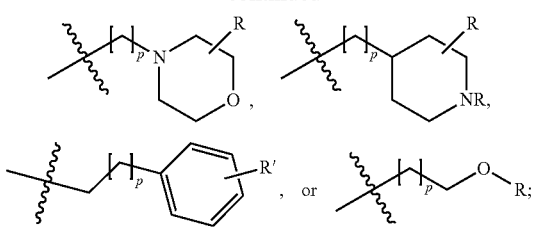

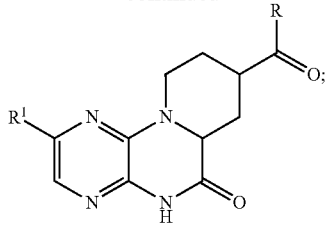

wherein R is at each occurrence independently H, or a substituted or unsubstituted $C_{1-4}$ alkyl (for example, methyl); R' is at each occurrence independently H, —OR, cyano, or a substituted or unsubstituted $C_{1-4}$ alkyl (for example, methyl); and p is 0-3.

In some such embodiments, $R^2$ is H, $C_{1-4}$ alkyl, $(C_{1-4}alkyl)(OR)$,

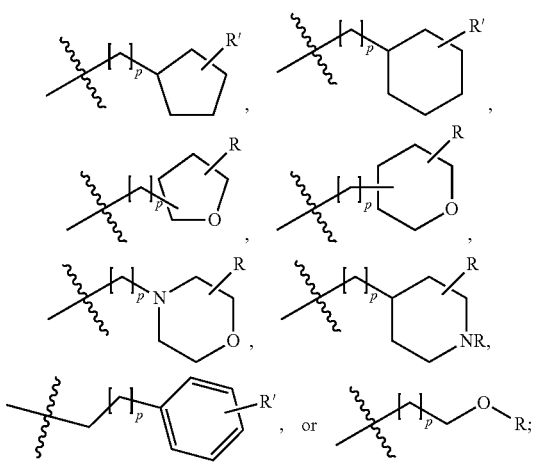

wherein R is at each occurrence independently H, or a substituted or unsubstituted $C_{1-2}$ alkyl; R' is at each occurrence independently H, —OR, cyano, or a substituted or unsubstituted $C_{1-2}$ alkyl; and p is 0-1.

In some other embodiments of compounds of formula (III), $R^2$ and one of $R^3$ and $R^4$ together with the atoms to which they are attached form a substituted or unsubstituted heterocyclyl. For example, in some embodiments, the compound of formula (III) is

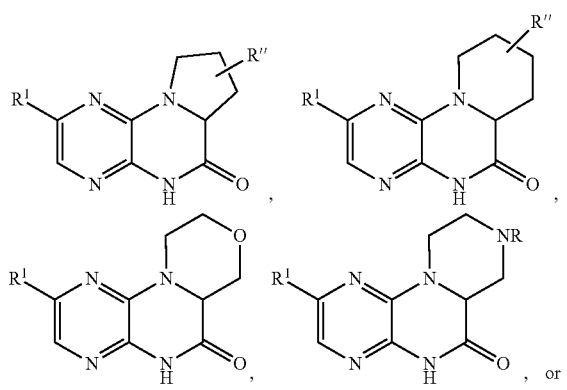

wherein R is at each occurrence independently H, or a substituted or unsubstituted $C_{1-4}$ alkyl; R" is H, OR, or a substituted or unsubstituted $C_{1-4}$ alkyl; and $R^1$ is as defined herein.

In some embodiments of compounds of formula (III), $R^3$ and $R^4$ are both H. In others, one of $R^3$ and $R^4$ is H and the other is other than H. In still others, one of $R^3$ and $R^4$ is $C_{1-4}$ alkyl (for example, methyl) and the other is H. In still others, both of $R^3$ and $R^4$ are $C_{1-4}$ alkyl (for example, methyl).

In some such embodiments described above, $R^1$ is substituted or unsubstituted aryl, or substituted or unsubstituted heteroaryl. For example, $R^1$ is phenyl, pyridyl, pyrimidyl, benzimidazolyl, indolyl, indazolyl, 1H-pyrrolo[2,3-b]pyridyl, 1H-imidazo[4,5-b]pyridyl, 1H-imidazo[4,5-b]pyridin-2(3H)-onyl, 3H-imidazo[4,5-b]pyridyl, or pyrazolyl, each optionally substituted. In some embodiments, $R^1$ is phenyl substituted with one or more substituents independently selected from the group consisting of substituted or unsubstituted $C_{1-8}$ alkyl, substituted or unsubstituted heterocyclyl, halogen, aminocarbonyl, cyano, hydroxyalkyl and hydroxy. In others, $R^1$ is pyridyl substituted with one or more substituents independently selected from the group consisting of cyano, substituted or unsubstituted $C_{1-8}$ alkyl, substituted or unsubstituted heterocyclyl, hydroxyalkyl, halogen, aminocarbonyl, —OR, and —$NR_2$, wherein each R is independently H, or a substituted or unsubstituted $C_{1-4}$ alkyl. In others, $R^1$ is 1H-pyrrolo[2,3-b]pyridyl or benzimidazolyl, optionally substituted with one or more substituents independently selected from the group consisting of substituted or unsubstituted $C_{1-8}$ alkyl, and —$NR_2$, wherein R is independently H, or a substituted or unsubstituted $C_{1-4}$ alkyl In certain embodiments, the compounds of formula (III) have an $R^1$ group set forth herein and an $R^2$ group set forth herein.

In some embodiments of compounds of formula (III), the compound at a concentration of 10 μM inhibits mTOR, DNA-PK, or PI3K or a combination thereof, by at least about 50%. Compounds of formula (III) may be shown to be inhibitors of the kinases above in any suitable assay system.

Representative TOR kinase inhibitors of formula (III) include compounds from Table C.

Table C.

6-(1H-pyrrolo[2,3-b]pyridin-3-yl)-4-(2-(tetrahydro-2H-pyran-4-yl)ethyl)-3,4-dihydropyrazino[2,3-b]pyrazin-2(1H)-one;

6-(4-methyl-6-(1H-1,2,4-triazol-3-yl)pyridin-3-yl)-4-((tetrahydro-2H-pyran-4-yl)methyl)-3,4-dihydropyrazino[2,3-b]pyrazin-2(1H)-one;

6-(5-fluoro-2-methyl-4-(1H-1,2,4-triazol-3-yl)phenyl)-4-((trans-4-methoxycyclohexyl)methyl)-3,4-dihydropyrazino[2,3-b]pyrazin-2(1H)-one;

6-(5-fluoro-2-methyl-4-(1H-1,2,4-triazol-3-yl)phenyl)-4-((cis-4-methoxycyclohexyl)methyl)-3,4-dihydropyrazino[2,3-b]pyrazin-2(1H)-one;

6-(6-(1H-1,2,4-triazol-3-yl)pyridin-3-yl)-4-((trans-4-methoxycyclohexyl)methyl)-3,4-dihydropyrazino[2,3-b]pyrazin-2(1H)-one;

6-(5-fluoro-2-methyl-4-(1H-1,2,4-triazol-3-yl)phenyl)-4-((trans-4-hydroxycyclohexyl)methyl)-3,4-dihydropyrazino[2,3-b]pyrazin-2(1H)-one;

6-(6-(1H-1,2,4-triazol-3-yl)pyridin-3-yl)-4-((cis-4-methoxycyclohexyl)methyl)-3,4-dihydropyrazino[2,3-b]pyrazin-2(1H)-one;

6-(6-(1H-1,2,4-triazol-3-yl)pyridin-3-yl)-4-((trans-4-hydroxycyclohexyl)methyl)-3,4-dihydropyrazino[2,3-b]pyrazin-2(1H)-one;

6-(6-(1H-1,2,4-triazol-3-yl)pyridin-3-yl)-4-(cis-4-hydroxycyclohexyl)-3,4-dihydropyrazino[2,3-b]pyrazin-2(1H)-one;

6-(6-(1H-1,2,4-triazol-3-yl)pyridin-3-yl)-4-((cis-4-hydroxycyclohexyl)methyl)-3,4-dihydropyrazino[2,3-b]pyrazin-2(1H)-one;

6-(5-fluoro-2-methyl-4-(1H-1,2,4-triazol-3-yl)phenyl)-4-(trans-4-methoxycyclohexyl)-3,4-dihydropyrazino[2,3-b]pyrazin-2(1H)-one;

6-(6-(1H-1,2,4-triazol-3-yl)pyridin-3-yl)-4-(trans-4-methoxycyclohexyl)-3,4-dihydropyrazino[2,3-b]pyrazin-2(1H)-one;

6-(6-(1H-1,2,4-triazol-3-yl)pyridin-3-yl)-4-(trans-4-hydroxycyclohexyl)-3,4-dihydropyrazino[2,3-b]pyrazin-2(1H)-one;

6-(5-fluoro-2-methyl-4-(1H-1,2,4-triazol-3-yl)phenyl)-4-((cis-4-hydroxycyclohexyl)methyl)-3,4-dihydropyrazino[2,3-b]pyrazin-2(1H)-one;

6-(6-(1H-1,2,4-triazol-3-yl)pyridin-3-yl)-4-(cis-4-methoxycyclohexyl)-3,4-dihydropyrazino[2,3-b]pyrazin-2(1H)-one;

6-(6-(1H-1,2,4-triazol-3-yl)pyridin-3-yl)-4-(2-methoxyethyl)-3,4-dihydropyrazino[2,3-b]pyrazin-2(1H)-one;

6-(6-(1H-1,2,4-triazol-3-yl)pyridin-3-yl)-4-isopropyl-3,4-dihydropyrazino[2,3-b]pyrazin-2(1H)-one;

6-(5-fluoro-2-methyl-4-(1H-1,2,4-triazol-3-yl)phenyl)-4-(cis-4-hydroxycyclohexyl)-3,4-dihydropyrazino[2,3-b]pyrazin-2(1H)-one;

6-(5-fluoro-2-methyl-4-(1H-1,2,4-triazol-3-yl)phenyl)-4-(cis-4-methoxycyclohexyl)-3,4-dihydropyrazino[2,3-b]pyrazin-2(1H)-one;

6-(5-fluoro-2-methyl-4-(1H-1,2,4-triazol-3-yl)phenyl)-4-(2-methoxyethyl)-3,4-dihydropyrazino[2,3-b]pyrazin-2(1H)-one;

6-(6-(1H-1,2,4-triazol-3-yl)pyridin-3-yl)-4-(tetrahydro-2H-pyran-4-yl)-3,4-dihydropyrazino[2,3-b]pyrazin-2(1H)-one;

6-(6-(1H-1,2,4-triazol-3-yl)pyridin-3-yl)-4-ethyl-3,4-dihydropyrazino[2,3-b]pyrazin-2(1H)-one;

6-(5-fluoro-2-methyl-4-(1H-1,2,4-triazol-3-yl)phenyl)-4-(trans-4-hydroxycyclohexyl)-3,4-dihydropyrazino[2,3-b]pyrazin-2(1H)-one;

6-(5-fluoro-2-methyl-4-(1H-1,2,4-triazol-3-yl)phenyl)-4-(tetrahydro-2H-pyran-4-yl)-3,4-dihydropyrazino[2,3-b]pyrazin-2(1H)-one;

6-(5-fluoro-2-methyl-4-(1H-1,2,4-triazol-3-yl)phenyl)-4-isopropyl-3,4-dihydropyrazino[2,3-b]pyrazin-2(1H)-one;

4-ethyl-6-(5-fluoro-2-methyl-4-(1H-1,2,4-triazol-3-yl)phenyl)-3,4-dihydropyrazino[2,3-b]pyrazin-2(1H)-one;

6-(3-fluoro-2-methyl-4-(1H-1,2,4-triazol-3-yl)phenyl)-4-(tetrahydro-2H-pyran-4-yl)-3,4-dihydropyrazino[2,3-b]pyrazin-2(1H)-one;

6-(3-fluoro-2-methyl-4-(1H-1,2,4-triazol-3-yl)phenyl)-4-(cis-4-methoxycyclohexyl)-3,4-dihydropyrazino[2,3-b]pyrazin-2(1H)-one;

6-(3-fluoro-2-methyl-4-(1H-1,2,4-triazol-3-yl)phenyl)-4-(trans-4-methoxycyclohexyl)-3,4-dihydropyrazino[2,3-b]pyrazin-2(1H)-one;

4-(2-methoxyethyl)-6-(4-methyl-6-(1H-1,2,4-triazol-3-yl)pyridin-3-yl)-3,4-dihydropyrazino[2,3-b]pyrazin-2(1H)-one;

6-(3-(1H-1,2,4-triazol-5-yl)phenyl)-4-(2-(tetrahydro-2H-pyran-4-yl)ethyl)-3,4-dihydropyrazino[2,3-b]pyrazin-2(1H)-one;

5-(8-(2-methoxyethyl)-6-oxo-5,6,7,8-tetrahydropyrazino[2,3-b]pyrazin-2-yl)-4-methylpicolinamide;

3-(6-oxo-8-(2-(tetrahydro-2H-pyran-4-yl)ethyl)-5,6,7,8-tetrahydropyrazino[2,3-b]pyrazin-2-yl)benzamide;

3-(6-oxo-8-(2-(tetrahydro-2H-pyran-4-yl)ethyl)-5,6,7,8-tetrahydropyrazino[2,3-b]pyrazin-2-yl)benzonitrile;

5-(8-(trans-4-methoxycyclohexyl)-6-oxo-5,6,7,8-tetrahydropyrazino[2,3-b]pyrazin-2-yl)-4-methylpicolinamide;

6-(1H-imidazo[4,5-b]pyridin-6-yl)-4-(2-(tetrahydro-2H-pyran-4-yl)ethyl)-3,4-dihydropyrazino[2,3-b]pyrazin-2(1H)-one;

6-(1H-indazol-6-yl)-4-(2-(tetrahydro-2H-pyran-4-yl)ethyl)-3,4-dihydropyrazino[2,3-b]pyrazin-2(1H)-one;

4-((1R,3S)-3-methoxycyclopentyl)-6-(2-methyl-6-(4H-1,2,4-triazol-3-yl)pyridin-3-yl)-3,4-dihydropyrazino[2,3-b]pyrazin-2(1H)-one;

4-((1S,3R)-3-methoxycyclopentyl)-6-(2-methyl-6-(4H-1,2,4-triazol-3-yl)pyridin-3-yl)-3,4-dihydropyrazino[2,3-b]pyrazin-2(1H)-one;

4-((1R,3R)-3-methoxycyclopentyl)-6-(2-methyl-6-(4H-1,2,4-triazol-3-yl)pyridin-3-yl)-3,4-dihydropyrazino[2,3-b]pyrazin-2(1H)-one;

4-((1S,3S)-3-methoxycyclopentyl)-6-(2-methyl-6-(4H-1,2,4-triazol-3-yl)pyridin-3-yl)-3,4-dihydropyrazino[2,3-b]pyrazin-2(1H)-one;

4-ethyl-6-(2-methyl-6-(4H-1,2,4-triazol-3-yl)pyridin-3-yl)-3,4-dihydropyrazino[2,3-b]pyrazin-2(1H)-one;

6-(1H-pyrrolo[2,3-b]pyridin-5-yl)-4-(2-(tetrahydro-2H-pyran-4-yl)ethyl)-3,4-dihydropyrazino[2,3-b]pyrazin-2(1H)-one;

6-(1H-indol-6-yl)-4-(2-(tetrahydro-2H-pyran-4-yl)ethyl)-3,4-dihydropyrazino[2,3-b]pyrazin-2(1H)-one;

6-(1H-indol-5-yl)-4-(2-(tetrahydro-2H-pyran-4-yl)ethyl)-3,4-dihydropyrazino[2,3-b]pyrazin-2(1H)-one;

4-(((1R,3S)-3-methoxycyclopentyl)methyl)-6-(2-methyl-6-(4H-1,2,4-triazol-3-yl)pyridin-3-yl)-3,4-dihydropyrazino[2,3-b]pyrazin-2(1H)-one;

4-(((1S,3R)-3-methoxycyclopentyl)methyl)-6-(2-methyl-6-(4H-1,2,4-triazol-3-yl)pyridin-3-yl)-3,4-dihydropyrazino[2,3-b]pyrazin-2(1H)-one;

6-(3-fluoro-2-methyl-4-(4H-1,2,4-triazol-3-yl)phenyl)-4-(2-(tetrahydro-2H-pyran-4-yl)ethyl)-3,4-dihydropyrazino[2,3-b]pyrazin-2(1H)-one;

6-(3-fluoro-2-methyl-4-(4H-1,2,4-triazol-3-yl)phenyl)-4-(2-methoxyethyl)-3,4-dihydropyrazino[2,3-b]pyrazin-2(1H)-one;

3,3-dimethyl-6-(4-methyl-6-(4H-1,2,4-triazol-3-yl)pyridin-3-yl)-4-((tetrahydro-2H-pyran-4-yl)methyl)-3,4-dihydropyrazino[2,3-b]pyrazin-2(1H)-one;

6-(6-(2-hydroxypropan-2-yl)pyridin-3-yl)-4-((1R,3S)-3-methoxycyclopentyl)-3,4-dihydropyrazino[2,3-b]pyrazin-2(1H)-one;

6-(6-(2-hydroxypropan-2-yl)pyridin-3-yl)-4-((1S,3R)-3-methoxycyclopentyl)-3,4-dihydropyrazino[2,3-b]pyrazin-2(1H)-one;

6-(6-(2-hydroxypropan-2-yl)pyridin-3-yl)-4-4(1S,3S)-3-methoxycyclopentyl)methyl)-3,4-dihydropyrazino[2,3-b]pyrazin-2(1H)-one;

6-(6-(2-hydroxypropan-2-yl)pyridin-3-yl)-4-((1R,3R)-3-methoxycyclopentyl)methyl)-3,4-dihydropyrazino[2,3-b]pyrazin-2(1H)-one;

6-(6-(2-hydroxypropan-2-yl)pyridin-3-yl)-4-((1S,3 S)-3-methoxycyclopentyl)-3,4-dihydropyrazino[2,3-b]pyrazin-2(1H)-one;

6-(6-(2-hydroxypropan-2-yl)pyridin-3-yl)-4-((1R,3R)-3-methoxycyclopentyl)-3,4-dihydropyrazino[2,3-b]pyrazin-2(1H)-one;

6-(6-(2-hydroxypropan-2-yl)pyridin-3-yl)-4-((1R,3 S)-3-methoxycyclopentyl)methyl)-3,4-dihydropyrazino[2,3-b]pyrazin-2(1H)-one;

6-(6-(2-hydroxypropan-2-yl)pyridin-3-yl)-4-((1S,3R)-3-methoxycyclopentyl)methyl)-3,4-dihydropyrazino[2,3-b]pyrazin-2(1H)-one;

6-(3-fluoro-4-(4H-1,2,4-triazol-3-yl)phenyl)-4-(2-methoxyethyl)-3,4-dihydropyrazino[2,3-b]pyrazin-2(1H)-one;

6-(3-fluoro-4-(4H-1,2,4-triazol-3-yl)phenyl)-4-(2-(tetrahydro-2H-pyran-4-yl)ethyl)-3,4-dihydropyrazino[2,3-b]pyrazin-2(1H)-one;

7'-(2-methyl-4-(4H-1,2,4-triazol-3-yl)phenyl)-1'-((tetrahydro-2H-pyran-4-yl)methyl)-1'H-spiro[cyclopentane-1,2'-pyrazino[2,3-b]pyrazin]-3'(4'H)-one;

7'-(2-methyl-4-(4H-1,2,4-triazol-3-yl)phenyl)-1'-((tetrahydro-2H-pyran-4-yl)methyl)-1'H-spiro[cyclobutane-1,2'-pyrazino[2,3-b]pyrazin]-3'(4'H)-one;

4-(cyclopropylmethyl)-6-(6-(2-hydroxypropan-2-yl)pyridin-3-yl)-3,4-dihydropyrazino[2,3-b]pyrazin-2(1H)-one;

7'-(2-methyl-4-(4H-1,2,4-triazol-3-yl)phenyl)-1'H-spiro[cyclopentane-1,2'-pyrazino[2,3-b]pyrazin]-3'(4'H)-one;

7'-(2-methyl-4-(4H-1,2,4-triazol-3-yl)phenyl)-1'H-spiro[cyclobutane-1,2'-pyrazino[2,3-b]pyrazin]-3'(4'H)-one;

7'-(2-methyl-4-(4H-1,2,4-triazol-3-yl)phenyl)-1'H-spiro[cyclopropane-1,2'-pyrazino[2,3-b]pyrazin]-3'(4'H)-one;

(R)-6-(4-(4H-1,2,4-triazol-3-yl)phenyl)-4-((tetrahydrofuran-2-yl)methyl)-3,4-dihydropyrazino[2,3-b]pyrazin-2(1H)-one;

(S)-6-(4-(4H-1,2,4-triazol-3-yl)phenyl)-4-((tetrahydrofuran-2-yl)methyl)-3,4-dihydropyrazino[2,3-b]pyrazin-2(1H)-one;

6-(1H-indazol-5-yl)-4-(2-(tetrahydro-2H-pyran-4-yl)ethyl)-3,4-dihydropyrazino[2,3-b]pyrazin-2(1H)-one;

4-(6-oxo-8-(2-(tetrahydro-2H-pyran-4-yl)ethyl)-5,6,7,8-tetrahydropyrazino[2,3-b]pyrazin-2-yl)benzamide;

4-(2-methoxyethyl)-3,3-dimethyl-6-(2-methyl-4-(4H-1,2,4-triazol-3-yl)phenyl)-3,4-dihydropyrazino[2,3-b]pyrazin-2(1H)-one;

4-ethyl-3,3-dimethyl-6-(2-methyl-4-(4H-1,2,4-triazol-3-yl)phenyl)-3,4-dihydropyrazino[2,3-b]pyrazin-2(1H)-one;

6-(2-methyl-4-(4H-1,2,4-triazol-3-yl)phenyl)-3,4-dihydropyrazino[2,3-b]pyrazin-2(1H)-one;

3,3-dimethyl-6-(2-methyl-6-(4H-1,2,4-triazol-3-yl)pyridin-3-yl)-4-((tetrahydro-2H-pyran-4-yl)methyl)-3,4-dihydropyrazino[2,3-b]pyrazin-2(1H)-one;

(R)-6-(6-(1-hydroxyethyl)pyridin-3-yl)-4-(2-(tetrahydro-2H-pyran-4-yl)ethyl)-3,4-dihydropyrazino[2,3-b]pyrazin-2(1H)-one;

3,3-dimethyl-6-(2-methyl-4-(4H-1,2,4-triazol-3-yl)phenyl)-4-((tetrahydro-2H-pyran-4-yl)methyl)-3,4-dihydropyrazino[2,3-b]pyrazin-2(1H)-one;

6-(6-(2-hydroxypropan-2-yl)-4-methylpyridin-3-yl)-4-(trans-4-methoxycyclohexyl)-3,4-dihydropyrazino[2,3-b]pyrazin-2(1H)-one;

6-(6-(2-hydroxypropan-2-yl)-4-methylpyridin-3-yl)-4-((tetrahydro-2H-pyran-4-yl)methyl)-3,4-dihydropyrazino[2,3-b]pyrazin-2(1H)-one;

3,3-dimethyl-6-(2-methyl-4-(4H-1,2,4-triazol-3-yl)phenyl)-3,4-dihydropyrazino[2,3-b]pyrazin-2(1H)-one;

3,3-dimethyl-6-(2-methyl-6-(4H-1,2,4-triazol-3-yl)pyridin-3-yl)-4-(2-(tetrahydro-2H-pyran-4-yl)ethyl)-3,4-dihydropyrazino[2,3-b]pyrazin-2(1H)-one;

6-(6-(2-hydroxypropan-2-yl)-2-methylpyridin-3-yl)-4-((tetrahydro-2H-pyran-4-yl)methyl)-3,4-dihydropyrazino[2,3-b]pyrazin-2(1H)-one;

6-(6-(2-hydroxypropan-2-yl)-2-methylpyridin-3-yl)-4-(trans-4-methoxycyclohexyl)-3,4-dihydropyrazino[2,3-b]pyrazin-2(1H)-one;

(S)-6-(6-(1-hydroxyethyl)pyridin-3-yl)-4-(2-(tetrahydro-2H-pyran-4-yl)ethyl)-3,4-dihydropyrazino[2,3-b]pyrazin-2(1H)-one;

3,3-dimethyl-6-(2-methyl-4-(4H-1,2,4-triazol-3-yl)phenyl)-4-(2-(tetrahydro-2H-pyran-4-yl)ethyl)-3,4-dihydropyrazino[2,3-b]pyrazin-2(1H)-one;

6-(6-(2-hydroxypropan-2-yl)pyridin-3-yl)-3,3-dimethyl-4-(2-(tetrahydro-2H-pyran-4-yl)ethyl)-3,4-dihydropyrazino[2,3-b]pyrazin-2(1H)-one;

6-(4-(2-hydroxypropan-2-yl)phenyl)-4-(trans-4-methoxycyclohexyl)-3,4-dihydropyrazino[2,3-b]pyrazin-2(1H)-one;

6-(4-(2-hydroxypropan-2-yl)phenyl)-4-((trans-4-methoxycyclohexyl)methyl)-3,4-dihydropyrazino[2,3-b]pyrazin-2(1H)-one;

4-(cis-4-methoxycyclohexyl)-6-(2-methyl-6-(4H-1,2,4-triazol-3-yl)pyridin-3-yl)-3,4-dihydropyrazino[2,3-b]pyrazin-2(1H)-one;

4-(trans-4-methoxycyclohexyl)-6-(2-methyl-6-(4H-1,2,4-triazol-3-yl)pyridin-3-yl)-3,4-dihydropyrazino[2,3-b]pyrazin-2(1H)-one;

6-(4-(2-hydroxypropan-2-yl)phenyl)-4-((tetrahydro-2H-pyran-4-yl)methyl)-3,4-dihydropyrazino[2,3-b]pyrazin-2(1H)-one;

4-(2-methoxyethyl)-6-(2-methyl-6-(4H-1,2,4-triazol-3-yl)pyridin-3-yl)-3,4-dihydropyrazino[2,3-b]pyrazin-2(1H)-one;

9-(6-(4H-1,2,4-triazol-3-yl)-3-pyridyl)-6,11,4a-trihydromorpholino[4,3-e]pyrazino[2,3-b]pyrazin-5-one;

6-(2-methyl-6-(4H-1,2,4-triazol-3-yl)pyridin-3-yl)-4-((tetrahydro-2H-pyran-4-yl)methyl)-3,4-dihydropyrazino[2,3-b]pyrazin-2(1H)-one;

5-(8-(cis-4-methoxycyclohexyl)-6-oxo-5,6,7,8-tetrahydropyrazino[2,3-b]pyrazin-2-yl)-6-methylpicolinonitrile;

6-(6-(4H-1,2,4-triazol-3-yl)pyridin-3-yl)-4-(2-(tetrahydro-2H-pyran-4-yl)ethyl)-3,4-dihydropyrazino[2,3-b]pyrazin-2(1H)-one;

9-(4-(4H-1,2,4-triazol-3-yl)-2-methylphenyl)-3-(2-methoxyacetyl)-6,11,4a-trihydropiperazino[1,2-e]pyrazino[2,3-b]pyrazin-5-one;

9-(4-(4H-1,2,4-triazol-3-yl)-2-methylphenyl)-6,11,4a-trihydropiperazino[1,2-e]pyrazino[2,3-b]pyrazin-5-one;

9-(4-(4H-1,2,4-triazol-3-yl)-2-methylphenyl)-3-(2-methoxyethyl)-6,11,4a-trihydropiperazino[1,2-e]pyrazino[2,3-b]pyrazin-5-one;

4-(cyclopentylmethyl)-6-(2-methyl-6-(4H-1,2,4-triazol-3-yl)pyridin-3-yl)-3,4-dihydropyrazino[2,3-b]pyrazin-2(1H)-one;

9-(6-(4H-1,2,4-triazol-3-yl)-2-methyl-3-pyridyl)-6,11,4a-trihydromorpholino[4,3-e]pyrazino[2,3-b]pyrazin-5-one;

4-(trans-4-hydroxycyclohexyl)-6-(6-(2-hydroxypropan-2-yl)pyridin-3-yl)-3,4-dihydropyrazino[2,3-b]pyrazin-2(1H)-one;

4-(cis-4-hydroxycyclohexyl)-6-(6-(2-hydroxypropan-2-yl)pyridin-3-yl)-3,4-dihydropyrazino[2,3-b]pyrazin-2(1H)-one;

6-(6-(2-hydroxypropan-2-yl)pyridin-3-yl)-4-((tetrahydrofuran-3-yl)methyl)-3,4-dihydropyrazino[2,3-b]pyrazin-2(1H)-one;

4-(cyclopentylmethyl)-6-(6-(2-hydroxypropan-2-yl)pyridin-3-yl)-3,4-dihydropyrazino[2,3-b]pyrazin-2(1H)-one;

6-(6-(2-hydroxypropan-2-yl)pyridin-3-yl)-4-neopentyl-3,4-dihydropyrazino[2,3-b]pyrazin-2(1H)-one;

6-(6-(2-hydroxypropan-2-yl)pyridin-3-yl)-4-isobutyl-3,4-dihydropyrazino[2,3-b]pyrazin-2(1H)-one;

3-methyl-6-(2-methyl-4-(4H-1,2,4-triazol-3-yl)phenyl)-4-(2-(tetrahydro-2H-pyran-4-yl)ethyl)-3,4-dihydropyrazino[2,3-b]pyrazin-2(1H)-one;

6-(6-(2-hydroxypropan-2-yl)pyridin-3-yl)-4-(piperidin-4-yl)-3,4-dihydropyrazino[2,3-b]pyrazin-2(1H)-one;

6-(6-(2-hydroxypropan-2-yl)pyridin-3-yl)-4-(2-(tetrahydro-2H-pyran-3-yl)ethyl)-3,4-dihydropyrazino[2,3-b]pyrazin-2(1H)-one;

8-(4-(4H-1,2,4-triazol-3-yl)-2-methylphenyl)(3 aS,2R)-2-methoxy-5,10,3a-trihydropyrazino[2,3-b]pyrrolidino[1,2-e]pyrazin-4-one;

8-(4-(4H-1,2,4-triazol-3-yl)-2-methylphenyl)(2R,3 aR)-2-methoxy-5,10,3a-trihydropyrazino[2,3-b]pyrrolidino[1,2-e]pyrazin-4-one;

8-(4-(4H-1,2,4-triazol-3-yl)-2-methylphenyl)(2S,3 aR)-2-methoxy-5,10,3a-trihydropyrazino[2,3-b]pyrrolidino[1,2-e]pyrazin-4-one;

8-(4-(4H-1,2,4-triazol-3-yl)-2-methylphenyl)(2S,3 aS)-2-methoxy-5,10,3a-trihydropyrazino[2,3-b]pyrrolidino[1,2-e]pyrazin-4-one;

6-(6-(2-hydroxypropan-2-yl)pyridin-3-yl)-4-(3-methoxypropyl)-3,4-dihydropyrazino[2,3-b]pyrazin-2(1H)-one;

(S)-6-(6-(2-hydroxypropan-2-yl)pyridin-3-yl)-4-((tetrahydrofuran-2-yl)methyl)-3,4-dihydropyrazino[2,3-b]pyrazin-2(1H)-one;

(R)-6-(6-(2-hydroxypropan-2-yl)pyridin-3-yl)-4-((tetrahydrofuran-2-yl)methyl)-3,4-dihydropyrazino[2,3-b]pyrazin-2(1H)-one;

6-(2-methyl-6-(4H-1,2,4-triazol-3-yl)pyridin-3-yl)-4-(2-(tetrahydro-2H-pyran-4-yl)ethyl)-3,4-dihydropyrazino[2,3-b]pyrazin-2(1H)-one;

9-(4-(4H-1,2,4-triazol-3-yl)-2-methylphenyl)-3-methyl-6,11,4a-trihydropiperazino[1,2-e]pyrazino[2,3-b]pyrazin-5-one;

9-(4-(4H-1,2,4-triazol-3-yl)phenyl)-6,11,4a-trihydromorpholino[4,3-e]pyrazino[2,3-b]pyrazin-5-one;

9-(4-(4H-1,2,4-triazol-3-yl)-2-methylphenyl)-6,11,4a-trihydropiperidino[1,2-e]pyrazino[2,3-b]pyrazin-5-one;

6-(6-(2-hydroxypropan-2-yl)pyridin-3-yl)-4-(trans-4-methoxycyclohexyl)-3,4-dihydropyrazino[2,3-b]pyrazin-2(1H)-one;

6-(6-(2-hydroxypropan-2-yl)pyridin-3-yl)-4-(cis-4-methoxycyclohexyl)-3,4-dihydropyrazino[2,3-b]pyrazin-2(1H)-one;

6-(6-(2-hydroxypropan-2-yl)pyridin-3-yl)-4-(2-morpholinoethyl)-3,4-dihydropyrazino[2,3-b]pyrazin-2(1H)-one;

6-(6-(2-hydroxypropan-2-yl)pyridin-3-yl)-4-phenethyl-3,4-dihydropyrazino[2,3-b]pyrazin-2(1H)-one;

6-(6-(2-hydroxypropan-2-yl)pyridin-3-yl)-4-(tetrahydro-2H-pyran-4-yl)-3,4-dihydropyrazino[2,3-b]pyrazin-2(1H)-one;

4-(cyclohexylmethyl)-6-(6-(2-hydroxypropan-2-yl)pyridin-3-yl)-3,4-dihydropyrazino[2,3-b]pyrazin-2(1H)-one;

6-(6-(2-hydroxypropan-2-yl)pyridin-3-yl)-4-((trans-4-methoxycyclohexyl)methyl)-3,4-dihydropyrazino[2,3-b]pyrazin-2(1H)-one;

6-(6-(2-hydroxypropan-2-yl)pyridin-3-yl)-4-((cis-4-methoxycyclohexyl)methyl)-3,4-dihydropyrazino[2,3-b]pyrazin-2(1H)-one;

(R)-6-(6-(2-hydroxypropan-2-yl)pyridin-3-yl)-4-(tetrahydrofuran-3-yl)-3,4-dihydropyrazino[2,3-b]pyrazin-2(1H)-one;

(S)-6-(6-(2-hydroxypropan-2-yl)pyridin-3-yl)-4-(tetrahydrofuran-3-yl)-3,4-dihydropyrazino[2,3-b]pyrazin-2(1H)-one;

6-(6-(2-hydroxypropan-2-yl)pyridin-3-yl)-4-phenyl-3,4-dihydropyrazino[2,3-b]pyrazin-2(1H)-one;

(S)-6-(6-(2-hydroxypropan-2-yl)pyridin-3-yl)-3-methyl-4-(2-(tetrahydro-2H-pyran-4-yl)ethyl)-3,4-dihydropyrazino[2,3-b]pyrazin-2(1H)-one;

9-[6-(1-hydroxy-isopropyl)-3-pyridyl]-6,11,4a-trihydromorpholino[4,3-e]pyrazino[2,3-b]pyrazin-5-one;

6-(6-(2-hydroxypropan-2-yl)pyridin-3-yl)-4-((tetrahydro-2H-pyran-4-yl)methyl)-3,4-dihydropyrazino[2,3-b]pyrazin-2(1H)-one;

6-(6-(2-hydroxypropan-2-yl)pyridin-3-yl)-4-(2-methoxyethyl)-3,4-dihydropyrazino[2,3-b]pyrazin-2(1H)-one;

6-(2-amino-7-methyl-1H-benzo[d]imidazol-5-yl)-4-(3-(trifluoromethyl)benzyl)-3,4-dihydropyrazino[2,3-b]pyrazin-2(1H)-one;

6-(6-(2-hydroxypropan-2-yl)pyridin-3-yl)-4-(3-(trifluoromethyl)benzyl)-3,4-dihydropyrazino[2,3-b]pyrazin-2(1H)-one;

9-(4-(4H-1,2,4-triazol-3-yl)-2-methylphenyl)-6,11,4a-trihydromorpholino[4,3-e]pyrazino[2,3-b]pyrazin-5-one;

6-(4-methyl-2-(methylamino)-1H-benzo[d]imidazol-6-yl)-4-(2-(tetrahydro-2H-pyran-4-yl)ethyl)-3,4-dihydropyrazino[2,3-b]pyrazin-2(1H)-one;

8-(4-(4H-1,2,4-triazol-3-yl)-2-methylphenyl)-5,10,3a-trihydropyrazino[2,3-b]pyrrolidino[1,2-e]pyrazin-4-one;

6-(4-(4H-1,2,4-triazol-3-yl)phenyl)-4-ethyl-3,4-dihydropyrazino[2,3-b]pyrazin-2(1H)-one;

6-(4-(4H-1,2,4-triazol-3-yl)phenyl)-4-((tetrahydro-2H-pyran-4-yl)methyl)-3,4-dihydropyrazino[2,3-b]pyrazin-2(1H)-one;

6-(6-(2-hydroxypropan-2-yl)pyridin-3-yl)-4-(2-(tetrahydro-2H-pyran-4-yl)ethyl)-3,4-dihydropyrazino[2,3-b]pyrazin-2(1H)-one;

6-(4-(4H-1,2,4-triazol-3-yl)phenyl)-4-(2-methoxyethyl)-3,4-dihydropyrazino[2,3-b]pyrazin-2(1H)-one;

6-(4-(4H-1,2,4-triazol-3-yl)phenyl)-4-(3-(trifluoromethyl)benzyl)-3,4-dihydropyrazino[2,3-b]pyrazin-2(1H)-one;

6-(2-methyl-4-(4H-1,2,4-triazol-3-yl)phenyl)-4-(2-(tetrahydro-2H-pyran-4-yl)ethyl)-3,4-dihydropyrazino[2,3-b]pyrazin-2(1H)-one;

6-(4-methyl-1H-benzo[d]imidazol-6-yl)-4-(2-(tetrahydro-2H-pyran-4-yl)ethyl)-3,4-dihydropyrazino[2,3-b]pyrazin-2(1H)-one;

6-(4-(2-hydroxypropan-2-yl)phenyl)-4-(2-(tetrahydro-2H-pyran-4-yl)ethyl)-3,4-dihydropyrazino[2,3-b]pyrazin-2(1H)-one; and 6-(4-(1H-1,2,4-triazol-5-yl)phenyl)-4-(2-(tetrahydro-2H-pyran-4-yl)ethyl)-3,4-dihydropyrazino[2,3-b]pyrazin-2(1H)-one, and pharmaceutically acceptable salts, clathrates, solvates, stereoisomers, tautomers, and prodrugs thereof.

In one embodiment, the TOR kinase inhibitors include compounds having the following formula (IV):

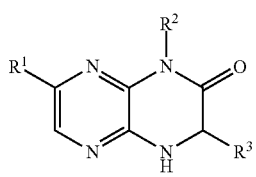

and pharmaceutically acceptable salts, clathrates, solvates, stereoisomers, tautomers, and prodrugs thereof, wherein:

$R^1$ is substituted or unsubstituted $C_{1-8}$ alkyl, substituted or unsubstituted aryl, substituted or unsubstituted cycloalkyl, substituted or unsubstituted heterocyclyl, or substituted or unsubstituted heterocyclylalkyl;

$R^2$ is H, substituted or unsubstituted $C_{1-8}$ alkyl, substituted or unsubstituted cycloalkyl, substituted or unsubstituted heterocyclyl, substituted or unsubstituted heterocyclylalkyl, substituted or unsubstituted aralkyl, or substituted or unsubstituted cycloalkylalkyl;

$R^3$ is H, or a substituted or unsubstituted $C_{1-8}$ alkyl, wherein in certain embodiments, the TOR kinase inhibitors do not include 7-(4-hydroxyphenyl)-1-(3-methoxybenzyl)-3,4-dihydropyrazino[2,3-b]pyrazin-2(1H)-one, depicted below:

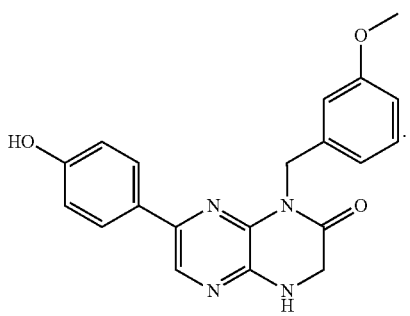 [SMILES: COc1cccc(CN2C(=O)CNc3ncc(-c4ccc(O)cc4)nc32)c1]

In some embodiments of compounds of formula (IV), $R^1$ is substituted or unsubstituted aryl or substituted or unsubstituted heteroaryl. For example, $R^1$ is phenyl, pyridyl, pyrimidyl, benzimidazolyl, 1H-pyrrolo[2,3-b]pyridyl, indazolyl, indolyl, 1H-imidazo[4,5-b]pyridyl, 1H-imidazo[4,5-b]pyridin-2(3H)-onyl, 3H-imidazo[4,5-b]pyridyl, or pyrazolyl, each optionally substituted. In some embodiments, $R^1$ is phenyl substituted with one or more substituents independently selected from the group consisting of substituted or unsubstituted $C_{1-8}$ alkyl (for example, methyl), substituted or unsubstituted heterocyclyl (for example, a substituted or unsubstituted triazolyl or pyrazolyl), aminocarbonyl, halogen (for example, fluorine), cyano, hydroxyalkyl and hydroxy. In other embodiments, $R^1$ is pyridyl substituted with one or more substituents independently selected from the group consisting of substituted or unsubstituted $C_{1-8}$ alkyl (for example, methyl), substituted or unsubstituted heterocyclyl (for example, a substituted or unsubstituted triazolyl), halogen, aminocarbonyl, cyano, hydroxyalkyl (for example, hydroxypropyl), —OR, and —$NR_2$, wherein each R is independently H, or a substituted or unsubstituted $C_{1-4}$ alkyl. In some embodiments, $R^1$ is 1H-pyrrolo[2,3-b]pyridyl or benzimidazolyl, optionally substituted with one or more substituents independently selected from the group consisting of substituted or unsubstituted $C_{1-8}$ alkyl, and —$NR_2$, wherein R is independently H, or a substituted or unsubstituted $C_{1-4}$ alkyl.

In some embodiments, $R^1$ is

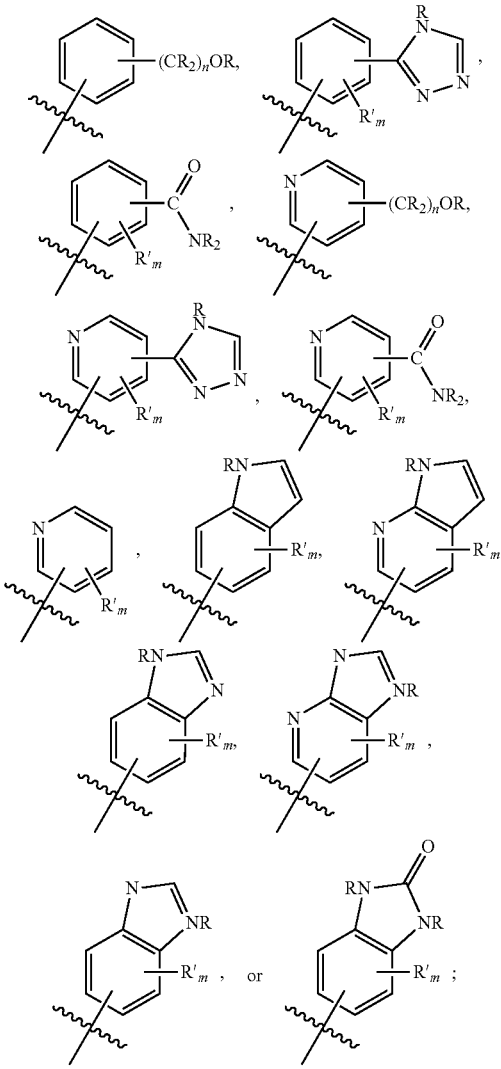

wherein R is at each occurrence independently H, or a substituted or unsubstituted $C_{1-4}$ alkyl (for example, methyl); R' is at each occurrence independently a substituted or unsubstituted $C_{1-4}$ alkyl (for example, methyl), halogen (for example, fluoro), cyano, —OR, or —$NR_2$; m is 0-3; and n is 0-3. It will be understood by those skilled in the art that any of the substitutents R' may be attached to any suitable atom of any of the rings in the fused ring systems.

In some embodiments of compounds of formula (IV), $R^1$ is

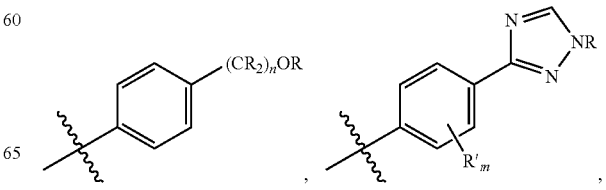

-continued

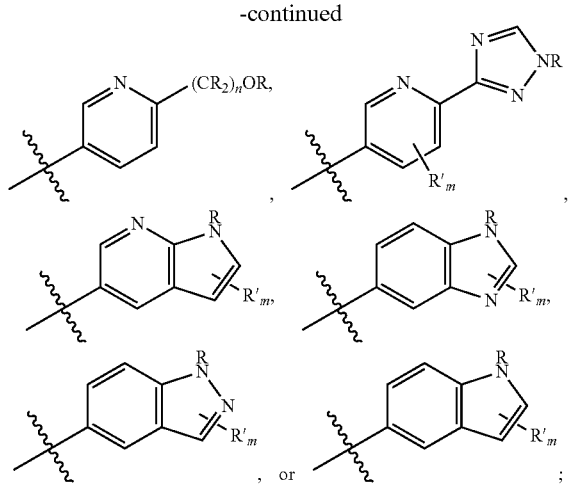

wherein R is at each occurrence independently H, or a substituted or unsubstituted $C_{1-4}$ alkyl; R' is at each occurrence independently a substituted or unsubstituted $C_{1-4}$ alkyl, halogen, cyano, —OR or —NR$_2$; m is 0-3; and n is 0-3.

In some embodiments of compounds of formula (IV), R$^2$ is H, substituted or unsubstituted $C_{1-8}$ alkyl, substituted or unsubstituted cycloalkyl, substituted or unsubstituted heterocyclyl, substituted or unsubstituted $C_{1-4}$ alkyl-heterocyclyl, substituted or unsubstituted $C_{1-4}$ alkyl-aryl, or substituted or unsubstituted $C_{1-4}$ alkyl-cycloalkyl. For example, R$^2$ is H, methyl, ethyl, n-propyl, isopropyl, n-butyl, sec-butyl, isobutyl, tert-butyl, n-pentyl, isopentyl, cyclopentyl, cyclohexyl, tetrahydrofuranyl, tetrahydropyranyl, ($C_{1-4}$ alkyl)-phenyl, ($C_{1-4}$ alkyl)-cyclopropyl, ($C_{1-4}$ alkyl)-cyclobutyl, ($C_{1-4}$ alkyl)-cyclopentyl, ($C_{1-4}$ alkyl)-cyclohexyl, ($C_{1-4}$ alkyl)-pyrrolidyl, ($C_{1-4}$ alkyl)-piperidyl, ($C_{1-4}$ alkyl)-piperazinyl, ($C_{1-4}$ alkyl)-morpholinyl, ($C_{1-4}$ alkyl)-tetrahydrofuranyl, or ($C_{1-4}$ alkyl)-tetrahydropyranyl, each optionally substituted.

In other embodiments, R$^2$ is H, $C_{1-4}$ alkyl, ($C_{1-4}$alkyl)(OR),

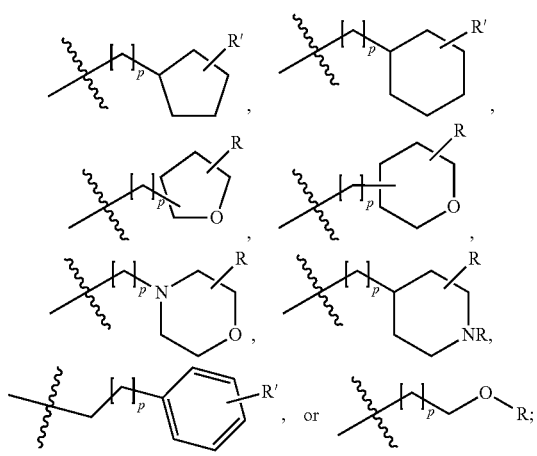

wherein R is at each occurrence independently H, or a substituted or unsubstituted $C_{1-4}$ alkyl (for example, methyl); R' is at each occurrence independently H, —OR, cyano, or a substituted or unsubstituted $C_{1-4}$ alkyl (for example, methyl); and p is 0-3.

In other embodiments of compounds of formula (IV), R$^2$ is H, $C_{1-4}$ alkyl, ($C_{1-4}$alkyl)(OR),

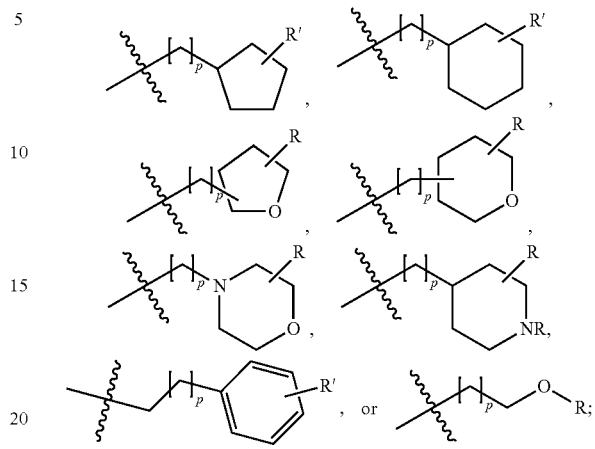

wherein R is at each occurrence independently H, or a substituted or unsubstituted $C_{1-2}$ alkyl; R' is at each occurrence independently H, —OR, cyano, or a substituted or unsubstituted $C_{1-2}$ alkyl; and p is 0-1.

In other embodiments of compounds of formula (IV), R$^3$ is H.

In some such embodiments described herein, R$^1$ is substituted or unsubstituted aryl, or substituted or unsubstituted heteroaryl. For example, R$^1$ is phenyl, pyridyl, pyrimidyl, benzimidazolyl, 1H-pyrrolo[2,3-b]pyridyl, indazolyl, indolyl, 1H-imidazo[4,5-b]pyridine, pyridyl, 1H-imidazo[4,5-b]pyridin-2(3H)-onyl, 3H-imidazo[4,5-b]pyridyl, or pyrazolyl, each optionally substituted. In some embodiments, R$^1$ is phenyl substituted with one or more substituents independently selected from the group consisting of substituted or unsubstituted $C_{1-8}$ alkyl, substituted or unsubstituted heterocyclyl, aminocarbonyl, halogen, cyano, hydroxyalkyl and hydroxy. In others, R$^1$ is pyridyl substituted with one or more substituents independently selected from the group consisting of $C_{1-8}$ alkyl, substituted or unsubstituted heterocyclyl, halogen, aminocarbonyl, cyano, hydroxyalkyl, —OR, and —NR$_2$, wherein each R is independently H, or a substituted or unsubstituted $C_{1-4}$ alkyl. In still others, R$^1$ is 1H-pyrrolo[2,3-b]pyridyl or benzimidazolyl, optionally substituted with one or more substituents independently selected from the group consisting of substituted or unsubstituted $C_{1-8}$ alkyl, and —NR$_2$, wherein R is independently H, or a substituted or unsubstituted $C_{1-4}$ alkyl.

In certain embodiments, the compounds of formula (IV) have an R$^1$ group set forth herein and an R$^2$ group set forth herein.

In some embodiments of compounds of formula (IV), the compound at a concentration of 10 μM inhibits mTOR, DNA-PK, PI3K, or a combination thereof by at least about 50%. Compounds of formula (IV) may be shown to be inhibitors of the kinases above in any suitable assay system.

Representative TOR kinase inhibitors of formula (IV) include compounds from Table D.

Table D.

7-(5-fluoro-2-methyl-4-(1H-1,2,4-triazol-3-yl)phenyl)-1-(((trans-4-methoxycyclohexyl)methyl)-3,4-dihydropyrazino[2,3-b]pyrazin-2(1H)-one;

7-(6-(1H-1,2,4-triazol-3-yl)pyridin-3-yl)-1-(cis-4-methoxycyclohexyl)-3,4-dihydropyrazino[2,3-b]pyrazin-2(1H)-one;

7-(1H-pyrrolo[2,3-b]pyridin-3-yl)-1-(2-(tetrahydro-2H-pyran-4-yl)ethyl)-3,4-dihydropyrazino[2,3-b]pyrazin-2(1H)-one;

7-(5-fluoro-2-methyl-4-(1H-1,2,4-triazol-3-yl)phenyl)-1-((cis-4-methoxycyclohexyl)methyl)-3,4-dihydropyrazino[2,3-b]pyrazin-2(1H)-one;

1-ethyl-7-(1H-pyrrolo[3,2-b]pyridin-5-yl)-3,4-dihydropyrazino[2,3-b]pyrazin-2(1H)-one;

7-(6-(1H-1,2,4-triazol-3-yl)pyridin-3-yl)-1-((cis-4-methoxycyclohexyl)methyl)-3,4-dihydropyrazino[2,3-b]pyrazin-2(1H)-one;

7-(1H-benzo[d]imidazol-4-yl)-1-(2-(tetrahydro-2H-pyran-4-yl)ethyl)-3,4-dihydropyrazino[2,3-b]pyrazin-2(1H)-one;

7-(1H-pyrrolo[2,3-b]pyridin-4-yl)-1-(2-(tetrahydro-2H-pyran-4-yl)ethyl)-3,4-dihydropyrazino[2,3-b]pyrazin-2(1H)-one;

7-(6-(1H-1,2,4-triazol-3-yl)pyridin-3-yl)-1-((trans-4-methoxycyclohexyl)methyl)-3,4-dihydropyrazino[2,3-b]pyrazin-2(1H)-one;

7-(6-(1H-1,2,4-triazol-3-yl)pyridin-3-yl)-1-((trans-4-hydroxycyclohexyl)methyl)-3,4-dihydropyrazino[2,3-b]pyrazin-2(1H)-one;

7-(6-(1H-1,2,4-triazol-3-yl)pyridin-3-yl)-1-(cis-4-hydroxycyclohexyl)-3,4-dihydropyrazino[2,3-b]pyrazin-2(1H)-one;

7-(5-fluoro-2-methyl-4-(1H-1,2,4-triazol-3-yl)phenyl)-1-(cis-4-hydroxycyclohexyl)-3,4-dihydropyrazino[2,3-b]pyrazin-2(1H)-one;

7-(6-(1H-1,2,4-triazol-3-yl)pyridin-3-yl)-1-(tetrahydro-2H-pyran-4-yl)-3,4-dihydropyrazino[2,3-b]pyrazin-2(1H)-one;

7-(6-(1H-1,2,4-triazol-3-yl)pyridin-3-yl)-1-(2-methoxyethyl)-3,4-dihydropyrazino[2,3-b]pyrazin-2(1H)-one;

7-(6-(1H-1,2,4-triazol-3-yl)pyridin-3-yl)-1-ethyl-3,4-dihydropyrazino[2,3-b]pyrazin-2(1H)-one;

7-(5-fluoro-2-methyl-4-(1H-1,2,4-triazol-3-yl)phenyl)-1-((cis-4-hydroxycyclohexyl)methyl)-3,4-dihydropyrazino[2,3-b]pyrazin-2(1H)-one;

7-(5-fluoro-2-methyl-4-(1H-1,2,4-triazol-3-yl)phenyl)-1-(tetrahydro-2H-pyran-4-yl)-3,4-dihydropyrazino[2,3-b]pyrazin-2(1H)-one;

7-(1H-indol-4-yl)-1-(2-(tetrahydro-2H-pyran-4-yl)ethyl)-3,4-dihydropyrazino[2,3-b]pyrazin-2(1H)-one;

7-(5-fluoro-2-methyl-4-(1H-1,2,4-triazol-3-yl)phenyl)-1-((trans-4-hydroxycyclohexyl)methyl)-3,4-dihydropyrazino[2,3-b]pyrazin-2(1H)-one;

7-(6-(1H-1,2,4-triazol-3-yl)pyridin-3-yl)-1-((cis-4-hydroxycyclohexyl)methyl)-3,4-dihydropyrazino[2,3-b]pyrazin-2(1H)-one;

7-(6-(1H-1,2,4-triazol-3-yl)pyridin-3-yl)-1-(trans-4-hydroxycyclohexyl)-3,4-dihydropyrazino[2,3-b]pyrazin-2(1H)-one;

7-(6-(1H-1,2,4-triazol-3-yl)pyridin-3-yl)-1-(trans-4-methoxycyclohexyl)-3,4-dihydropyrazino[2,3-b]pyrazin-2(1H)-one;

7-(6-(1H-1,2,4-triazol-3-yl)pyridin-3-yl)-1-isopropyl-3,4-dihydropyrazino[2,3-b]pyrazin-2(1H)-one;

7-(5-fluoro-2-methyl-4-(1H-1,2,4-triazol-3-yl)phenyl)-1-(trans-4-methoxycyclohexyl)-3,4-dihydropyrazino[2,3-b]pyrazin-2(1H)-one;

7-(5-fluoro-2-methyl-4-(1H-1,2,4-triazol-3-yl)phenyl)-1-(trans-4-hydroxycyclohexyl)-3,4-dihydropyrazino[2,3-b]pyrazin-2(1H)-one;

7-(5-fluoro-2-methyl-4-(1H-1,2,4-triazol-3-yl)phenyl)-1-(2-methoxyethyl)-3,4-dihydropyrazino[2,3-b]pyrazin-2(1H)-one;

7-(5-fluoro-2-methyl-4-(1H-1,2,4-triazol-3-yl)phenyl)-1-isopropyl-3,4-dihydropyrazino[2,3-b]pyrazin-2(1H)-one;

1-ethyl-7-(5-fluoro-2-methyl-4-(1H-1,2,4-triazol-3-yl)phenyl)-3,4-dihydropyrazino[2,3-b]pyrazin-2(1H)-one;

7-(2-hydroxypyridin-4-yl)-1-(2-(tetrahydro-2H-pyran-4-yl)ethyl)-3,4-dihydropyrazino[2,3-b]pyrazin-2(1H)-one;

1-isopropyl-7-(4-methyl-6-(1H-1,2,4-triazol-3-yl)pyridin-3-yl)-3,4-dihydropyrazino[2,3-b]pyrazin-2(1H)-one;

5-(8-isopropyl-7-oxo-5,6,7,8-tetrahydropyrazino[2,3-b]pyrazin-2-yl)-4-methylpicolinamide;

7-(1H-indazol-4-yl)-1-(2-(tetrahydro-2H-pyran-4-yl)ethyl)-3,4-dihydropyrazino[2,3-b]pyrazin-2(1H)-one;

7-(2-aminopyrimidin-5-yl)-1-(2-(tetrahydro-2H-pyran-4-yl)ethyl)-3,4-dihydropyrazino[2,3-b]pyrazin-2(1H)-one;

7-(2-aminopyridin-4-yl)-1-(2-(tetrahydro-2H-pyran-4-yl)ethyl)-3,4-dihydropyrazino[2,3-b]pyrazin-2(1H)-one;

7-(6-(methylamino)pyridin-3-yl)-1-(2-(tetrahydro-2H-pyran-4-yl)ethyl)-3,4-dihydropyrazino[2,3-b]pyrazin-2(1H)-one;

7-(6-hydroxypyridin-3-yl)-1-(2-(tetrahydro-2H-pyran-4-yl)ethyl)-3,4-dihydropyrazino[2,3-b]pyrazin-2(1H)-one;

7-(4-(1H-pyrazol-3-yl)phenyl)-1-(2-methoxyethyl)-3,4-dihydropyrazino[2,3-b]pyrazin-2(1H)-one;

7-(pyridin-3-yl)-1-(2-(tetrahydro-2H-pyran-4-yl)ethyl)-3,4-dihydropyrazino[2,3-b]pyrazin-2(1H)-one;

7-(1H-indazol-4-yl)-1-(2-methoxyethyl)-3,4-dihydropyrazino[2,3-b]pyrazin-2(1H)-one;

7-(1H-indazol-6-yl)-1-(2-methoxyethyl)-3,4-dihydropyrazino[2,3-b]pyrazin-2(1H)-one;

7-(pyrimidin-5-yl)-1-(2-(tetrahydro-2H-pyran-4-yl)ethyl)-3,4-dihydropyrazino[2,3-b]pyrazin-2(1H)-one;

7-(6-methoxypyridin-3-yl)-1-(2-(tetrahydro-2H-pyran-4-yl)ethyl)-3,4-dihydropyrazino[2,3-b]pyrazin-2(1H)-one;

1-(2-methoxyethyl)-7-(1H-pyrrolo[2,3-b]pyridin-5-yl)-3,4-dihydropyrazino[2,3-b]pyrazin-2(1H)-one;

1-ethyl-7-(1H-pyrrolo[2,3-b]pyridin-5-yl)-3,4-dihydropyrazino[2,3-b]pyrazin-2(1H)-one;

1-ethyl-7-(1H-indazol-4-yl)-3,4-dihydropyrazino[2,3-b]pyrazin-2(1H)-one;

7-(pyridin-4-yl)-1-(2-(tetrahydro-2H-pyran-4-yl)ethyl)-3,4-dihydropyrazino[2,3-b]pyrazin-2(1H)-one;

7-(6-aminopyridin-3-yl)-1-(2-(tetrahydro-2H-pyran-4-yl)ethyl)-3,4-dihydropyrazino[2,3-b]pyrazin-2(1H)-one;

1-methyl-7-(2-methyl-6-(4H-1,2,4-triazol-3-yl)pyridin-3-yl)-3,4-dihydropyrazino[2,3-b]pyrazin-2(1H)-one;

2-(2-hydroxypropan-2-yl)-5-(8-(trans-4-methoxycyclohexyl)-7-oxo-5,6,7,8-tetrahydropyrazino[2,3-b]pyrazin-2-yl)pyridine 1-oxide;

4-methyl-5-(7-oxo-8-((tetrahydro-2H-pyran-4-yl)methyl)-5,6,7,8-tetrahydropyrazino[2,3-b]pyrazin-2-yl)picolinamide;

5-(8-((cis-4-methoxycyclohexyl)methyl)-7-oxo-5,6,7,8-tetrahydropyrazino[2,3-b]pyrazin-2-yl)-4-methylpicolinamide;

7-(1H-pyrazol-4-yl)-1-(2-(tetrahydro-2H-pyran-4-yl)ethyl)-3,4-dihydropyrazino[2,3-b]pyrazin-2(1H)-one;

1-(trans-4-methoxycyclohexyl)-7-(4-methyl-6-(1H-1,2,4-triazol-3-yl)pyridin-3-yl)-3,4-dihydropyrazino[2,3-b]pyrazin-2(1H)-one;

3-((7-(2-methyl-6-(4H-1,2,4-triazol-3-yl)pyridin-3-yl)-2-oxo-3,4-dihydropyrazino[2,3-b]pyrazin-1(2H)-yl)methyl)benzonitrile;

1-((trans-4-methoxycyclohexyl)methyl)-7-(4-methyl-6-(1H-1,2,4-triazol-3-yl)pyridin-3-yl)-3,4-dihydropyrazino[2,3-b]pyrazin-2(1H)-one;

3-(7-oxo-8-(2-(tetrahydro-2H-pyran-4-yl)ethyl)-5,6,7,8-tetrahydropyrazino[2,3-b]pyrazin-2-yl)benzamide;

5-(8-((trans-4-methoxycyclohexyl)methyl)-7-oxo-5,6,7,8-tetrahydropyrazino[2,3-b]pyrazin-2-yl)-4-methylpicolinamide;

3-((7-(6-(2-hydroxypropan-2-yl)pyridin-3-yl)-2-oxo-3,4-dihydropyrazino[2,3-b]pyrazin-1 (2H)-yl)methyl)benzonitrile;

7-(6-(2-hydroxypropan-2-yl)pyridin-3-yl)-1-((1R,3R)-3-methoxycyclopentyl)-3,4-dihydropyrazino[2,3-b]pyrazin-2(1H)-one;

7-(6-(2-hydroxypropan-2-yl)pyridin-3-yl)-1-((1S,3R)-3-methoxycyclopentyl)-3,4-dihydropyrazino[2,3-b]pyrazin-2(1H)-one;

7-(6-(2-hydroxypropan-2-yl)pyridin-3-yl)-1-((1S,3 S)-3-methoxycyclopentyl)-3,4-dihydropyrazino[2,3-b]pyrazin-2(1H)-one;

7-(6-(2-hydroxypropan-2-yl)pyridin-3-yl)-1-((1R,3 S)-3-methoxycyclopentyl)-3,4-dihydropyrazino[2,3-b]pyrazin-2(1H)-one;

7-(1H-indazol-6-yl)-1-(2-(tetrahydro-2H-pyran-4-yl)ethyl)-3,4-dihydropyrazino[2,3-b]pyrazin-2(1H)-one;

7-(2-methyl-6-(4H-1,2,4-triazol-3-yl)pyridin-3-yl)-1-(2-morpholinoethyl)-3,4-dihydropyrazino[2,3-b]pyrazin-2(1H)-one;

1-(trans-4-hydroxycyclohexyl)-7-(2-methyl-6-(4H-1,2,4-triazol-3-yl)pyridin-3-yl)-3,4-dihydropyrazino[2,3-b]pyrazin-2(1H)-one;

1-(cis-4-hydroxycyclohexyl)-7-(2-methyl-6-(4H-1,2,4-triazol-3-yl)pyridin-3-yl)-3,4-dihydropyrazino[2,3-b]pyrazin-2(1H)-one;

7-(6-(2-hydroxypropan-2-yl)pyridin-3-yl)-1-(2-morpholinoethyl)-3,4-dihydropyrazino[2,3-b]pyrazin-2(1H)-one;

1-isopropyl-7-(2-methyl-6-(4H-1,2,4-triazol-3-yl)pyridin-3-yl)-3,4-dihydropyrazino[2,3-b]pyrazin-2(1H)-one;

7-(1H-imidazo[4,5-b]pyridin-6-yl)-1-(2-(tetrahydro-2H-pyran-4-yl)ethyl)-3,4-dihydropyrazino[2,3-b]pyrazin-2(1H)-one;

1-((cis-4-methoxycyclohexyl)methyl)-7-(2-methyl-6-(1H-1,2,4-triazol-3-yl)pyridin-3-yl)-3,4-dihydropyrazino[2,3-b]pyrazin-2(1H)-one;

1-(trans-4-hydroxycyclohexyl)-7-(6-(2-hydroxypropan-2-yl)pyridin-3-yl)-3,4-dihydropyrazino[2,3-b]pyrazin-2(1H)-one;

1-(cis-4-hydroxycyclohexyl)-7-(6-(2-hydroxypropan-2-yl)pyridin-3-yl)-3,4-dihydropyrazino[2,3-b]pyrazin-2(1H)-one;

4-(7-oxo-8-(2-(tetrahydro-2H-pyran-4-yl)ethyl)-5,6,7,8-tetrahydropyrazino[2,3-b]pyrazin-2-yl)benzamide;

7-(1H-indazol-5-yl)-1-(2-(tetrahydro-2H-pyran-4-yl)ethyl)-3,4-dihydropyrazino[2,3-b]pyrazin-2(1H)-one;

7-(1H-pyrrolo[2,3-b]pyridin-5-yl)-1-(2-(tetrahydro-2H-pyran-4-yl)ethyl)-3,4-dihydropyrazino[2,3-b]pyrazin-2(1H)-one;

7-(2-methyl-6-(4H-1,2,4-triazol-3-yl)pyridin-3-yl)-1-(tetrahydro-2H-pyran-4-yl)-3,4-dihydropyrazino[2,3-b]pyrazin-2(1H)-one;

1-((1S,3R)-3-methoxycyclopentyl)-7-(2-methyl-6-(4H-1,2,4-triazol-3-yl)pyridin-3-yl)-3,4-dihydropyrazino[2,3-b]pyrazin-2(1H)-one;

1-((1R,3R)-3-methoxycyclopentyl)-7-(2-methyl-6-(4H-1,2,4-triazol-3-yl)pyridin-3-yl)-3,4-dihydropyrazino[2,3-b]pyrazin-2(1H)-one;

1-((1R,3S)-3-methoxycyclopentyl)-7-(2-methyl-6-(4H-1,2,4-triazol-3-yl)pyridin-3-yl)-3,4-dihydropyrazino[2,3-b]pyrazin-2(1H)-one;

1-((1S,3S)-3-methoxycyclopentyl)-7-(2-methyl-6-(4H-1,2,4-triazol-3-yl)pyridin-3-yl)-3,4-dihydropyrazino[2,3-b]pyrazin-2(1H)-one;

7-(1H-indol-5-yl)-1-(2-(tetrahydro-2H-pyran-4-yl)ethyl)-3,4-dihydropyrazino[2,3-b]pyrazin-2(1H)-one;

1-ethyl-7-(2-methyl-6-(4H-1,2,4-triazol-3-yl)pyridin-3-yl)-3,4-dihydropyrazino[2,3-b]pyrazin-2(1H)-one;

7-(1H-indol-6-yl)-1-(2-(tetrahydro-2H-pyran-4-yl)ethyl)-3,4-dihydropyrazino[2,3-b]pyrazin-2(1H)-one;

7-(4-(2-hydroxypropan-2-yl)phenyl)-1-(trans-4-methoxycyclohexyl)-3,4-dihydropyrazino[2,3-b]pyrazin-2(1H)-one;

7-(6-(2-hydroxypropan-2-yl)pyridin-3-yl)-1-(tetrahydro-2H-pyran-4-yl)-3,4-dihydropyrazino[2,3-b]pyrazin-2(1H)-one;

1-((trans-4-methoxycyclohexyl)methyl)-7-(2-methyl-6-(1H-1,2,4-triazol-3-yl)pyridin-3-yl)-3,4-dihydropyrazino[2,3-b]pyrazin-2(1H)-one;

7-(6-(2-hydroxypropan-2-yl)pyridin-3-yl)-1-((cis-4-methoxycyclohexyl)methyl)-3,4-dihydropyrazino[2,3-b]pyrazin-2(1H)-one;

1-(2-methoxyethyl)-7-(4-methyl-2-(methylamino)-1H-benzo[d]imidazol-6-yl)-3,4-dihydropyrazino[2,3-b]pyrazin-2(1H)-one;

7-(7-methyl-2-oxo-2,3-dihydro-1H-benzo[d]imidazol-5-yl)-1-((tetrahydro-2H-pyran-4-yl)methyl)-3,4-dihydropyrazino[2,3-b]pyrazin-2(1H)-one;

7-(2-methyl-4-(4H-1,2,4-triazol-3-yl)phenyl)-3,4-dihydropyrazino[2,3-b]pyrazin-2(1H)-one;

1-(2-methoxyethyl)-7-(4-methyl-6-(1H-1,2,4-triazol-3-yl)pyridin-3-yl)-3,4-dihydropyrazino[2,3-b]pyrazin-2(1H)-one;

1-benzyl-7-(2-methyl-4-(4H-1,2,4-triazol-3-yl)phenyl)-3,4-dihydropyrazino[2,3-b]pyrazin-2(1H)-one;

7-(3-fluoro-4-(4H-1,2,4-triazol-3-yl)phenyl)-1-(2-methoxyethyl)-3,4-dihydropyrazino[2,3-b]pyrazin-2(1H)-one;

7-(3-fluoro-4-(4H-1,2,4-triazol-3-yl)phenyl)-1-(2-(tetrahydro-2H-pyran-4-yl)ethyl)-3,4-dihydropyrazino[2,3-b]pyrazin-2(1H)-one;

7-(3-fluoro-2-methyl-4-(1H-1,2,4-triazol-3-yl)phenyl)-1-(2-methoxyethyl)-3,4-dihydropyrazino[2,3-b]pyrazin-2(1H)-one;

1-(trans-4-methoxycyclohexyl)-7-(2-methyl-6-(4H-1,2,4-triazol-3-yl)pyridin-3-yl)-3,4-dihydropyrazino[2,3-b]pyrazin-2(1H)-one;

7-(6-(2-hydroxypropan-2-yl)pyridin-3-yl)-1-(trans-4-methoxycyclohexyl)-3,4-dihydropyrazino[2,3-b]pyrazin-2(1H)-one;

7-(5-fluoro-2-methyl-4-(1H-1,2,4-triazol-3-yl)phenyl)-1-(2-(tetrahydro-2H-pyran-4-yl)ethyl)-3,4-dihydropyrazino[2,3-b]pyrazin-2(1H)-one;

7-(3-fluoro-2-methyl-4-(1H-1,2,4-triazol-3-yl)phenyl)-1-(2-(tetrahydro-2H-pyran-4-yl)ethyl)-3,4-dihydropyrazino[2,3-b]pyrazin-2(1H)-one;

1-(2-methoxyethyl)-7-(2-methyl-6-(4H-1,2,4-triazol-3-yl)pyridin-3-yl)-3,4-dihydropyrazino[2,3-b]pyrazin-2(1H)-one;

7-(6-(2-hydroxypropan-2-yl)pyridin-3-yl)-1-((trans-4-methoxycyclohexyl)methyl)-3,4-dihydropyrazino[2,3-b]pyrazin-2(1H)-one;

1-(cyclopentylmethyl)-7-(6-(2-hydroxypropan-2-yl)pyridin-3-yl)-3,4-dihydropyrazino[2,3-b]pyrazin-2(1H)-one;

7-(4-(2-hydroxypropan-2-yl)phenyl)-1-(2-methoxyethyl)-3,4-dihydropyrazino[2,3-b]pyrazin-2(1H)-one;

(S)-7-(6-(1-hydroxyethyl)pyridin-3-yl)-1-(2-(tetrahydro-2H-pyran-4-yl)ethyl)-3,4-dihydropyrazino[2,3-b]pyrazin-2(1H)-one;

(R)-7-(6-(1-hydroxyethyl)pyridin-3-yl)-1-(2-(tetrahydro-2H-pyran-4-yl)ethyl)-3,4-dihydropyrazino[2,3-b]pyrazin-2(1H)-one;

7-(2-methyl-6-(4H-1,2,4-triazol-3-yl)pyridin-3-yl)-1-((tetrahydro-2H-pyran-4-yl)methyl)-3,4-dihydropyrazino[2,3-b]pyrazin-2(1H)-one;

7-(4-(2-hydroxypropan-2-yl)phenyl)-1-(2-(tetrahydro-2H-pyran-4-yl)ethyl)-3,4-dihydropyrazino[2,3-b]pyrazin-2(1H)-one;

7-(6-(2-hydroxypropan-2-yl)pyridin-3-yl)-1-(4-(trifluoromethyl)benzyl)-3,4-dihydropyrazino[2,3-b]pyrazin-2(1H)-one;

7-(6-(2-hydroxypropan-2-yl)pyridin-3-yl)-1-(3-(trifluoromethyl)benzyl)-3,4-dihydropyrazino[2,3-b]pyrazin-2(1H)-one;

7-(6-(2-hydroxypropan-2-yl)pyridin-3-yl)-1-(3-methoxypropyl)-3,4-dihydropyrazino[2,3-b]pyrazin-2(1H)-one;

7-(4-methyl-6-(1H-1,2,4-triazol-3-yl)pyridin-3-yl)-1-(2-(tetrahydro-2H-pyran-4-yl)ethyl)-3,4-dihydropyrazino[2,3-b]pyrazin-2(1H)-one;

7-(6-(2-hydroxypropan-2-yl)pyridin-3-yl)-1-(2-methoxyethyl)-3,4-dihydropyrazino[2,3-b]pyrazin-2(1H)-one;

7-(6-(2-hydroxypropan-2-yl)pyridin-3-yl)-1-((tetrahydro-2H-pyran-4-yl)methyl)-3,4-dihydropyrazino[2,3-b]pyrazin-2(1H)-one;

7-(4-methyl-2-(methylamino)-1H-benzo[d]imidazol-6-yl)-1-((tetrahydro-2H-pyran-4-yl)methyl)-3,4-dihydropyrazino[2,3-b]pyrazin-2(1H)-one;

7-(2-amino-4-methyl-1H-benzo[d]imidazol-6-yl)-1-((tetrahydro-2H-pyran-4-yl)methyl)-3,4-dihydropyrazino[2,3-b]pyrazin-2(1H)-one;

7-(2-methyl-6-(4H-1,2,4-triazol-3-yl)pyridin-3-yl)-1-(2-(tetrahydro-2H-pyran-4-yl)ethyl)-3,4-dihydropyrazino[2,3-b]pyrazin-2(1H)-one;

(R)-7-(6-(2-hydroxypropan-2-yl)pyridin-3-yl)-3-methyl-1-(2-(tetrahydro-2H-pyran-4-yl)ethyl)-3,4-dihydropyrazino[2,3-b]pyrazin-2(1H)-one;

(S)-7-(6-(2-hydroxypropan-2-yl)pyridin-3-yl)-3-methyl-1-(2-(tetrahydro-2H-pyran-4-yl)ethyl)-3,4-dihydropyrazino[2,3-b]pyrazin-2(1H)-one;

7-(6-(2-hydroxypropan-2-yl)pyridin-3-yl)-3,3-dimethyl-1-(2-(tetrahydro-2H-pyran-4-yl)ethyl)-3,4-dihydropyrazino[2,3-b]pyrazin-2(1H)-one;

7-(2-amino-4-methyl-1H-benzo[d]imidazol-6-yl)-1-(2-(tetrahydro-2H-pyran-4-yl)ethyl)-3,4-dihydropyrazino[2,3-b]pyrazin-2(1H)-one;

7-(6-(2-hydroxypropan-2-yl)pyridin-3-yl)-1-(2-(tetrahydro-2H-pyran-4-yl)ethyl)-3,4-dihydropyrazino[2,3-b]pyrazin-2(1H)-one;

7-(2-methyl-4-(1H-1,2,4-triazol-3-yl)phenyl)-1-(2-(tetrahydro-2H-pyran-4-yl)ethyl)-3,4-dihydropyrazino[2,3-b]pyrazin-2(1H)-one;

7-(4-(1H-1,2,4-triazol-5-yl)phenyl)-1-(2-(tetrahydro-2H-pyran-4-yl)ethyl)-3,4-dihydropyrazino[2,3-b]pyrazin-2(1H)-one;

1-(1-hydroxypropan-2-yl)-7-(2-methyl-6-(1H-1,2,4-triazol-3-yl)pyridin-3-yl)-3,4-dihydropyrazino[2,3-b]pyrazin-2(1H)-one; and 1-(2-hydroxyethyl)-7-(2-methyl-6-(1H-1,2,4-triazol-3-yl)pyridin-3-yl)-3,4-dihydropyrazino[2,3-b]pyrazin-2(1H)-one, and pharmaceutically acceptable salts, clathrates, solvates, stereoisomers, tautomers, and prodrugs thereof.

4.4 Methods for Making TOR Kinase Inhibitors

The TOR kinase inhibitors can be obtained via standard, well-known synthetic methodology, see e.g., March, J. Advanced Organic Chemistry; Reactions Mechanisms, and Structure, 4th ed., 1992. Starting materials useful for preparing compounds of formula (III) and intermediates therefore, are commercially available or can be prepared from commercially available materials using known synthetic methods and reagents.

Particular methods for preparing compounds of formula (I) are disclosed in U.S. Pat. No. 7,981,893, issued Jul. 19, 2011, incorporated by reference herein in its entirety. Particular methods for preparing compounds of formula (II) are disclosed in U.S. Pat. No. 7,968,556, issued Jun. 28, 2011, incorporated by reference herein in its entirety. Particular methods for preparing compounds of formula (III) and (IV) are disclosed in U.S. Publication No. 2010/0216781, filed Oct. 26, 2009, and U.S. Publication No. 2011/0137028, filed Oct. 25, 2010, incorporated by reference herein in its entirety.

4.5 Methods of Use

Provided herein are methods for treating or preventing a solid tumor, non-Hodgkin lymphoma or multiple myeloma, comprising administering an effective amount of a TOR kinase inhibitor to a patient having a solid tumor, non-Hodgkin lymphoma or multiple myeloma. In one embodiment, the solid tumor, non-Hodgkin lymphoma or multiple myeloma, is rapamycin resistant.

In one embodiment, the non-Hodgkin lymphoma is diffuse large B-cell lymphoma (DLBCL), follicular lymphoma (FL), acute myeloid leukemia (AML), mantle cell lymphoma (MCL), or ALK$^+$ anaplastic large cell lymphoma. In one embodiment, the non-Hodgkin lymphoma is advanced solid non-Hodgkin lymphoma.

In one embodiment, the solid tumor is a neuroendocrine tumor. In certain embodiments, the neuroendocrine tumor is a neuroendocrine tumor of gut origin. In certain embodiments, the neuroendocrine tumor is of non-pancreatic origin. In certain embodiments, the neuroendocrine tumor is non-pancreatic of gut origin. In certain embodiments, the neuroendocrine tumor is of unknown primary origin. In certain embodiments, the neuroendocrine tumor is a symptomatic endocrine producing tumor or a nonfunctional tumor. In certain embodiments, the neuroendocrine tumor is locally unresectable, metastatic moderate, well differentiated, low (grade 1) or intermediate (grade 2).

In one embodiment, the solid tumor is non-small cell lung cancer (NSCLC).

In another embodiments the solid tumor is glioblastoma multiforme (GBM).

In another embodiment, the solid tumor is hepatocellular carcinoma (HCC).

In another embodiment, the solid tumor is breast cancer. In one embodiment, the breast cancer is estrogen receptor positive (ER+, ER+/Her2− or ER+/Her2+). In one embodiment, the breast cancer is estrogen receptor negative (ER−/Her2+). In one embodiment, the breast cancer is triple negative (TN) (breast cancer that does not express the genes and/or protein corresponding to the estrogen receptor (ER), progesterone receptor (PR), and that does not overexpress the Her2/neu protein).

In another embodiment, the solid tumor is colorectal cancer (CRC).

In another embodiment, the solid tumor is salivary cancer.

In another embodiment, the solid tumor is pancreatic cancer.

In another embodiment, the solid tumor is adenocystic cancer.

In another embodiment, the solid tumor is adrenal cancer.

In another embodiment, the solid tumor is esophageal cancer, renal cancer, leiomyosarcoma, or paraganglioma.

In one embodiment, the solid tumor is an advanced solid tumor.

In one embodiment, the advanced solid tumor is a neuroendocrine tumor. In certain embodiments, the neuroendocrine tumor is a neuroendocrine tumor of gut origin. In certain embodiments, the neuroendocrine tumor is of non-pancreatic origin. In certain embodiments, the neuroendocrine tumor is non-pancreatic of gut origin. In certain embodiments, the neuroendocrine tumor is of unknown primary origin. In certain embodiments, the neuroendocrine tumor is a symptomatic endocrine producing tumor or a nonfunctional tumor. In certain embodiments, the neuroendocrine tumor is locally unresectable, metastatic moderate, well differentiated, low (grade 1) or intermediate (grade 2).

In one embodiment, the advanced solid tumor is non-small cell lung cancer (NSCLC).

In another embodiments the advanced solid tumor is glioblastoma multiforme (GBM).

In another embodiment, the advanced solid tumor is hepatocellular carcinoma (HCC).

In another embodiment, the advanced solid tumor is breast cancer. In one embodiment, the advanced solid tumor is estrogen receptor positive (ER+, ER+/Her2− or ER+/Her2+) breast cancer. In one embodiment, the advanced solid tumor is ER+/Her2− breast cancer. In one embodiment, the advanced solid tumor is ER+/Her2+ breast cancer.

In one embodiment, the advanced solid tumor is ER−/Her2+ breast cancer. In one embodiment, the advanced solid tumor is triple negative (TN) breast cancer.

In another embodiment, the advanced solid tumor is colorectal cancer (CRC).

In another embodiment, the advanced solid tumor is salivary cancer.

In another embodiment, the advanced solid tumor is pancreatic cancer.

In another embodiment, the advanced solid tumor is adenocystic cancer.

In another embodiment, the advanced solid tumor is adrenal cancer.

In another embodiment, the advanced solid tumor is esophageal cancer, renal cancer, leiomyosarcoma, or paraganglioma.

In one embodiment, the non-Hodgkin lymphoma is diffuse large B-cell lymphoma (DLBCL).

In one embodiment, provided herein are methods for achieving a Response Evaluation Criteria in Solid Tumors (RECIST 1.1) of complete response, partial response or stable disease in a patient comprising administering an effective amount of a TOR kinase inhibitor to a patient having a solid tumor, such as an advanced solid tumor. In another embodiment, provided herein are methods to increase Progression Free Survival rates, as determined by Kaplan-Meier estimates.

In one embodiment, provided herein are methods for preventing or delaying a Response Evaluation Criteria in Solid Tumors (RECIST 1.1) of progressive disease in a patient, comprising administering an effective amount of a TOR kinase inhibitor to a patient having a solid tumor, such as an advanced solid tumor. In one embodiment the prevention or delaying of progressive disease is characterized or achieved by a change in overall size of the target lesions, of for example, between −30% and +20% compared to pre-treatment. In another embodiment, the change in size of the target lesions is a reduction in overall size of more than 30%, for example, more than 50% reduction in target lesion size compared to pre-treatment. In another, the prevention is characterized or achieved by a reduction in size or a delay in progression of non-target lesions compared to pre-treatment. In one embodiment, the prevention is achieved or characterized by a reduction in the number of target lesions compared to pre-treatment. In another, the prevention is achieved or characterized by a reduction in the number or quality of non-target lesions compared to pre-treatment. In one embodiment, the prevention is achieved or characterized by the absence or the disappearance of target lesions compared to pre-treatment. In another, the prevention is achieved or characterized by the absence or the disappearance of non-target lesions compared to pre-treatment. In another embodiment, the prevention is achieved or characterized by the prevention of new lesions compared to pre-treatment. In yet another embodiment, the prevention is achieved or characterized by the prevention of clinical signs or symptoms of disease progression compared to pre-treatment, such as cancer-related cachexia or increased pain.

In certain embodiments, provided herein are methods for decreasing the size of target lesions in a patient compared to pre-treatment, comprising administering an effective amount of a TOR kinase inhibitor to a patient having a solid tumor, such as an advanced solid tumor.

In certain embodiments, provided herein are methods for decreasing the size of a non-target lesion in a patient compared to pre-treatment, comprising administering an effective amount of a TOR kinase inhibitor to a patient having a solid tumor, such as an advanced solid tumor.

In certain embodiments, provided herein are methods for achieving a reduction in the number of target lesions in a patient compared to pre-treatment, comprising administering an effective amount of a TOR kinase inhibitor to a patient having a solid tumor, such as an advanced solid tumor.

In certain embodiments, provided herein are methods for achieving a reduction in the number of non-target lesions in a patient compared to pre-treatment, comprising administering an effective amount of a TOR kinase inhibitor to a patient having a solid tumor, such as an advanced solid tumor.

In certain embodiments, provided herein are methods for achieving an absence of all target lesions in a patient, comprising administering an effective amount of a TOR kinase inhibitor to a patient having a solid tumor, such as an advanced solid tumor.

In certain embodiments, provided herein are methods for achieving an absence of all non-target lesions in a patient, comprising administering an effective amount of a TOR kinase inhibitor to a patient having a solid tumor, such as an advanced solid tumor.

In certain embodiments, provided herein are methods for treating a solid tumor, such as an advanced solid tumor, the methods comprising administering an effective amount of a TOR kinase inhibitor to a patient having a solid tumor, such as an advanced solid tumor, wherein the treatment results in a complete response, partial response or stable disease, as determined by Response Evaluation Criteria in Solid Tumors (RECIST 1.1).

In certain embodiments, provided herein are methods for treating a solid tumor, such as an advanced solid tumor, the methods comprising administering an effective amount of a TOR kinase inhibitor to a patient having a solid tumor, such as an advanced solid tumor, wherein the treatment results in a reduction in target lesion size, a reduction in non-target lesion size and/or the absence of new target and/or non-target lesions, compared to pre-treatment.

In certain embodiments, provided herein are methods for treating a solid tumor, such as an advanced solid tumor, the methods comprising administering an effective amount of a TOR kinase inhibitor to a patient having a solid tumor, such as an advanced solid tumor, wherein the treatment results in prevention or retarding of clinical progression, such as cancer-related cachexia or increased pain.

In another embodiment, provided herein are methods for inducing a therapeutic response characterized with the International Workshop Criteria (IWC) for NHL (see Cheson B D, Pfistner B, Juweid, M E, et. al. Revised Response Criteria for Malignant Lymphoma. J. Clin. Oncol: 2007: (25) 579-586) of a patient, comprising administering an effective amount of a TOR kinase inhibitor to a patient having non-Hodgkin lymphoma. In another embodiment, provided herein are methods for achieving complete remission, partial remission or stable disease, as determined by the International Workshop Criteria (IWC) for NHL in a patient, comprising administering an effective amount of a TOR kinase inhibitor to patient having non-Hodgkin lymphoma. In another embodiment, provided herein are methods for achieving an increase in overall survival, progression-free survival, event-free survival, time to progression, disease-free survival or lymphoma-free survival as determined by the International Workshop Criteria (IWC) for NHL in a patient, comprising administering an effective amount of a TOR kinase inhibitor to patient having non-Hodgkin lymphoma.

In another embodiment, provided herein are methods for inducing a therapeutic response assessed with the International Uniform Response Criteria for Multiple Myeloma (IURC) (see Durie B G M, Harousseau J- L, Miguel J S, et al. International uniform response criteria for multiple myeloma. Leukemia, 2006; (10) 10:1-7) of a patient, comprising administering an effective amount of a TOR kinase inhibitor to a patient having multiple myeloma. In another embodiment, provided herein are methods for achieving a stringent complete response, complete response, or very good partial response, as determined by the International Uniform Response Criteria for Multiple Myeloma (IURC) in a patient, comprising administering an effective amount of a TOR kinase inhibitor to patient having multiple myeloma. In another embodiment, provided herein are methods for achieving an increase in overall survival, progression-free survival, event-free survival, time to progression, or disease-free survival in a patient, comprising administering an effective amount of a TOR kinase inhibitor to patient having multiple myeloma.

In another embodiment, provided herein are methods for inducing a therapeutic response assessed with the Response Assessment for Neuro-Oncology (RANO) Working Group for GBM (see Wen P., Macdonald, D R., Reardon, D A., et al. Updated response assessment criteria for highgrade gliomas: Response assessment in neuro-oncology working group. J. Clin. Oncol. 2010; 28: 1963-1972) of a patient, comprising administering an effective amount of a TOR kinase inhibitor to a patient having glioblastoma multiforme. In one embodiment, RANO will be used to establish the proportion of subjects progression-free at 6 months from Day 1 relative to efficacy evaluable subjects in the GBM type.

In another embodiment, provided herein are methods for improving the Eastern Cooperative Oncology Group Performance Status (ECOG) of a patient, comprising administering an effective amount of a TOR kinase inhibitor to a patient having a tumor, such as an advanced solid tumor.

In another embodiment, provided herein are methods for inducing a therapeutic response assessed by Positron Emission Tomography (PET) outcome of a patient, comprising administering an effective amount of a TOR kinase inhibitor to a patient having a tumor, such as an advanced solid tumor. In certain embodiments, provided herein are methods for treating a solid tumor, such as an advanced solid tumor, the methods comprising administering an effective amount of a TOR kinase inhibitor to a patient having a solid tumor, such as an advanced solid tumor, wherein the treatment results in a reduction in tumor metabolic activity, for example, as measured by PET imaging.

In another embodiment, provided herein are methods for inducing a therapeutic response assessed by a reduction in carcinoid syndrome-related symptoms, such as diarrhea and/or flushing, and/or a reduction in endocrine hormone markers, such as chromogranin, gastrin, serotonin, and/or glucagon.

In one embodiment, provided herein are methods for inhibiting phosphorylation of S6RP, 4E-BP1 and/or AKT in a patient having a solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer or adrenal cancer), non-Hodgkin lymphoma or multiple myeloma, comprising administering an effective amount of a TOR kinase inhibitor to said patient. In another embodiment, the solid tumor is esophageal cancer, renal cancer, leiomyosarcoma, or paraganglioma. In some such embodiments, the inhibition of phosphorylation is assessed in a biological sample of the patient, such as in circulating blood and/or tumor cells, skin biopsies and/or tumor biopsies or aspirate. In such embodiments, the amount of inhibition of phosphorylation is assessed by comparison of the amount of phospho-S6RP, 4E-BP1 and/or AKT before and after administration of the TOR kinase inhibitor. In certain embodiments, provided herein are methods for measuring inhibition of phosphorylation of S6RP, 4E-BP1 or AKT in a patient having a solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer or adrenal cancer), non-Hodgkin lymphoma or multiple myeloma, comprising administering an effective amount of a TOR kinase inhibitor to said patient, measuring the amount of phosphorylated S6RP, 4E-BP1 and/or AKT in said patient, and comparing said amount of phosphorylated S6RP, 4E-BP1 and/or AKT to that of said patient prior to administration of an effective amount of a TOR kinase inhibitor. In another embodiment, the solid tumor is esophageal cancer, renal cancer, leiomyosarcoma, or paraganglioma. In some embodiments, the inhibition of phosphorylation of S6RP, 4E-BP1 and/or AKT is assessed in B-cells, T-cells and/or monocytes.

In certain embodiments, provided herein are methods for inhibiting phosphorylation of S6RP, 4E-BP1 and/or AKT in a biological sample of a patient having a solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer or adrenal cancer), non-Hodgkin lymphoma or multiple myeloma, comprising administering an effective amount of a TOR kinase inhibitor to said patient and comparing the amount of phosphorylated S6RP, 4E-BP1 and/or AKT in a biological sample of a patient obtained prior to and after administration of said TOR kinase inhibitor, wherein less phosphorylated S6RP, 4E-BP1 and/or AKT in said biological sample obtained after administration of said TOR kinase inhibitor relative to the amount of phosphorylated S6RP, 4E-BP1 and/or AKT in said biological sample obtained prior to administration of said TOR kinase inhibitor indicates inhibition. In another embodiment, the solid tumor is esophageal cancer, renal cancer, leiomyosarcoma, or paraganglioma. In some embodiments, the inhibition of phosphorylation of S6RP, 4E-BP1 and/or AKT is assessed in B-cells, T-cells and/or monocytes.

In one embodiment, provided herein are methods for inhibiting DNA-dependent protein kinase (DNA-PK) activity in a patient having a solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer or adrenal cancer), non-Hodgkin lymphoma or multiple myeloma, comprising administering an effective amount of a TOR kinase inhibitor to said patient. In another embodiment, the solid tumor is esophageal cancer, renal cancer, leiomyosarcoma, or paraganglioma. In some embodiments, DNA-PK inhibition is assessed in the skin of the patient having a solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer or adrenal cancer), non-Hodgkin lymphoma or multiple myeloma, in one example in a UV light-irradiated skin sample of said patient. In another embodiment, the solid tumor is esophageal cancer, renal cancer, leiomyosarcoma, or paraganglioma. In another embodiment, DNA-PK inhibition is assessed in a tumor biopsy or aspirate of a patient having a solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer or adrenal cancer), non-Hodgkin lymphoma or multiple myeloma. In one embodiment, inhibition is assessed by measuring the amount of phosphorylated DNA-PK S2056 (also known as pDNA-PK S2056) before and after administration of the TOR kinase inhibitor. In another embodiment, the solid tumor is esophageal cancer, renal cancer, leiomyosarcoma, or paraganglioma. In certain embodiments, provided herein are methods for measuring inhibition of phosphorylation of DNA-PK S2056 in a skin sample of a patient having a solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer or adrenal cancer), non-Hodgkin lymphoma or multiple myeloma, comprising administering an effective amount of a TOR kinase inhibitor to said patient, measuring the amount of phosphorylated DNA-PK S2056 present in the skin sample and comparing said amount of phosphorylated DNA-PK S2056 to that in a skin sample from said patient prior to administration of an effective amount of a TOR kinase inhibitor. In another embodiment, the solid tumor is esophageal cancer, renal cancer, leiomyosarcoma, or paraganglioma. In one embodiment, the skin sample is irradiated with UV light.

In certain embodiments, provided herein are methods for inhibiting DNA-dependent protein kinase (DNA-PK) activity in a skin sample of a patient having a solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer or adrenal cancer), non-Hodgkin lymphoma or multiple myeloma, comprising administering an effective amount of a TOR kinase inhibitor to said patient and comparing the amount of phosphorylated DNA-PK in a biological sample of a patient obtained prior to and after administration of said TOR kinase inhibitor, wherein less phosphorylated DNA-PK in said biological sample obtained after administration of said TOR kinase inhibitor relative to the amount of phosphorylated DNA-PK in said biological sample obtained prior to administration of said TOR kinase inhibitor indicates inhibition. In another embodiment, the solid tumor is esophageal cancer, renal cancer, leiomyosarcoma, or paraganglioma.

In some embodiments, the TOR kinase inhibitor is a compound as described herein. In one embodiment, the TOR kinase inhibitor is a compound of formula (I), (II), (III), or (IV). In one embodiment, the TOR kinase inhibitor is a compound of formula (I), (Ia), (Ib), (Ic), (Id), (Ie), (If), (Ig), (II), (IIa), (IIb), (IIc), (IId), (III), or (IV). In one embodiment, the TOR kinase inhibitor is a compound from Table A, B, C or D. In one embodiment, the TOR kinase inhibitor is Compound 1 (a TOR kinase inhibitor set forth herein having molecular formula $C_{21}H_{27}N_5O_3$). In one embodiment, the TOR kinase inhibitor is Compound 2 (a TOR kinase inhibitor set forth herein having molecular formula $C_{16}H_{16}N_8O$). In one embodiment, Compound 1 is 7-(6-(2-hydroxypropan-2-yl)pyridin-3-yl)-1-((1r,4r)-4-methoxycyclohexyl)-3,4-dihydropyrazino-[2,3-b]pyrazin-2(1H)-one. In another embodiment, Compound 2 is 1-ethyl-7-(2-methyl-6-(1H-1,2,4-triazol-3-yl)pyridin-3-yl)-3,4-dihydropyrazino[2,3-b]pyrazin-2(1H)-one.

A TOR kinase inhibitor can be combined with radiation therapy or surgery. In certain embodiments, a TOR kinase inhibitor is administered to patient who is undergoing radiation therapy, has previously undergone radiation therapy or will be undergoing radiation therapy. In certain embodiments, a TOR kinase inhibitor is administered to a patient who has undergone tumor removal surgery.

Further provided herein are methods for treating patients who have been previously treated for a solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer or adrenal cancer), non-Hodgkin lymphoma or multiple myeloma, but are non-responsive to standard therapies, as well as those who have not previously been treated. In another embodiment, the solid tumor is esophageal cancer, renal cancer, leiomyosarcoma, or paraganglioma. Further provided herein are methods for treating patients who have undergone surgery in an attempt to treat the condition at issue, as well as those who have not. Because patients with a solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer or adrenal cancer), non-Hodgkin lymphoma or multiple myeloma have heterogenous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapy that can be effectively used to treat an individual patient with a solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer or adrenal cancer), non-Hodgkin lymphoma or multiple myeloma. In another embodiment, the solid tumor is esophageal cancer, renal cancer, leiomyosarcoma, or paraganglioma.

In certain embodiments, the methods provided herein comprise the use of a kit comprising a TOR kinase inhibitor provided herein.

In certain embodiments, provided herein are methods for treating or preventing a solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer or adrenal cancer), non-Hodgkin lymphoma or multiple myeloma, comprising administering an effective amount of a TOR kinase inhibitor to a patient having a solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer or adrenal cancer), non-Hodgkin lymphoma or multiple myeloma, wherein said TOR kinase inhibitor is a component of a kit provided herein. In another embodiment, the solid tumor is esophageal cancer, renal cancer, leiomyosarcoma, or paraganglioma.

In certain embodiments, provided herein are methods for monitoring the response to TOR kinase inhibitor treatment of a patient having a solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer or adrenal cancer), non-Hodgkin lymphoma or multiple myeloma, comprising administering an effective amount of a TOR kinase inhibitor to a patient having a solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer or adrenal cancer), non-Hodgkin lymphoma or multiple myeloma and assessing inhibition of disease progression, inhibition of tumor growth, reduction of primary and/or secondary tumor(s), relief of tumor-related symptoms, improvement in quality of life, inhibition of tumor secreted factors (including tumor secreted hormones, such as those that contribute to carcinoid syndrome), delayed appearance of primary and/or secondary tumor(s), slowed development of primary and/or secondary tumor(s), decreased occurrence of primary and/or secondary tumor(s), slowed or decreased severity of secondary effects of disease, arrested tumor growth and/or regression of tumors, inhibition of phosphorylation of S6RP, 4E-BP1 and/or AKT, or inhibition of DNA-dependent protein kinase (DNA-PK) activity, wherein said TOR kinase inhibitor and means for assessing treatment response are components of a kit provided herein. In another embodiment, the solid tumor is esophageal cancer, renal cancer, leiomyosarcoma, or paraganglioma. Inhibition of phosphorylation of S6RP, 4E-BP1, and/or AKT can be measured in blood, skin, tumor, and/or circulating tumor cells (CTCs) in blood by various methodology including flow cytometry, ELISA, immunohistochemistry (IHC), immunofluorescence (IF) using phosphoraltion-specific antibodies Inhibition of DNA-PK activity can be measured in blood, skin, and/or circulating tumor cells (CTCs) in blood by monitoring phosphorylation of substrates of DNA-PK, such as DNA-PK itself and XRCC4. Inhibition of DNA-PK activity can also be measured by monitoring accumulation of double strand DNA damage in tissues and/or cells such as those mentioned above.

In further embodiments, the solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer or adrenal cancer), non-Hodgkin lymphoma or multiple myeloma is that in which the PI3K/mTOR pathway is activated. In another embodiment, the solid tumor (esophageal cancer, renal cancer, leiomyosarcoma, or paraganglioma) is that in which the PI3K/mTOR pathway is activated. In certain embodiments, the solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer or adrenal cancer), non-Hodgkin lymphoma or multiple myeloma is that in which the PI3K/mTOR pathway is activated due to PTEN loss, a PIK3CA mutation or EGFR overexpression, or a combination thereof. In another embodiment, the solid tumor (for example, esophageal cancer, renal cancer, leiomyosarcoma, or paraganglioma) is that in which the PI3K/mTOR pathway is activated due to PTEN loss, a PIK3CA mutation or EGFR overexpression, or a combination thereof.

4.6 Pharmaceutical Compositions and Routes of Administration

Provided herein are compositions comprising an effective amount of a TOR kinase inhibitor and compositions comprising an effective amount of a TOR kinase inhibitor and a pharmaceutically acceptable carrier or vehicle. In some embodiments, the pharmaceutical composition described herein are suitable for oral, parenteral, mucosal, transdermal or topical administration.

The TOR kinase inhibitors can be administered to a patient orally or parenterally in the conventional form of preparations, such as capsules, microcapsules, tablets, granules, powder, troches, pills, suppositories, injections, suspensions and syrups. Suitable formulations can be prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrator (e.g., starch, carboxymethylcellulose, hydroxypropyl-starch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g, sodium benzoate, sodium bisulfite, methylparaben or propylparaben), a stabilizer (e.g., citric acid, sodium citrate or acetic acid), a suspending agent (e.g., methylcellulose, polyvinyl pyrroliclone or aluminum stearate), a dispersing agent (e.g., hydroxypropylmethylcellulose), a diluent (e.g., water), and base wax (e.g., cocoa butter, white petrolatum or polyethylene glycol). The effective amount of the TOR kinase inhibitor in the pharmaceutical composition may be at a level that will exercise the desired effect; for example, about 0.005 mg/kg of a patient's body weight to about 10 mg/kg of a patient's body weight in unit dosage for both oral and parenteral administration.

The dose of a TOR kinase inhibitor to be administered to a patient is rather widely variable and can be patient to the judgment of a health-care practitioner. In general, the TOR kinase inhibitors can be administered one to four times a day in a dose of about 0.005 mg/kg of a patient's body weight to about 10 mg/kg of a patient's body weight in a patient, but the above dosage may be properly varied depending on the age, body weight and medical condition of the patient and the type of administration. In one embodiment, the dose is about 0.01 mg/kg of a patient's body weight to about 5 mg/kg of a patient's body weight, about 0.05 mg/kg of a patient's body weight to about 1 mg/kg of a patient's body weight, about 0.1 mg/kg of a patient's body weight to about 0.75 mg/kg of a patient's body weight or about 0.25 mg/kg of a patient's body weight to about 0.5 mg/kg of a patient's body weight. In one embodiment, one dose is given per day In another embodiment, two doses are given per day. In any given case, the amount of the TOR kinase inhibitor administered will depend on such factors as the solubility of the active component, the formulation used and the route of administration.

In another embodiment, provided herein are methods for the treatment or prevention of a disease or disorder comprising the administration of about 0.375 mg/day to about 750 mg/day, about 0.75 mg/day to about 375 mg/day, about 3.75 mg/day to about 75 mg/day, about 7.5 mg/day to about 55 mg/day or about 18 mg/day to about 37 mg/day of a TOR kinase inhibitor to a patient in need thereof. In a particular embodiment, the methods disclosed herein comprise the administration of 15 mg/day, 30 mg/day, 45 mg/day or 60 mg/day of a TOR kinase inhibitor to a patient in need thereof. In another, the methods disclosed herein comprise administration of 0.5 mg/day, 1 mg/day, 2 mg/day, 4 mg/day, 8 mg/day, 16 mg/day, 20 mg/day, 25 mg/day, 30 mg/day or 40 mg/day of a TOR kinase inhibitor to a patient in need thereof.

In another embodiment, provided herein are methods for the treatment or prevention of a disease or disorder comprising the administration of about 0.1 mg/day to about 1200 mg/day, about 1 mg/day to about 100 mg/day, about 10 mg/day to about 1200 mg/day, about 10 mg/day to about 100 mg/day, about 100 mg/day to about 1200 mg/day, about 400 mg/day to about 1200 mg/day, about 600 mg/day to about 1200 mg/day, about 400 mg/day to about 800 mg/day or about 600 mg/day to about 800 mg/day of a TOR kinase inhibitor to a patient in need thereof. In a particular embodiment, the methods disclosed herein comprise the administration of 0.1 mg/day, 0.5 mg/day, 1 mg/day, 10 mg/day, 15 mg/day, 20 mg/day, 30 mg/day, 40 mg/day, 45 mg/day, 50 mg/day, 60 mg/day, 75 mg/day, 100 mg/day, 125 mg/day, 150 mg/day, 200 mg/day, 250 mg/day, 300 mg/day, 400 mg/day, 600 mg/day or 800 mg/day of a TOR kinase inhibitor to a patient in need thereof.

In another embodiment, provided herein are unit dosage formulations that comprise between about 0.1 mg and about 2000 mg, about 1 mg and 200 mg, about 35 mg and about 1400 mg, about 125 mg and about 1000 mg, about 250 mg and about 1000 mg, or about 500 mg and about 1000 mg of a TOR kinase inhibitor.

In a particular embodiment, provided herein are unit dosage formulation comprising about 0.1 mg, 0.25 mg, 0.5 mg, 1 mg, 5 mg, 10 mg, 15 mg, 20 mg, 30 mg, 45 mg, 50 mg, 60 mg, 75 mg, 100 mg, 125 mg, 150 mg, 200 mg, 250 mg, 300 mg, 400 mg, 600 mg or 800 mg of a TOR kinase inhibitor.

In another embodiment, provided herein are unit dosage formulations that comprise 0.1 mg, 0.25 mg, 0.5 mg, 1 mg, 2.5 mg, 5 mg, 10 mg, 15 mg, 20 mg, 30 mg, 35 mg, 50 mg, 70 mg, 100 mg, 125 mg, 140 mg, 175 mg, 200 mg, 250 mg, 280 mg, 350 mg, 500 mg, 560 mg, 700 mg, 750 mg, 1000 mg or 1400 mg of a TOR kinase inhibitor. In a particular embodiment, provided herein are unit dosage formulations that comprise 10 mg, 15 mg, 20 mg, 30 mg, 45 mg or 60 mg of a TOR kinase inhibitor.

A TOR kinase inhibitor can be administered once, twice, three, four or more times daily.

A TOR kinase inhibitor can be administered orally for reasons of convenience. In one embodiment, when administered orally, a TOR kinase inhibitor is administered with a meal and water. In another embodiment, the TOR kinase inhibitor is dispersed in water or juice (e.g., apple juice or orange juice) and administered orally as a suspension. In another embodiment, when administered orally, a TOR kinase inhibitor is administered in a fasted state.

The TOR kinase inhibitor can also be administered intradermally, intramuscularly, intraperitoneally, percutaneously, intravenously, subcutaneously, intranasally, epidurally, sublingually, intracerebrally, intravaginally, transdermally, rectally, mucosally, by inhalation, or topically to the ears, nose, eyes, or skin. The mode of administration is left to the discretion of the health-care practitioner, and can depend in-part upon the site of the medical condition.

In one embodiment, provided herein are capsules containing a TOR kinase inhibitor without an additional carrier, excipient or vehicle.

In another embodiment, provided herein are compositions comprising an effective amount of a TOR kinase inhibitor and a pharmaceutically acceptable carrier or vehicle, wherein a pharmaceutically acceptable carrier or vehicle can comprise an excipient, diluent, or a mixture thereof. In one embodiment, the composition is a pharmaceutical composition.

The compositions can be in the form of tablets, chewable tablets, capsules, solutions, parenteral solutions, troches, suppositories and suspensions and the like. Compositions can be formulated to contain a daily dose, or a convenient fraction of a daily dose, in a dosage unit, which may be a single tablet or capsule or convenient volume of a liquid. In one embodiment, the solutions are prepared from water-soluble salts, such as the hydrochloride salt. In general, all of the compositions are prepared according to known methods in pharmaceutical chemistry. Capsules can be prepared by mixing a TOR kinase inhibitor with a suitable carrier or diluent and filling the proper amount of the mixture in capsules. The usual carriers and diluents include, but are not limited to, inert powdered substances such as starch of many different kinds, powdered cellulose, especially crystalline and microcrystalline cellulose, sugars such as fructose, mannitol and sucrose, grain flours and similar edible powders.

Tablets can be prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. In one embodiment, the pharmaceutical composition is lactose-free. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant might be necessary in a tablet formulation to prevent the tablet and punches from sticking in the die. The lubricant can be chosen from such slippery solids as talc, magnesium and calcium stearate, stearic acid and hydrogenated vegetable oils. Tablet disintegrators are substances that swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethyl cellulose, for example, can be used as well as sodium lauryl sulfate. Tablets can be coated with sugar as a flavor and sealant, or with film-forming protecting agents to modify the dissolution properties of the tablet. The compositions can also be formulated as chewable tablets, for example, by using substances such as mannitol in the formulation.

When it is desired to administer a TOR kinase inhibitor as a suppository, typical bases can be used. Cocoa butter is a traditional suppository base, which can be modified by addition of waxes to raise its melting point slightly. Water-miscible suppository bases comprising, particularly, polyethylene glycols of various molecular weights are in wide use.

The effect of the TOR kinase inhibitor can be delayed or prolonged by proper formulation. For example, a slowly soluble pellet of the TOR kinase inhibitor can be prepared and incorporated in a tablet or capsule, or as a slow-release implantable device. The technique also includes making pellets of several different dissolution rates and filling capsules with a mixture of the pellets. Tablets or capsules can be coated with a film that resists dissolution for a predictable period of time. Even the parenteral preparations can be made long-acting, by dissolving or suspending the TOR kinase inhibitor in oily or emulsified vehicles that allow it to disperse slowly in the serum.

4.7. Kits

In certain embodiments, provided herein are kits comprising a TOR kinase inhibitor. In particular embodiments, provided herein are kits comprising a unit dosage form comprising a TOR kinase inhibitor in a sealed container, wherein the unit dosage form comprises about 1 mg to about 100 mg of a TOR kinase inhibitor. In particular embodiments, provided herein are kits comprising a unit dosage form comprising a TOR kinase inhibitor in a sealed container, wherein the unit dosage form comprises about 5 mg, about 20 mg or about 50 mg of a TOR kinase inhibitor.

In other embodiments, provide herein are kits comprising a TOR kinase inhibitor and means for monitoring patient response to administration of said TOR kinase inhibitor. In certain embodiments, the patient has a solid tumor, non-Hodgkin lymphoma or multiple myeloma. In particular embodiments, the patient response measured is inhibition of disease progression, inhibition of tumor growth, reduction of primary and/or secondary tumor(s), relief of tumor-related symptoms, improvement in quality of life, inhibition of tumor secreted factors (including tumor secreted hormones, such as those that contribute to carcinoid syndrome), delayed appearance of primary and/or secondary tumor(s), slowed development of primary and/or secondary tumor(s), decreased occurrence of primary and/or secondary tumor(s), slowed or decreased severity of secondary effects of disease, arrested tumor growth and/or regression of tumors.

In other embodiments, provide herein are kits comprising a TOR kinase inhibitor and means for monitoring patient response to administration of said TOR kinase inhibitor, wherein said response is Response Evaluation Criteria in Solid Tumors (RECIST 1.1), International Workshop Criteria (IWC) for NHL, International Uniform Response Criteria for Multiple Myeloma (IURC), Eastern Cooperative Oncology Group Performance Status (ECOG) or Response Assessment for Neuro-Oncology (RANO) Working Group for GBM.

In other embodiments, provided herein are kits comprising a TOR kinase inhibitor and means for measuring the amount of inhibition of phosphorylation of S6RP, 4E-BP1 and/or AKT in a patient. In certain embodiments, the kits comprise means for measuring inhibition of phosphorylation of S6RP, 4E-BP1 and/or AKT in circulating blood or tumor cells and/or skin biopsies or tumor biopsies/aspirates of a patient. In certain embodiments, provided herein are kits comprising a TOR kinase inhibitor and means for measuring the amount of inhibition of phosphorylation as assessed by comparison of the amount of phospho-S6RP, 4E-BP1 and/or AKT before, during and/or after administration of the TOR kinase inhibitor. In certain embodiments, the patient has a solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer or adrenal cancer), non-Hodgkin lymphoma or multiple myeloma. In another embodiment, the solid tumor is esophageal cancer, renal cancer, leiomyosarcoma, or paraganglioma.

In other embodiments, provided herein are kits comprising a TOR kinase inhibitor and means for measuring the amount of inhibition of DNA-dependent protein kinase (DNA-PK) activity in a patient. In certain embodiments, the kits comprise means for measuring the amount of inhibition of DNA-dependent protein kinase (DNA-PK) activity in a skin sample and/or a tumor biopsy/aspirate of a patient. In one embodiment, the kits comprise a means for measuring the amount of pDNA-PK S2056 in a skin sample and/or a tumor biopsy/aspirate of a patient. In one embodiment, the skin sample is irradiated by UV light. In certain embodiments, provided herein are kits comprising a TOR kinase inhibitor and means for measuring the amount of inhibition of DNA-dependent protein kinase (DNA-PK) activity before, during and/or after administration of the TOR kinase inhibitor. In certain embodiments, provided herein are kits comprising a TOR kinase inhibitor and means for measuring the amount of phosphorylated DNA-PK S2056 before, during and/or after administration of the TOR kinase inhibitor. In certain embodiments, the patient has a solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer or adrenal cancer), non-Hodgkin lymphoma or multiple myeloma. In another embodiment, the solid tumor is esophageal cancer, renal cancer, leiomyosarcoma, or paraganglioma.

Inhibition of phosphorylation of S6RP, 4E-BP1, and/or AKT can be measured in blood, skin, tumor, and/or circulating tumor cells (CTCs) in blood by various methodology including flow cytometry, ELISA, immunohistochemistry (IHC) using phosphorylation-specific antibodies. Inhibition of DNA-PK activity can be measured in blood, skin, and/or circulating tumor cells (CTCs) in blood by monitoring phosphorylation of substrates of DNA-PK, such as DNA-PK itself and XRCC4. Inhibition of DNA-PK activity can also be measured by monitoring accumulation of double strand DNA damage in tissues and/or cells such as those mentioned above.

In certain embodiments, the kits provided herein comprise an amount of a TOR kinase inhibitor effective for treating or preventing a solid tumor (for example, a neuroendocrine tumor, non-small cell lung cancer, glioblastoma multiforme, hepatocellular carcinoma, breast cancer, colorectal cancer, salivary cancer, pancreatic cancer, adenocystic cancer or adrenal cancer), non-Hodgkin lymphoma or multiple myeloma. In another embodiment, the solid tumor is esophageal cancer, renal cancer, leiomyosarcoma, or paraganglioma. In certain embodiments, the kits provided herein comprise a TOR kinase inhibitor having the molecular formula $C_{16}H_{16}N_8O$. In certain embodiments, the kits provided herein comprise Compound 1.

In certain embodiments, the kits provided herein further comprise instructions for use, such as for administering a TOR kinase inhibitor and/or monitoring patient response to administration of a TOR kinase inhibitor.

5. EXAMPLES

5.1 Biological Examples

5.1.1 Biochemical Assays mTOR HTR-FRET Assay. The following is an example of an assay that can be used to determine the TOR kinase inhibitory activity of a test compound. TOR kinase inhibitors were dissolved in DMSO and prepared as 10 mM stocks and diluted appropriately for the experiments. Reagents were prepared as follows:

"Simple TOR buffer" (used to dilute high glycerol TOR fraction): 10 mM Tris pH 7.4, 100 mM NaCl, 0.1% Tween-20, 1 mM DTT. Invitrogen mTOR (cat#PV4753) was diluted in this buffer to an assay concentration of 0.200 µg/mL.

ATP/Substrate solution: 0.075 mM ATP, 12.5 mM $MnCl_2$, 50 mM Hepes, pH 7.4, 50 mM β-GOP, 250 nM Microcystin LR, 0.25 mM EDTA, 5 mM DTT, and 3.5 µg/mL GST-p70S6.

Detection reagent solution: 50 mM HEPES, pH 7.4, 0.01% Triton X-100, 0.01% BSA, 0.1 mM EDTA, 12.7 µg/mL Cy5-αGST Amersham (Cat#PA92002V), 9 ng/mL α-phospho p70S6 (Thr389) (Cell Signaling Mouse Monoclonal #9206L), 627 ng/mL α-mouse Lance Eu (Perkin Elmer Cat#AD0077).

To 20 µL of the Simple mTor buffer is added 0.5 µL of test compound in DMSO. To initiate the reaction 5 µL of ATP/Substrate solution was added to 20 µL of the Simple TOR buffer solution (control) and to the compound solution prepared above. The assay was stopped after 60 min by adding 5 µL of a 60 mM EDTA solution; 10 µL of detection reagent solution was then added and the mixture was allowed to sit for at least 2 hours before reading on a Perkin-Elmer Envision Microplate Reader set to detect LANCE Eu TR-FRET (excitation at 320 nm and emission at 495/520 nm).

TOR kinase inhibitors were tested in the mTor HTR-FRET assay and were found to have activity therein, with certain compounds having an $IC_{50}$ below 10 µM in the assay, with some compounds having an $IC_{50}$ between and 0.005 nM and 250 nM, others having an $IC_{50}$ between and 250 nM and 500 nM, others having an $IC_{50}$ between 500 nM and 1 µM, and others having an $IC_{50}$ between 1 µM and 10 µM.

DNA-PK Assay. DNA-PK assays were performed using the procedures supplied in the Promega DNA-PK assay kit (catalog #V7870). DNA-PK enzyme was purchased from Promega (Promega cat#V5811).

Selected TORKi have, or are expected to have, an $IC_{50}$ below 10 µM in this assay, with some TORKi having an $IC_{50}$ below 1 µM, and others having an $IC_{50}$ below 0.10 µM.

5.1.2 Cell Based Assays

Materials and Methods. Cell lines and cell culture: Human glioblastoma and lung cancer cell lines are purchased from American Type Culture Collection (ATCC) and maintained in RPMI 1640 plus 10% bovine calf serum (FCS) or recommended special culture medium. The non-small cell lung cancer cells can include the following cell lines NCI-H460, NCI-H838, NCI-H1792, NCI-H520, NCI-H1993, NCI-H1944, NCI-H1975, NCI-H1395, A549, NCI-H2122, NCI-H1703, NCI-H1299, NCI-H647, NCI-H358, SK-LU-1, NCI-H1734, NCI-H1693, NCI-H226, NCI-H23, NCI-H2030, NCI-H1755, Calu-6, Calu-1, SW1573, NCI-H2009, NCI-H441, HOP92, NCI-H2110, NCI-H727, NCI-H1568, Calu-3, NCI-H2228, NCI-H2444, NCI-H1563, NCI-H1650, NCI-H1437, NCI-H650, NCI-H1838, NCI-H2291, NCI-H28 and NCI-H596. Additional cell lines that TOR kinase inhibitors can be tested against include HT-3, HeLaSF, Hela S3, SKG-IIIa, SiHa, MS751, BOKU, C-33-A, C-4-II, Ca-Ski, DoTc2-4510, ME-180, OMC-1, SW756, and TC-YIK.

Glioblastoma cell lines obtained from, for example, ATCC (for example A-172, T98G, DBTRG-05MG, M059K, M059J, LN18, LN-229, TIME, G44, and U87 MG, U-118 MG, U-138 MG cells) can be engineered to express the EGFRvIII mutation or overexpress EGFR by methods known in the art. The cell lines can also been engineered to express EGFRvIII or overexpress EGFR, and express PTEN simultaneously. Additionally, cell lines with EGFR overexpression and EGFRvIII mutation can be established from human tumors (patient samples). (See for example A. Lal et al, *Cancer Res*, 62:3335 (2002), J. J. Kelly et al, *Stem Cells* 27(8):1722 (2009), M. Y. Wang et al, *Cancer Res*. 66:7864 (2006)).

Cell Viability Assay for NSCLC Lines. Cell viability was assessed using the Cell Titer-Glo Luminescent Cell Viability from Promega. The assay is a homogenous method of determining the number of viable cells in culture based on quantitation of the adenosine triphosphate (ATP) present, an indicator of metabolically active cells. The homogenous assay procedure involves adding the single reagent (CellTiter-Glo Reagent) directly to cells cultured in serum-supplemented medium. Cells were plated into a 96-well flat bottom plate (Costar Catalog Number 33595) at densities that were previously optimized for each cell line. The cells were incubated overnight in 5% $CO_2$ at 37° C. The following day, compound dilutions were prepared and all concentrations were assayed in triplicate. The cells were incubated with Compound 1 (0.03 µM, 0.1 µM, 0.3 µM, 1 µM, 3 µM, 10 µM and 30 µM for NSCLC cells) in 5% $CO_2$ at 37° C. for 3 days. After a 3-day incubation period, 100 µL of CellTiter-Glo reagent was added to each well for 2 minutes with shaking and further incubated for 10 minutes (no shaking) at room temperature to stabilize the signal. The luminescence was measured on the VICTOR X2 multilabel plate reader. The percent growth inhibition was calculated using the DMSO control in the same plate (no compound) response as 100% cell growth. The average values from triplicates were plotted to obtain $IC_{50}$ values using software XLfit from IDBS. The formula used for determining $IC_{50}$ in XLfit was model number 205, which utilizes a 4 Parameter Logistic Model or Sigmoidal Dose-Response Model to calculate the $IC_{50}$ values. All $IC_{50}$ values are reported as an average from either two independent experiments or a single experiment. Results for Compound 1 for selected NSCLC cells lines are set forth in Table 1.

TABLE 1

| NSCLC Cell Line | IC$_{50}$ µM |
|---|---|
| NCI-H1568 | 0.226 |
| NCI-H2228 | 0.264 |
| NCI-H727 | 0.288 |
| Calu-3 | 0.302 |
| NCI-H460 | 0.37 |
| NCI-H838 | 0.39 |
| NCI-H2110 | 0.456 |
| NCI-H520 | 0.499 |
| NCI-H520 | 0.50 |
| NCI-H1993 | 0.50 |
| NCI-H1792 | 0.54 |
| NCI-H1944 | 0.55 |
| NCI-H1395 | 0.60 |
| NCI-H549 | 0.77 |
| NCI-H2444 | 0.778 |
| NCI-H2122 | 0.90 |
| NCI-H1703 | 0.92 |
| NCI-H1975 | 0.96 |
| NCI-H1437 | 0.975 |
| NCI-H1299 | 1.23 |
| NCI-H647 | 1.36 |
| NCI-H358 | 1.42 |
| SK-LU-1 | 1.44 |
| NCI-H1734 | 1.55 |
| NCI-H1693 | 1.58 |
| NCI-H226 | 1.75 |
| HOP62 | 2.007 |
| NCI-H596 | 2.196 |
| NCI-H23 | 2.21 |
| NCI-H2030 | 2.23 |
| NCI-H1755 | 3.03 |
| Calu-6 | 4.52 |
| Calu-1 | 4.74 |
| SW1573 | 7.21 |
| NCI-H2009 | 26.01 |
| NCI-H441 | >30 |
| HOP92 | >30 |
| NCI-H1563 | >30 |
| NCI-H1650 | >30 |
| NCI-H1838 | >30 |
| NCI-H2291 | >30 |
| NCI-H28 | >30 |
| NCI-H650 | >30 |

Growth Inhibition Assay for HCC and NHL Lines. All HCC and NHL cell lines were maintained and tested in the culture media indicated in Table 2 and 3. The seeding density for each cell line was optimized to ensure assay linearity in 384-well plates.

Compound 1 was dissolved in dimethyl sulfoxide (DMSO) to prepare a 10 mM stock solution. A serial titration was performed to produce a working concentration range of 1.5 µM to 10 mM. Aliquots to produce final concentrations of 1.5 nM to 10 µM were spotted via an acoustic dispenser (EDC ATS-100) into an empty 384-well plate. Compound 1 was spotted in a 10-point serial dilution fashion (3-fold dilution) in duplicate within the plate. The DMSO concentration was kept constant for a final assay concentration of 0.1% DMSO. Plates were replicated for use with different cell lines and testing periods. After compound plate replication, all plates were sealed (Agilent ThermoLoc) and stored at −20° C. for up to 1 month. Repeat testing of Compound 1 in the control cell line (A549) resulted in consistent GI$_{50}$ and IC$_{50}$ values regardless of plate replication sequence or storage time at −20° C., suggesting Compound 1 is stable under the storage conditions used in the current study for at least 1 month. When ready for testing, plates were removed from the freezer, thawed, and unsealed just prior to the addition of the test cells. Prior to testing, cells were grown and expanded in culture flasks to provide sufficient amounts of starting material. Cells were then diluted to the appropriate densities and added directly to the compound-spotted 384-well plates. Cells were allowed to grow for 96 hours at 37° C./5% CO$_2$. At the time when compound was added (t$_0$), initial cell number was assessed via a viability assay (Cell Titer-Glo) by quantifying the level of luminescence generated by ATP present in viable cells. After 96 hours, cell viability of compound-treated cells was assessed via Cell Titer-Glo and luminescence measurement. Cell lines were assayed for growth inhibition by Compound 1 in at least 3 independent tests. A control cell line (the lung tumor cell line, A549) was included in each of the assays. The compound response against this control cell line was monitored closely to enable comparison of the data generated through the assay period. All data were normalized and presented as a percentage of the DMSO-treated cells. Results were then expressed as a GI$_{50}$ value. The GI$_{50}$ value corrects for the cell count at time zero. In addition, the IC$_{50}$ value of Compound 1 for each cell line was calculated. Results for Compound 1 for selected HCC cell lines are set forth in Table 2.

TABLE 2

| HCC Cell Line | GI$_{50}$ µM | IC$_{50}$ µM | Growth Medium |
|---|---|---|---|
| Hep3B | 0.26 ± 0.07 | 0.34 ± 0.11 | DMEM + 10% FBS |
| HepG2 | 0.24 ± 0.06 | 0.32 ± 0.13 | DMEM + 10% FBS |
| HuH-7 | 0.07 ± 0.03 | 0.10 ± 0.04 | DMEM + 10% FBS |
| PLC-PRF-5 | 0.31 ± 0.07 | 0.43 ± 0.07 | DMEM + 10% FBS |
| SK-HEP-1 | 0.27 ± 0.04 | 0.33 ± 0.07 | DMEM + 10% FBS |
| SNU-182 | 0.08 ± 0.03 | 0.26 ± 0.1 | RPMI 1640 + 10% FBS |
| SNU-387 | 1.26 ± 0.47 | 2.47 ± 0.93 | RPMI 1640 + 10% FBS |
| SNU-398 | 0.28 ± 0.06 | 0.29 ± 0.05 | RPMI 1640 + 10% FBS |
| SNU-423 | 0.30 ± 0.05 | 0.48 ± 0.06 | RPMI 1640 + 10% FBS |
| SNU-449 | 0.37 ± 0.07 | 0.48 ± 0.11 | RPMI 1640 + 10% FBS |
| SNU-475 | 0.46 ± 0.09 | 0.69 ± 0.14 | RPMI 1640 + 10% FBS |

DMEM = Dulbecco's Modified Eagle's Medium;
FBS = fetal bovine serum.

Apoptosis Assay for NHL Lines. Prior to testing, cells were grown and expanded in culture flasks to provide sufficient amounts of starting material. Cells were then diluted to their desired densities and added directly to compound-spotted 384-well plates. Cells were allowed to grow for 24 hours in 5% CO$_2$ at 37° C. The apoptotic response was assessed by quantifying the activities of caspase 3 and caspase 7 (Caspase 3/7-Glo) in treated cells and control cells at the 24-hour time point. All data was normalized and represented as a value relative to the DMSO-treated cells. Results were then expressed as CalX, which is the minimum compound concentration required to double the levels of caspase 3/7 relative to those of the DMSO-treated cells during their treatment period.

Figure 1B:
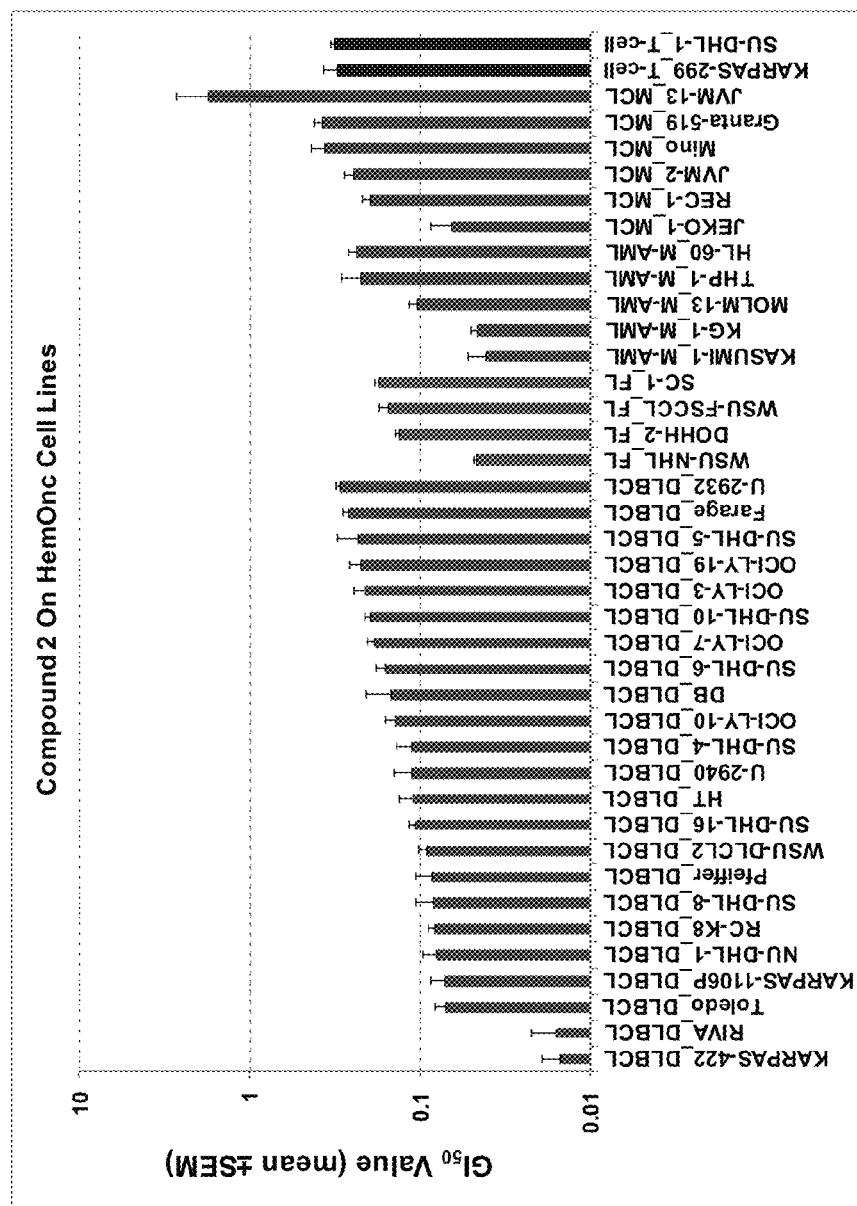
Figure 2:
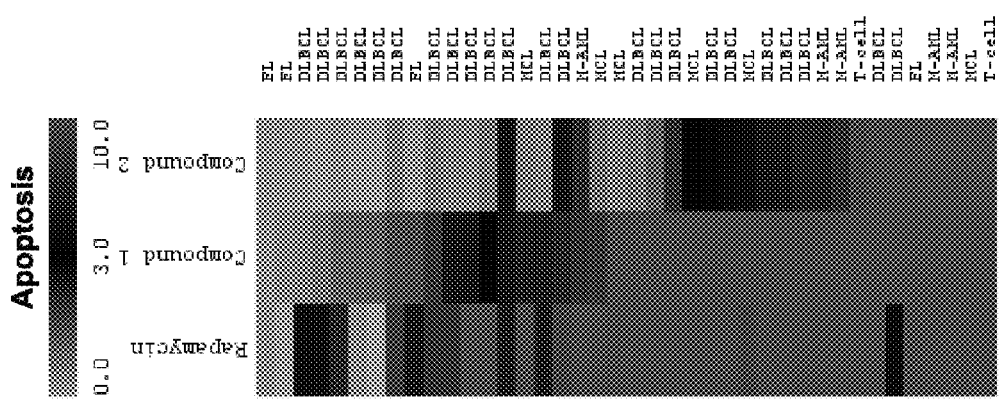
FIG. 2 depicts the effects of Compound 1 and Compound 2 on apoptosis of certain NHL cell lines.
Figure 3:
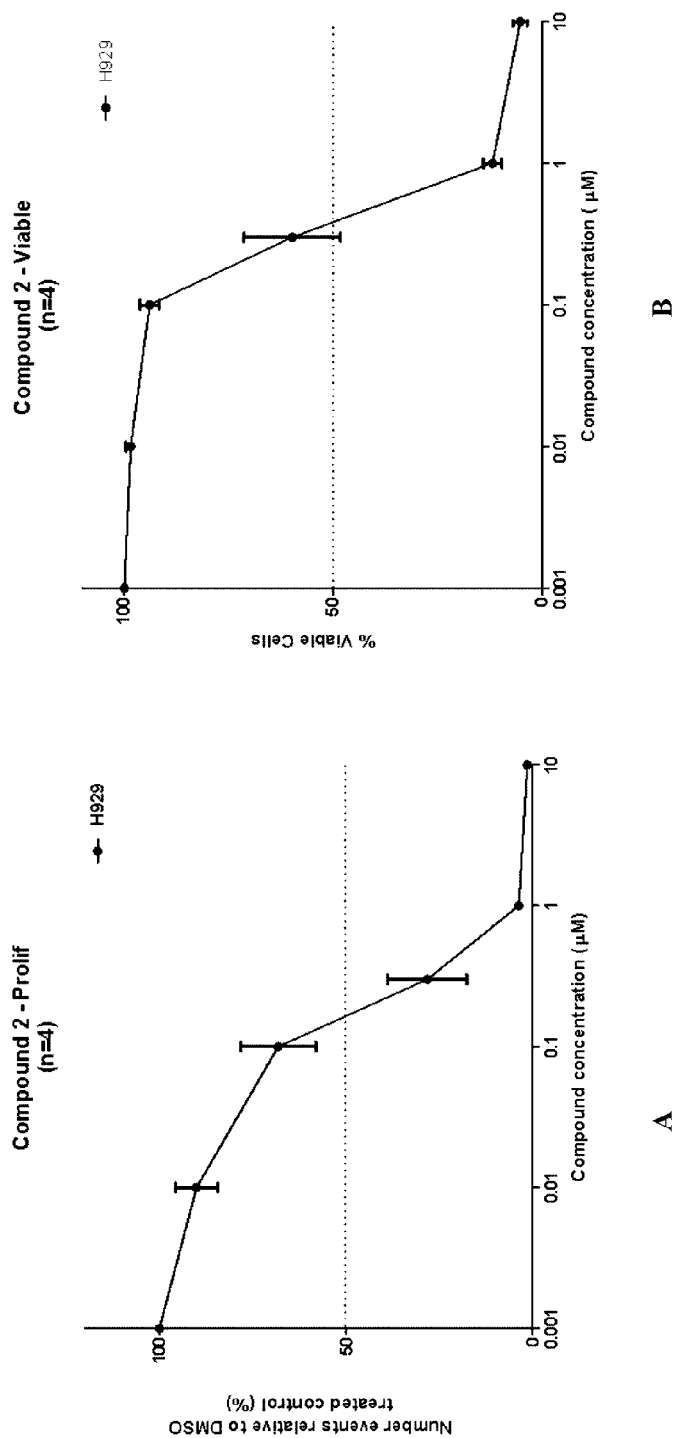
FIG. 3 depicts the effects of Compound 2 on the proliferation (A) and viability (B) of certain multiple myeloma cell lines.
Figure 4:
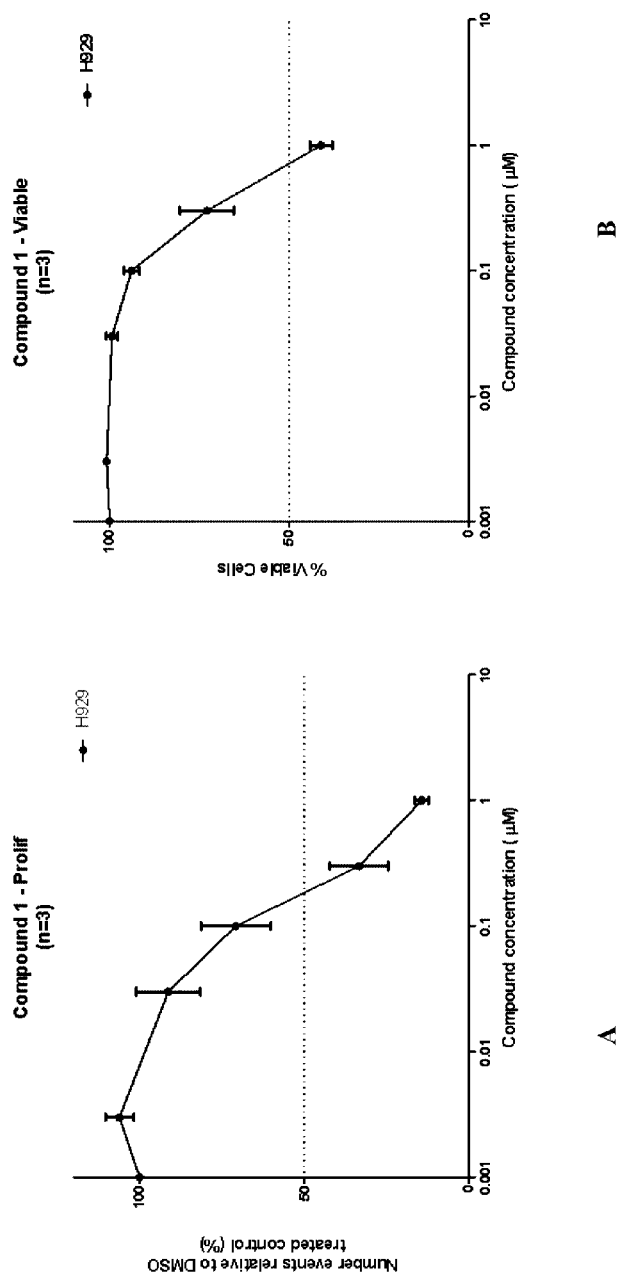
FIG. 4 depicts the effects of Compound 1 on the proliferation (A) and viability (B) of certain multiple myeloma cell lines.
Figure 5:
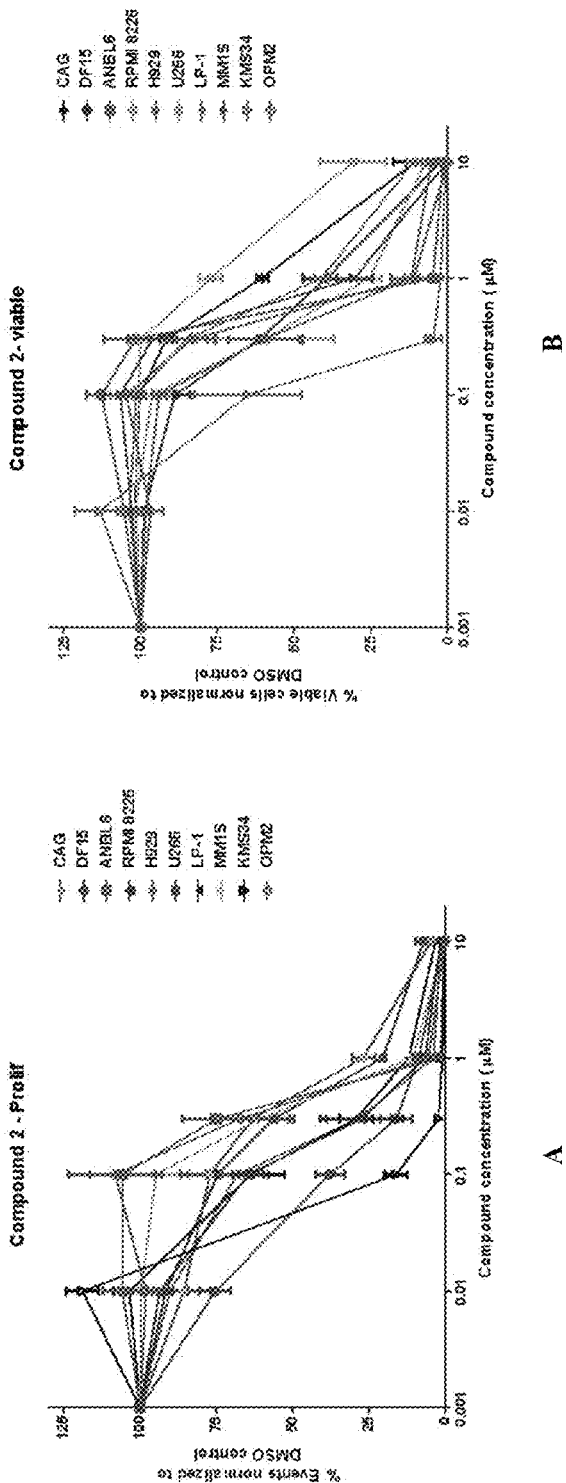
FIG. 5 depicts the effects of Compound 2 on the proliferation (A) and viability (B) of certain multiple myeloma cell lines.
Figure 6:
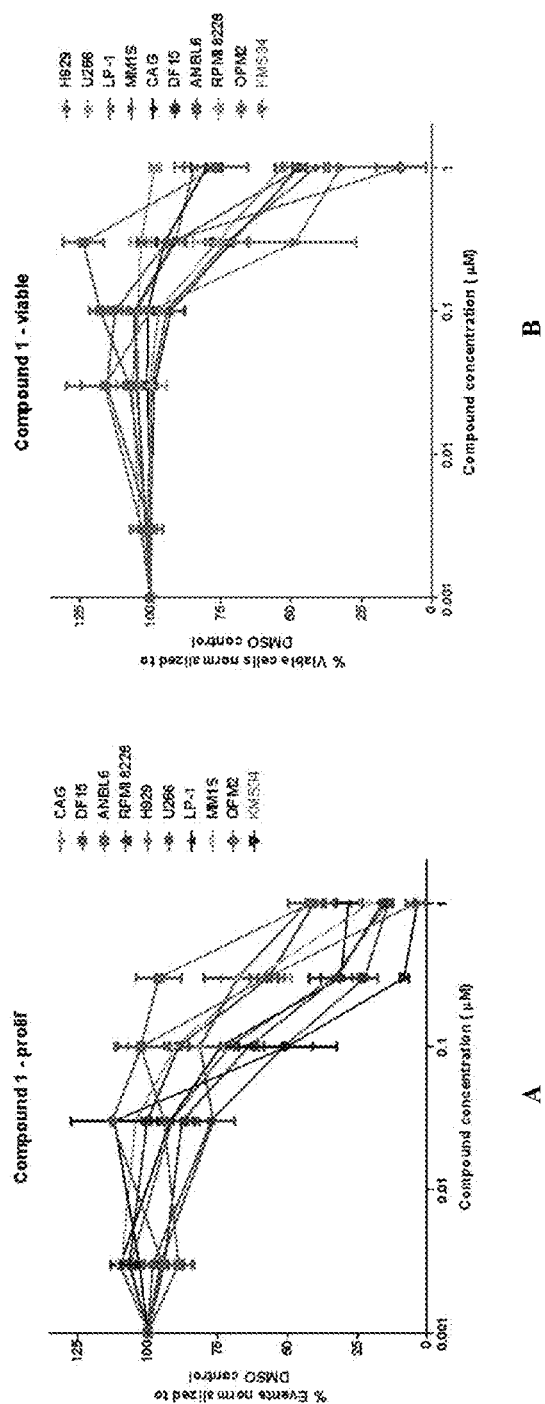
FIG. 6 depicts the effects of Compound 1 on the proliferation (A) and viability (B) of certain multiple myeloma cell lines.

Results for Compound 1 for inhibition of proliferation of selected NHL cell lines are set forth in Table 3 and for Compound 1 and Compound 2 in FIG. 1A and FIG. 1B, and results for Compound 1 and Compound 2 for apoptosis of selected NHL cell lines are set forth in FIG. 2. As can be seen, Compound 1 and Compound 2 induce apoptosis in multiple NHL cell lines in vitro.

TABLE 3

| Cell Line | Disease | Subtype | Proliferation (n ≥ 3) | | Apoptosis (n = 1) | |
|---|---|---|---|---|---|---|
| | | | $GI_{50}$ | $IC_{50}$ | CalX | Apoptotic |
| KARPAS-422 | NHL | DLBCL | 0.02 ± 0.01 | 0.02 ± 0.01 | 5.16 | N/Y |
| RIVA | NHL | DLBCL | 0.02 ± 0.01 | 0.1 ± 0.05 | 3.84 | N/Y |
| KASUMI-1 | Leukemia | M-AML | 0.04 ± 0.02 | 0.12 ± 0.03 | 6.52 | N/Y |
| WSU-NHL | NHL | FL | 0.05 ± 0 | 0.07 ± 0 | 0.16 | Y |
| KG-1 | Leukemia | M-AML | 0.06 ± 0.02 | 0.37 ± 0.04 | 10 | N |
| JEKO-1 | NHL | MCL | 0.07 ± 0.04 | 0.1 ± 0.05 | 0.56 | Y |
| Toledo | NHL | DLBCL | 0.07 ± 0.02 | 0.44 ± 0.02 | 3.48 | N/Y |
| KARPAS-1106P | NHL | DLBCL | 0.07 ± 0.03 | 0.07 ± 0.03 | 0.25 | Y |
| NU-DHL-1 | NHL | DLBCL | 0.08 ± 0.03 | 0.11 ± 0.05 | 0.41 | Y |
| RC-K8 | NHL | DLBCL | 0.08 ± 0.01 | 0.15 ± 0.03 | 6.51 | N/Y |
| SU-DHL-8 | NHL | DLBCL | 0.08 ± 0.04 | 0.1 ± 0.04 | 0.07 | Y |
| Pfeiffer | NHL | DLBCL | 0.09 ± 0.04 | 0.19 ± 0.07 | 10 | N |
| WSU-DLCL2 | NHL | DLBCL | 0.09 ± 0.02 | 0.09 ± 0.02 | 0.19 | Y |
| MOLM-13 | Leukemia | M-AML | 0.11 ± 0.02 | 0.14 ± 0.02 | 7.24 | N/Y |
| SU-DHL-16 | NHL | DLBCL | 0.11 ± 0.02 | 0.11 ± 0.02 | 0.11 | Y |
| HT | NHL | DLBCL | 0.11 ± 0.04 | 0.17 ± 0.05 | 5.62 | N/Y |
| U-2940 | NHL | DLBCL | 0.11 ± 0.07 | 0.18 ± 0.1 | 0.43 | Y |
| SU-DHL-4 | NHL | DLBCL | 0.11 ± 0.04 | 0.12 ± 0.05 | 5.15 | N/Y |
| DOHH-2 | NHL | FL | 0.13 ± 0.02 | 0.16 ± 0.03 | 0.14 | Y |
| OCI-LY-10 | NHL | DLBCL | 0.14 ± 0.04 | 0.19 ± 0.04 | 0.7 | Y |
| DB | NHL | DLBCL | 0.15 ± 0.1 | 0.17 ± 0.09 | 5.44 | N/Y |
| WSU-FSCCL | NHL | FL | 0.16 ± 0.04 | 0.19 ± 0.04 | 0.16 | Y |
| SU-DHL-6 | NHL | DLBCL | 0.16 ± 0.04 | 0.2 ± 0.06 | 10 | N |
| SC-1 | NHL | FL | 0.18 ± 0.01 | 0.2 ± 0.01 | 10 | N |
| OCI-LY-7 | NHL | DLBCL | 0.19 ± 0.03 | 0.25 ± 0.03 | 0.07 | Y |
| SU-DHL-10 | NHL | DLBCL | 0.2 ± 0.02 | 0.2 ± 0.03 | 0.54 | Y |
| REC-1 | NHL | MCL | 0.2 ± 0.04 | 0.26 ± 0.05 | 0.79 | Y |
| OCI-LY-3 | NHL | DLBCL | 0.21 ± 0.06 | 0.29 ± 0.07 | 0.67 | Y |
| OCI-LY-19 | NHL | DLBCL | 0.22 ± 0.06 | 0.35 ± 0.08 | 1.13 | Y |
| THP-1 | Leukemia | M-AML | 0.23 ± 0.11 | 0.57 ± 0.16 | 7.57 | N/Y |
| SU-DHL-5 | NHL | DLBCL | 0.23 ± 0.13 | 0.26 ± 0.14 | 0.59 | Y |
| HL-60 | Leukemia | M-AML | 0.24 ± 0.06 | 0.38 ± 0.13 | 10 | N |
| JVM-2 | NHL | MCL | 0.26 ± 0.05 | 0.44 ± 0.18 | 3.2 | N/Y |
| Farage | NHL | DLBCL | 0.27 ± 0.03 | 0.28 ± 0.04 | 0.47 | Y |
| U-2932 | NHL | DLBCL | 0.3 ± 0.03 | 0.45 ± 0.01 | 2.04 | Y |
| SU-DHL-1 | ALCL | T-cell | 0.32 ± 0.02 | 0.39 ± 0.03 | 10 | N |
| KARPAS-299 | ALCL | T-cell | 0.33 ± 0.12 | 0.47 ± 0.22 | 9.61 | N/Y |
| Mino | NHL | MCL | 0.37 ± 0.13 | 0.48 ± 0.1 | 0.53 | Y |
| Granta-519 | NHL | MCL | 0.38 ± 0.08 | 0.96 ± 0.1 | 10 | N |
| JVM-13 | NHL | MCL | 1.77 ± 1.61 | 3.49 ± 2.48 | 4.27 | N/Y |

Cell Proliferation and Viability Assay for MM Lines. Prior to use, cells were washed and maintained in medium for 5 days. Cells were seeded out at a density of $0.3 \times 10^6$ cells/mL in a 12-well plate and treated with Compound 1 or Compound 2 for 5 days. 7AAD detection fluorescence-activated cell sorting (FACS) flow cytometry was used in the analysis. Results are shown in FIGS. 3-6 and Tables 4-5.

TABLE 4

Proliferation

| Cell Line | $IC_{50}$ μM Compound 1 | $IC_{50}$ μM Compound 2 |
|---|---|---|
| H929 | 0.19 | 0.13 |
| KMS34 | 0.1 | 0.07 |
| DF15 | 0.1 | 0.05 |
| LP-1 | 0.22 | 0.16 |
| RPMI | 0.17 | 0.15 |
| MM1.S | 0.44 | 0.0.37 |
| CAG | 0.8 | 0.41 |
| Anbl 6 | | 0.37 |
| U266 | 0.56 | 0.32 |
| OPM2 | 0.33 | 0.37 |

TABLE 5

Viability

| Cell Line | $IC_{50}$ μM Compound 1 | $IC_{50}$ μM Compound 2 |
|---|---|---|
| H929 | 0.73 μM | 0.40 μM |
| KMS34 | 0.42 | 0.12 |
| DF15 | 0.85 | 0.57 |
| LP-1 | | 0.83 |
| RPMI | 1.1 | 0.45 |
| MM1.S | 1.01 | 0.85 |
| CAG | 2.6 | 1.5 |
| Anbl 6 | | 0.78 |
| U266 | | 4.29 |
| OPM2 | 0.6 | 0.51 |

Growth Inhibition Assay for Breast Cancer (BC) (Compound 1). All breast cancer cell lines were maintained and tested in appropriate culture media. The seeding density for each cell line was optimized to ensure assay linearity in 384-well plates.

Increasing concentrations of Compound 1 were spotted via an acoustic dispenser (EDC ATS-100) into an empty 384-well plate. Compound 1 was spotted in a 10-point serial dilution fashion (3-fold dilution) in duplicate within the plate. The dimethyl sulfoxide (DMSO) concentration was kept constant for a final assay concentration of 0.1% DMSO. Plates were replicated for use against different cell lines and testing periods. After compound plate replication, all plates were sealed (Agilent ThermoLoc) and stored at −20° C. for up to 1 month. When ready for testing, plates were removed from the freezer, thawed, and unsealed just prior to the addition of the test cell.

Prior to testing, cells were grown and expanded in culture flasks to provide sufficient amounts of starting material. Cells were then diluted to their desired densities and added directly to the Compound 1-spotted 384-well plates. Cells were allowed to grow for 96 hours at 37° C./5% $CO_2$. At the time of setup ($t_0$), initial cell number was assessed via a viability assay (Cell Titer-Glo) and read for luminescence. After 96 hours, cell viability of Compound 1-treated cells was assessed via Cell Titer-Glo and read for luminescence.

Figure 7A:
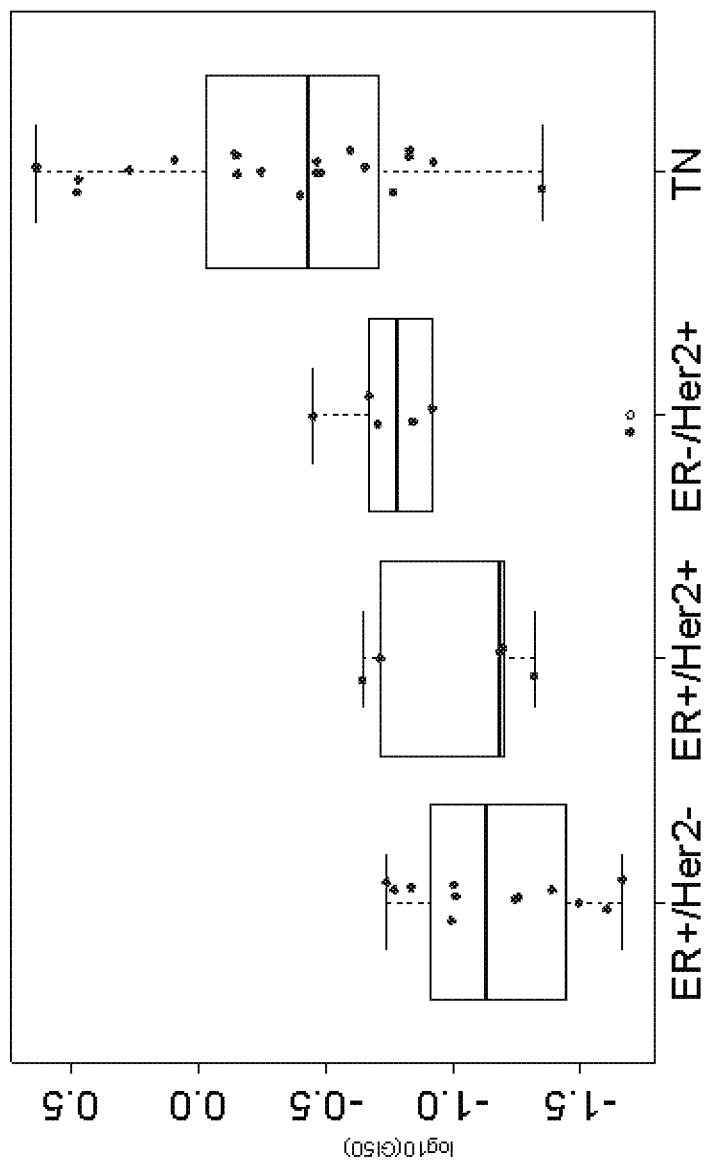
FIG. 7A depicts the potency of Compound 1 in different subtypes (ER+/Her2−, ER+/Her2+, ER−/Her2+ and triple negative (TN)) of breast cancer cells lines.
Figure 7B:
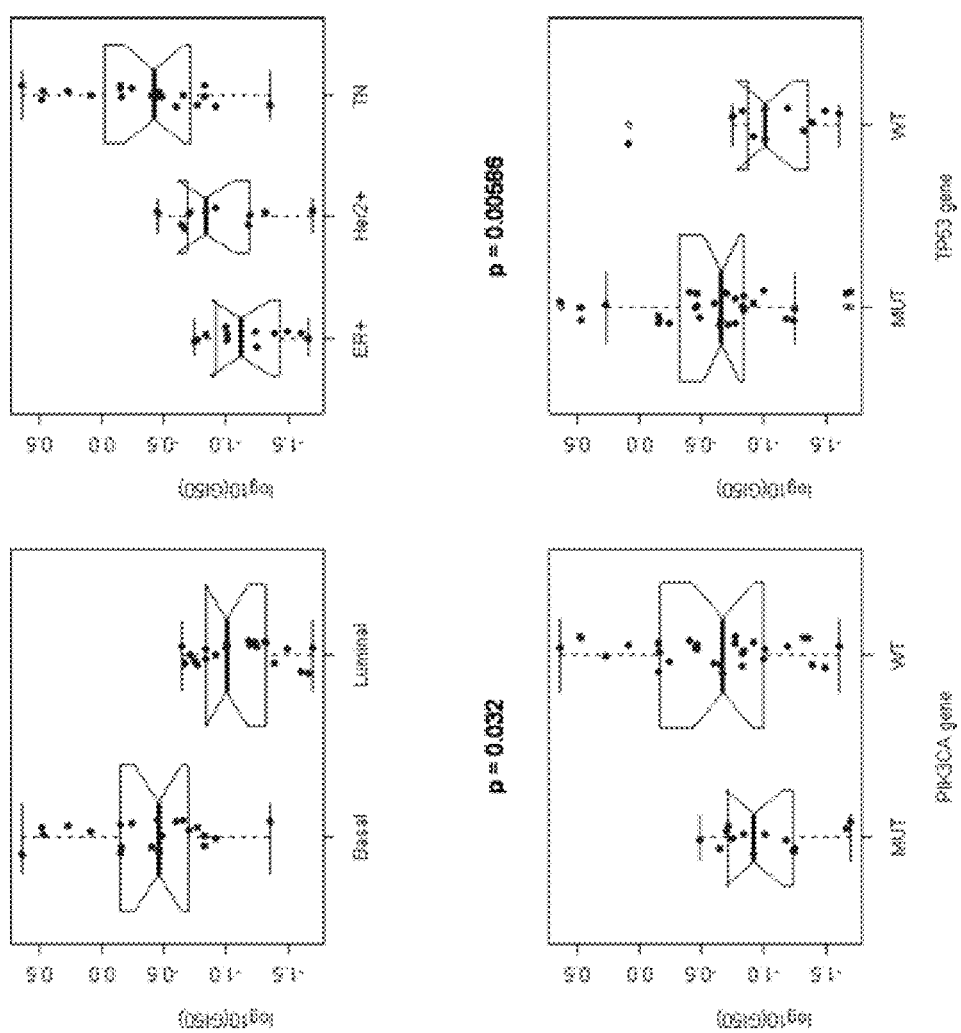
FIG. 7B depicts the correlation of Compound 1 sensitivity to ER, HER, PIK3CA, and TP53 status in breast cancer cell lines.

Cell lines were assayed for growth inhibition by Compound 1 for at least two independent tests. All data was normalized and represented as a percentage of the DMSO-treated control cells. Results were then expressed as a $GI_{50}$, which is the compound concentration required to inhibit cell growth in treated cells to 50% of the growth of the untreated control cells during the 96 hours of treatment (Table 6). The potency of Compound 1 in different subtypes of breast cancer cell lines is shown in FIG. 7A, while the correlation of Compound 1 sensitivity to ER, HER, PIK3CA, and TP53 status is shown in FIG. 7B. As can be seen from the data, the potency of Compound 1 strongly correlates with luminal cell type in breast cancer.

TABLE 6

| Breast Cancer Cell Line | ER | Her2 | Molec. Subtype | Tumor Subtype | PTEN | PIK3CA | TP53 | $GI_{50}$ (uM) | SD |
|---|---|---|---|---|---|---|---|---|---|
| BT-483 | + | − | Luminal | ER+ | + | E542K | M246I or mut | 0.0217 | |
| HCC1500 | + | − | Luminal | ER+ | + | WT | WT | 0.0248 | 0.0045 |
| ZR-75-1 | + | − | Luminal | ER+ | − | WT | WT | 0.0321 | 0.0098 |
| MDA-MB-175-VII | + | − | Luminal | ER+ | + | WT | WT | 0.0408 | 0.0332 |
| T47D | + | − | Luminal | ER+ | + | H1047R | L194F | 0.0553 | 0.0196 |
| EFM-19 | + | − | Luminal | ER+ | + | H1047L | H193R | 0.0572 | 0.0171 |
| KPL-1 | + | − | Luminal | ER+ | + | E545K | WT | 0.0973 | 0.0071 |
| HCC1428 | + | − | Luminal | ER+ | + | WT | WT | 0.0984 | 0.0095 |
| MDA-MB-134-VI | + | − | Luminal | ER+ | + | WT | E285K or WT | 0.101 | 0.0423 |
| CAMA-1 | + | − | Luminal | ER+ | + | WT | R280T | 0.1458 | 0.0899 |
| MDA-MB-415 | + | − | Luminal | ER+ | − | WT | Y236C | 0.1691 | 0.0192 |
| MCF7 | + | − | Luminal | ER+ | + | E545K | WT | 0.1807 | 0.0909 |
| HCC202 | − | + | Luminal | Her2+ | + | E545K | 283 > FS | 0.0201 | 0.0196 |
| UACC-812 | + | + | Luminal | Her2+ | + | WT | WT | 0.0478 | 0.016 |
| ZR-75-30 | + | + | Luminal | Her2+ | + | WT | WT | 0.0634 | 0.0098 |
| MDA-MB-361 | + | + | Luminal | Her2+ | + | E545K, K567R | E56X or S166* or WT | 0.0657 | 0.0345 |
| SK-BR-3 | − | + | Luminal | Her2+ | + | WT | R175H | 0.1212 | 0.0553 |
| MDA-MB-453 | − | + | Luminal | Her2+ | + | H1047R | H368del or WT | 0.1432 | 0.0295 |
| EFM-192A | + | + | Luminal | Her2+ | + | C420R | 270fs | 0.1922 | 0.0375 |
| HCC1954 | − | + | Basal | Her2+ | + | H1047R | Y163C | 0.1972 | 0.0899 |
| AU565 | − | + | Luminal | Her2+ | + | WT | R175H or WT | 0.213 | |
| BT-474 | + | + | Luminal | Her2+ | + | K111N or WT | E285K | 0.2261 | |
| HCC1569 | − | + | Basal | Her2+ | − | WT | E294* and 227fs | 0.3557 | 0.3023 |
| MCF12A | − | − | Basal | TN | + | WT | unk | 0.0444 | 0.0221 |
| CAL-51 | − | − | Basal | TN | − | E542K | WT | 0.119 | 0.0224 |
| MCF10A | − | − | Basal | TN | + | WT | WT | 0.1471 | 0.172 |
| BT-549 | − | − | Basal | TN | − | WT | R249S | 0.1492 | 0.104 |
| HCC70 | − | − | Basal | TN | − | WT | R248Q or WT | 0.1716 | 0.1492 |
| MDA-MB-435 | − | − | Basal | TN | + | WT | G266E | 0.222 | 0.1168 |
| CAL-85-1 | − | − | Basal | TN | + | WT | K132E | 0.253 | 0.0027 |
| BT-20 | − | − | Basal | TN | − | H1047R and P539R | K132Q or WT | 0.33 | |
| HCC1143 | − | − | Basal | TN | + | WT | R248Q or WT | 0.3427 | 0.2513 |
| HS578T | − | − | Basal | TN | + | WT | V157F | 0.3429 | 0.0046 |
| HCC2157 | − | − | Basal | TN | − | WT | R248W or WT | 0.3992 | 0.322 |
| HCC1187 | − | − | Basal | TN | + | WT | G108del | 0.5674 | 0.2614 |
| HCC1937 | − | − | Basal | TN | − | WT | R306* | 0.697 | 0.3973 |
| CAL-120 | − | − | Basal | TN | + | WT | mut or WT | 0.7002 | 0.0835 |
| MDA-MB-231 | − | − | Basal | TN | + | WT | R280K | 0.7105 | 0.0544 |
| NCI/ADR-RES | − | − | Basal | TN | + | WT | unk | 0.9441 | 0.2325 |
| DU4475 | − | − | Basal | TN | − | WT | WT | 1.2392 | 0.5476 |

TABLE 6-continued

| Breast Cancer Cell Line | ER | Her2 | Molec. Subtype | Tumor Subtype | PTEN | PIK3CA | TP53 | $GI_{50}$ (uM) | SD |
|---|---|---|---|---|---|---|---|---|---|
| MDA-MB-468 | − | − | Basal | TN | − | WT | R273H | 1.8556 | 0.038 |
| HCC38 | − | − | Basal | TN | − | WT | R273L | 2.9544 | 0.0419 |
| MDA-MB-436 | − | − | Basal | TN | − | WT | R273H or 202fs | 2.9873 | 0.018 |
| MDA-MB-157 | − | − | Basal | TN | + | WT | A88fs*52 or S261del | 4.341 | 1.1704 |

ER = estrogen receptor
Her2 = human epidermal growth factor receptor 2
TN = triple negative (estrogen receptor negative, progesterone receptor negative, human epidermal growth factor rector 2 negative)
WT = wild type status
Mut = mutant
Unk = unknown
SD = Standard deviation.

Growth Inhibition Assay for Cell Lines with Varying Sensitivity to Rapamycin (Compound 1). Cells were plated in 96-well plates at densities determined for each cell line and the following day were treated with a range of Compound 1 concentrations. The cells were incubated for 3 days at 37° C. and then 20 ml of WST-1 (Roche) for PC-3, A549, HCT 116, U87-MG, MDA-MB-231, and NCI-H23) or 100 ml CellTiter-Glo reagent (Promega) for NCI-H460, T47D) was added to each well and the assay was completed according to manufacturer protocols. The percentage inhibition at each concentration of compound was normalized to the DMSO control values. The percentage inhibition was determined for each replicate and then the 3 values were averaged for each set of triplicate wells. All data were analyzed using XLfit from IDBS. The formula used for determining $IC_{50}$ in Xlfit was model number 205, which utilizes a 4-parameter logistic model or sigmoidal dose-response model to calculate $IC_{50}$ values. $IC_{50}$ values are reported as an average.

Figure 8:
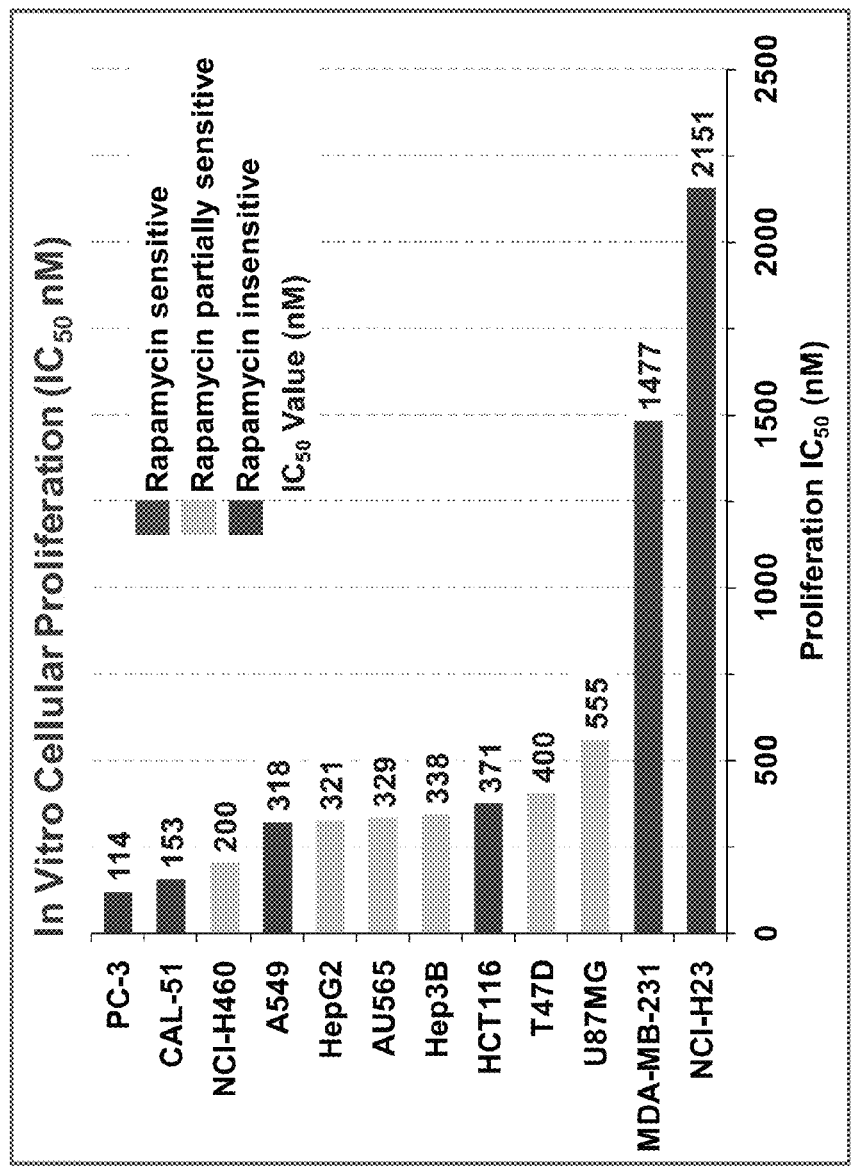
FIG. 8 depicts the effects of Compound 1 on proliferation of cell lines with varying sensitivity to rapamycin.

Rapamycin effects on proliferation tend to plateau in most cell lines. The sensitivity to Rapamycin was determined by the level of inhibition where this plateau occurs and assigned as follows: sensitive 100-55% inhibition; partially sensitive 54-31% inhibition and insensitive 0-30%. As can be seen in FIG. 8 Compound 1 shows potent cell growth inhibition, including in cell types that are partially sensitive, or insensitive to Rapamycin.

5.1.3 In Vivo Assays

Figure 9:
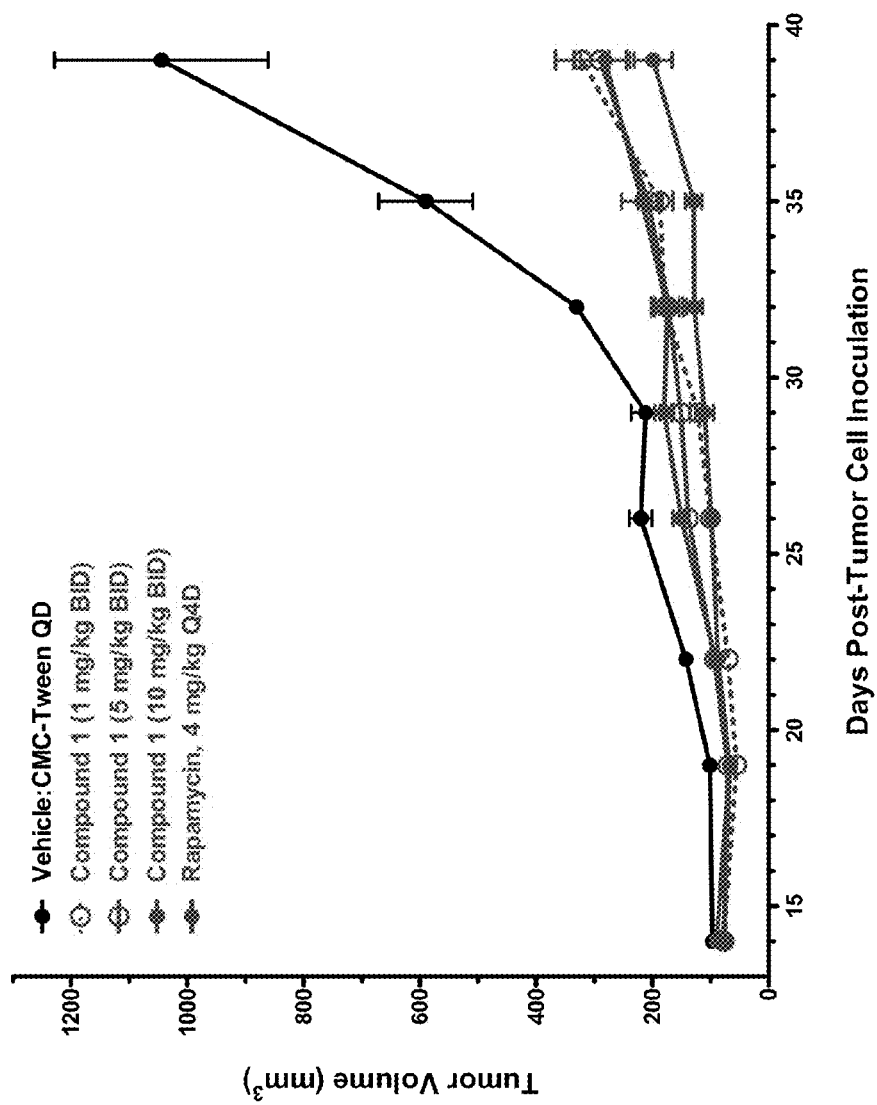
FIG. 9 depicts anti-tumor activity of Compound 1 in a NCI-H441 non-small cell lung cancer model.

NCI-H441 NSCLC In Vivo Tumor Growth Model. A xenograft study was conducted with NCI-H441 tumor-bearing mice. SCID mice were inoculated subcutaneously with NCI-H441 cells in the flank region above the right hind leg. Following inoculation of the animals, the tumors were allowed to grow to about 100 mm³ prior to randomization. On Day 14 following tumor cell inoculation, the mice bearing NCI-H441 tumors ranging between 87 and 136 mm³ were pooled together and randomized into various treatment groups. Compound 1 was formulated in 0.5% CMC and 0.25% Tween 80 in water (as a suspension). The animals were orally administered vehicle (CMC-Tween) or Compound 1 twice daily (BID) for up to 26 days. Doses of Compound 1 ranged between 1 and 10 mg/kg. The positive control rapamycin (4 mg/kg, Q3D) was administered via the intraperitoneal (IP) route. Rapamycin was prepared as solution in 2% ethanol, 45% polyethyleneglycol 400, and 53% saline. Tumors were measured twice a week using calipers and tumor volumes were calculated using the formula of $W^2 \times L/2$. Statistical analysis was performed using a one-way analysis of variance (ANOVA) followed by Dunnett's post-hoc comparison with the vehicle-treated control group. Results are set forth in FIG. 9, wherein it is shown that Compound 1 significantly inhibited NCI-H441 NSCLC tumor growth in vivo.

In Vivo Evaluation of Compound 1 in Low Passage Tumorgraft Models of Non-Small Cell Lung Cancer (NSCLC). The objective of the study was to evaluate the single agent efficacy of Compound 1 in non-small cell lung cancer (NCSLC) models. The antitumor activity of Compound 1 was evaluated in low passage non-small cell lung cancer (NSCLC) tumorgraft models. The tumorgrafts were developed by directly implanting the human tumor fragments into immunocompromised mice and then subsequently passaged in vivo. The tumors from these primary tumorgrafts have preserved biological and morphological characteristics of the original human tumors. The antitumor activity of Compound 1 was evaluated at three dose levels (1, 5 and 10 mg/kg) with once daily dosing for 28 days. During the course of the study antitumor activity was evaluated by measuring the tumors. Compound 1 significantly inhibited the growth of NSCLC primary tumor grafts in vivo.

U87MG Human Glioblastoma Xenograft Model (Compound 1). Efficacy Studies: Groups of female SCID mice bearing U87MG tumors (n=8-10/group) were dosed orally with vehicle or Compound 1 throughout the study, starting when tumor volumes reached approximately 200 mm³. The twice daily (BID) dose groups were dosed with a 10-hour separation between morning and evening doses. In the positive control group, rapamycin was administered Q3D via intraperitoneal (IP) route. At the end of each study, plasma and/or tumor samples were collected.

TABLE 7A

Design of Efficacy Study with twice daily dosing for 18 days

| Dose Group | Dosing Schedule | Dosing Duration |
|---|---|---|
| Vehicle (n = 9) | BID | 18 days |
| Rapamycin 4 mg/kg (n = 7) | Q3D | 18 days |
| Compound 1 5 mg/kg (n = 9) | BID | 18 days |

TABLE 7A-continued

Design of Efficacy Study with twice daily dosing for 18 days

| Dose Group | Dosing Schedule | Dosing Duration |
|---|---|---|
| Compound 1 10 mg/kg (n = 9) | BID | 18 days |
| Compound 1 25 mg/kg (n = 9) | Q2D | 18 days |

TABLE 7B

Design of Efficacy Study with once daily dosing for 3 weeks

| Dose Group | Dosing Schedule | Dosing Duration |
|---|---|---|
| Vehicle (n = 10) | QD | 3 weeks |
| Rapamycin 4 mg/kg (n = 6) | Q3D | 3 weeks |
| Compound 1 0.5 mg/kg (n = 10) | QD | 3 weeks |
| Compound 1 1 mg/kg (n = 10) | QD | 3 weeks |
| Compound 1 3 mg/kg (n = 10) | QD | 3 weeks |
| Compound 1 5 mg/kg (n = 10) | QD | 3 weeks |

Cell Line and Culture. U87MG cell line was obtained from American Tissue Culture Collection (ATCC) (Gaithersberg, Md.) and grown in growth medium containing MEM, 2 mM L-glutamine, 0.1 mM non-essential amino acids and 1 mM sodium pyruvate and 10% fetal bovine serum (FBS). The cells were detached from tissue culture flasks using trypsin-EDTA. After centrifugation, the cell pellets were suspended in phosphate buffered saline (PBS) and counted using a hemocytometer. The final volume was adjusted to $5 \times 10^6$ cells/0.1 mL of PBS.

Tumor Cell Inoculation. Mice were anesthetized with inhaled isoflurane and then inoculated with U87MG tumor cells subcutaneously on the right hind leg with 0.1 mL of a single cell suspension in PBS using a sterile 1 mL syringe fitted with a 26 gauge needle. Following inoculation, the mice were returned to microisolator cages Randomization of Animals. Following inoculation, tumors were allowed to grow to about 200 mm$^3$ prior to randomization. The typical number of days required for tumors to reach 200 mm$^3$ was 14-15 days. The tumor of each animal was measured and animals with tumors ranging between 175-250 mm$^3$ were included in the study. Animals from the pool were then distributed randomly into various cages and the cages were randomly assigned to vehicle, positive control, or test article groups. All of the mice were tagged with metal ear tags on the right ear.

Test Article Preparation and Administration. Suspensions of Compound 1 were prepared in aqueous 0.5% CMC and 0.25% Tween-80. The formulations were homogenized using a Teflon™ pestle and mortar (Potter-Elvehjem tissue grinder). Between the doses, the formulated compound was stored under constant stirring using a magnetic stirrer at 4° C. in the dark. The test article and vehicle were administered by oral gavage. The positive control, rapamycin, was prepared as solution in 2% ethanol, 45% polyethyleneglycol 400, and 53% saline and administered by IP injection. Sterile syringes and gavage needles were used for compound administration. All of the procedures including injections were done in biosafety cabinets disinfected with 70% ethanol prior to use.

Tumor Measurements. Tumor volumes were determined prior to the initiation of treatment and were considered as the starting volumes. Thereafter, tumors were measured twice a week for the duration of the study. The long and short axes of each tumor were measured using a digital caliper in millimeters. Tumor volumes were calculated using the formula: width$^2$×length/2. The tumor volumes were expressed in cubic millimeters (mm$^3$).

Tumor Growth Delay (TGD) Calculations. Tumor growth delay is the difference in days for treated versus control tumors to reach a volume of 1000 mm$^3$. The TGD was calculated from the data plotted in a graph format.

Body Weight Measurements. Initial body weights were recorded prior to the initiation of treatment using a digital scale. The percent body weight change during the course of the study was calculated using initial body weight measurements. Body weights of each animal were measured twice a week at the same time as the tumor measurements. Body weights were measured more frequently if significant decreases were noted during the course of the study.

Mechanism of action studies. To determine the mechanism of action of Compound 1, mice bearing U87MG tumors of approximately 500 mm$^3$ were dosed orally with vehicle or Compound 1 at 5 mg/kg BID for 4 days. The positive control, rapamycin, was dosed at 4 mg/kg Q3D for 4 days. Two hours after the 7$^{th}$ dose of Compound 1 on day 4, animals were euthanized and tumors were dissected out and snap frozen in liquid nitrogen. In the rapamycin-treated group tumors were collected at 2 hour after the 2$^{nd}$ dose on day 4. The tumors were processed for immunohistochemistry (IHC) or TUNEL.

Immunohistochemistry. Five to ten micron (5-10 µm) thick cryostat sections were used for IHC. The expression of the cell proliferation marker Ki67 was evaluated by IHC using anti-Ki67 antibody. Anti-CD31 antibody was used to determine blood vessel density and is a measurement of tumor angiogenesis. Frozen sections were fixed in 4% paraformaldehyde for 10 minutes at room temperature, washed in PBS, blocked and permeabilized with normal goat serum and triton X-100. Sections were then incubated with primary antibody (overnight) followed by incubation with secondary antibody (60 minutes). The sections were washed, counterstained with Hoechst stain and mounted with antifade reagent. For double labeling methods (Ki67 and CD31), cocktails of primary and secondary antibodies were used for incubation. Positive and negative controls were included in each assay. Positive controls included the sections that were known to be reactive with the antibody. Negative controls included omission of primary or secondary antibody. The sections were visualized with a Nikon E800 microscope equipped with fluorescence detection equipment and a digital camera attached to a computer.

Apoptosis TUNEL Assay. To detect apoptotic cells, fluorescence in situ cell death detection kit (Roche Biosciences) was used. Five to ten micron (5-10 µm) thick cryostat sections were fixed in 4% paraformaldehyde for 15 minutes at room temperature, washed, permeabilized with 0.3% triton X-100 and 0.1% sodium citrate in PBS for 10 minutes. Sections were then washed in PBS and incubated with a labeling solution containing TdT enzyme for 1 hour at 37° C. in the dark. The sections were washed in PBS, counterstained with Hoechst dye (0.4 µg/mL) at room temperature for 10 minutes and mounted in Prolong Gold antifade reagent.

Quantitation of Immunohistochemistry. The tissues sections processed for apoptosis or immunostained for proliferating cells (Ki67) or blood vessels were quantitated using Metamorph software. Using 20× objective, 5 different fields from each section, 2-4 sections from each tumor, and 3-4 tumors from each treatment group or control were used for quantitation. The area of interest was expressed as the percent threshold area of the total area.

Figure 11:
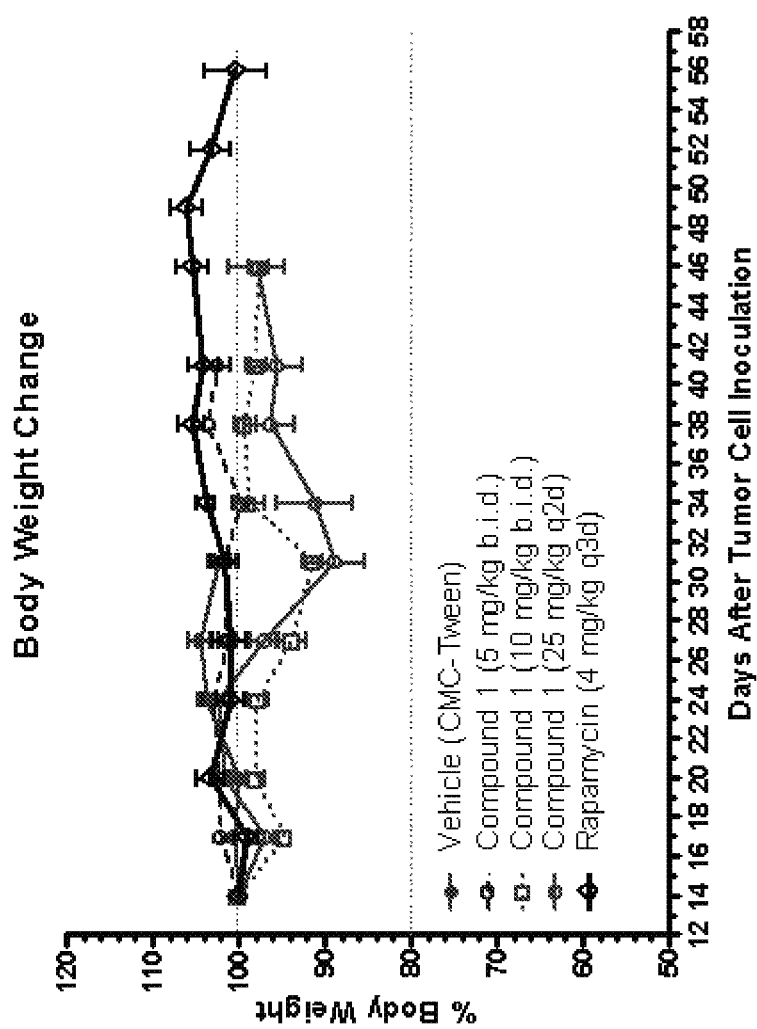
FIG. 11 depicts the body weight change of mice in the U87MG human glioblastoma xenograft model.

Results. The antitumor activity of Compound 1 was initially tested at 5 and 10 mg/kg BID and 25 mg/kg Q2D (FIG. 10A). Dosing started on Day 14 when tumor volumes ranged between 230-250 mm$^3$ and continued until Day 31. By Day 31, the vehicle-treated group measured 2404±185.6 mm$^3$. All animals in the positive control group that received rapamycin (4 mg/kg, Q3D) had significantly (p<0.001) smaller tumors when compared with the vehicle group on Day 31. At the beginning of the dosing period, all of the Compound 1-treated groups showed tumor regression, and this persisted until the end of the dosing period on Day 31. The average tumor volumes of Compound 1-treated groups on Day 24 were smaller than their respective starting volumes on Day 14 (149±9, 96±4 and 101±8 mm$^3$ Day 24 versus 231±4, 235±4 and 238±5 mm$^3$ on Day 14 for 5 and 10 mg/kg BID, and 25 mg/kg Q2D respectively). The average tumor volumes of Compound 1-treated groups on Day 31 were smaller than their respective starting volumes on Day 14 (208±31, 96±13 and 116±15 mm$^3$ Day 31 versus 231±4, 235±4 and 238±5 mm$^3$ on Day 14 for 5 and 10 mg/kg BID and 25 mg/kg Q2D, respectively). The tumor volumes from the 5 and 10 mg/kg BID and 25 mg/kg Q2D Compound 1-treated animals were reduced by 91, 96, and 95%, respectively, compared with the vehicle control group. On Day 31 the vehicle control animals were euthanized. The animals in the Compound 1 and rapamycin treated groups were allowed to survive without any further dosing to observe the kinetics of tumor re-growth following cessation of test article administration. Immediately following cessation of dosing, tumor growth resumed. The animals in each group were euthanized when tumor volumes reached about 2000 mm$^3$. Tumor growth delay (TGD) was 11, 20, and 17 days for the 5 mg/kg BID, 10 mg/kg BID, and 25 mg/kg Q2D groups, respectively. No significant change in body weight was observed in the groups dosed with vehicle, Compound 1 at 5 mg/kg BID, or the positive control. Compound 1-treated mice (10 mg/kg BID and 25 mg/kg Q2D) lost about 10% of their initial body mass by the end of the first cycle (p<0.01). As soon as dosing ceased, the animals immediately gained weight (FIG. 11). Conclusion: Treatment with Compound 1 significantly inhibited U87MG glioblastoma tumor growth in vivo.

A second study was designed to determine the lowest efficacious dose of Compound 1 with QD dosing and the corresponding plasma exposure (expressed as AUC) in the U87MG tumor xenograft model (FIG. 10B). Dosing was initiated on Day 14 when average tumor volumes ranged between 171 mm$^3$ and 179 mm$^3$. By the end of the 3-week dosing period on Day 34, vehicle-treated tumors reached an average volume of 2308±240 mm$^3$. Rapamycin significantly inhibited tumor growth (p<0.001) on day 34. Following Compound 1 treatment, dose-dependent antitumor activity was observed. Significant (p<0.001) tumor volume reduction was achieved at all dose levels tested. The lowest efficacious dose as determined by 65% tumor volume inhibition was 1 mg/kg QD. No statistically significant change in body weight was observed in any of the groups in the study.

Apoptotic Activity of Compound 1. To determine if Compound 1 induces apoptosis in U87MG tumors, vehicle, Compound 1 and rapamycin-treated tumor sections were processed for TUNEL which labels apoptotic cells. In this assay, terminal deoxynucleotidyl transferase (TdT) incorporates the FITC-labeled nucleotides to the ends of DNA strand breaks in situ (Gavrieli Y et. al., J Cell Biol 119:493-501 (1992)). FITC-labeled nucleotides (representing the cells with DNA strand breaks, a hallmark of apoptosis) can be detected using a microscope equipped with a fluorescence attachment. Relatively very few (<0.1%) TUNEL-positive cells were observed in vehicle-treated U87MG tumors (FIG. 10C). The number of TUNEL-positive cells in the tumors treated with Compound 1 and rapamycin were comparable (FIG. 10C). There was more than a four-fold increase in TUNEL-positive cells in Compound 1-treated tumors compared with vehicle control-treated tumors. These data suggest that apoptosis contributes to the observed antitumor activity of Compound 1 in vivo.

Antiproliferative and Antiangiogenic Activity of Compound 1. Immunohistochemistry with anti-Ki67 antibody was utilized to determine if Compound 1 inhibited tumor growth by blocking the proliferation of tumor cells in vivo. Ki67 is a nuclear antigen expressed in proliferating cells. A strong correlation between the fraction of cells in S phase and the Ki67 index has been demonstrated (Vielh P et. al., Am J Clin Pathol 94:681-686 (1990); Gasparini G et al., Int J Cancer 57:822-829 (1994)). Tumor sections were co-stained with anti-CD31 antibody to determine the antiangiogenic activity of the compound. CD31 (also called PECAM-1) antibody recognizes a CD31 molecule expressed on the endothelial cell membranes and is involved in their adhesive interactions (DeLisser H M, et al., Am J Pathol 151(3):671-677 (1997)). Nuclei were counter-stained with Hoechst dye. The proliferating cells and microvessels were quantitated using Metamorph software and expressed as a percent of the threshold area. In vehicle-treated U87MG tumors, there was a significant number of cells (about 20%, expressed as Ki67-positive threshold area) were proliferating (FIG. 10D). There was a 59% reduction (p<0.001) in the number of proliferating cells in the Compound 1-treated tumors compared with vehicle-treated tumors. About 11% of the threshold area comprised of CD31-positive vessels in the vehicle control U87MG tumor sections as determined by CD31 immunohistochemistry. CD31-positive blood vessels in Compound 1-treated U87MG tumors were significantly reduced (50%, p<0.001) when compared with vehicle-treated tumors (FIG. 10E). These data suggest that Compound 1 inhibited proliferation of U87MG tumor cells and angiogenesis in the tumors.

U87MG Human Glioblastoma Xenograft Model (Compound 2). Efficacy Studies: Groups of female SCID mice bearing U87MG tumors (n=8-10/group) were dosed orally with vehicle or Compound 2 (doses ranged between 0.05 and 1 mg/kg) throughout the study, starting when tumor volumes reached approximately 170-180 mm$^3$. The twice daily (BID) dose groups were dosed with a 10-hour separation between morning and evening doses. In the positive control group, rapamycin was administered every third day (Q3D) via intraperitoneal (IP) route. At the end of each study, plasma and/or tumor samples were collected.

TABLE 8

Design of Efficacy Study

| Study | Dose Group (n) | Dosing Schedule | Dosing Duration |
|---|---|---|---|
| A | Vehicle (n = 9) | QD | 3 weeks |
|   | Rapamycin 4 mg/kg (n = 6) | Q3D | 3 weeks |
|   | Compound 2 0.1 mg/kg (n = 9) | QD | 3 weeks |
|   | Compound 2 0.5 mg/kg (n = 9) | QD | 3 weeks |
|   | Compound 2 1 mg/kg (n = 9) | QD | 3 weeks |
| B | Vehicle (n = 9) | BID | 3 weeks |
|   | Rapamycin 4 mg/kg (n = 6) | Q3D | 3 weeks |
|   | Compound 2 0.05 mg/kg (n = 9) | BID | 3 weeks |

TABLE 8-continued

Design of Efficacy Study

| Study | Dose Group (n) | Dosing Schedule | Dosing Duration |
|---|---|---|---|
| | Compound 2 0.1 mg/kg (n = 9) | BID | 3 weeks |
| | Compound 2 0.3 mg/kg (n = 9) | BID | 3 weeks |

BID = twice daily;
Q3D = once in 3 days;
QD = once daily.

Cell Line and Culture. U87MG cell line was obtained from American Tissue Culture Collection (ATCC) (Gaithersburg, Md.) and grown in growth medium containing MEM, 2 mM L-glutamine, 0.1 mM non-essential amino acids, and 1 mM sodium pyruvate plus 10% FBS. The cells were detached from tissue culture flasks using trypsin-EDTA. After centrifugation, the cell pellets were suspended in PBS and cells counted using a hemocytometer. The final volume was adjusted to $5 \times 10^6$ cells/0.1 mL of PBS.

Tumor Cell Inoculation. Mice were anesthetized with inhaled isoflurane and then inoculated with U87MG tumor cells subcutaneously above the right hind leg with 0.1 mL of a single cell suspension in PBS using a sterile 1 mL syringe fitted with a 26-gauge needle. Following inoculation, the mice were returned to microisolator cages Randomization of Animals. Following inoculation of animals, tumors were allowed to grow to approximately 200 mm³ prior to randomization of mice. The typical number of days required for tumors to reach 200 mm³ was 14-15 days. The tumor of each animal was measured and animals with tumors ranging between 170 and 180 mm³ were included in the study. Animals from the study pool were then distributed randomly into various cages and the cages were randomly assigned to vehicle, positive control, or test article groups. All of the mice were tagged with metal ear tags on the right ear. A typical group consisted of 9-10 animals.

Test Article Preparation and Administration. Suspensions of Compound 2 were prepared in aqueous 0.5% CMC and 0.25% Tween-80. The formulations were homogenized using a Teflon™ pestle and mortar (Potter-Elvehjem tissue grinder). For different dose levels, the formulated compound was diluted from highest dose level to lowest. Between the doses, the formulated compound was stored under constant stirring using a magnetic stirrer at 4° C. in the dark. The test article and vehicle were administered by oral gavage. The positive control, rapamycin, was prepared as a solution in 2% ethanol, 45% polyethyleneglycol 400, and 53% saline and administered by IP injection. Sterile syringes and gavage needles were used for compound administration. All of the procedures including injections were done in biosafety cabinets disinfected with 70% ethanol prior to use.

Tumor Measurements. Tumor volumes were determined prior to the initiation of treatment and were considered as the starting volumes. Thereafter, tumors were measured twice a week for the duration of the study. The long and short axes of each tumor were measured using a digital caliper in millimeters. Tumor volumes were calculated using the formula: width²×length/2. The tumor volumes were expressed in mm³.

Body Weight Measurements. Initial body weights were recorded prior to the initiation of treatment using a digital scale. The percentage body weight change during the course of the study was calculated using initial body weight measurements. Body weights of each animal were measured twice a week at the same time as the tumor measurements. Body weights were measured more frequently if significant decreases were noted during the course of the study.

Figure 12:
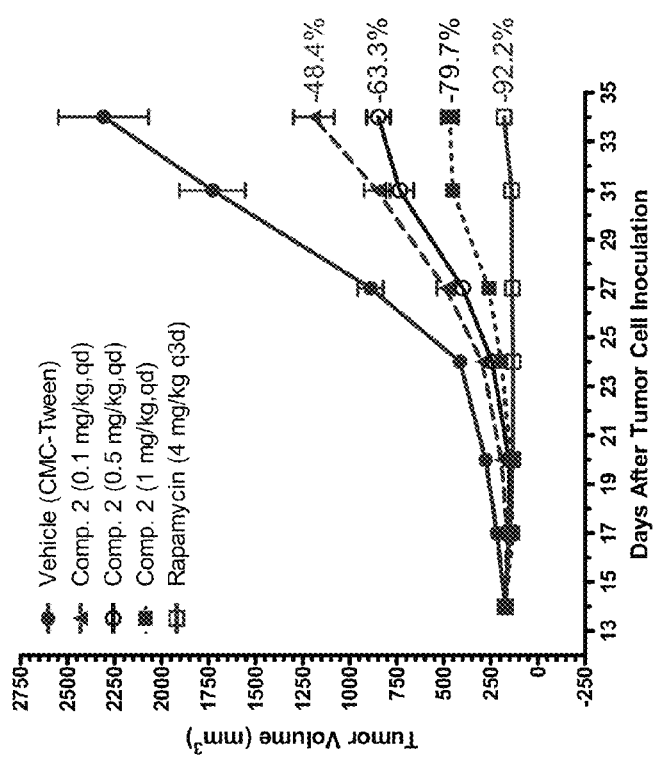
FIG. 12 depicts anti-tumor activity of Compound 2 in a U87MG human glioblastoma xenograft model with once daily dosing paradigms.

Results. The antitumor activity of Compound 2 was tested with QD dosing at 0.1, 0.5, and 1 mg/kg (FIG. 12). Dosing started on Day 14 when tumor volumes ranged between 170 and 180 mm³ and continued until Day 34. By Day 34, the vehicle-treated group measured 2309±240 mm³. All animals in the positive control group that received rapamycin (4 mg/kg, Q3D) had significantly (p<0.001) smaller tumors when compared with the vehicle group on Day 34. Tumor inhibition for each treatment group is shown in FIG. 10 as a percentage and represents the difference in average tumor volume between Compound 2-treated mice and vehicle-treated mice on Day 34. Dose-dependent tumor inhibition was achieved with Compound 2. The average tumor volumes of all Compound 2-treated groups were significantly smaller (p<0.001) than in vehicle-treated control mice on Day 34. The lowest efficacious dose as determined by approximately 65% tumor volume inhibition was observed at the 0.5 mg/kg dose level.

Figure 13:
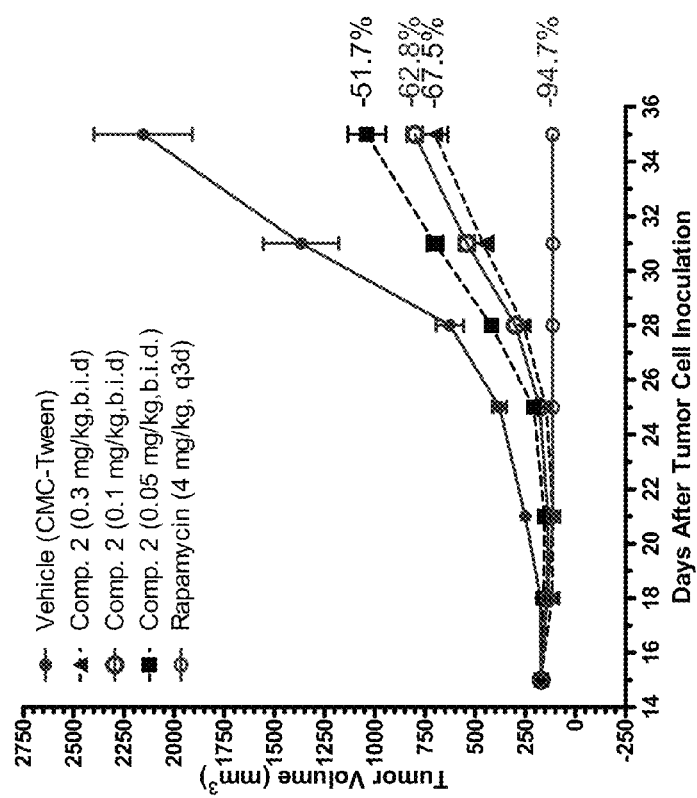
FIG. 13 depicts anti-tumor activity of Compound 2 in a U87MG human glioblastoma xenograft model with twice daily dosing.

The antitumor activity of Compound 2 was tested with BID dosing at 0.05, 0.1, and 0.3 mg/kg (FIG. 13). Dosing was initiated on Day 15 when average tumor volumes ranged between 170 and 180 mm³. By the end of the 3-week dosing period on Day 35, vehicle-treated tumors reached an average volume of 2155±245 mm³. The positive control rapamycin significantly inhibited tumors (p<0.001) on Day 35 when compared to the vehicle control. Dose-dependent tumor inhibition was achieved with Compound 2 (FIG. 13). The average tumor volumes of all of Compound 2-treated groups were significantly smaller (p<0.001) than vehicle control on Day 35. The tumor inhibition presented in FIG. 13 for each treatment group represents the percentage difference in average tumor volumes between the Compound 2-treated and vehicle-treated control mice on Day 35. The lowest efficacious dose that achieved approximately 65% tumor volume inhibition was observed between the 0.1 and 0.3 mg/kg dose level.

Figure 14:
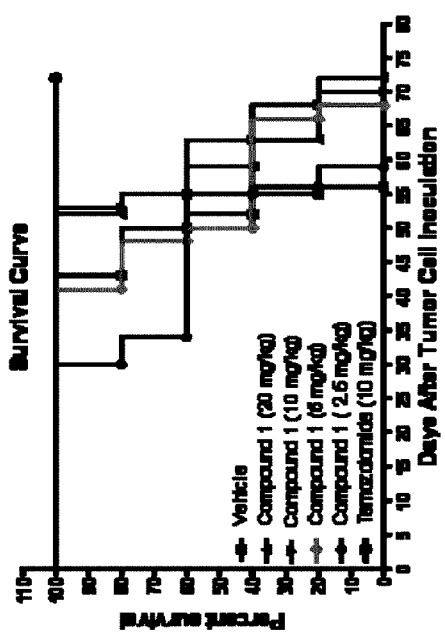
FIG. 14 depicts the Kaplan-Meier survival plot for Compound 1 in a U87MG intracranial glioblastoma model.

U87MG Intracranial Glioblastoma Model (Compound 1). An intracranial glioblastoma study was conducted with U87MG cells transfected with luciferase (U87-MG-Luc). Nude mice were inoculated intracranially with U87MG-Luc cells into the brain. Following inoculation of animals, the tumors were allowed to grow for 7 days. On day 7 following tumor cell inoculation, the mice were imaged using Xenogen imaging system. The mice having tumors with an average flux ranging between $6.29 \times 10^7$ and $1.59 \times 10^8$ photons/sec were pooled together and randomized into various treatment groups. Compound 1 was formulated in 0.5% CMC and 0.25% Tween 80 in water (as a suspension). The animals were orally administered vehicle (CMC-Tween) or Compound 1 once daily (QD) for up to 6 weeks. Doses of Compound 1 ranged between 2.5 and 20 mg/kg. The positive control Temozolomide (10 mg/kg, QD) was administered via intra peritoneal (IP) route. Temozolomide was formulated in 5% N-methylpyrrolidone, 45% PEG400 and 50% saline. The animals were imaged for bioluminescence once a week using Xenogen imaging system and monitored for survival. Statistical analysis was performed using a log-rank test between Compound-treated and vehicle-treated control groups. Compound 1 significantly prolonged the life of mice with intracranial glioblastoma (See FIG. 14).

G144 Cancer Stem Cell Derived Intracranial Glioblastoma Model (Compound 1). An intracranial glioblastoma study was conducted with G144 glioblastoma cells transfected with luciferase (G144-Luc). Nude mice were inoculated intracranially with G144-Luc cells into the brain.

Figure 15:
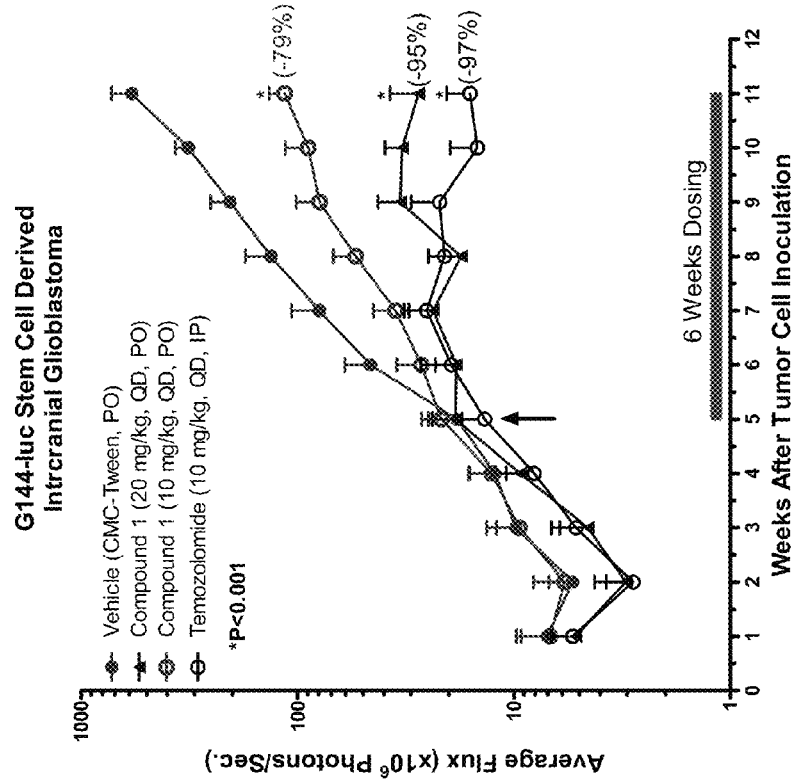
FIG. 15 depicts anti-tumor activity of Compound 1 in a G144 cancer stem cell derived intracranial glioblastoma model.

Following inoculation of animals, the tumors were allowed to grow for 5 weeks. At the end of 5 weeks following tumor cell inoculation, the mice were imaged using Xenogen imaging system. The mice having tumors with an average flux ranging between $3.71 \times 10^6$ and $3.87 \times 10^7$ photons/sec were pooled together and randomized into various treatment groups. Compound 1 was formulated in 0.5% CMC and 0.25% Tween 80 in water (as a suspension). The animals were orally administered vehicle (CMC-Tween) or Compound 1 once daily (QD) for up to 6 weeks. Doses of 10 mg/kg and 20 mg/kg Compound 1 were used. The positive control Temozolomide (TMZ) (10 mg/kg, QD) was administered via intra peritoneal (IP) route. Temozolomide was formulated in 5% N-methylpyrrolidone, 45% PEG400 and 50% saline. The animals were monitored for tumor growth by imaging for bioluminescence once a week using Xenogen imaging system. Statistical analysis was performed using a one-way analysis of variance (ANOVA) followed by Dunnett's post-hoc comparison with the vehicle-treated control groups. Compound 1 significantly inhibited the intracranial tumor growth (see FIG. 15).

Figure 16:
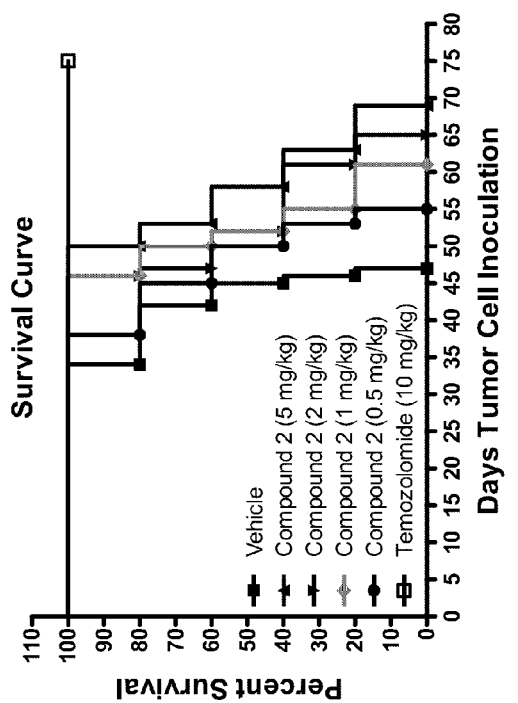
FIG. 16 depicts the Kaplan-Meier survival plot for Compound 2 in a U87MG intracranial glioblastoma model.

U87MG Intracranial Glioblastoma Model (Compound 2). An intracranial glioblastoma study was conducted with U87MG cells transfected with luciferase (U87-MG-Luc). Nude mice were inoculated intracranially with U87MG-Luc cells into the brain. Following inoculation of animals, the tumors were allowed to grow for 7 days. On day 7 following tumor cell inoculation, the mice were imaged using Xenogen imaging system. The mice having tumors with an average flux ranging between $2.94 \times 10^7$ and $1.89 \times 10^8$ photons/sec were pooled together and randomized into various treatment groups. Compound 2 was formulated in 0.5% CMC and 0.25% Tween 80 in water (as a suspension). The animals were orally administered vehicle (CMC-Tween) or. Compound 2 once daily (QD) for up to 6 weeks. Doses of Compound 2 ranged between 0.5 and 5 mg/kg. The positive control Temozolomide (10 mg/kg, QD) was administered via intra peritoneal (IP) route. Temozolomide was formulated in 5% N-methylpyrrolidone, 45% PEG400 and 50% saline. The animals were imaged for bioluminescence once a week using Xenogen imaging system and monitored for survival. Statistical analysis was performed using a log-rank test between. Compound 2-treated and vehicle-treated control groups. Compound 2 significantly prolonged the life of mice with intracranial glioblastoma (see FIG. 16).

Hepatocellular Carcinoma (Hep3B2.1-7) Orthotopic Study. Hep3B2.1-7 human liver tumor cells were cultured in RPMI 1640 cell culture medium, supplemented with 10% FBS, 1% Glutamax and 1% penicillin-streptomycin. The cells were harvested by trypsinization, washed twice in HBSS and counted. The cells were then resuspended in HBSS:Matrigel™ (1:1, v/v) to a final concentration of $2 \times 10^8$ cells/mL. Prior to inoculation (while the animal was anesthetized via injectable Ketamil (10 mg/mL)/Xylazil (0.9 mg/mL) anesthetic), the skin on the incision site was swabbed with alcohol and an incision was made into the skin directly over the liver to expose the main lobe of the liver. The needle was introduced into the main lobe of the liver, where $2 \times 10^6$ Hep3B2.1-7 cells (in 10 µL with 50% Matrigel™) were discharged. Fourteen days post-inoculation, a satellite group of mice were culled to assess the presence of tumors in the liver.

Compound 1 powder was suspended in 0.5% CMC/0.25% Tween80 to achieve a stock concentration of 2 mg/mL. Briefly, Compound 1 was weighed and a volume of 0.5% CMC/0.25% Tween80 was added to achieve a 2 mg/mL stock solution. The mixture was then vortexed, followed by homogenization with a mortar and pestle to achieve a fine suspension. The stock was prepared freshly for each dose and diluted with 0.5% CMC/0.25% Tween80 to achieve the required concentration for dosing.

The mice in each group received daily oral (p.o.) treatment with either Vehicle Control (0.5% CMC/0.25% Tween80; Group 1) or Compound 1 (1, 5 or 10 mg/kg; Groups 4, 5 and 6, respectively). Treatments began on Day 0 and continued for three weeks.

The Vehicle Control and Test Articles were administered in a dosing volume of 5 mL/kg. Each animal's body weight was measured immediately prior to dosing. The volume of dosing solution administered to each animal was calculated and adjusted based on individual body weight.

Figure 17:
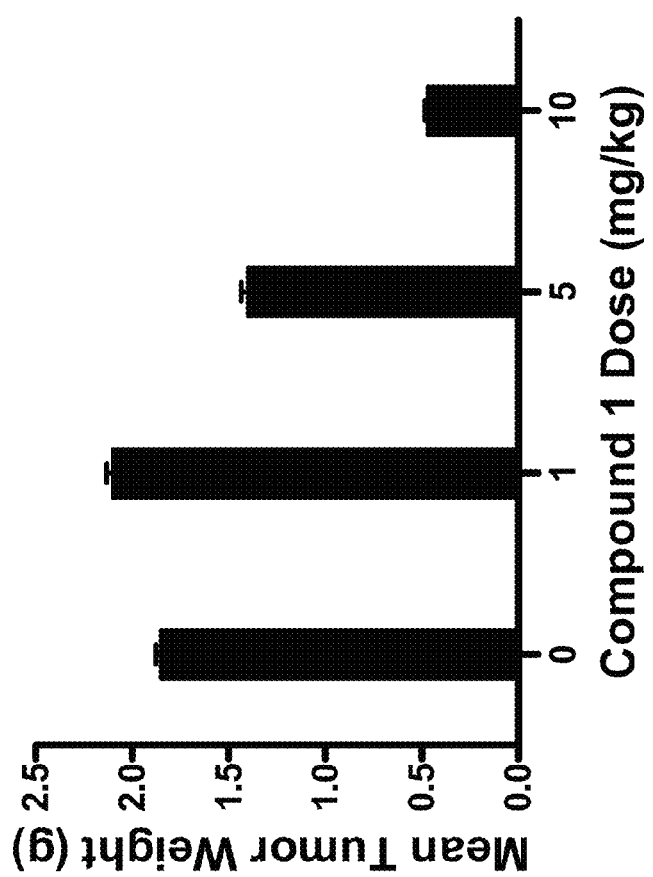
FIG. 17 depicts the efficacy of Compound 1 in the Hep3B2.1-7 orthotopic liver model.
Figure 18:
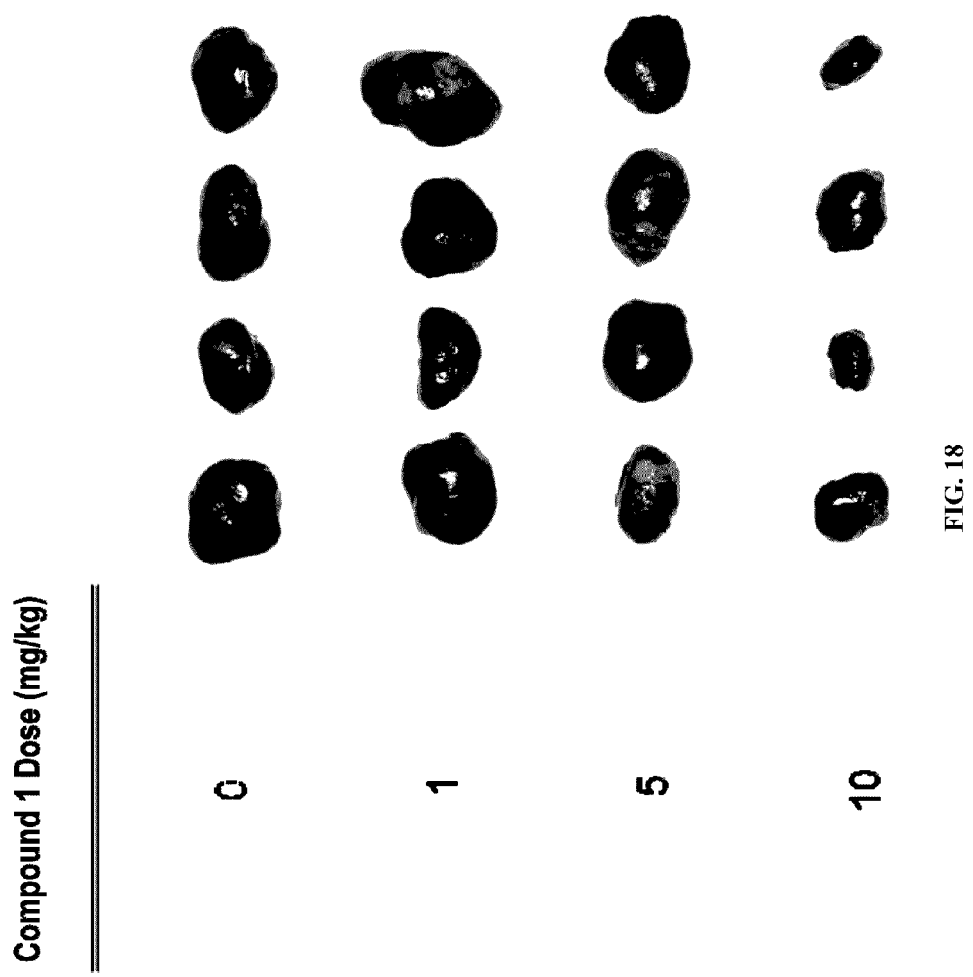
FIG. 18 depicts the effect of Compound 1 on tumor size in the Hep3B2.1-7 orthotopic liver model.

Samples were collected at termination of the study or earlier if mice were culled due to ethical reasons. One hour post-final dose, all mice receiving Vehicle Control (Group 1) and Compound 1 (Groups 4-6, inclusive) were bled via terminal cardiac bleed into Lithium Heparin collection tubes. The samples were centrifuged (2000 rcf) for 15 minutes at 4° C. The plasma component was collected into fresh cryovials and stored at −80° C. The intact liver and tumor was excised and weighed. The tumor was removed from the liver and weighed separately. Each tumor was cut into three portions, one portion being preserved in 10% neutral buffered formalin for paraffin embedding, and the remaining two portions snap frozen in liquid nitrogen and stored at −80° C. Compound 1 exhibited significant tumor growth inhibition at 10 mg/kg (see FIGS. 17-18).

Human Plasma Cell Myeloma (NCI-H929) Study. Female SCID mice (Fox Chase SCID®, CB17/Icr-Prkce$^{scid}$, Charles River) were 8 weeks old at the beginning of the study. The animals were fed ad libitum water (reverse osmosis, 1 ppm Cl) and NIH 31 Modified and Irradiated Lab Diet® consisting of 18.0% crude protein, 5.0% crude fat, and 5.0% crude fiber.

NCI-H929 plasma cell myeloma cells were obtained from the American Type Culture Collection, and were maintained at Piedmont as exponentially growing suspension cultures in RPMI 1640 medium supplemented with 20% fetal bovine serum, 2 mM glutamine, 100 units/mL penicillin G sodium, 100 µg/mL streptomycin sulfate, 25 µg/mL gentamicin, and 50 µM β-mercaptoethanol. The tumor cells were grown in tissue culture flasks in a humidified incubator at 37° C., in an atmosphere of 5% $CO_2$ and 95% air.

The NCI-H929 tumor cells used for implantation were harvested during log phase growth and resuspended at a concentration of $5 \times 10^7$ cells/mL in 50% Matrigel (BD Biosciences). Each SCID mouse was injected subcutaneously in the right flank with $1 \times 10^7$ NCI-H929 tumor cells (0.2 mL cell suspension). Tumors were calipered in two dimensions to monitor growth as their mean volume approached 100-150 mm³. Tumor size, in mm³, was calculated from:

$$\text{Tumor Volume} = \frac{w^2 \times l}{2}$$

where w=width and l=length, in mm, of the tumor. Tumor weight was estimated with the assumption that 1 mg is equivalent to 1 mm³ of tumor volume.

Fourteen days after tumor cell implantation, on Day 1 (D1) of the study, mice were sorted into treatment groups. Tumors were calipered twice weekly during the study.

Compound 1 was a powder that was stored desiccated at room temperature, protected from light. It was suspended in 0.5% carboxymethyl cellulose: 0.25% Tween®80 in deionized water (Vehicle) for dosing. Compound 1 suspensions were prepared every other day; between treatments, the compound was maintained in suspension at 4° C. by continuous magnetic stirring, protected from light.

Compound 1 was administered via oral gavage (p.o.) once daily for twenty-eight days (qd×28). Treatment efficacy was determined from the calculated tumor volumes on Day 12. MTV(n), the median tumor volume for the number of animals, n, evaluable on the day of analysis, was determined for each group. Percent tumor growth inhibition (% TGI) was defined as the difference between the MTV of the control group and the MTV of the drug-treated group, expressed as a percentage of the MTV of the control group:

$$\% \ TGI = \left( \frac{MTV_{control} - MTV_{drug\text{-}treated}}{MTV_{control}} \right) \times 100 = [1 - (MTV_{drug\text{-}treated} / MTV_{control})] \times 100$$

Each animal was to be euthanized when its neoplasm reached the endpoint volume (2000 mm$^3$). For each animal whose tumor reached the endpoint volume, the time to endpoint (TTE) was calculated by the following equation:

$$TTE = \frac{\log_{10}(\text{endpoint volume}) - b}{m}$$

where TTE is expressed in days, endpoint volume is in mm$^3$, b is the intercept, and m is the slope of the line obtained by linear regression of a log-transformed tumor growth data set.

Animals were weighed daily on Day 1-5, then twice weekly until the completion of the study. On Day 14, at 1 hour before the 14$^{th}$ dose, mice in each group were sampled for 0.25 mL blood from the mandibular vein, without anesthesia, and with sodium heparin as anti-coagulant. The same mice were euthanized 1 hour after the 14$^{th}$ dose, and full volume blood was to be collected by cardiac puncture under CO$_2$ anesthesia. The blood was processed for plasma, which was stored at −80° C. The tumor was excised from each euthanized animal, trisected, and the three parts were snap frozen in liquid N$_2$ in separate containers. Significant tumor growth inhibition was observed with 10 mg/kg Compound 1 (see FIG. 19). Significant tumor growth delay was observed at 3 mg/kg and 10 mg/kg Compound 1 (see FIG. 19).

HCT-116 Human Colorectal Cancer Xenograft Model. The HCT-116 cell line was obtained from American Tissue Culture Collection (ATCC) (Gaithersberg, Md.) and grown in growth medium containing McCoy's 5A medium with 2 mM L-glutamine adjusted to contain 90% and 10% of fetal bovine serum. The cells were detached from tissue culture flasks using trypsin-EDTA. After centrifugation, the cell pellets were suspended in phosphate buffered saline (PBS) and counted using a hemocytometer. Matrigel was added to the cell suspension to adjust the final volume to 2×10$^6$ cells/0.1 mL of 1:1 mixture of Matrigel: PBS.

Female 6-8 weeks old CB17 SCID mice were obtained from Charles River Laboratories at a body weight of 17-20 g. Mice were anesthetized with inhaled isoflurane and then inoculated with HCT-116 tumor cells subcutaneously on the right hind leg with 0.1 mL of a single cell suspension using a sterile 1 mL syringe fitted with a 26 gauge needle. Following inoculation, the mice were returned to microisolator cages. The tumors were allowed to grow to about 100 mm$^3$ prior to randomization. The typical number of days required for tumors to reach 100 mm$^3$ was 7 to 8 days. The tumor of each animal was measured and animals with tumors ranging between 100 and 150 mm$^3$ were included in the study. The animals were distributed randomly into various cages and the cages were randomly assigned to vehicle, positive control, or test article groups. All of the mice were tagged with metal ear tags on the right ear. A typical group consisted of 8 to 10 animals.

Compound 1 was formulated in 0.5% CMC and 0.25% Tween 80 in water (as a suspension). The formulations were homogenized using a Teflon pestle and mortar (Potter-Elvehjem tissue grinder). Between the doses, the formulated compound was stored under constant stirring using a magnetic stirrer at 4° C. in the dark. The test article and vehicle were administered by oral gavage. The positive control (rapamycin) was prepared as solution in 2% ethanol, 45% polyethyleneglycol 400, and 53% saline and administered by IP injection. Vehicle and the test article were dosed in a volume of 5 mL/kg. The positive control rapamycin was dosed in a volume of 10 mL/kg. Sterile syringes and gavage needles were used for compound administration. All the procedures including injections were done in biosafety cabinets sprayed with ethanol prior to use.

Groups of female SCID mice bearing HCT-116 tumors (n=9-10/group) were dosed orally with vehicle or Compound 1 (1 mg/kg to 50 mg/kg) twice daily (BID), once daily (QD), every second day (Q2D), every third day (Q3D) or every 5th day (Q5D) throughout the study starting when the tumor volumes reached approximately 100 mm$^3$. The BID dose groups were dosed with a 10 h separation between the morning and evening doses. In the positive control group, rapamycin (n=6/group) was administered via the intraperitoneal (IP) route Q3D. At the end of each study, plasma and/or tumor samples were collected.

Tumor volumes were determined prior to the initiation of treatment and were considered as the starting volumes. Thereafter, tumors were measured twice a week for the duration of the study. The long and short axes of each tumor were measured using a digital caliper in millimeters. The tumor volumes were calculated using the formula: width$^2$× length/2 (using long [L] and short [W] axes of tumors). The tumor volumes were expressed in cubic millimeters (mm$^3$). Tumor volume data are expressed as mean±SE. The difference in tumor volume between vehicle and treatment group was expressed in percent volume reduction=100−tumor volume of treated/tumor volume of control×100. Statistical analysis was done using Graphpad Prism. Comparison between multiple groups was done using one-way ANOVA with Newman-Keuls post-test with a 95% significance level.

Initial body weights were recorded prior to the initiation of treatment using a digital scale. The percent body weight change during the course of study was calculated using initial body weight. Body weights of each animal were measured twice a week at the same time that tumor measurements were taken. Body weights were measured more frequently if significant decreases were noted during the course of the study. Statistical analysis for the body weight was performed using one-way ANOVA followed by Dunnett's comparison to the initial body weight of each group.

Figure 20:
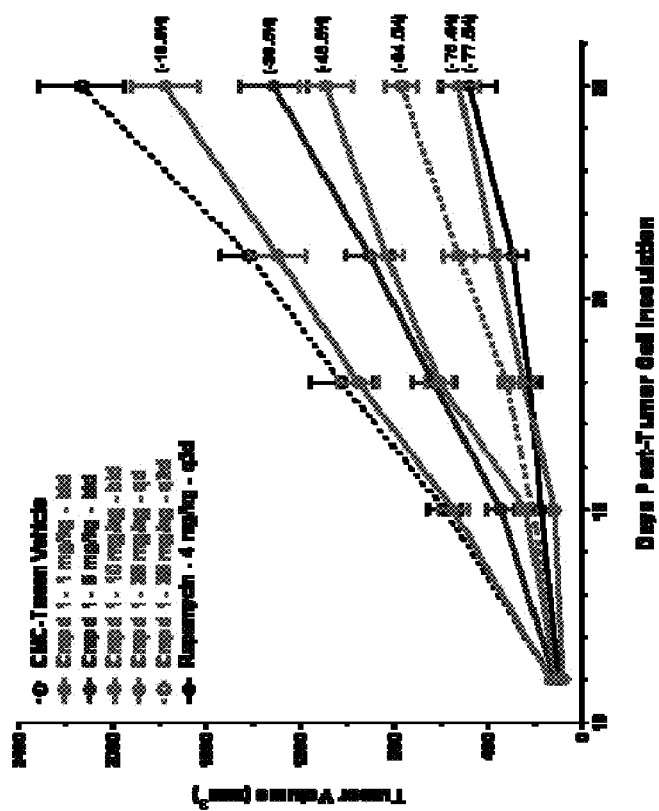
FIG. 20 depicts the anti-tumor activity of Compound 1 in the HCT-116 human colorectal cancer xenograft model in SCID mice.

The antitumor activity of Compound 1 was tested at doses of 1 mg/kg, 5 mg/kg and 10 mg/kg BID and 25 mg/kg QD and Q2D and is shown in FIG. 20. Dosing was initiated on Day 11 when the tumor volumes ranged between 75 and 125 mm³. By the end of the dosing period on Day 25, the vehicle-treated group reached an average volume of 2132±182 mm³. All animals in the positive control group that received rapamycin (4 mg/kg, Q3D) showed significantly (p<0.001) smaller tumors when compared with vehicle on the last day. Significant (p<0.001) tumor growth inhibition with Compound 1 was observed at 5 mg/kg (BID), 10 mg/kg (BID), and 25 mg/kg (QD and Q2D). In the BID dosing paradigm, inhibition of tumor growth followed a dose response in that increasing the dose resulted in increased tumor growth inhibition. The minimum dose required to obtain >65% tumor volume reduction compared to the vehicle control was 25 mg/kg QD. Approximately 50% tumor volume reduction was observed at the 10 mg/kg BID dose level. Body weight loss was observed for the 10 mg/kg BID (16.9%) and 25 mg/kg QD (14%) dose groups. No significant change in body weight was observed in any other group. The studies demonstrate that treatment with Compound 1 significantly inhibits HCT-116 colorectal tumor growth in a dose and schedule-dependent manner.

5.2 Clinical Studies

5.2.1 A Phase 1/2, Multi-Center, Open-Label, Dose Finding Study to Assess the Safety, Tolerability, Pharmacokinetics and Preliminary Efficacy of Compound 1 Administered Orally to Subjects with Advanced Solid Tumors, Non-Hodgkin Lymphoma or Multiple Myeloma Compound 1 will be administered orally to subjects with solid tumors, non-Hodgkin lymphoma or multiple myeloma. The study is designed as a Phase 1/2 trial consisting of two parts: dose escalation (Part A) and dose expansion (Part B).

Compound 1 will be administered orally to determine safety and tolerability and to define the non-tolerated dose (NTD) and the maximum tolerated dose (MTD).

Evaluations will include the extent of inhibition of phosphorylation of S6RP (Ser235/236 and/or Ser240/244) and/or 4EB-P1 (Thr37/46) for mTORC1 activity and AKT (Ser473) and/or other relevant biomarkers for mTORC2 activity in peripheral blood samples and tumor biopsies following treatment with Compound 1, and the efficacy of Compound 1.

The study population will consist of men and women, 18 years or older, with advanced NHL, MM, neuroendocrine tumors (the latter also accepting subjects aged 12 years or older) or advanced unresectable solid tumors, including subjects who have progressed on (or not been able to tolerate) standard therapy or for whom no standard anticancer therapy exists.

For both the dose escalation and dose expansion parts of this protocol, inclusion criteria are: (1) Understand and voluntarily sign an informed consent document prior to any study related assessments/procedures are conducted; (2) Men and women, 18 years or older, with histologically or cytologically-confirmed, advanced NHL, MM, or advanced unresectable solid tumors including subjects who have progressed on (or not been able to tolerate) standard anticancer therapy or for whom no standard anticancer therapy exists; (3) Eastern Cooperative Oncology Group Performance Status (ECOG) PS of 0 or 1 for subjects with solid tumors, and 0-2 for hematologic malignancies; (4) Subjects must have the following laboratory values: Absolute Neutrophil Count (ANC)≥1.5×10⁹/L, Hemoglobin (Hgb)≥9 g/dl, Platelets (plt) ≥100×10⁹/L, Potassium within normal limits or correctable with supplements, AST/SGOT and ALT/SGPT≤2.5×Upper Limit of Normal (ULN) or ≤5.0×ULN if liver tumor is present, Serum bilirubin≤1.5×ULN or ≤2×ULN if liver tumor is present, Serum creatinine≤1.5×ULN or 24-hour clearance≥50 mL/min, Negative serum or urine pregnancy test within 48 hours before starting study treatment in females of childbearing potential; and (5) Able to adhere to the study visit schedule and other protocol requirements For the dose expansion part (Part B) of this protocol, inclusion criteria are: (1) Retrieval of formalin-fixed, paraffin embedded (FFPE) archival tumor tissue, either in tumor blocks or sectioned/mounted specimens for gene mutation and/or IHC biomarker assay for all tumors except MM. Only in exceptional circumstances may an exemption waiver be granted by the Sponsor for other tumor types; (2) Satisfactory Screening biopsy for gene mutation and/or IHC biomarker assay for accessible tumors for all tumors except NSCLC and NET (optional) and GBM; (3) Histologically-confirmed tumors of the following types, all with measurable disease. Type-specific criteria are in addition to, or supersede, above criteria where applicable: (a) Glioblastoma multiforme (GBM) or gliosarcoma, excluding WHO Grade IV oligoastrocytoma (has received prior treatment including radiation and/or chemotherapy, with radiation completed >12 weeks prior to Day 1; planned salvage surgical tumor resection on Day 15±7 days, anticipated to yield ≥200 mg tumor tissue; no prior or scheduled Gliadel® wafer implant unless area of assessment and planned resection is outside the region previously implanted; no prior interstitial brachytherapy or stereotactic radiosurgery unless area of assessment and planned resection is outside the region previously treated; no enzyme-inducing anti-epileptic drugs (EIAED) such as carbamazepine, phenyloin, phenobarbital, or primidone within 14 days before Day 1; able to undergo repeated magnetic resonance imaging (MRI) scans; Availability of adequate FFPE archival tumor material (for PD biomarkers)); (b) Hepatocellular carcinoma (HCC) (Plt count≥60× 10⁹/L if portal hypertension is present; Child-Pugh score of less than 10 (i.e., class B liver function or better); at least 4 weeks from last dose of α-interferon and/or ribivirin; at least 4 weeks from prior percutaneous ethanol injection, radiofrequency ablation, transarterial embolization, or cryotherapy with documentation of progressive or recurrent disease); (c) Gastrointestinal neuroendocrine tumor (NET) of non-pancreatic origin (locally unresectable or metastatic moderate or well differentiated, low (grade 1) or intermediate (grade 2), non-pancreatic NET either of gut origin or of unknown primary; pancreatic, bronchial, and other NET with origins in organs above the diaphragm (e.g., laryngeal, pharyngeal, thyroid), pheochromocytomas, paragangliomas, adenocarcinoid and goblet carcinoid tumors, and poorly differentiated, high grade (eg., small cell or large cell) tumors are excluded; subjects aged 12 years or older; symptomatic endocrine-producing tumors and nonfunctional tumors are both allowed; concurrent therapy with somatostatin analogs is required (the subject must be on a stable dose for at least two months with documented progressive disease on therapy); evidence of radiologic disease progression within 12 months prior to Cycle 1, Day 1; no receptor targeted radiolabeled therapy within 3 months prior to Cycle 1, Day 1; no liver-directed therapy within 4 weeks prior to Cycle 1, Day 1, unless a site of measurable disease other than the treated lesion is present; screening and on-study tumor biopsies are optional in this cohort; archival tumor collection should be requested, but is not mandatory in this cohort); (d) Hormone receptor-positive breast cancer (HRPBC) (unresectable locally advanced or metastatic carcinoma of the breast; ER positive, and HER2/neu negative (0 or 1+), tumor; measurable disease according to RECIST v1.1; must have received at least one prior line of hormonal therapy or at least one year of aromatase therapy in the adjuvant setting, or six months of aromatase inhibitor therapy for metastatic disease; bisphosphonates or denusomab are allowed in stable doses; cohort may be expanded to enroll a minimum of 5 subjects each with tumors containing PIK3CA mutations; (e) Multiple Myeloma (MM) (measurable levels of myeloma paraprotein in serum (>0.5 g/dL) or urine (>0.2 g excreted in a 24-hour collection sample); absolute neutrophil count (ANC)≥1.0×10$^9$/L; platelets (plt)≥60×10$^9$/L in subjects in whom <50% of bone marrow mononuclear cells are plasma cells or ≥30×10$^9$/L in subjects in whom ≥50% of bone marrow mononuclear cells are plasma cells); (f) Diffuse large B-cell lymphoma (DLBCL) (histologically proven diffuse large B-cell non-Hodgkin's lymphoma; platelets (plt)≥60×10$^9$/L for subjects in whom <50% of bone marrow mononuclear cells are lymphoma cells, or ≥30×10$^9$/L for subjects in whom ≥50% of bone marrow mononuclear cells are lymphoma cells; at least 4 weeks from last dose of therapeutic glucocorticosteroids; adrenal replacement doses of glucocorticosteroids (up to the equivalent of 10 mg daily prednisone) are allowed).

For both the dose escalation and dose expansion parts of this protocol, exclusion criteria are: (1) Symptomatic central nervous system metastases (excluding GBM; subjects with brain metastases that have been previously treated and are stable for 6 weeks are allowed); (2) Known acute or chronic pancreatitis; (3) Subjects with any peripheral neuropathy ≥NCI CTCAE grade 2; (4) Subjects with persistent diarrhea or malabsorption≥NCI CTCAE grade 2, despite medical management; (5) Impaired cardiac function or clinically significant cardiac diseases, including any of the following: LVEF <45% as determined by MUGA scan or ECHO, Complete left bundle branch, or bifasicular, block, Congenital long QT syndrome, Persistent or clinically meaningful ventricular arrhythmias or atrial fibrillation, QTcF>460 msec on screening ECG (mean of triplicate recordings), Unstable angina pectoris or myocardial infarction ≤3 months prior to starting Compound 1, Other clinically significant heart disease such as congestive heart failure requiring treatment or uncontrolled hypertension (blood pressure≥160/95 mmHg); (6) Subjects with diabetes on active treatment or subjects with either of the following: (a) fasting blood glucose≥126 mg/dL (7.0 mmol/L), or (b) HbA1c≥6.5%; (7) Other concurrent severe and/or uncontrolled concomitant medical conditions (e.g., active or uncontrolled infection) that could cause unacceptable safety risks or compromise compliance with the protocol; (8) Prior systemic cancer-directed treatments or investigational modalities ≤5 half lives or 4 weeks, whichever is shorter, prior to starting study drug or who have not recovered from side effects of such therapy; (9) Subjects who have undergone major surgery ≤2 weeks prior to starting study drug or who have not recovered from side effects of such therapy; (10) Women who are pregnant or breast feeding; Adults of reproductive potential not employing two forms of birth control: (a) females of childbearing potential must agree to use two adequate forms of contraception methods simultaneously (one must be non-hormonal) from the time of giving informed consent until 28 days after the last dose of Compound 1. Females of child-bearing potential, defined as sexually mature women who have not undergone a hysterectomy or bilateral oophorectomy, or who have not been naturally postmenopausal (ie., who have not menstruated at all) for at least 24 consecutive months; (b) males (with partners who are female with child-bearing potential must agree that they or their partners will use at least two effective contraceptive methods (including one barrier method) when engaging in reproductive sexual activity throughout the study, and will avoid conceiving for 28 days after taking the last dose of Compound 1; (11) Subjects with known HIV infection; (12) Known chronic hepatitis B or C virus (HBV/HCV) infection, unless comorbidity in subjects with HCC; (13) Any significant medical condition, laboratory abnormality, or psychiatric illness that would prevent the subject from participating in the study; (14) Any condition including the presence of laboratory abnormalities, which places the subject at unacceptable risk if he/she were to participate in the study; (15) Any condition that confounds the ability to interpret data from the study.

For the dose expansion part (Part B) of this protocol, exclusion criteria are: (1) Concurrent active second malignancy for which the patient is receiving therapy, excluding non-melanomatous skin cancer or carcinoma in situ of the cervix.

Compound 1 will be supplied in appropriate strengths (e.g., 2.5 mg, 10 mg, and 20 mg) containing only the active pharmaceutical ingredient in reddish-brown gelatin capsules for oral administration. No other excipients will be used in the product capsules.

Compound 1 will be administered orally, in an uninterrupted once-daily schedule with no rest period between cycles. A dose of 7.5 mg/day of Compound 1 will be the starting dose in this protocol. Each dose will be taken in the morning, with the subject having fasted overnight (minimum of 6 hours). Food intake will be delayed until at least one hour after dosing on the days Compound 1 is taken at home. On clinic visit days, Compound 1 will be administered in the clinic after any predose tests have been completed. Food will be taken after all fasting tests have been completed but in no case sooner than 60 minutes after dosing (3 hours after dosing on Day 8). In cases where troublesome GI symptoms, fatigue or other symptoms persist beyond the end of Cycle 1, dosing may be moved to the end of day, providing the subject can maintain at least a 3-hour separation between the last intake of food and Compound 1 administration. Compound 1 may be taken up to 12 hours late if dosing has been delayed on a single day; otherwise that day's dose should be omitted.

In Part A, subjects will receive single and multiple ascending dose levels of Compound 1 to measure pharmacokinetics (PK) and to identify the maximum tolerated dose (MTD). A modified accelerated titration design (Simon R, Freidlin B, Rubinstein L, et al. Accelerated Titration Designs for Phase I Clinical. Trials in Oncology, Journal of the National Cancer Institute, (1997) Vol. 89, No. 15.) will be used to establish initial toxicity. During the accelerated course, initial cohorts of one subject will be given Compound 1 at dose increments of 100% until the first instance of first-course grade 2 or higher toxicity, at which point the accelerated part will be terminated, and this particular cohort will be expanded to 6 subjects. Subsequently, a standard escalation dosing schedule with approximately 50% dose increments and 6 subjects per cohort will be initiated in order to establish the non-tolerated dose (NTD) and MTD. Smaller increments and additional subjects within a dose cohort may also be evaluated.

A dose will be considered to be non-tolerated if 2 evaluable subjects in a dose cohort experience dose-limiting toxicity (DLT). When a NTD is defined, dose escalation will be stopped. The MTD will be defined as the last dose tested below the NTD with 0 or 1 out of 6 evaluable subjects experiencing DLT during Cycle 1. An intermediate dose (i.e., one between the NTD and the last dose level before the NTD) or additional subjects within any dose cohort may be required to determine the MTD more precisely.

In Part B, subjects may start Compound 1 at the MTD and/or a lower dose level based on safety, PK and PD data from Part A. Approximately 150 subjects will be treated and evaluated for safety and preliminary antitumor activity after every two cycles of therapy. Tumor types include non-small cell lung cancer (NSCLC), glioblastoma multiforme (GBM), hepatocellular carcinoma (HCC), gastrointestinal neuroendocrine tumor of non-pancreatic origin (NET), diffuse large B-cell lymphoma (DLBCL), multiple myeloma (MM), and hormone receptor positive breast cancer (HRPBC). Up to 20 subjects will be enrolled in each tumor type.

During the first cycle only in Part A, each subject will be administered a single dose of Compound 1 (Day −1), followed by a 48-hour observation and PK sampling period, followed on Day 1 by daily uninterrupted dosing for 28 days (Cycle 1=30 days). In subsequent Part A cycles, subjects are treated in 28-day cycles with continuous dosing from Day 1 to 28. In Part B, subjects will receive continuous dosing for 28 days from the beginning—there is neither an initial observation period nor a 48-hour PK collection.

Therapy may be discontinued if there is evidence of disease progression, but subjects can continue to receive Compound 1 as long as the Investigator considers they are deriving benefit from treatment. Therapy will be discontinued if there is unacceptable toxicity or if the subject decides to withdraw from the study.

When a dose reduction is indicated, the next lower dose level will be selected. Two dose reductions are allowed. For the starting dose level (7.5 mg) in Part A, reductions will be in 2.5 mg decrements. In Part B, the starting dose level will be 45 mg QD; dose reductions to 30 mg and 15 mg QD are permitted. If any subject continues to experience unacceptable toxicity after 2 dose reductions in Part A, Compound 1 will be discontinued permanently. In Part B, subjects may dose reduce up to 2 levels (i.e., to 15 mg) and increase again if clinically appropriate; subsequent dose reductions are permitted in the event of recurrent toxicity but, in such circumstances, it is not permitted to reescalate the dose again.

Subjects will be evaluated for efficacy every 2 cycles through cycle 6 and every 3 cycles thereafter. The primary efficacy variable is response. Tumor assessments, including imaging (CT, MRI and/or PET) of the chest and abdomen and other sites as appropriate, will be performed during Screening. Subjects with brain lesions will also have brain scans at Screening and during follow-up tumor assessments. After Screening, tumor assessments (for all tumors except multiple myeloma) will be performed on completion of Cycles 2, 4 and 6 (i.e., on Cycles 3, 5 and 7/Day 1±7 days) and then every 3 months thereafter (e.g., Cycle 10 and 13/Day 1±7 days). Tumor assessment (for multiple myeloma and only NHL/DLBCL with known or suspected marrow involvement) (bone marrow aspiration and biopsy, with PD biomarker analysis, cytogenetic analysis if abnormally present at Screening) will be performed on completion of Cycles 4, 8, 12 and 16 only (i.e., on Cycles 5, 9, 13 and 17/Day 1±7 days). Cytogenetics need not be repeated if normal at Screening. Tumor response will be based on Response Evaluation Criteria in Solid Tumors (RECIST 1.1), International Workshop Criteria (IWC) for NHL/DLBCL or International Uniform Response Criteria (IURC) for Multiple Myeloma, and RANO for GBM, using the post resection MRI scan as the baseline. Given the difficulty in assessing tumor response following salvage surgery, the primary efficacy endpoint for GBM will be the proportion of subjects progression-free at 6 months from Day 1 relative to efficacy evaluable subjects in the GBM type. Subjects will be evaluated for tumor response on completion of Cycle 2, 4, 6, and so on. A descriptive analysis of evidence of anti-tumor activity will be provided based on clinical and radiographic assessments by the investigator, which includes assessment of target lesion, non-target lesion, new lesion and overall response.

The efficacy variable of focus for Part A will be best overall response. Other preliminary efficacy variables will be summarized using frequency tabulations for categorical variables or descriptive statistics for continuous variables.

For Part B, efficacy variables to be analyzed include tumor response at the end of treatment, the proportion of subject alive and progression-free, and duration of response. Efficacy variables will mature when last subject of a treatment arm or cohort have withdrawn from the study or completed 6 cycles.

Progression Free Survival rates will be computed using the Kaplan-Meier estimates. Duration of response will also be reported in subjects who respond, using tumor specific evaluation criteria. Two-sided 90% CIs of the response rate, and of the PFS rate at time of each scheduled response assessment (ie., Cycles 2, 4, 6, etc.) will be provided by tumor type.

Other preliminary efficacy variables, including ECOG performance status, CTC, and PET outcomes, will be summarized using frequency tabulations for categorical variables or descriptive statistics for continuous variables.

Parameters to be explored include mTOR biomarker inhibition in blood and tumor, histopathologic response, correlations with pharmacogenomic findings and percentage of inhibition of pAKT (Ser473), phospho-S6RP (Ser235/236 and/or Ser240/244), phospho-4EB-P1 (Thr37/46), and/or other relevant biomarkers in peripheral blood samples and tumor, adverse events and clinical outcome. The pharmacodynamic (PD) measurements are incorporated in this study to evaluate target inhibition of mTORC1 and mTORC2 pathways, the consequences of such inhibition, and PK/PD relationships. In Parts A and B, biomarker analysis will involve measuring pAKT (mTORC2) in protein lysates derived from isolated platelets. Levels of p4EB-P1 and pS6RP (mTORC1), and pAKT (mTORC2), will be measured by flow cytometry using whole blood samples. Likewise, in Parts A and B, pAKT, p4EB-P1, p56, Ki67 and/or other relevant markers to assess Compound 1 activity will be measured in serial tumor biopsies from subjects with accessible disease when possible. The changes of each biomarker will be determined by comparing the levels of biomarkers in pre- and post-treatment samples and, where possible, correlate these with drug exposure in blood, and tissue if available, and tumor response over time. Full details of all statistical analyses and modeling for these outcomes will be described in the statistical analysis plan and final study report.

The safety variables for this study are adverse events, clinical laboratory variables, 12-lead ECGs (centrally reviewed), LVEF assessments, physical examinations and vital signs. In Part A, the decision to either evaluate a higher dose level or declare a MTD will be determined by the Safety Review Committee (SRC) each time all clinical and laboratory safety data for a given cohort is available for review. The SRC will also determine the dose, doses, or schedule appropriate for Part B. During Part B, the SRC will continue to review safety data regularly and make recommendations about the study continuation, as appropriate.

In certain embodiments, patients undergoing the clinical protocol provide herein will show a positive tumor response, such as inhibition of tumor growth or a reduction in tumor size. In certain embodiments, patients undergoing the clinical protocol provide herein will show an improvement in brain lesions, such as a decrease in number or size. In certain embodiments, patients undergoing the clinical protocol provide herein will achieve a Response Evaluation Criteria in Solid Tumors (RECIST 1.1) of complete response, partial response or stable disease. In certain embodiments, patients undergoing the clinical protocol provided herein will prevent a Response Evaluation Criteria in Solid Tumors (RECIST 1.1) of progressive disease. In certain embodiments, patients undergoing the clinical protocol provide herein will show an improvement in International Workshop Criteria (IWC) or International Uniform Response Criteria (IURC). In certain embodiments, patients undergoing the clinical protocol provide herein will show an improvement in Response Assessment for Neuro-Oncology (RANO) Working Group criteria. In certain embodiments, patients undergoing the clinical protocol provide herein will show an improvement in ECOG performance status or PET outcomes.

TOR Pathway Biomarker Measurements in Whole Blood. Blood samples received from clinical sites were aliquoted into a 96-deepwell plate and rested for 1 hour at 37° C. The samples were stimulated with anti-IgD and LPS for 15 minutes at 37° C. The red blood cells were lysed and the white blood cells were fixed with BD Lyse/Fix Buffer at a ratio of 15:1 buffer to blood for 10 minutes at 37° C. The plates were centrifuged, aspirated, and 1 mL of ice-cold methanol was added to the wells containing fixed white blood cells to permeabilize the cells for intracellular staining. The plates were stored overnight at −80° C. The plates were thawed, centrifuged, aspirated and washed twice with PBS+0.5% BSA. The cells were stained with antibodies specific for the surface markers CD3, CD14, and CD19, and for mTOR pathway markers, including pS6 (S235/236), p4EBP1 (T37/46), and pAKT (S473). The cells were washed twice with PBS and fixed with 1.6% PFA.

Sample analysis: The samples were analyzed on an 8 color cytometer. Control wells of 8-peak rainbow beads (Spherotech Libertyville, Ill.) were acquired at multiple points during sample acquisition. The median fluorescence intensity (MFI) was computed for each marker from the fluorescence intensity levels in T cells, B cells, and monocytes. The MFI were normalized using the 8-peak rainbow beads and presented as ERF (Equivalent number of Reference Fluorophores). ERFs were calculated from the MFIs using a linear regression transformation carried out on a log-log scale using the rainbow calibration particles with 8 intensities on 8 colors. The percent change from baseline for pS6, p4EBP1, and pAKT in stimulated and non-stimulated T cells, B cells, and monocytes was determined for each patient. The baseline value was an average of two visits (screening and cycle 1/day −1 at 0 hr pre-dose) when available.

Part A: Accelerated Dose Escalation Results. 28 subjects were treated across 5 dose levels: 7.5 (n=1), 15 (n=2), 30 (n=9), 45 (n=7) and 60 mg (n=8). Baseline characteristics were typical for phase 1 oncology trials. Although ECOG 2 was allowed, >95% of subjects had ECOG 0 or 1. Diverse tumor types were enrolled with the most common being CRC, breast, and pancreas. Half of the patients had received more than 3 prior therapies (see. FIG. 21).

Five dose levels were evaluated. The first grade 2 related toxicity was observed at the $3^{rd}$ dose level (30 mg) and thereafter cohorts were expanded to a minimum of 6 subjects with 50% dose escalation increments. Additional subjects were backfilled into all cohorts except dose level 1. Grade 3 hyperglycemia was reported as a DLT at 30 mg and grade 3 rash as a DLT at 45 mg. In response, the protocol DLT criteria were modified to allow for medical management of rash and hyperglycemia prior to considering these events as DLT in subsequent patients. Fatigue and mucositis were reported as DLT at 60 mg and this dose was considered the NTD; the MTD was determined to be 45 mg once daily and this was the dose taken forward in Part B. (see FIG. 22)

Figure 22:
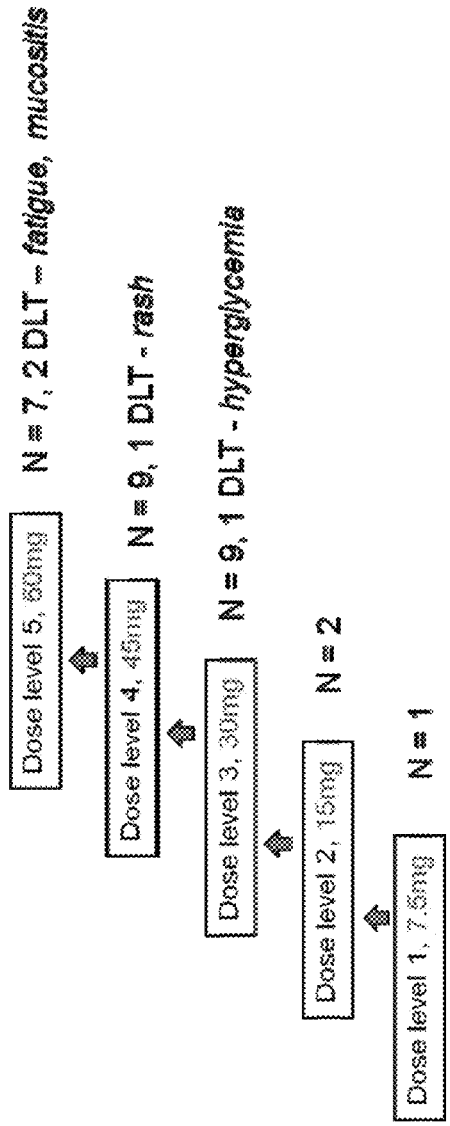
FIG. 22 depicts the Part A Accelerated (1+5) Dose Escalation design and DLT definition.
Figure 23:
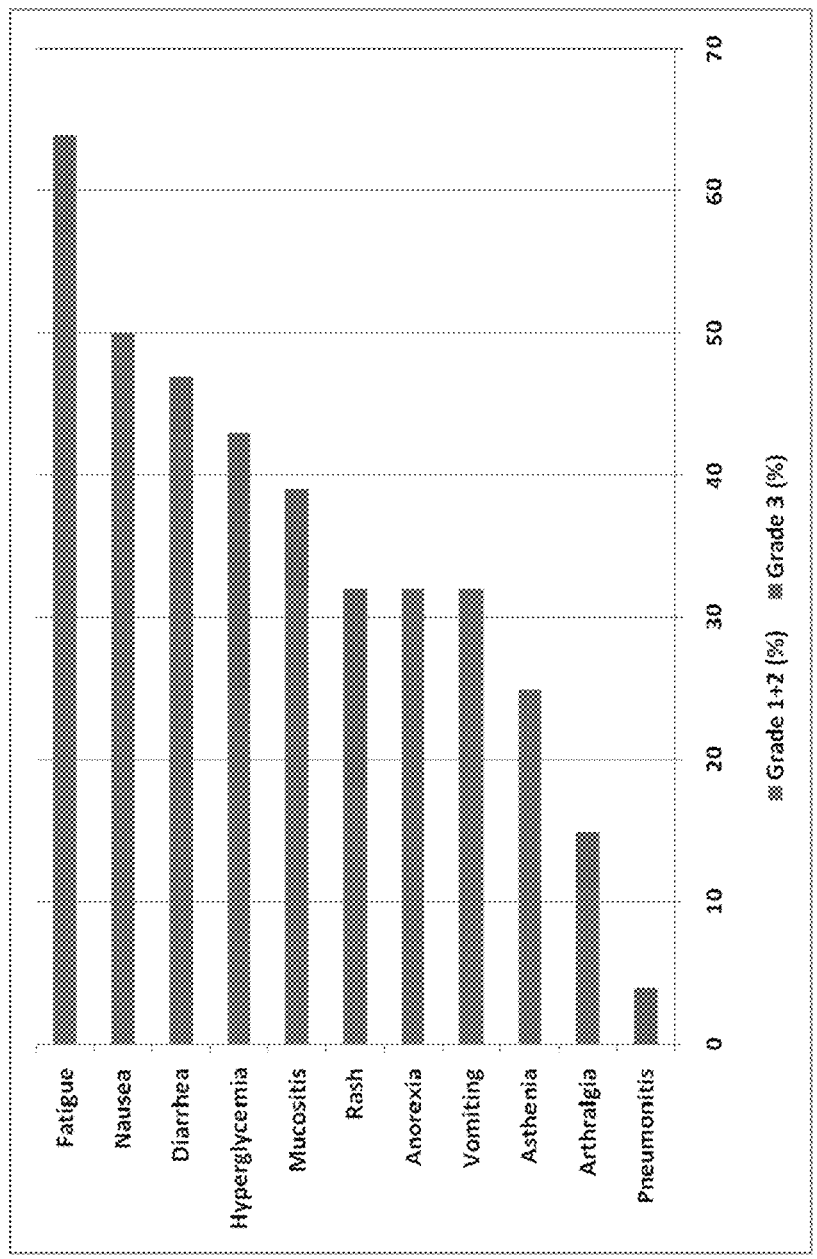
FIG. 23 depicts the most frequent Compound 1 related adverse events (overall frequency>20%) and all related grade 3/4 events (N=28).

The most frequent Compound 1-related events (>20%) as well as all related grade 3/4 events are shown in FIG. 22). Fatigue, GI toxicity (including mucositis/stomatitis), hyperglycemia, rash and arthralgia were the most frequent events. One case of grade 3 interstitial pneumonitis requiring hospitalization occurred. Compound 1 dosing was held and the pneumonitis responded to steroid treatment. The maximum tolerated dose (MTD) was 45 mg QD. (see FIG. 23).

Hyperglycemia was reported frequently with onset often occurring during cycle 1. Hyperglycemia was associated with elevations of insulin and c-peptide (FIG. 24) and was dose related. Daily fingerstick glucose monitoring was implemented early in the trial with rapid intervention with metformin and/or insulin at first occurrence of hyperglycemia. Hyperglycemia was generally manageable and patients were able to continue on Compound 1 treatment at the same or a lowered dose.

Figure 25:
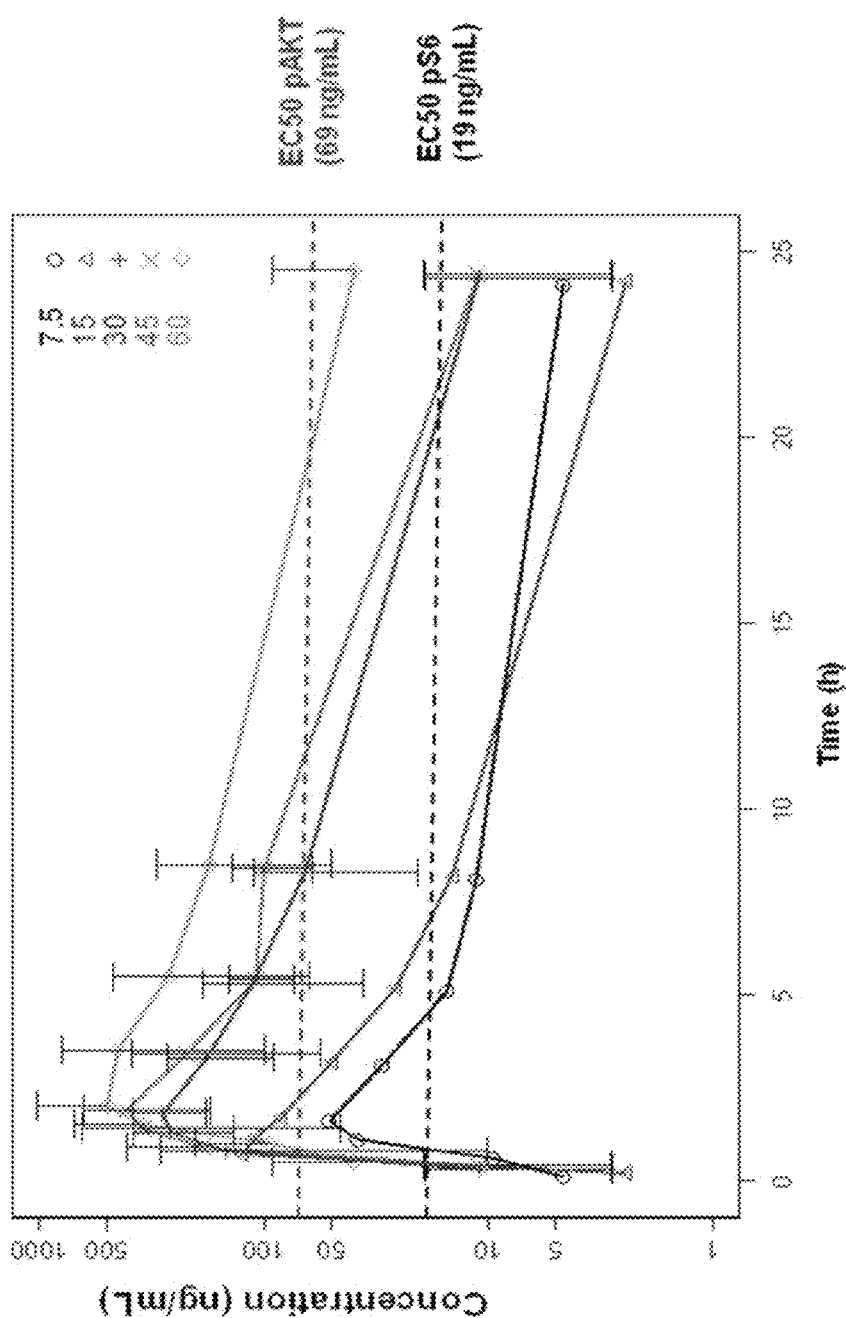
FIG. 25 depicts the mean (±SD) Steady-State plasma concentrations for Compound 1 on day 15 in human subjects.

Dose proportional drug exposure was observed, although there was a high level of intersubject variability in exposure. At dose levels of 30 mg and higher, exposures exceeded the levels estimated to provide >50% inhibition of TORC1 (pS6) and TORC2 (pAKT) pathways for at least 8 hours post dosing based on preclinical xenograft models. There was only minimal drug accumulation after 15 days of dosing. Dose proportional exposure was observed with a terminal half life of 4 to 8 hrs (mean steady state $C_{max}$ 485 ng/mL, $AUC_{0-24}$ 2371 ng$^x$hr/mL at 45 mg) (see FIG. 25)

Figure 26:
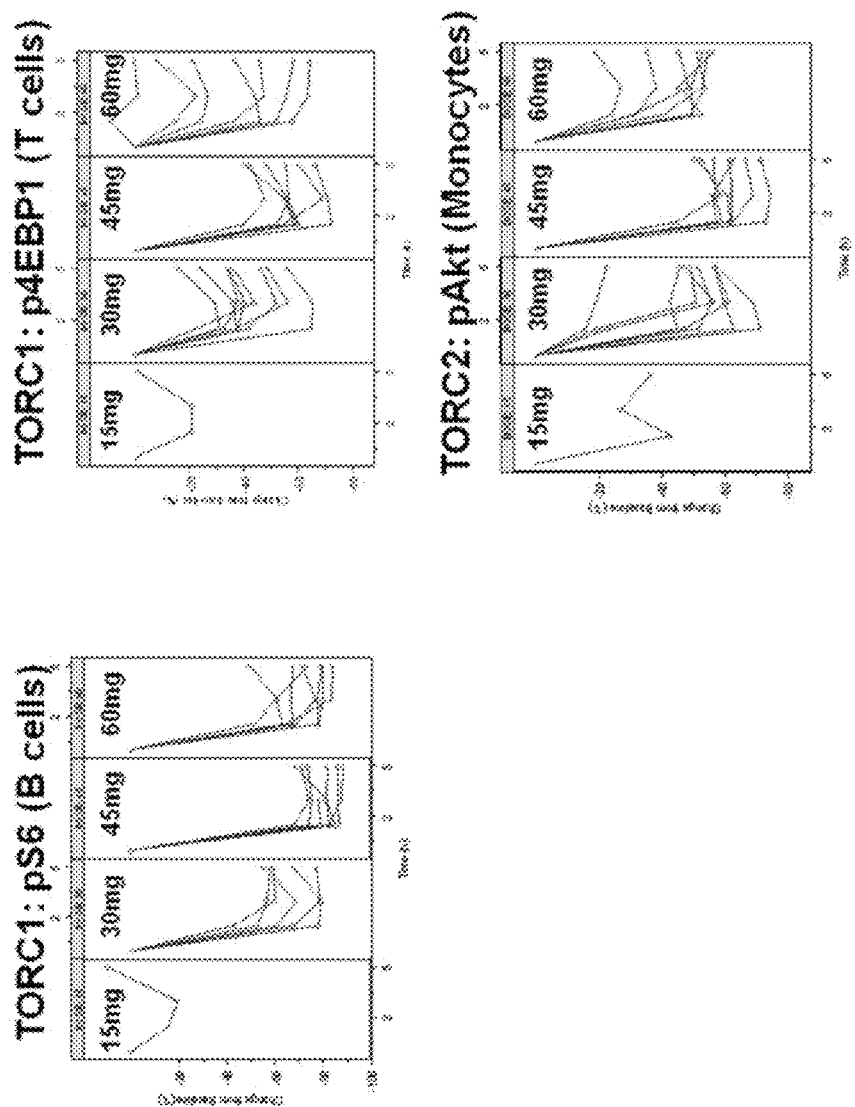
FIG. 26 depicts the dose-related TOR pathway inhibition in blood of human subjects.

TOR pathway biomarker inhibition was monitored in blood samples using a stimulated assay (FIG. 26). TORC1 inhibition was monitored by measurement of changes in p4EBP1 and pS6 and TORC2 by pAkt. Data was obtained after the first dose of Compound 1 and sampling timepoints were pre-dose, 1.5, 3, and 5 hours post dose. Biomarker inhibition was monitored in B cells, T cells, and monocytes and the cell type with the most consistent findings was selected for presentation. Consistent inhibition of both TORC1 and TORC2 biomarkers was observed for up to 5 hours post dose at Compound 1 doses of 30 mg and higher as predicted by preclinical modeling and human exposures achieved. In general, inhibition of the TORC1 marker, pS6, was more complete and durable than the p4EBP1 marker. Inhibition of pAkt confirmed Compound 1 activity against the TORC2 pathway and differentiates this agent from rapalogs which are predominantly TORC1 inhibitors and have been shown to trigger feedback upregulation of pAkt. PK/PD analysis demonstrated a dose dependent relationship between Compound 1 exposure and mTOR kinase inhibition.

Figure 27:
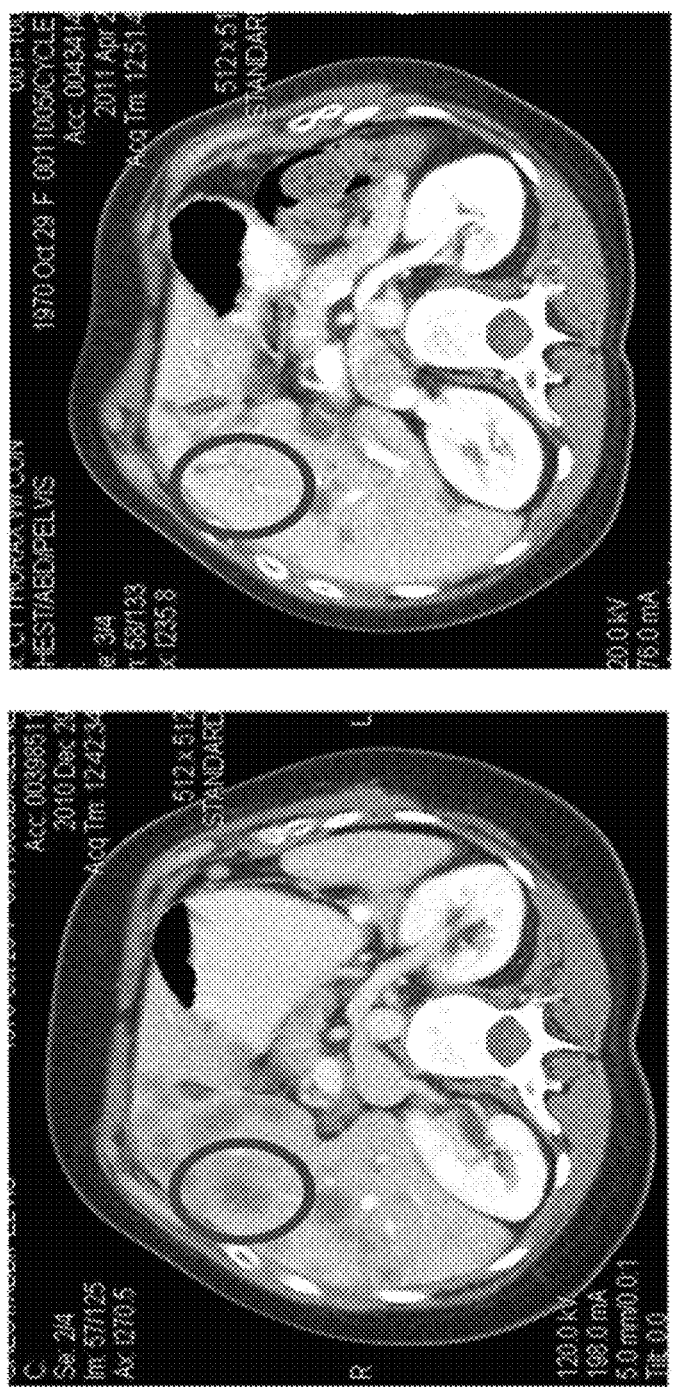
FIG. 27 depicts the radiological response for a patient having ER+/Her2− breast cancer. This subject demonstrated a 30% reduction in target lesions at the first restaging after 2 cycles of therapy.
Figure 28:
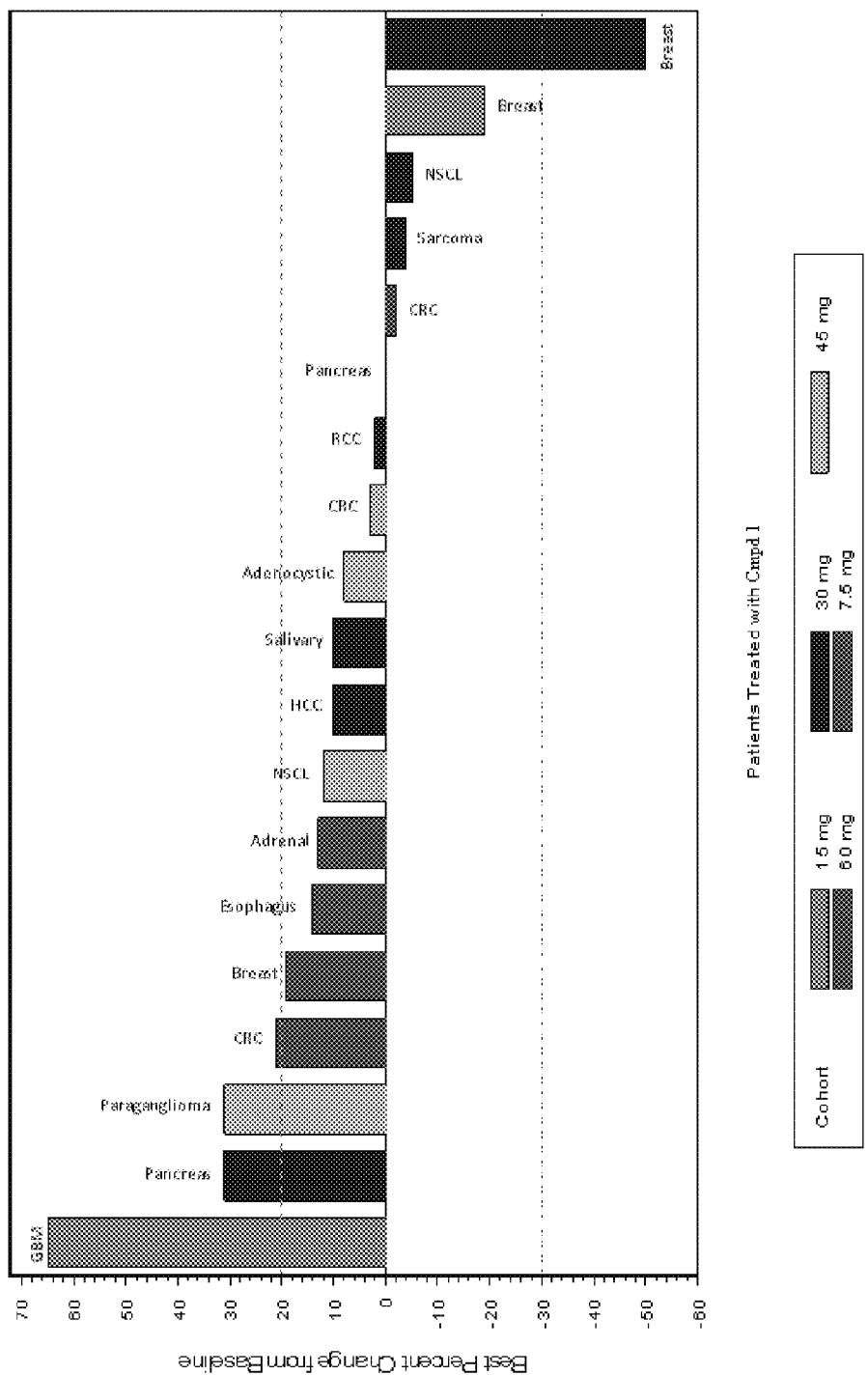
FIG. 28 depicts the best Target Lesion Responses (n=19; 9 subjects without restaging (7 early withdrawal/PD; 1 ineligible; 1 myeloma)).

Fifteen subjects showed target lesion responses in the stable range (see FIG. 28), of which 1 breast cancer subject showed greater than 30% regression of target lesions (see FIG. 27). The 2 subjects with the greatest tumor regression both had ER+ breast cancer. One subject with breast cancer completed more than 11 cycles of study treatment and demonstrated a confirmed PR, while a second subject with ER+ breast cancer completed nearly 6 cycles of study treatment and demonstrated SD at the time of first restaging scans (after 2 cycles of treatment).

Figure 29:
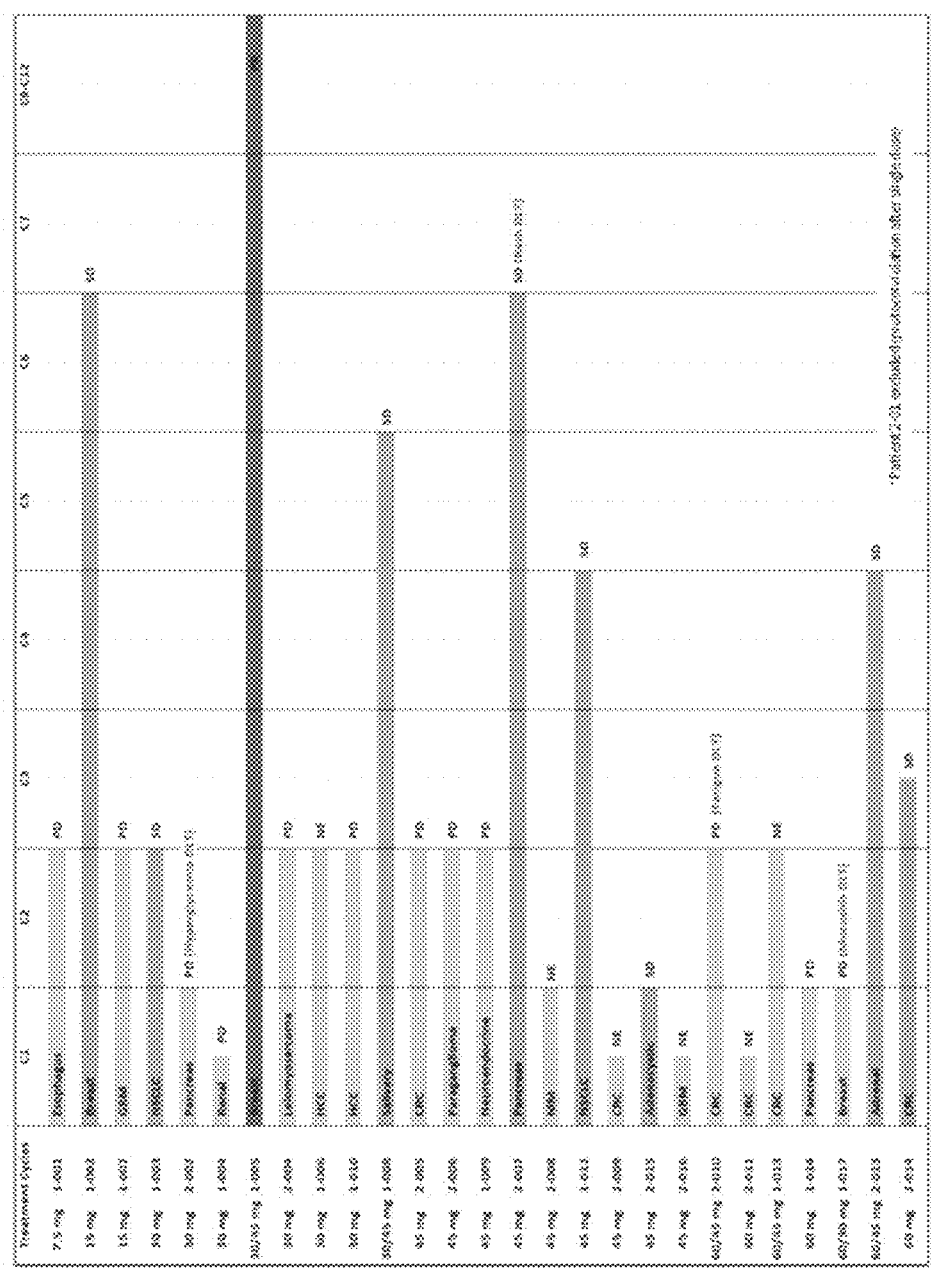
FIG. 29 depicts dose Level, Treatment Duration and Best Overall Response (n=27*).

The Dose Level, Treatment Duration and Best Overall Response is shown in FIG. 29. One subject with breast cancer demonstrated complete PR and completed more than 11 cycles of study treatment. The subject was dose escalated from 30 to 45 mg. Eight subjects had Stable Disease at the time of their first restaging scans (after 2 cycles of treatment). The longest duration of SD was 24 weeks. Tumors with SD included NSCLC (2), breast, salivary, pancreas, adenocystic, adrenal and colorectal cancer (CRC). SD was observed at doses ranging from 15 to 60 mg.

The ER+/Her2− breast cancer subject achieving Partial Response (see FIG. 27) lasting at least 11 months, and completing more than 11 cycles of study treatment, demonstrated a 30% reduction in target lesions at the first restaging after 2 cycles of therapy; demonstrated further regression at each subsequent restaging with a maximum 50% reduction after 10 cycles of therapy; and was subsequently removed from the study due to clinical progression manifest by worsening pulmonary symptoms during the 12th cycle. The duration of Partial Response from first restaging scan to last scan was 220 days (7.2 months or 7.9 cycles) and the duration of partial response from first restaging scan to last dose was 271 days (8.9 months or 9.7 cycles). The time to progression from first dose to last scan was 277 days (9.1 months or 9.9 cycles) and the time to progression from first dose to last dose was 328 days (10.8 months or 11.7 cycles).

Compound 1 was well tolerated with toxicities comparable to other drugs targeting this pathway. Evidence of TORC1/TORC2 pathway inhibition was observed as well as preliminary signals of anti-tumor activity, including the partial response and stable disease described above. Expansion cohorts in selected hematologic and solid tumors will evaluate Compound 1 at the MTD of 45 mg QD.

Part B: Dose Expansion Findings (based on Sep. 20, 2012 findings).

TOR Pathway Biomarker Inhibition: In all cohorts, TORC1 and TORC2 inhibition was observed in blood, as measured by inhibition of pAkt and p4EPB1 formation, when measured at baseline (average of screening and Cycle 1/Day 1 (t=0 h) and in Cycle 1/Day 1 (t=1.5 h after dosing), and in Cycle 1/Day 15 (t=0 h and 1.5 h). The data was analyzed by Paired t test and P values <0.001 were obtained when comparing baseline and Cycle 1/Day 1 (t=1.5 h after dosing), and between Cycle 1/Day 15 (t=0 h) and Cycle 1/Day 15 (t=1.5 h).

NSCLC Patients: TORC1 inhibition (as measured by percent change from baseline for p4EPB1) and TORC2 inhibition (as measured by percent change from baseline for pAkt/tAkt) were observed in majority of patients. Clear signals of clinical activity were seen in NSCLC patients. In 17 evaluable patients, best target lesions responses up to 35% reduction were observed, with 11 patients meeting at least Stable Disease and 1 patient meeting Partial Response RECIST 1.1 criteria. Four patients completed at least 6 cycles of study treatment and one patient remains on study drug after 10 cycles.

HCC Patients: TORC1 inhibition (as measured by percent change from baseline for p4EPB1) and TORC2 inhibition (as measured by percent change from baseline for pAkt/tAkt) were observed in majority of patients. Some signals of clinical activity were seen in HCC patients. In 14 evaluable patients, best target lesions responses up to 47% reduction were observed, with 5 patients meeting at least Stable Disease and 2 patients meeting Partial Response RECIST 1.1 criteria. Eight patients completed at least 4 cycles of study treatment.

DLBCL Patients: TORC1 inhibition (as measured by percent change from baseline for p4EPB1) and TORC2 inhibition (as measured by percent change from baseline for pAkt) was observed in the first patient analyzed. Some signals of clinical activity were seen in DLBCL patients. In 11 evaluable patients, best target lesions responses up to 75% reduction were observed, with 1 patient meeting at least Stable Disease and 2 patients meeting Partial Response RECIST 1.1 criteria. Restaging tumor assessments are pending in most treated subjects. Nine patients remain on study drug, and are ongoing at up to 6 cycles.

GBM Patients: TORC1 inhibition (as measured by percent change from baseline for p4EPB1) and TORC2 inhibition (as measured by percent change from baseline for pAkt) were observed in majority of patients. No signs of clinical activity, defined as a 6-month Progression-Free Survival, were observed in 10 evaluable GBM patients.

MM Patients: TORC1 inhibition (as measured by percent change from baseline for p4EPB1) and TORC2 inhibition (as measured by percent change from baseline for pAkt) were observed in 2 patients. No tumor responses were seen in MM patients. In 11 evaluable patients, none met Partial Response using IURCMM criteria, after up to 9 cycles of treatment. Two patients remain on study drug after 9 cycles.

NET Patients: Some signals of clinical activity were seen in NET patients. Six patients with sufficient follow up met Stable Disease RECIST 1.1 criteria. Thirteen patients remain on study drug, and are ongoing at up to 5 cycles. Preliminary signals of activity include improvements in carcinoid syndrome-related symptoms in some patients with refractory baseline symptoms, reductions in endocrine hormone markers (chromogranin, gastrin, serotonin, glucagon) in some patients, and reductions in tumor metabolic activity, as measured by PET imaging, in the majority of subjects.

Breast Cancer patients: Five subjects have initiated study drug in the expansion phase. Biomarker and response information will be collected.

5.2.2 Phase 1A/1B, Multi-Center, Open-Label, Dose Finding Study to Assess the Safety, Tolerability, Pharmacokinetics and Preliminary Efficacy of Compound 2 Administered Orally to Subjects with Glioblastoma Multiforme or Gliosarcoma Compound 2 will be administered orally to subjects with glioblastoma multiforme or gliosarcoma. The safety and tolerability of Compound 2 in humans, as well as the efficacy, will be evaluated in this study. The study will be conducted in two parts: dose escalation (Part A) and dose expansion (Part B). Subjects will be enrolled sequentially in Part A. Enrollment in Part B will be stratified by tumor type.

The primary objectives of this study are to: A. Determine the safety and tolerability of Compound 2 when administered orally and to define the NTD and the MTD. B. Determine the PK of Compound 2. The secondary objectives of this study are to: A. Evaluate the extent of inhibition of phosphorylation of S6RP and/or 4E-BP1 for mTORC1 activity and AKT and/or other relevant biomarkers for mTORC2 activity, in blood, skin and/or tumor biopsies/aspirates, when available before and during treatment with Compound 2. B. Evaluate the inhibition of DNA-PK activity in skin samples irradiated by UV light and/or tumor biopsies/aspirates using pDNA-PK S2056 and/or other relevant biomarkers for DNA damage pathways before and during Compound 2 treatment. C. Provide information on the efficacy of Compound 2.

Compound 2 will be available in four strengths (0.25 mg, 1.0 mg, 5.0 mg and 10 mg) presented in gelatin capsules containing only the active pharmaceutical ingredient. The capsules will be packaged in high density polyethylene (HDPE) bottles, fitted with induction seals and child-resistant polypropylene closures.

The primary endpoints of this study are: a) The following safety endpoints: DLTs, NTD and MTD, evaluated using the NCI CTCAE criteria Version 4; b) PK endpoints: $C_{max}$, AUC, $t_{max}$, $t_{1/2}$, CL/F, Vz/F and Accumulation Index of Compound 2. The secondary endpoints of this study are: a) Biomarker inhibition, determined by change in the levels of phosphorylation of S6RP, and/or 4E-BP1, and/or AKT, and/or other relevant biomarkers in blood, skin and/or tumor biopsies/aspirates, when available; b) Inhibition of UV-stimulated DNA-PK activity determined by levels of pDNA-PK and/or other relevant biomarkers in skin and/or tumor biopsies/aspirates, when available; c) Antitumor efficacy, determined by response rates of each tumor type using tumorappropriate response criteria.

Between 30 and 60 subjects will be enrolled in Part A, designed to establish initial toxicity.

Part B will consist of approximately 100 subjects with prespecified types of advanced solid tumors such as glioblastoma multiforme to further assess the safety profile of Compound 2 and provide efficacy information. Tumor response rate will be assessed by tumor type and dose level. The Part B population will be defined by the efficacy seen during Part A and by data from ongoing preclinical studies.

The overall study design will be comprised of a Screening Period (Day −28 to Day 1), a Treatment and Evaluation Period (28-day QD (and/or BID) cycles until tumor progression, unacceptable toxicity or subject/physician decision to discontinue administration of Compound 2) and an End of Treatment and Follow-up Period (end of treatment procedures within 21 days of last dose; follow-up for 28 days after last dose for final safety assessment).

Subjects will start Compound 2 QD or BID dosing (or other suitable regimen) on Cycle 1 Day 1 and receive daily treatment in 28-day cycles. Compound 2 may be discontinued when there is evidence of tumor progression, but subjects can continue to receive study drug as long as the Investigator considers they are deriving benefit. Compound 2 administration will be discontinued when there is unacceptable toxicity, or the subject decides to withdraw from the study.

Compound 2 will be administered orally either once or twice daily (or other suitable dosing regimen) with no rest period between cycles. Each QD dose will be taken in the morning with at least 200 mL of water, with the subject having fasted overnight (minimum of 6 hours). Food intake will be delayed until at least 90 minutes after dosing on the days Compound 2 is taken at home. On clinic visit days, the morning Compound 2 dose will be administered in the clinic after any predose tests have been completed. Food may be taken after all fasting tests have been completed but in no case earlier than 90 minutes after dosing (3 hours after dosing on Day 15). For subjects receiving Compound 2 QD where troublesome related GI symptoms, fatigue or other symptoms persist beyond the end of Cycle 1, dosing may be moved to later in the day providing the subject can maintain a 3-hour separation between Compound 2 administration and the last intake of food and a 90-minute delay before ingesting further food. Compound 2 may be taken up to 12 hours late if dosing has been delayed on a single day; otherwise that dose should be omitted.

Compound 2 will be administered initially as a QD regimen.

Doses will be administered in an escalating manner following satisfactory review of safety data from the lower doses. There will be a minimum of 28 days after the first dose has been administered to the last subject between dose escalations. Within each cohort, enrollment will be staggered so that there is a minimum of 24 hours between Cycle 1 Day 1 for each subject in order to evaluate initial toxicity.

Each cycle of Compound 2 lasts 28 days and there is no rest period between cycles. Subjects may be discontinued when there is evidence of disease progression but subjects can continue to receive Compound 2 for as long as they derive benefit from treatment, as judged by the Investigator. Compound 2 administration will be discontinued when there is unacceptable toxicity or if the subject decides to withdraw from the study.

In Part A, cohorts of subjects will initially receive QD ascending doses of Compound 2 to measure PK and to identify the MTD. In Part A, 0.5 mg QD is the Compound 2 starting dose. A modified accelerated titration design (Simon, R., Freidlin, B., Rubinstein, L., et al. Accelerated titration designs for Phase I clinical. trials in oncology, *J Nat Canc Institute* 1997; 89, (15): 1138-1147) will be used to establish initial toxicity. During the accelerated phase, initial cohorts of one subject will be given Compound 2 at dose increments of 100% until the first instance of first-Cycle grade 2 or higher toxicity suspected to be drug-related, at which point the accelerated phase will stop and this particular cohort will be expanded to a total of 6 subjects. Subsequently, a standard escalation dosing schedule with approximately 50% dose increments and 6 subjects per cohort will be initiated in order to establish the NTD and MTD. Smaller increments and additional subjects within a dose cohort may also be evaluated, if necessary, based on toxicity, PK/PD results or tumor biopsy findings.

Based on interim PK and PD results from initial dose cohorts, a twice-daily (BID) dosing regimen will also be evaluated in Part A. This will be initiated in cohorts of 6 subjects at or below a total daily dose level already shown to be tolerable, but divided into two equal doses administered approximately 12 hours apart. Thereafter, dose escalation for QD and BID dosing cohorts may occur independently. Intermittent dosing schedules of comparable or lower dose intensity than continuous daily dosing may also be considered for evaluation.

A dose will be considered to be non-tolerated if 2 or more out of 6 evaluable subjects in a dose cohort experience DLT during Cycle 1. When a NTD is defined, dose escalation will be stopped. The MTD will be defined as the last dose tested below the NTD with 0 or 1 out of 6 evaluable subjects experiencing DLT during Cycle 1. An intermediate dose (i.e., one between the NTD and the last dose level before the NTD) or additional subjects within any dose cohort may be required to more precisely determine the MTD more precisely, as may alternate regimens if emerging PK-PD results suggest these may be appropriate.

In Part B, subjects may start Compound 2 on a QD or BID regimen at the MTD and/or lower dose levels based on safety, PK and PD data from Part A. In Part B, approximately 100 subjects will be evaluated for safety and antitumor activity after every two cycles of therapy.

All subjects who receive at least one dose of Compound 2 will be evaluable for safety. In Part A, a subject evaluable for dose-limiting toxicity (DLT) is defined as one who, in the first 28 days after Cycle 1 dosing began, either (a) received at least 21 of the planned 28 doses of Compound 2 at the cohort-specified dose and has sufficient data for safety evaluation by the SRC, or (b) experienced study drug-related DLT. Non-evaluable subjects will be replaced in the dosing cohort. In Part B, an efficacy evaluable subject for tumor response is defined as one who received at least one cycle of Compound 2, and have baseline and at least one post-baseline efficacy assessment.

In Parts A and B, dose reductions are permitted in any cycle, including Cycle 1. Dose reductions that occur in Cycle 1 during Part A will constitute DLT, but subjects will be allowed to continue on study drug at the reduced dose. National Cancer Institute Common Terminology Criteria for Adverse Events (NCI CTCAE) Version 4, 2009 will be used to grade AEs.

When a dose reduction is indicated, the next lower dose level will be on a QD or BID schedule will be selected. For BID dose reductions below the starting dose of 10 mg BID, 8 mg BID and 4 mg BID will be selected. Two dose reductions are allowed. Additional PK evaluations may be conducted at modified dose level(s) in order to characterize intrasubject PK profiles with alternate doses.

In Part A, intrasubject dose escalation beyond the dose initially assigned to a subject is not permitted in Cycle 1. Those continuing to take Compound 2 beyond Cycle 1 may, have the dose level increased providing the alternative dose level has been shown to be well tolerated by at least one cohort of other subjects in this study. In these instances, additional PK evaluation at the higher dose level may be conducted. In Part B, no dose escalation beyond the MTD is allowed.

In the following, statistical analyses will be performed by study phase, dose level, dosing regimen and tumor cohort as needed or applicable.

The study population definitions are as follows: (a) Intent-to-Treat (ITT) Population—All subjects who take at least one dose of Compound 2; (b) Safety Population—All subjects who take at least one dose of Compound 2, which is the same as ITT population for this study; (c) Efficacy Evaluable (EE) Population—All ITT subjects who meet eligibility criteria, complete at least one cycle of Compound 2, and have baseline and at least one valid post-baseline efficacy assessment.

Subject enrollment will be curtailed when up to 20 evaluable subjects have been enrolled in each tumor type and dose level/regimen. In Part B as a whole, sample sizes are not based on statistical calculation but rather on clinical empirical and practical considerations traditionally used for Phase 1 studies of this kind.

All efficacy evaluable subjects in the Part B portion will be included for efficacy analysis. Efficacy will be analyzed by each tumor type once all subjects have withdrawn from the study or completed 6 cycles. Two-sided ninety-five percent confidence intervals of the response rate will be provided by tumor type. A case-by-case description of all subjects who exhibited a complete or partial response during the Part A segment will be provided. A descriptive analysis of other evidence of anti-tumor activity will be provided based on clinical, radiographic, and biologic assessments of efficacy.

All treated subjects will be included for the efficacy analysis. The primary efficacy variable is tumor respons, based on investigator's assessment using RANO criteria, using the post resection MRI scan as the baseline. Given the difficulty in assessing tumor response following salvage surgery, the primary efficacy endpoint for GBM will be the proportion of subjects progression-free at 6 months from Day 1 relative to efficacy evaluable subjects in the GBM type. Other supplementary efficacy variables, including CTC assessments, will be summarized using frequency tabulations for categorical variables or descriptive statistics for continuous variables.

For both the dose escalation and dose expansion parts of this protocol, inclusion criteria are: (a) Understand and voluntarily sign an informed consent document before any study-related assessments/procedures are conducted; (b) Men and women, 18 years or older, with histological or cytological confirmation of glioblasoma multiforme or gliosarcoma, including those who have progressed on (or not been able to tolerate) standard anticancer therapy or for whom no other conventional therapy exists; (c) Consent to screening tumor biopsy (Part A optional; Part B mandatory except as specified for individual tumor types below); (d) ECOG PS of 0 or 1; (e) The following laboratory values: (1) Absolute neutrophil count (ANC)≥1.5×109/L; (2) Hemoglobin (Hgb)≥9 g/dl; (3) Platelets (plt)≥100×109/L; (4) Potassium within normal range, or correctable with supplements; (5) AST/SGOT and ALT/SGPT≤2.5×Upper Limit of Normal (ULN) or ≤5.0×ULN if liver tumor is present; (6) Serum total bilirubin≤1.5×ULN or ≤2×ULN if liver tumor is present; (7) Serum creatinine≤1.5×ULN, or 24-hr clearance≥50 mL/min; and (8) Negative serum or urine pregnancy test within 72 hrs before starting study treatment in females of childbearing potential; and (f) Able to adhere to the study visit schedule and other protocol requirements.

For the dose expansion part (Part B) of this protocol, inclusion criteria are: (a) Subject consent to retrieve formalin-fixed, paraffin-embedded (FFPE) archival tumor tissue, either in tumor blocks or sectioned/mounted specimens; and (b) Histologically-confirmed glioblasoma multiforme or gliosarcoma, excluding WHO Grade IV oligoastrocytoma (has received prior treatment including radiation and/or chemotherapy, with radiation completed >12 weeks prior to Day 1; planned salvage surgical tumor resection on Day 15±7 days, anticipated to yield ≥300 mg tumor tissue. Screening tumor biopsy is not required; no prior or scheduled Gliadel® wafer implant unless area of assessment and planned resection is outside the region previously implanted; no prior interstitial brachytherapy or stereotactic radiosurgery unless area of assessment and planned resection is outside the region previously treated; no enzyme-inducing anti-epileptic drugs (EIAED) such as carbamazepine, phenyloin, phenobarbital, or primidone within 14 days before Day 1; and able to undergo repeated magnetic resonance imaging (MRI) scans).

For both the dose escalation and dose expansion parts of this protocol, exclusion criteria are: (a) Symptomatic central nervous system metastases; (b) Known acute or chronic pancreatitis; (c) Any peripheral neuropathy ≥NCI CTCAE grade 2; (d) Persistent diarrhea or malabsorption ≥NCI CTCAE grade 2, despite medical management. Impaired ability to swallow; (e) Impaired cardiac function or clinically significant cardiac diseases; (f) Diabetes mellitus on active treatment; (g) Other concurrent severe and/or uncontrolled concomitant medical conditions (e.g. active or uncontrolled infection) that could cause unacceptable safety risks or compromise compliance with the protocol; (h) Prior systemic cancer-directed treatments or investigational modalities ≤5 half lives or 4 weeks, whichever is shorter, prior to starting study drug or who have not recovered from side effects of such therapy; (i) Major surgery ≤2 weeks prior to starting study drug or who have not recovered from side effects of such therapy; (j) Pregnancy or breast feeding;

(k) Adults of reproductive potential not employing two forms of birth control; (l) Known HIV infection; (m) Known chronic hepatitis B or C virus (HBV/HCV) infection, unless this is comorbidity in subjects with HCC; (n) Any significant medical condition, laboratory abnormality, or psychiatric illness, including the inability to swallow capsules, that would prevent subjects from participating in the study; (o) Any condition including the presence of laboratory abnormalities, which places subjects at unacceptable risk if they were to participate in the study; (p) Any condition that confounds the ability to interpret study data; or (q) Concurrent active second malignancy for which the subject is receiving therapy, excluding non-melanomatous skin cancer or carcinoma in situ of the cervix.

For the dose expansion part (Part B) of this protocol, exclusion criteria are: Prior treatment with agents targeting both mTOR complexes (dual TORC1+TORC2 inhibitors) and/or PI3K/AKT pathways. However, prior treatment with isolated TORC1 inhibitors (e.g., rapalogs) is allowed in both parts of this study.

In certain embodiments, patients undergoing the clinical protocol provide herein will show a positive tumor response, such as inhibition of tumor growth or a reduction in tumor size. In certain embodiments, patients undergoing the clinical protocol provide herein will show an improvement in the Response Assessment for Neuro-Oncology (RANO) Working Group regarding response criteria for high-grade gliomas.

Effect of Compound 2 on Ultraviolet B-Stimulated Human Skin. The inhibitory effect of Compound 2 on DNA-PK was evaluated by assessing the phosphorylation status of DNA-PK S2056 following UV irradiation of human skin before and during Compound 2 treatment. The minimal erythema dose (MED) was determined for each subject during screening. To determine the MED, each subject received UV-irradiation to 6 areas on their buttock. The UV dose on each area was increased incrementally from the previous dose. The starting UV dose was dependent on the subject's skin type according to Fitzpatrick classification. The spectrum of UV-irradiation is UV light B spectrum (UVB). MED determination was done approximately 22 to 24 hours post UVB exposure.

During screening, and after MED determination, subjects received a 2×MED UV dose to one site on the buttock. Two punch biopsies (approximately 4 mm in diameter by 0.8 mm in depth) were taken, one from the UV irradiated site and one from adjacent non-UV irradiated skin. The punch biopsies were taken at 4 (±15 minutes) hours post UV exposure. On Cycle 1 Day 15 to 22, subjects received a 2×MED UV dose to one site on the opposite buttock. Two punch biopsies (approximately 4 mm in diameter by 0.8 mm in depth) were taken, one from the UV irradiated site and one from adjacent non-UV irradiated skin. The punch biopsies were taken at 4 (±15 minutes) hours post UV exposure and 2 (±15 minutes) hours post Compound 2 dose. All skin samples were immediately placed into 10% formalin, fixed for 24 hours, and subsequently transferred to 70% ethanol. The specimens were embedded in paraffin within 48-72 hours. Skin specimens from the biopsies were analyzed for phospho-DNA-PK using an IHC assay. Phospho-DNA-PK was quantified using a combination of percentage and intensity subjective grading scales and/or objective scoring using an automated system, i.e. Aperio, with a nuclear algorithm to evaluate staining.

UV Exposure Equipment: The DermaPal UV unit (manufactured by Daavlin) uses a FS Fluorescent Sunlamp and exposure was regulated by a built-in digital timer. The DermaPal was adapted to position a 12 oz styrofoam coffee cup over the bulbs, which thus became a device establishing all exposure distances and preventing unwanted exposure. A separate device consisting of six graded neutral density filters was supplied to provide a graded series of UV doses to establish each patient's MED. A kodacel filter was used in conjunction with this device.

A number of references have been cited, the disclosures of which are incorporated herein by reference in their entirety. The embodiments disclosed herein are not to be limited in scope by the specific embodiments disclosed in the examples which are intended as illustrations of a few aspects of the disclosed embodiments and any embodiments that are functionally equivalent are encompassed by the present disclosure. Indeed, various modifications of the embodiments disclosed herein are in addition to those shown and described herein will become apparent to those skilled in the art and are intended to fall within the scope of the appended claims.

What is claimed is:

1. A method for treating a solid tumor, comprising administering an effective amount of 7-(6-(2-hydroxypropan-2-yl)pyridin-3-yl)-1-(trans-4-methoxycyclohexyl)-3,4-dihydropyrazino[2,3-b]pyrazin-2(1H)-one or a pharmaceutically acceptable salt, stereoisomer or tautomer thereof, to a patient having a solid tumor, wherein the solid tumor is non-small cell lung cancer or breast cancer, and wherein the solid tumor is rapamycin resistant.

2. The method of claim 1, wherein the solid tumor is an advanced solid tumor.

3. The method of claim 1, wherein the breast cancer is ER+/Her2-, ER+/Her2+, ER-/Her2+ or triple negative (TN).

4. The method of claim 1, wherein the solid tumor is non-small cell lung cancer.

5. The method of claim 1, wherein the solid tumor is breast cancer.

* * * * *